US008575208B2

(12) United States Patent
Farmer et al.

(10) Patent No.: US 8,575,208 B2
(45) Date of Patent: Nov. 5, 2013

(54) INHIBITORS OF SERINE PROTEASES

(75) Inventors: Luc Farmer, Foxborough, MA (US); Randy Scott Bethiel, Lexington, MA (US); Dylan Jacobs, Everett, MA (US); Robert B. Perni, Marlborough, MA (US); John Maxwell, Hingham, MA (US); Kevin Cottrell, Cambridge, MA (US); Summer Halas, Seattle, WA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 751 days.

(21) Appl. No.: 12/528,952

(22) PCT Filed: Feb. 20, 2008

(86) PCT No.: PCT/US2008/002395
§ 371 (c)(1),
(2), (4) Date: Apr. 22, 2010

(87) PCT Pub. No.: WO2008/106058
PCT Pub. Date: Sep. 4, 2008

(65) Prior Publication Data
US 2010/0272681 A1    Oct. 28, 2010

Related U.S. Application Data

(60) Provisional application No. 60/903,814, filed on Feb. 27, 2007.

(51) Int. Cl.
*A61K 31/4025*    (2006.01)
*C07D 207/08*    (2006.01)

(52) U.S. Cl.
USPC .......................... 514/409; 548/409; 548/410

(58) Field of Classification Search
USPC ................................. 548/409, 410; 514/409
See application file for complete search history.

(56) References Cited

U.S. PATENT DOCUMENTS

| | | | |
|---|---|---|---|
| 4,499,082 A | 2/1985 | Shenvi et al. |
| 4,720,484 A | 1/1988 | Vincent et al. |
| 4,880,780 A | 11/1989 | Trainor et al. |
| 5,053,519 A | 10/1991 | Teetz et al. |
| 5,231,084 A | 7/1993 | Hock et al. |
| 5,371,072 A | 12/1994 | Webb et al. |
| 5,384,410 A | 1/1995 | Kettner |
| 5,468,858 A | 11/1995 | Berlin et al. |
| 5,484,801 A | 1/1996 | Al-Razzak et al. |
| 5,496,927 A | 3/1996 | Kolb et al. |
| 5,502,061 A | 3/1996 | Hui et al. |
| 5,559,158 A | 9/1996 | Al-Razzak et al. |
| 5,610,193 A | 3/1997 | Al-Razzak et al. |
| 5,656,600 A | 8/1997 | Abelman et al. |
| 5,656,627 A | 8/1997 | Bemis et al. |
| 5,672,582 A | 9/1997 | Veber et al. |
| 5,716,929 A | 2/1998 | Bemis et al. |
| 5,725,878 A | 3/1998 | Al-Razzak et al. |
| 5,736,520 A | 4/1998 | Bey et al. |
| 5,756,466 A | 5/1998 | Bemis et al. |
| 5,760,029 A | 6/1998 | Jadhav et al. |
| 5,807,876 A | 9/1998 | Armistead et al. |
| 5,847,135 A | 12/1998 | Bemis et al. |
| 5,849,866 A | 12/1998 | Kolb |
| 5,861,267 A | 1/1999 | Su |
| 5,866,684 A | 2/1999 | Attwood et al. |
| 5,948,436 A | 9/1999 | Al-Razzak et al. |
| 5,973,111 A | 10/1999 | Bemis et al. |
| 5,990,276 A | 11/1999 | Zhang et al. |
| 6,015,912 A * | 1/2000 | Wang et al. .................... 548/408 |
| 6,018,020 A | 1/2000 | Attwood et al. |
| 6,025,147 A | 2/2000 | Bemis et al. |
| 6,025,516 A | 2/2000 | Ramaswamy et al. |
| 6,037,157 A | 3/2000 | Norbeck |
| 6,046,195 A | 4/2000 | Haworth et al. |
| 6,054,472 A | 4/2000 | Armistead et al. |
| 6,060,469 A | 5/2000 | Baker et al. |
| 6,103,711 A | 8/2000 | Bemis et al. |
| 6,117,639 A | 9/2000 | Germann et al. |
| 6,130,315 A | 10/2000 | Kolb |
| 6,143,715 A | 11/2000 | Llinas-Brunet et al. |

(Continued)

FOREIGN PATENT DOCUMENTS

DE    3211676    10/1983
EP    0417721    3/1991

(Continued)

OTHER PUBLICATIONS

Akahoshi, F., "Chymase Inhibitors and their Therapeutic Potential", Drugs of the Future, 27(8) (2009), pp. 765-770.
Anonymous, VPI internet press release Sep. 7, 2004.
Anonymous, newsrx internet article, May 31, 2004.
Arasappan, A., "Hepatitis C Virus NS3-4A Serine Protease Inhibitors: SAR of P'2 Moiety with Improved Potency", Bioorg. & Med. Chem. Let, vol. 15, (2005), pp. 4180-4184.
Avolio, S., "Inhibitors of hepatitis C virus NS3/4A: α-Ketoamide based macrocyclic inhibitors," Bioorganic & Medicinal Chemistry Letters (2009), 19, pp. 2295-2298.

(Continued)

*Primary Examiner* — Kamal Saeed
*Assistant Examiner* — Janet L Coppins
(74) *Attorney, Agent, or Firm* — Honigman Miller Schwarz and Cohn; Kathryn D. Soulier; Jonathan P. O'Brien

(57) ABSTRACT

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

11 Claims, No Drawings

(56) References Cited

U.S. PATENT DOCUMENTS

| | | |
|---|---|---|
| 6,153,579 A | 11/2000 | Kim et al. |
| 6,172,077 B1 | 1/2001 | Curtis et al. |
| 6,183,121 B1 | 2/2001 | Kim et al. |
| 6,211,338 B1 | 4/2001 | Malcolm et al. |
| 6,225,320 B1 | 5/2001 | Kulagowski et al. |
| 6,251,583 B1 | 6/2001 | Zhang et al. |
| 6,265,380 B1 | 7/2001 | Tung et al. |
| 6,268,207 B1 | 7/2001 | Bailey et al. |
| 6,274,613 B1 | 8/2001 | Plant et al. |
| 6,303,287 B1 | 10/2001 | Kim et al. |
| 6,323,180 B1 | 11/2001 | Llinas-Brunet et al. |
| 6,329,417 B1 | 12/2001 | Llinas-Brunet et al. |
| 6,344,465 B1 | 2/2002 | Armistead et al. |
| 6,348,608 B1 | 2/2002 | Shi |
| 6,399,771 B1 | 6/2002 | Plant et al. |
| 6,410,531 B1 | 6/2002 | Llinas-Brunet et al. |
| 6,420,380 B2 | 7/2002 | Llinas-Brunet et al. |
| 6,420,522 B1 | 7/2002 | Bemis et al. |
| 6,498,178 B2 | 12/2002 | Stamos et al. |
| 6,528,276 B1 | 3/2003 | Germann et al. |
| 6,534,523 B1 | 3/2003 | Llinas-Brunet et al. |
| 6,541,496 B1 | 4/2003 | Armistead et al. |
| 6,548,555 B1 | 4/2003 | Curatolo et al. |
| 6,608,027 B1 | 8/2003 | Tsantrizos et al. |
| 6,608,067 B1 | 8/2003 | Tung et al. |
| 6,617,309 B2 | 9/2003 | Tung et al. |
| 6,653,127 B1 | 11/2003 | Malcolm et al. |
| 6,653,295 B2 | 11/2003 | Glunz et al. |
| 6,699,855 B2 | 3/2004 | Zhang et al. |
| 6,727,366 B2 | 4/2004 | Han et al. |
| 6,767,991 B1 | 7/2004 | Llinas-Brunet et al. |
| 6,774,212 B2 | 8/2004 | Han |
| 6,800,434 B2 | 10/2004 | Saksena et al. |
| 6,824,769 B2 | 11/2004 | Chaturvedi et al. |
| 6,833,442 B2 | 12/2004 | Shibasaki et al. |
| 6,838,475 B2 | 1/2005 | Arasappan et al. |
| 6,846,802 B2 | 1/2005 | Chen et al. |
| 6,846,806 B2 | 1/2005 | Priestley |
| 6,867,284 B1 | 3/2005 | Matassa et al. |
| 6,872,805 B2 | 3/2005 | Campbell et al. |
| 6,909,000 B2 | 6/2005 | Farmer et al. |
| 6,911,428 B2 | 6/2005 | Zhu et al. |
| 6,914,122 B2 | 7/2005 | Venkatraman et al. |
| 6,919,423 B2 | 7/2005 | Llinas-Brunet et al. |
| 6,939,692 B2 | 9/2005 | Bathe et al. |
| 6,939,854 B2 | 9/2005 | Priestley |
| 7,012,066 B2 | 3/2006 | Saksena et al. |
| 7,034,178 B2 | 4/2006 | Faber et al. |
| 7,091,184 B2 | 8/2006 | Llinas-Brunet et al. |
| 7,105,302 B2 | 9/2006 | Bathe et al. |
| 7,109,172 B2 | 9/2006 | Britt et al. |
| 7,119,073 B2 | 10/2006 | Colarusso et al. |
| 7,122,627 B2 | 10/2006 | Priestley |
| 7,169,760 B2 | 1/2007 | Saksena et al. |
| 7,208,600 B2 | 4/2007 | Cottrell et al. |
| 7,241,796 B2 | 7/2007 | Farmer et al. |
| 7,244,721 B2 | 7/2007 | Saksena et al. |
| 7,250,520 B2 | 7/2007 | Wallace |
| 7,273,885 B2 | 9/2007 | Pitlik et al. |
| 7,288,624 B2 | 10/2007 | Bemis et al. |
| 7,365,092 B2 | 4/2008 | Cottrell et al. |
| 7,371,372 B2 | 5/2008 | Chaturvedi et al. |
| 7,378,422 B2 | 5/2008 | Perni et al. |
| 7,381,827 B2 | 6/2008 | Tanoury et al. |
| 7,388,017 B2 | 6/2008 | Tung et al. |
| 7,504,378 B2 | 3/2009 | Llinas-Brunet et al. |
| 7,592,316 B2 | 9/2009 | Njoroge et al. |
| 2002/0016294 A1 | 2/2002 | Venkatraman et al. |
| 2002/0016442 A1 | 2/2002 | Llinas-Brunet et al. |
| 2002/0032175 A1 | 3/2002 | Tung et al. |
| 2002/0037998 A1 | 3/2002 | Llinas-Brunet et al. |
| 2002/0042046 A1 | 4/2002 | Kim et al. |
| 2002/0045729 A1 | 4/2002 | Kerres et al. |
| 2002/0065248 A1 | 5/2002 | Zhang et al. |
| 2002/0068702 A1 | 6/2002 | Lim-Wilby |
| 2002/0102235 A1 | 8/2002 | Arasappan et al. |
| 2002/0107181 A1 | 8/2002 | Chen et al. |
| 2002/0111378 A1 | 8/2002 | Stamos et al. |
| 2002/0123468 A1 | 9/2002 | Han |
| 2002/0142449 A1 | 10/2002 | Kwong et al. |
| 2002/0147160 A1 | 10/2002 | Bhat et al. |
| 2002/0160962 A1 | 10/2002 | Saksena et al. |
| 2002/0177725 A1 | 11/2002 | Priestley et al. |
| 2002/0183249 A1 | 12/2002 | Taylor et al. |
| 2002/0187488 A1 | 12/2002 | Lin et al. |
| 2003/0008828 A1 | 1/2003 | Priestley et al. |
| 2003/0036501 A1 | 2/2003 | Saksena et al. |
| 2003/0064962 A1 | 4/2003 | Glunz et al. |
| 2003/0068369 A1 | 4/2003 | McAllister et al. |
| 2003/0083467 A1 | 5/2003 | Germann et al. |
| 2003/0100768 A1 | 5/2003 | Han et al. |
| 2003/0119752 A1 | 6/2003 | Farmer et al. |
| 2003/0144257 A1 | 7/2003 | Biggadike et al. |
| 2003/0153788 A1 | 8/2003 | Kobayashi et al. |
| 2003/0181363 A1 | 9/2003 | Llinas-Brunet et al. |
| 2003/0186895 A1 | 10/2003 | Llinas-Brunet et al. |
| 2003/0186952 A1 | 10/2003 | Crew et al. |
| 2003/0187018 A1 | 10/2003 | Llinas-Brunet et al. |
| 2003/0191067 A1 | 10/2003 | Llinas-Brunet et al. |
| 2003/0195362 A1 | 10/2003 | Kempf et al. |
| 2003/0216325 A1 | 11/2003 | Saksena et al. |
| 2003/0236242 A1 | 12/2003 | Perni et al. |
| 2004/0006237 A1 | 1/2004 | Dolitzky et al. |
| 2004/0018986 A1 | 1/2004 | Pitlik et al. |
| 2004/0048774 A1 | 3/2004 | Saunders et al. |
| 2004/0058982 A1 | 3/2004 | Harris et al. |
| 2004/0067901 A1 | 4/2004 | Bhat et al. |
| 2004/0072788 A1 | 4/2004 | Bhat et al. |
| 2004/0077600 A1 | 4/2004 | Tung et al. |
| 2004/0082574 A1 | 4/2004 | Wang et al. |
| 2004/0105820 A1 | 6/2004 | Weers et al. |
| 2004/0110747 A1 | 6/2004 | Altman |
| 2004/0142876 A1 | 7/2004 | Colarusso et al. |
| 2004/0171626 A1 | 9/2004 | Beaulieu et al. |
| 2004/0180815 A1 | 9/2004 | Nakajima et al. |
| 2004/0186125 A1 | 9/2004 | Poupart et al. |
| 2004/0224900 A1 | 11/2004 | Bailey et al. |
| 2004/0229817 A1 | 11/2004 | Duggal et al. |
| 2004/0229818 A1 | 11/2004 | Llinas-Brunet et al. |
| 2004/0266731 A1 | 12/2004 | Tung et al. |
| 2005/0020503 A1 | 1/2005 | Llinas-Brunet et al. |
| 2005/0049220 A1 | 3/2005 | Stuyver et al. |
| 2005/0059606 A1 | 3/2005 | Saksena et al. |
| 2005/0062522 A1 | 3/2005 | Haider et al. |
| 2005/0080005 A1 | 4/2005 | Llinas-Brunet et al. |
| 2005/0080017 A1 | 4/2005 | Cottrell et al. |
| 2005/0090450 A1 | 4/2005 | Farmer et al. |
| 2005/0107304 A1 | 5/2005 | Britt et al. |
| 2005/0112093 A1 | 5/2005 | Ette et al. |
| 2005/0119189 A1 | 6/2005 | Cottrell et al. |
| 2005/0119318 A1 | 6/2005 | Hudyma et al. |
| 2005/0120398 A1 | 6/2005 | Kalkeri et al. |
| 2005/0136400 A1 | 6/2005 | Lin et al. |
| 2005/0137139 A1 | 6/2005 | Perni et al. |
| 2005/0153877 A1 | 7/2005 | Miao et al. |
| 2005/0187165 A1 | 8/2005 | Scola et al. |
| 2005/0187192 A1 | 8/2005 | Fleming et al. |
| 2005/0192212 A1 | 9/2005 | Llinas-Brunet et al. |
| 2005/0197299 A1 | 9/2005 | Babine et al. |
| 2005/0197301 A1 | 9/2005 | Njoroge et al. |
| 2005/0215486 A1 | 9/2005 | Cottrell et al. |
| 2005/0222236 A1 | 10/2005 | Tsantrizos et al. |
| 2005/0249702 A1 | 11/2005 | Njoroge et al. |
| 2005/0287514 A1 | 12/2005 | Byrn |
| 2006/0003317 A1 | 1/2006 | Perni et al. |
| 2006/0003942 A1 | 1/2006 | Tung et al. |
| 2006/0046956 A1 | 3/2006 | Sannigrahi et al. |
| 2006/0089385 A1 | 4/2006 | Cui et al. |
| 2006/0105978 A1 | 5/2006 | Chu et al. |
| 2006/0205672 A1 | 9/2006 | Saksena et al. |
| 2006/0211629 A1 | 9/2006 | Britt et al. |
| 2007/0087973 A1 | 4/2007 | Tanoury et al. |
| 2007/0105781 A1 | 5/2007 | Lyons et al. |
| 2007/0161789 A1 | 7/2007 | Cottrell et al. |

(56) References Cited

U.S. PATENT DOCUMENTS

| | | |
|---|---|---|
| 2007/0179167 A1 | 8/2007 | Cottrell et al. |
| 2007/0191381 A1 | 8/2007 | Tung et al. |
| 2007/0212683 A1 | 9/2007 | Connelly |
| 2007/0218012 A1 | 9/2007 | Bittorf et al. |
| 2007/0218138 A1 | 9/2007 | Bittorf et al. |
| 2007/0225297 A1 | 9/2007 | Perni et al. |
| 2007/0231262 A1 | 10/2007 | Lin et al. |
| 2007/0243166 A1 | 10/2007 | Llinas-Brunet et al. |
| 2007/0244334 A1 | 10/2007 | Tanoury et al. |
| 2007/0292933 A1 | 12/2007 | Pitlik et al. |
| 2008/0045480 A1 | 2/2008 | Farmer et al. |
| 2008/0070972 A1 | 3/2008 | Kadiyala et al. |
| 2008/0125376 A1 | 5/2008 | Cottrell et al. |
| 2008/0167480 A1 | 7/2008 | Wallace |
| 2008/0267915 A1 | 10/2008 | Lin et al. |
| 2008/0311079 A1 | 12/2008 | Perni et al. |
| 2009/0022688 A1 | 1/2009 | Farmer et al. |
| 2009/0143312 A1 | 6/2009 | Tung et al. |
| 2009/0191555 A1 | 7/2009 | Lin et al. |
| 2009/0247468 A1 | 10/2009 | Bittorf et al. |

FOREIGN PATENT DOCUMENTS

| | | |
|---|---|---|
| EP | 0675112 | 10/1995 |
| JP | 09124691 | 5/1997 |
| WO | WO 92/12140 | 7/1992 |
| WO | WO 93/25574 | 12/1993 |
| WO | WO 94/14436 | 7/1994 |
| WO | WO 95/09614 | 7/1994 |
| WO | WO 95/07696 | 3/1995 |
| WO | WO 96/11697 | 4/1996 |
| WO | WO 97/17364 | 5/1997 |
| WO | WO 97/40028 | 10/1997 |
| WO | WO 97/43310 | 11/1997 |
| WO | WO 98/13365 | 4/1998 |
| WO | WO 98/17679 | 4/1998 |
| WO | WO 98/22496 | 5/1998 |
| WO | WO 98/40381 | 9/1998 |
| WO | WO 98/46630 | 10/1998 |
| WO | WO 99/07733 | 2/1999 |
| WO | WO 99/07734 | 2/1999 |
| WO | WO 99/38888 | 8/1999 |
| WO | WO 99/50230 | 10/1999 |
| WO | WO 99/64442 | 12/1999 |
| WO | WO 00/09543 | 2/2000 |
| WO | WO 00/09558 | 2/2000 |
| WO | WO 00/09588 | 2/2000 |
| WO | WO 00/23421 | 4/2000 |
| WO | WO 00/31129 | 6/2000 |
| WO | WO 00/56331 | 9/2000 |
| WO | WO 00/59929 | 10/2000 |
| WO | WO 01/02424 | 1/2001 |
| WO | WO 01/07407 | 2/2001 |
| WO | WO 01/32691 | 5/2001 |
| WO | WO 01/40262 | 6/2001 |
| WO | WO 01/40266 | 6/2001 |
| WO | WO 01/58929 | 8/2001 |
| WO | WO 01/64678 | 9/2001 |
| WO | WO 01/74768 | 10/2001 |
| WO | WO 01/77113 | 10/2001 |
| WO | WO 01/81325 | 11/2001 |
| WO | WO 02/07761 | 1/2002 |
| WO | WO 02/08187 | 1/2002 |
| WO | WO 02/08198 | 1/2002 |
| WO | WO 02/08244 | 1/2002 |
| WO | WO 02/08251 | 1/2002 |
| WO | WO 02/08256 | 1/2002 |
| WO | WO 02/18369 | 3/2002 |
| WO | WO 02/48116 | 6/2002 |
| WO | WO 02/48157 | 6/2002 |
| WO | WO 02/48172 | 6/2002 |
| WO | WO 02/060926 | 8/2002 |
| WO | WO 02/079234 | 10/2002 |
| WO | WO 03/003804 | 1/2003 |
| WO | WO 03/006490 | 1/2003 |
| WO | WO 03/020298 | 3/2003 |
| WO | WO 03/062228 | 7/2003 |
| WO | WO 03/062265 | 7/2003 |
| WO | WO 03/064416 | 8/2003 |
| WO | WO 03/064455 | 8/2003 |
| WO | WO 03/064456 | 8/2003 |
| WO | WO 03/087092 | 10/2003 |
| WO | WO 2004/026896 | 4/2004 |
| WO | WO 2004/030670 | 4/2004 |
| WO | WO 2004/032827 | 4/2004 |
| WO | WO 2004/037855 | 5/2004 |
| WO | WO 2004/039833 | 5/2004 |
| WO | WO 2004/072243 | 8/2004 |
| WO | WO 2004/089974 | 10/2004 |
| WO | WO 2004/092161 | 10/2004 |
| WO | WO 2004/093798 | 11/2004 |
| WO | WO 2004/094452 | 11/2004 |
| WO | WO 2004/103996 | 12/2004 |
| WO | WO 2004/113365 | 12/2004 |
| WO | WO 2005/007681 | 1/2005 |
| WO | WO 2005/010029 | 2/2005 |
| WO | WO 2005/021584 | 3/2005 |
| WO | WO 2005/028501 | 3/2005 |
| WO | WO 2005/028502 | 3/2005 |
| WO | WO 2005/030796 | 4/2005 |
| WO | WO 2005/035525 | 4/2005 |
| WO | WO 2005/037214 | 4/2005 |
| WO | WO 2005/037860 | 4/2005 |
| WO | WO 2005/042570 | 5/2005 |
| WO | WO 2005/046712 | 5/2005 |
| WO | WO 2005/051410 | 6/2005 |
| WO | WO 2005/051980 | 6/2005 |
| WO | WO 2005/054430 | 6/2005 |
| WO | WO 2005/058821 | 6/2005 |
| WO | WO 2005/070955 | 8/2005 |
| WO | WO 2005/073195 | 8/2005 |
| WO | WO 2005/073216 | 8/2005 |
| WO | WO 2005/077969 | 8/2005 |
| WO | WO 2005/085242 | 9/2005 |
| WO | WO 2005/085275 | 9/2005 |
| WO | WO 2005/087721 | 9/2005 |
| WO | WO 2005/087725 | 9/2005 |
| WO | WO 2005/087731 | 9/2005 |
| WO | WO 2005/095403 | 10/2005 |
| WO | WO 2005 107745 | 11/2005 |
| WO | WO 2005/113581 | 12/2005 |
| WO | WO 2005/123076 | 12/2005 |
| WO | WO 2006/000085 | 1/2006 |
| WO | WO 2006/007448 | 1/2006 |
| WO | WO 2006/007700 | 1/2006 |
| WO | WO 2006/007708 | 1/2006 |
| WO | WO 2007/016589 | 2/2007 |
| WO | WO 2007/025307 | 3/2007 |
| WO | WO-2007/025307 A2 * | 3/2007 ........... C07D 498/10 |
| WO | WO 2008/106058 | 9/2008 |

OTHER PUBLICATIONS

Bastos, M., "Inhibitors of Human Heart Chymase Based on a Peptide Library", Proc. Natl. Acad. Sci. USA, vol. 92 (1995), pp. 6738-6742.

Beak, P., "Complex Induced Proximity Effects: Enantioselective Syntheses Based on Asymmetric Deprotonations of N-Boc-Pyrrolidines", J. Amer. Chem. Soc., vol. 116 (1994), pp. 3231-3239.

Behrens, C., "Selective Transformations of 2,3-Epoxy alcohols and Related Derivatives. Strategies for Nucleophilic Attack at Carbon-3 or Carbon-2", J. Org.Chem., vol. 50 (1985), pp. 5696-5704.

Bergmeier, S.C., "Synthesis of Bicyclic Proline Analogs Using a formal [3+2] Intramolecular Aziridine-Allylsilane Cycloaddition Reaction", Tetrahedron, vol. 55, No. 26 (1999), pp. 8025-8038.

Blair, W., "5th Antiviral Drug Discovery and Development Summit," Expert opinion on investigational drugs (2004), 13 (8), pp. 1065-1069.

Blankley, C.J., "Synthesis and Structure-Activity Relationships of Potent New Abgiotensin Converting Enzyme Inhibitors Containing Saturated Bicyclic Amino Acids", J. of Medicinal Chem., vol. 30 (1987).

(56) References Cited

OTHER PUBLICATIONS

Cacciola, J., "The Synthesis of Lysine α-Ketoamide Thrombin Inhibitors via an Epoxy Amide Ring Opening", Tetrahedron Let., vol. 38, No. 33 (1997), pp. 5741-5744.
Chawla, et al., "Challenges in Polymorphism of Pharmaceuticals", CRIPS vol. 5, No. 1, Jan.-Mar. 2004, 4 pages.
Chen, S., "Synthesis and Evaluation of Tripeptidyl α-Ketoamides as Human Rhinovirus 3C Protease Inhibitors", Bioorg. & Med. Chem. Letters, vol. 13, No. 20 (2003), pp. 3531-3536.
Chen, S., "Discovery of Small-Molecule Inhibitors of HCV NS3-4A Protease as Potential Therapeutic Agents against HCV Infection," Current Medicinal Chemistry (2005), 12(20), pp. 2317-2342.
Chen, S., "P1 and P1' Optimization of [3,4]-Bicycloproline P2 Incorporated Tetrapeptidyl α-ketoamide Based HCV Protease Inhibitors," Letters in Drug Design and Discovery (2005), 2(2), pp. 118-123.
Cheng, W., "Stereoselective Synthesis of Unnatural Spiroisoxazolinoproline-Based Acids and Derivatives", J. Org. Chem., (2002), pp. 5673-5677.
Collado, I., "Stereocontrolled Synthesis of 4-Substituted (±)-Kainic Acids", Journal of Organic Chem., vol. 63 (1998).
Davis, G. "Future Options for the Management of Hepatitis C", Seminars in Liver Disease, vol. 19, Supp. 1 (1999), pp. 103-112.
Dixon, S. M., "A Spiroisoazolinoproline-based Amino Acid Scaffold for Solid Phase and One-Bead—One-Compound Library Synthesis" Journal of Combinatorial Chemistry, 9 (2007) pp. 143-157.
Dunsdon, R., "Solid Phase Synthesis of Aminoboronic Acids: Potent Inhibitors of the Hepatitis C Virus NS3 Proteinase", Bioorganic & Medicinal Chemistry Letters, 10 (2000), pp. 1577-1579.
Elemes, "Synthesis of enantiopure α-deuterated Boc-L amino acids," J. Chemical Society, Perkin Trans. vol. 1 (1995) pp. 537-540.
Esch, P.M., "Reductive Cyclization of Carbon-Centered Glycine Radicals; A Novel Synthetic route to Cyclic α-Amino Acids", Tetrahedron, vol. 48, No. 22 (1992), pp. 4659-4676.
Farmer, L., "Inhibitors of Hepatitis C Virus NS3-4A Protease: P2 Proline Variants," Letters in Drug Design and Discovery (2005), 2, pp. 497-502.
Forestier, Current status of subjects receiving peg-interferon-alfa-2a (PEG-IFN) and ribavirin (RBV) after a 14-day study of the hepatitis C protease inhibitor telaprevir (VX-950), with PEG-IFN, Hepatology, vol. 44, Supp. 2 (2006), p. 614A.
Freireich, E., "Quantitative Comparison of Toxicity of Anticancer Agents in Mouse, Rat, Hamster, Dog, Monkey and Man", Cancer Chemother. Rep., vol. 50 No. 219 (1966), pp. 219-244.
Gallagher, D., "Complex-Induced Proximity Effects: Evidence for a Prelithiation Complex and a Rate-Determining Deprotonation in the Asymmetric Lithiation of Boc-Pyrrolidine by an i-PrLi/(−) Sparteine Complex", J. Org. Chem., vol. 60 (1995), pp. 7092-7093.
Gallagher, D., "Chiral Organolithium Complexes: The Effect of Ligand Structure on the Enantioselective Deprotonation of Boc-Pyrrolidine", J. Org. Chem., vol. 60 (1995), pp. 8148-8154.
Garrison, G., "Novel 3,7-Diheterabicyclo[3.3.1]nonanes that Possess Predominant Class III Antiarrhythmic Activity in 1-4 Day Post Infarction Dog Models: X-ray Diffraction Analysis of 3-[4-(1 H-Imidazol-1-yl)benzoyl]-7-isopropyl-3,7-diazabicyclo[3.3.1]nonane Dihydroperchlorate", J. Med. Chem, vol. 39, No. 13 (1996), pp. 2559-2570.
Golina, S., "Vulcanisation of Poly(diethyl-n-butylamino) Phosphazenes", Internat'l. Polymer Science & Tech., vol. 18, No. 3 (1991), pp. T20-T22.
Han, W., "α-Ketoamides, α-Ketoesters and α-Diketones as HCV NS3 Protease Inhibitors", Bioorganic & Medicinal Chemistry Letters 10 (2000), pp. 711-713.
Janssen, H.L.A., "Suicide Associated with α-Interferon Therapy for Chronic Viral Hepatitis", J. Hepatol., 21 (1994), pp. 241-243.
Johansson, A., "Acyl Sulfonamides as Potent Protease Inhibitors of the Hepatitis C Virus Full-Length NS3 (Protease-Helicase/NTPase): A comparative Study of Different C-Terminals", Bioorganic & Medicinal Chemistry, 11 (2003), pp. 2551-2568.

Johansson, P., "Potent inhibitors of the hepatitis C virus NS3 protease: Use of a novel P2 cyclopentane-derived template," Bioorganic & Medicinal Chemistry (2006), 14, pp. 5136-5151.
Kakei, H., "Catalytic Asymmetric Epoxidation of α, β-Unsaturated Esters Using an Yttrium-Biphenyldiol Complex", J. Am. Chem. Soc., vol. 127 (2005), pp. 8962-8963.
Kalkeri, G., "Expression of HCV Protease in the Liver of Mice Results in Liver Injury Which can be Inhibited by VX-950, a Vertex HCV Protease Inhibitor," AALSD Abstracts, Hepatology (2004), 40(1), pp. 281A.
Kamandi, E., "Die Synthese von β-Phenyl-Isoserinen Durch Ammonolyse von β-Phenyl-Glycidestern, I", Archiv de Pharmazie, vol. 307 No. 11 (1974), pp. 871-878.
Kao, J.H., "Efficacy of Consensus Interferon in the Treatment of Chronic Hepatitis", J. Gastroenterol. Hepatol, 15 (2000), pp. 1418-1423.
Kerrick, S., "Asymmetric Deprotonations: Enantioselective Syntheses of 2-Substituted (tert-Butoxycarbonyl) pyrrolidines", J. Amer. Chem. Soc., vol. 113 (1991), pp. 9703-9710.
Kieffer, T., "Genetic Heterogeneity in the HCV NS3 Protease of Untreated Genotype 1 Patients has Little Effect on the Sensitivity to VX-950", Hepatol, vol. 42 (2005), p. 537A.
Kieffer, T., "Wild-Type HCV NS3 Protease Re-Emerges During Follow-up After 14 days of Dosing with VX-950 in Patients with Genotype 1 HCV", J. Hepatol, vol. 44 Supp. 2 (2006), p. S7.
Kieffer, T., "Combination of Telaprevir (VX-950) and Peg-Ifn-Alfa Suppresses both Wild-Type Virus and Resistance Variants in HCV Genotype 1-Infected Patients in a 14-Day Phase 18 Study", Hepatol. 44, Supp.2 (2006), p. 222A.
Kieffer, Genetic Heterogeneity in the HCV Ns3 Protease of Untreated Genotype 1 Patients Has Little Effect on the Sensitivity of the VX-950, 12th Internat'l. Conf. on Hep. C Virus and Related Viruses, Montreal, Canada, Oct. 2-6, 2005.
Kim, J., "Hepatitis C Virus NS3 RNA Helicase Domain with a bound Oligonucleotide: The Crystal Structure Provides Insights into the Mode of Unwinding", Structure, vol. 6, No. 1, (1998), pp. 89-100.
Kim, J., "Crystal structure of the hepatitis C virus NS3 protease domain complexed with a synthetic NS4A cofactor peptide," Cell, vol. 87 (1996), pp. 343-355; [and Kim, J. "Erratum," Cell, vol. 89, No. 1 (1997), p. 159.
Kino, R., "Remarkable Effect of tris(4-fluorphenyl)phosphine Oxide on the Stabilization of Chiral Lanthanum Complex Catalysis. A New and Practical Protocol for the Highly Enantioselective Epoxidation of Conjugated Enones", Org. Biomol. Chem., vol. 2 (2004), pp. 1822-1824.
Kwong, A.D., "Structure and Function of Hepatitis C Virus NS3 Helicase", Top Microbiol. Immunol., vol. 242, (2000), pp. 171-196.
Kwong, A.D., "Hepatitis C Virus NS3/4A Protease" Antiviral Res. 41 (1998) pp. 1-18.
Kwong, A.D., "Erratum to 'Hepatitis C Virus NS3/4A Protease'", Antiviral Res., vol. 41 (1999), pp. 67-84.
Kwong, A.D., "An Orally Bioavailable Inhibitor of the HCV NS3-4a Protease; a Potential HCV Therapeutic", 5th Antivir. Drug Disc. and Devel. Summit, (Mar. 30, 2004).
Kwong, A.D., "HCV Protease Inhibitors: Activity and Resistance," 13th Conference on Retroviruses and Opp. Infections (CROI), Denver, CO, (Feb. 5-8, 2006).
Kwong, A.D., "Beyond Interferon and Ribavirin: Antiviral Therapies for Hepatitis C Virus", Drug Disc. Today: Ther. Strategies, vol. 3 (2006), pp. 211-220.
Kwong, A.D., "VX 950: A Novel Hepatitis C Protease Inhibitor", HepDART (2005).
Lamar, J., "Novel P4 Truncated Tripeptidyl α-ketoamides as HCV Protease Inhibitors", Bio. & Med. Chem. Let, vol. 14 No. 1 (2004), pp. 263-266.
Landro, J.A. "Mechanistic Role of an NS4A Peptide Cofactor with the Truncated NS3 Protease of Hepatitis C Virus: Elucidation of the NS4A Stimulatory Effect via Kinetic Analysis and Inhibitor Mapping", Biochemistry, 36 (1997) pp. 9340-9348.
Laplante, S., "NMR Line-Broadening and Transferred NOESY as a Medicinal Chemistry Tool for Studying Inhibitors of the Hepatitis C Virus NS3 Protease Domain", Bioorganic & Medicinal Chemistry Letters, 10 (2000), pp. 2271-2274.

(56) References Cited

OTHER PUBLICATIONS

Lavanchy, D., "Global Surveillance and control of Hepatitis C", J. Viral Hepatitis, 6 (1999), pp. 35-47.
Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", 12th Internat'l Symposium on Viral Hep. and Liver Dis., (2006).
Lawitz, E., "28 Days of the Hepatitis C Protease Inhibitor VX-950, in Combination with Peginterferon-alfa-2a and Ribavirin, is Well-Tolerated and Demonstrates Robust Antiviral Effects", Gastroenterol., vol. 131, No. 3 (2006), pp. 950-951.
Lehmann, Über die chemischen and biologischen Eigenschaften einiger α-Aminoketone, Helvetica Chimica Acta., vol. 33 (1950), pp. 1217-1226.
Lin, C., "Structure-Based Mutagenesis Study of Hepatitis C Virus NS3 Helicase", J. Virol., vol. 73, No. 10 (1999), pp. 8798-8807.
Lin, K., "Combination of a Hepatitis C Virus NS3-NS4A Protease Inhibitor and α Interferon Synergistically Inhibits Viral RNA Replication and Facilitates Viral RNA Clearance in Replicon Cells", Antimicrob. Agents Chemo, vol. 48 (2004), pp. 4784-4792.
Lin, K., "VX-950, a Novel Hepatitis C Virus (HCV) NS3-4A Protease Inhibitor, Exhibits Potent Antiviral Activities in HCV Replicon Cells", Antimicrob. Agents Chemo, vol. 50, No. 5 (2006), pp. 1813-1822.
Lin, K., "VX-950: A Tight-Binding HCV Protease Inhibitor with a Superior Sustained Inhibitory Response in HCV Replicon Cells", Hepatol, vol. 38 (2003), p. 222A.
Lin, C., "Discovery and Development of VX-950, a Novel, Covalent and Reversible Inhibitor of Hepatitis C Virus NS3-4A Serine Protease", Infect. Disord. Drug Targets, vol. 6, No. 1 (2006), pp. 3-16.
Lin, C., "In Vitro Resistance Studies of Hepatitis C Virus Serine Protease Inhibitors, VX-950 and BILN 2061", J. Biol. Chem., vol. 279, No. 17 (2004), pp. 17508-17514.
Llinas-Brunet, M., "Highly Potent and Selective Peptide-Based Inhibitors of the Hepatitis C Virus Serine Protease: Towards Smaller Inhibitors", Bioorganic & Medicinal Chemistry Letters, 10 (2000), pp. 2267-2270.
Llinas-Brunet, M., "Peptide-Based Inhibitors of the Hepatitis C Virus Serine Protease", Bioorganic & Medicinal Chemistry Letters, 8 (1998), pp. 1713-1718.
Llinas-Brunet, M., "Studies on the C-Terminal of Hexapeptide Inhibitors of the Hepatitis C virus Serine Protease", Bioorganic & Medicinal Chemistry Letters, 8 (1998), pp. 2719-2724.
Lohmann, F. "Replication of Subgenomic Hepatitis C Virus RNAs in a Hepatoma Cell Line", Science, 285.5454 (1999) p. 110.
Marigo, M., "Asymmetric Organocatalytic Epoxidation of α,β-Unsaturated Aldehydes with Hydrogen Peroxide", J. Am. Chem. Soc., vol. 127, No. 19 (2005), pp. 6964-6965.
Markland, W., "Broad-Spectrum Antiviral Activity of the IMP Dehydrogenase Inhibitor VX-497: a Comparison with Ribavirin and Demonstration of Antiviral Additivity with Alpha Interferon", Antimicrob. Ag. Chem., vol. 44, No. 4 (2000), pp. 859-866.
McLaren, R., "Infrared Observations of Circumstellar Ammonia in OH/IR Supergiants," Astrophysical Journal (1980), 240(3, Pt. 2), pp. L161-L163.
Mehdi, The Inhibition of Human Neutrophil Elastase and Cathepsin G by Peptidyl 1,2-Dicarbonyl Derivatives, Biochem & Biophys. Res. Comm., vol. 166, No. 2 (1990), pp. 595-660.
Monn, J., "A Concise, Stereocontrolled Thiazolium Ylide Approach to Kainic Acid", J. Organic Chem., vol. 59, No. 10 (1994), pp. 2773-2778.
Moradpour, D., "Current and Evolving Therapies for Hepatitis C", Eur. J. Gastroenterol. Hepatol., vol. 11 (1999), pp. 1199-1202.
Morgenstern, J., "Polynucleotide Modulation of the Protease, Nucleoside Triphosphatase, and Helicase Activities of a Hepatitis C Virus NS3-NS4A Complex Isolated from Transfected COS Cells", J. Virol., vol. 71, No. 5 (1997), pp. 3767-3775.
Newman, A., "Solid-state Analysis of the Active Pharmaceutical Ingredient in Drug Products", vol. 8, No. 19 (2003), pp. 898-905.
Patent Abstracts of Japan, vol. 1997, No. 9, Sep. 30, 1997.

Perni, R., "NS3-4A Protease as a Target for Interfering with Hepatitis C Virus Replication", Drug News Perspect., vol. 13, No. 2 (2000), pp. 69-77.
Perni, R.B., "Inhibitors of Hepatitis C Virus NS3-4A Protease 1. Non-Charged Tetrapeptide Variants", Bioorganic & Medicinal Chemistry Letters, 13 (2003), pp. 4059-4063.
Perni, R.B., "Inhibitors of Hepatitis C Virus NS3-4A Protease 2. Warhead SAR and Optimization", Bioorganic & Medicinal Chemistry Letters, 14 (2004), pp. 1441-1446.
Perni, R.B., "Inhibitors of Hepatitis C Virus NS3-4A Part 3: P2 Proline Variants", Bioorganic & Medicinal Chemistry Letters, 14 (2004), pp. 1939-1942.
Perni, Preclinical Profile of VX-950, a Potent, Selective, and Orally Bioavailable Inhibitor of Hepatitis C Virus NS3-4A Serine Protease, Antimicrob. Agents Chemo., vol. 50, No. 3, Mar. 2006, pp. 899-909.
Perni, R. "VX-950: The Discovery of an Inhibitor of the Hepatitis C NS3-4A Protease and a Potential Hepatitis C Virus Therapeutic", Hepatology, vol. 38 (2003) p. 624A.
Perni, R., "Toward Smaller HCV NW-4A Protease Inhibitors: 3-Substituted Proline-based Tripeptide Scaffolds," Abstracts of Papers, 229th ACS National Meeting, San Diego, CA, United States, Mar. 13-17, 2005, MEDI-350.
Perni, R., "The Design of Inhibitors of the HCV NS3-4A Protease: The Identification of a Clinical Development Candidate, VX-950," ACS National Medicinal Chemistry Symposium, Madison, WI, Jun. 2004.
Perni, R., "Inhibitors of Hepatitis C Virus NS3-4A Protease. Effect of P4 Capping Groups on Inhibitory Potency and Pharmacokinetics," Bioorganic & Medicinal Chemistry Letters (2007), 17(12), pp. 3406-3411.
Perni, R., "Properties and Preclinical Profile of VX-950, an Orally Bioavailable Inhibitor of the Hepatitis C Virus (HCV) Protease and a Potential Anti-HCV Therapeutic," 10th International Symposium on Hepatitis C and Related Viruses, Kyoto, Japan, Dec. 2-6, 2003.
Perni, R., "The Importance of Backbone Hydrogen Bonds in Binding a Tetrapeptide Scaffold to the HCV NS3-4A Protease," American Chemical Society's 229th National Meeting, San Diego, CA, Mar. 13-17, 2005.
Pippel, D., "Complex-Induced Proximity Effects: Steroselective Carbon-Carbon Bond Formation in Chiral Auxiliary Mediated β-Lithiation-Substitution Sequences of β-Substituted Secondary Carboxamides", J. Org. Chem., vol. 63 (1998), pp. 2-3.
Poliakov, A. "Structure-Activity Relationships for the Selectivity of Hepatitis C Virus NS3 Protease Inhibitors", Biochimica et Biophysica Acta, 1672 (2004), pp. 51-59.
Ramachandran, R., "Anti-Viral Activity of VX-950 Resolves Expression of an HCV-Associated Gene Signature", J. Hepatol, vol. 44, Supp. 2 (2006), p. S223.
Reesink, H., "Initial Results of a Phase 1B, Multiple-Dose Study of VX-950, a Hepatitis C Virus Protease Inhibitor", Gastroent., vol. 128, No. 4, Supp. 2 (2005), pp. A696-A697.
Reesink, H., "Rapid Decline of Viral RNA in Hepatitis C Patients Treated with VX-950: A Phase 1b, Placebo-Controlled Randomized Study", Gastroenterol., vol. 131, No. 4 (2006), pp. 997-1002.
Reesink, H., "Final Results of a Phase 1B, Multiple-Dose Study of VX-950, a Hepatitis C Virus Protease Inhibitor", Hepatology, vol. 42, No. 4, Supp. 1 (2005), pp. 234A-235A.
Reesink, H., "Initial Results of a 14-Day Study of the Hepatitis C Virus Inhibitor Protease VX-950, in combination with Peginterferon-Alpha-2a", J. Hepatol., vol. 44, Supp. 2 (2006), p. S272.
Renault, P.F., "Side Effects of Alpha Interferon", Seminars in Liver disease, 9 (1989), pp. 273-277.
Rodriguez-Torres, M., "Current Status of Subjects Receiving Peg-Interferon-Alfa-2A (PEG-IFN) and Ribavirin (RBV) Follow-on Therapy After 28-Day Treatment with the Hepatitis C Protease Inhibitor Telaprevir (VX-950), PEG-IFN and RBV", Hepatol., vol. 44, Supp. 2 (2006), p. 532A.
Sagnard, I., "Enantioselective Synthesis of Cyclopropane α-Amino Acids: Synthesis of N-Box-cis-(2S,3R,4S)-3,4-Methanoproline and N-Boc-(2S,3R,4S)-3,4-Methanoglutamic Acid", Tetrahedron, vol. 36, No. 18 (1995), pp. 3149-3152.

(56) References Cited

OTHER PUBLICATIONS

Schneider, F. "Enhanced Plasma Concentration by Selective Deuteration of Rofecoxib in Rats," Arzeimittel-Forschung (Drug. Res.) vol. 56 (4) (2006), pp. 295-300.
Schneider, F. "Changed Phosphodiestarase Selectivity and Enhanced in vitro Efficacy by Selective Deuteraton of Sildenafil," Arzeimittel-Forschung (Drug. Res.) vol. 57 (6) (2007), pp. 293-298.
Taber, D., "Asymmetric Nucleophilic Epoxidation", Org. Chem. Highlights, (2004).
Takamizawa, A., "Structure and Organization of the Hepatitis C Virus Genome Isolated from Human Carriers", J. Virol., 65 (1991), pp. 1105-1113.
Taliani, M., "A continuous Assay of Hepatitis C Virus Protease Based on Resonance Energy Transfer Depsipeptide Substrates", Anal. Biochem., vol. 240 (1996), pp. 60-67.
Tan, S., "Strategies for Hepatitis C Therapeutic Intervention: Now and Next", Current Op. in Pharmacology, vol. 4, No. 5 (2004), pp. 465-470.
Tazulakhova, E.B., "Russian Experience in Screening, Analysis and Clinical Application of Novel Interferon Inducers", J. Interferon Cytokine Res., 21 (2001), pp. 65-73.
Thomson, J., "Hepatitis C Virus NS3-4A Protease Inhibitors: countering Viral Subversion in vitro and Showing Promise in the Clinic", Curr. Opin. Drug Discov. Devel., vol. 9, No. 5 (2006), pp. 606-617.
Toom, L., "Microwave-Assisted Raney Nickel Reduction of Bispidinone Thioketals to N,N'-Dialkylbispidines", Synthesis, vol. 12 (2006), pp. 2064-2068.
Udding, J.H., "Transition Metal-Catalyzed Chlorine Transfer Cyclizations of Carbon-Centered Glycine Radicals; A Novel Synthetic Route to Cyclic α-Amino Acids", Tetrahedron, vol. 50, No. 6 (1994), pp. 1907-1918.
Victor, F., "P1 and P3 optimization of novel bicycloproline P2 bearing tetrapeptidyl α-ketoamide based HCV protease inhibitors", Biorganic & Medicinal Chemistry Letters, 14 (2004), pp. 257-261.
Vishweshwar, P., "Pharmaceutical Co-Crystals", J. Pharm. Sci., vol. 95, No. 3 (2006), pp. 499-516.
Walker, M.A., "Hepatitis C Virus: An Overview of Current Approaches and Progress", DDT, 4 (1999), pp. 518-529.
Wang, Z., "Asymmetric Epoxidation of trans-β-Methylstyrene and 1-Phenylcyclohexene Using a D-Fructose-Derived Ketone: (R,R)-trans-β-Methylstyrene Oxide and (R,R)-1-Phenylcyclohexene Oxide", Org. Syntheses, vol. 80 (2003), pp. 9-13.
Weiland, O., "Interferon Therapy in Chronic Hepatitis C Virus Infection", FEMS Microiol. Rev., 14 (1994), pp. 279-288.
White, P.W. "Blunting the Swiss Army Knife of Hepatitis C Virus: Inhibitors of NS3/4A Protease" Progress in Medicinal Chemistry 44 (2006), pp. 65-107.
Yao, N., "Molecular views of viral polyprotein processing revealed by the crystal structure of the hepatitis C virus bifunctional protease-helicase," Structure (1999), 7, pp. 1353-1363.
Yasuda, M., "Synthesis of Conformationally Defined Glutamic Acid Analogues from Readily Available Diels-Alder Adducts", Chem. and Pharm. Bulletin (1995) pp. 1318-1324.
Yip, Y. Discovery of a Novel Bicycloproline P2 Bearing Peptidyl α-Ketoamide LY514962 as HCV Protease Inhibitor, Bio. & Med. Chem. Let, vol. 14, No. 1 (2005), pp. 251-256.
Yip, Y., "P4 and P1' Optimization of Bicycloproline P2 Bearing Tetrapeptidyl α-Ketoamides as HCV Protease Inhibitors", Bio. & Med. Chem. Let, vol. 14, No. 9 (2004), pp. 5007-5011.
Yun, C. "Oxidation of the antihistaminic drug terfenadine in human liver microsomes: Role of Cytochrome P-450 3A(4) in N-dealkylation and C-hydroxylation", Drug metabolism and Disposition, 21(3) (1993) pp. 403-409.
ISR dated May 2, 2002 from PCT/US2001/26008.
ISR dated Jun. 12, 2006 from PCT/US2005/039240.
ISR dated Feb. 6, 2007 from PCT/US2006/029988.
ISR dated Feb. 15, 2007 from PCT/US2006/0033770.
ISR dated Jul. 23, 2007 from PCT/US2007/006320.
ISR dated Aug. 3, 2007 from PCT/US2007/004995.
ISR dated Nov. 16, 2007 from PCT/US2007/64294.
ISR dated Dec. 27, 2007 from PCT/US2006/032481.
ISR dated Jul. 7, 2008 from PCT/US2008/002541.
ISR dated Jan. 16, 2009 from PCT/US2008/002395.

\* cited by examiner

SEQUENCE LISTING

<160> NUMBER OF SEQ ID NOS: 6

<210> SEQ ID NO 1
<211> LENGTH: 695
<212> TYPE: PRT
<213> ORGANISM: Hepatitis C virus
<220> FEATURE:
<221> NAME/KEY: MISC_FEATURE
<222> LOCATION: (1)..(10)
<223> OTHER INFORMATION: Histidine tag

<400> SEQUENCE: 1

```
Met Ser His His His His His Ala Met Ala Pro Ile Thr Ala Tyr
1               5                   10                  15

Ala Gln Gln Thr Arg Gly Leu Leu Gly Cys Ile Ile Thr Ser Leu Thr
                20                  25                  30

Gly Arg Asp Lys Asn Gln Val Glu Gly Glu Val Gln Ile Val Ser Thr
            35                  40                  45

Ala Thr Gln Thr Phe Leu Ala Thr Cys Ile Asn Gly Val Cys Trp Thr
        50                  55                  60

Val Tyr His Gly Ala Gly Thr Arg Thr Ile Ala Ser Pro Lys Gly Pro
65                  70                  75                  80

Val Ile Gln Met Tyr Thr Asn Val Asp Gln Asp Leu Val Gly Trp Pro
                85                  90                  95

Ala Pro Gln Gly Ser Arg Ser Leu Thr Pro Cys Thr Cys Gly Ser Ser
            100                 105                 110

Asp Leu Tyr Leu Val Thr Arg His Ala Asp Val Ile Pro Val Arg Arg
        115                 120                 125

Arg Gly Asp Ser Arg Gly Ser Leu Leu Ser Pro Arg Pro Ile Ser Tyr
    130                 135                 140

Leu Lys Gly Ser Ser Gly Gly Pro Leu Leu Cys Pro Ala Gly His Ala
145                 150                 155                 160

Val Gly Leu Phe Arg Ala Ala Val Cys Thr Arg Gly Val Thr Lys Ala
                165                 170                 175

Val Asp Phe Ile Pro Val Glu Asn Leu Glu Thr Thr Met Arg Ser Pro
            180                 185                 190

Val Phe Thr Asp Asn Ser Ser Pro Pro Ala Val Pro Gln Ser Phe Gln
        195                 200                 205

Val Ala His Leu His Ala Pro Thr Gly Ser Gly Lys Ser Thr Lys Val
    210                 215                 220

Pro Ala Ala Tyr Ala Ala Gln Gly Tyr Lys Val Leu Val Leu Asn Pro
225                 230                 235                 240

Ser Val Ala Ala Thr Leu Gly Phe Gly Ala Tyr Met Ser Lys Ala His
                245                 250                 255

Gly Val Asp Pro Asn Ile Arg Thr Gly Val Arg Thr Ile Thr Thr Gly
            260                 265                 270

Ser Pro Ile Thr Tyr Ser Thr Tyr Gly Lys Phe Leu Ala Asp Gly Gly
        275                 280                 285

Cys Ser Gly Gly Ala Tyr Asp Ile Ile Ile Cys Asp Glu Cys His Ser
    290                 295                 300

Thr Asp Ala Thr Ser Ile Leu Gly Ile Gly Thr Val Leu Asp Gln Ala
305                 310                 315                 320

Glu Thr Ala Gly Ala Arg Leu Val Val Leu Ala Thr Ala Thr Pro Pro
                325                 330                 335

Gly Ser Val Thr Val Ser His Pro Asn Ile Glu Glu Val Ala Leu Ser
```

```
                340             345             350
Thr Thr Gly Glu Ile Pro Phe Tyr Gly Lys Ala Ile Pro Leu Glu Val
        355                 360                 365

Ile Lys Gly Gly Arg His Leu Ile Phe Cys His Ser Lys Lys Cys
370                 375                 380

Asp Glu Leu Ala Ala Lys Leu Val Ala Leu Gly Ile Asn Ala Val Ala
385                 390                 395                 400

Tyr Tyr Arg Gly Leu Asp Val Ser Val Ile Pro Thr Asn Gly Asp Val
                405                 410                 415

Val Val Val Ser Thr Asp Ala Leu Met Thr Gly Phe Thr Gly Asp Phe
                420                 425                 430

Asp Ser Val Ile Asp Cys Asn Thr Cys Val Thr Gln Thr Val Asp Phe
                435                 440                 445

Ser Leu Asp Pro Thr Phe Thr Ile Glu Thr Thr Thr Leu Pro Gln Asp
    450                 455                 460

Ala Val Ser Arg Thr Gln Arg Arg Gly Arg Thr Gly Arg Gly Lys Pro
465                 470                 475                 480

Gly Ile Tyr Arg Phe Val Ala Pro Gly Glu Arg Pro Ser Gly Met Phe
                485                 490                 495

Asp Ser Ser Val Leu Cys Glu Cys Tyr Asp Ala Gly Cys Ala Trp Tyr
                500                 505                 510

Glu Leu Met Pro Ala Glu Thr Thr Val Arg Leu Arg Ala Tyr Met Asn
            515                 520                 525

Thr Pro Gly Leu Pro Val Cys Gln Asp His Leu Glu Phe Trp Glu Gly
            530                 535                 540

Val Phe Thr Gly Leu Thr His Ile Asp Ala His Phe Leu Ser Gln Thr
545                 550                 555                 560

Lys Gln Ser Gly Glu Asn Phe Pro Tyr Leu Val Ala Tyr Gln Ala Thr
                565                 570                 575

Val Cys Ala Arg Ala Gln Ala Pro Pro Pro Ser Trp Asp Gln Met Trp
            580                 585                 590

Lys Cys Leu Ile Arg Leu Lys Pro Thr Leu His Gly Pro Thr Pro Leu
            595                 600                 605

Leu Tyr Arg Leu Gly Ala Val Gln Asn Glu Val Thr Leu Thr His Pro
610                 615                 620

Ile Thr Lys Tyr Ile Met Thr Cys Met Ser Ala Asp Leu Glu Val Val
625                 630                 635                 640

Thr Ser Thr Trp Val Leu Val Gly Gly Val Leu Ala Ala Leu Ala Ala
                645                 650                 655

Tyr Cys Leu Ser Thr Gly Cys Val Val Ile Val Gly Arg Ile Val Leu
                660                 665                 670

Ser Gly Lys Pro Ala Ile Ile Pro Asp Arg Glu Val Leu Tyr Gln Glu
                675                 680                 685

Phe Asp Glu Met Glu Glu Cys
                690                 695

<210> SEQ ID NO 2
<211> LENGTH: 10
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid
```

-continued

```
<400> SEQUENCE: 2

Glu Asp Val Val Xaa Cys Ser Met Ser Tyr
1               5                   10

<210> SEQ ID NO 3
<211> LENGTH: 16
<212> TYPE: PRT
<213> ORGANISM: Artificial
<220> FEATURE:
<223> OTHER INFORMATION: Synthetically generated peptide

<400> SEQUENCE: 3

Lys Lys Gly Ser Val Val Ile Val Gly Arg Ile Val Leu Ser Gly Lys
1               5                   10                  15

<210> SEQ ID NO 4
<211> LENGTH: 23
<212> TYPE: PRT
<213> ORGANISM: Artificial
<220> FEATURE:
<223> OTHER INFORMATION: Synthetically generated peptide

<400> SEQUENCE: 4

Lys Lys Gly Ser Val Val Ile Val Gly Arg Ile Val Leu Ser Gly Lys
1               5                   10                  15

Pro Ala Ile Ile Pro Lys Lys
            20

<210> SEQ ID NO 5
<211> LENGTH: 15
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: (alpha) aminobutyric acid
<220> FEATURE:
<221> NAME/KEY: MOD_RES
<222> LOCATION: (12)..(12)
<223> OTHER INFORMATION: Asp(EDANS)

<400> SEQUENCE: 5

Glu Asp Val Val Xaa Cys Ser Met Ser Tyr Thr Asp Lys Lys Lys
1               5                   10                  15

<210> SEQ ID NO 6
<211> LENGTH: 14
<212> TYPE: PRT
<213> ORGANISM: Artificial
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: FITC-2-aminohexanoic acid
<220> FEATURE:
<221> NAME/KEY: MOD_RES
<222> LOCATION: (6)..(6)
<223> OTHER INFORMATION: (alpha) aminobutyric acid

<400> SEQUENCE: 6

Xaa Glu Asp Val Val Xaa Cys Ser Met Ser Tyr Thr Lys Lys
1               5                   10
```

INHIBITORS OF SERINE PROTEASES

CLAIM OF PRIORITY

This application is a national phase entry of PCT/US2008/002395, filed Feb. 20, 2008 which claims the benefit of the U.S. Provisional Application No 60/903,814, filed on Feb. 27, 2007. The entire contents of the documents are incorporated herein in their entirety.

FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States", Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear to resolve the infection spontaneously. In almost 70% of instances; however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology-Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decrease viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. However, interferons have significant side effects [M. A. Walker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (≈25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

This invention relates to compounds of formula I

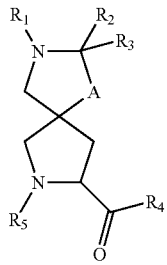

or a pharmaceutically acceptable salt thereof.

$R_1$ is $—Z^A R_8$, wherein each $Z^A$ is independently a bond or an optionally substituted branched or straight $C_{1-12}$ aliphatic chain wherein up to three carbon units of $Z^A$ are optionally and independently replaced by —C(O)—, —C(S)—, —C(O)NR$^A$—, —C(O)NR$^A$NR$^A$—, —C(O)O—, —NR$^A$C(O)O—, —O—, —NR$^A$C(O)NR$^A$—, —NR$^A$NR$^A$—, —S—, —SO—, —SO$_2$—, —NR$^A$—, —SO$_2$NR$^A$—, or —NR$^A$SO$_2$NR$^A$— provided that —O—, —NR$^A$NR$^A$—, —NR$^A$C(O)NR$^A$—, or —NR$^A$SO$_2$NR$^A$— is not directly bound to the nitrogen ring atom of formula I. Each $R_8$ is independently $R^A$, halo, —OH, —CN, —NO$_2$, —NH$_2$, or —OCF$_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

$R_2$ and $R_3$ are $—Z^B R_9$, wherein each $Z^B$ is independently a bond or an optionally substituted branched or straight $C_{1-6}$ aliphatic chain wherein up to three carbon units of $Z^B$ are optionally and independently replaced by —C(O)—, —C(S)—, —C(O)NR$^B$—, —C(O)NR$^B$NR$^B$—, —C(O)O—, —NR$^B$C(O)O—, —NR$^B$C(O)NR$^B$—, —NR$^B$NR$^B$—, —S—, —SO—, —SO$_2$—, —NR$^B$—, —SO$_2$NR$^B$—, or —NR$^B$SO$_2$NR$^B$—. Each $R_9$ is independently $R^B$, halo, —OH, —CN, —NO$_2$, —NH$_2$, or —OCF$_3$. Each $R^B$ is independently hydrogen, an optionally substituted aliphatic, an optionally substituted cycloaliphatic, an optionally substituted aryl, or an optionally substituted heteroaryl.

Alternatively, $R_2$ and $R_3$, together form an oxo group.

A is —O—, or —CR$_6$R$_7$—, wherein each $R_6$ and $R_7$ is $—Z^C R_{10}$, wherein each $Z^C$ is independently a bond or an optionally substituted branched or straight $C_{1-6}$ aliphatic chain wherein up to three carbon units of $Z^C$ are optionally and independently replaced by —C(O)—, —C(S)—, —C(O)NR$^C$—, —C(O)NR$^C$NR$^C$—, —C(O)O—, —NR$^C$C(O)O—, —NR$^C$C(O)NR$^C$—, —NR$^C$NR$^C$—, —S—, —SO—, —SO$_2$—, —NR$^C$—, —SO$_2$NR$^C$—, or —NR$^C$SO$_2$NR$^C$—. Each $R_{10}$ is independently $R^C$, halo, —OH, —CN, —NO$_2$, —NH$_2$, or —OCF$_3$. Each $R^C$ is independently hydrogen, an optionally substituted aliphatic, an optionally substituted cycloaliphatic, an optionally substituted aryl, or an optionally substituted heteroaryl.

$R_4$ is $—Z^D R_{11}$, wherein each $Z^D$ is independently a bond or an optionally substituted branched or straight $C_{1-12}$ aliphatic chain wherein up to three carbon units of $Z^D$ are optionally and independently replaced by —C(O)—, —C(S)—, —C(O)NR$^D$—, —C(O)NR$^D$NR$^D$—, —C(O)O—, —NR$^D$C(O)O—, —O—, —NR$^D$C(O)NR$^D$—, —NR$^D$NR$^D$—, —S—, —SO—, —SO$_2$—, —NR$^D$—, —SO$_2$NR$^D$—, or —NR$^D$SO$_2$NR$^D$—, provided that —SO—, —SO$_2$—, or —SO$_2$NR$^D$— is not directly bound to the carbonyl adjacent to $R_4$. Each $R_{11}$ is independently $R^D$, halo, —OH, —CN, —NO$_2$, —NH$_2$, or —OCF$_3$. Each $R^D$ is independently hydrogen, an optionally substituted aliphatic, an optionally substituted cycloaliphatic, an optionally substituted heterocycloaliphatic, an optionally substituted aryl, or an optionally substituted heteroaryl.

$R_5$ is $—Z^E R_{12}$, wherein each $Z^E$ is independently a bond or an optionally substituted branched or straight $C_{1-12}$ aliphatic chain wherein up to three carbon units of $Z^E$ are optionally and independently replaced by —C(O)—, —C(S)—, —C(O)NR$^E$—, —C(O)NR$^E$NR$^E$—, —C(O)O—, —NR$^E$C(O)O—, —O—, —NR$^E$C(O)NR$^E$—, —NR$^E$NR$^E$—, —S—, —SO—, —SO$_2$—, —NR$^E$—, —SO$_2$NR$^E$—, or —NR$^E$SO$_2$NR$^E$—. Each $R_{12}$ is independently $R^E$, halo, —OH, —CN, —NO$_2$, —NH$_2$, or —OCF$_3$. Each $R^E$ is independently hydrogen, an optionally substituted aliphatic, an optionally substituted cycloaliphatic, an optionally substituted heterocycloaliphatic, an optionally substituted aryl, or an optionally substituted heteroaryl.

In some aspects, the invention features a pharmaceutical composition comprising a compound of formula I or a pharmaceutically acceptable salt thereof in an amount effective to inhibit a serine protease; and an acceptable carrier, adjuvant or vehicle. The composition may include an additional agent selected from an immunomodulatory agent; an antiviral agent; a second inhibitor of HCV protease; an inhibitor of another target in the HCV life cycle; a cytochrome P-450 inhibitor; or combinations thereof. The immunomodulatory agent is α-, β-, or γ-interferon or thymosin; said antiviral agent is ribavirin, amantadine, or telbivudine; or said inhibitor of another target in the HCV life cycle is an inhibitor of HCV helicase, polymerase, or metalloprotease. Cytochrome P-450 inhibitor may be ritonavir.

In other aspects, a method of inhibiting the activity of a serine protease comprising the step of contacting said serine protease with a compound of formula I. The serine protease may be an HCV NS3 protease. The methods also include treating an HCV infection in a patient by administering a compound of formula I. The method may also include administering to said patient an additional agent selected from an immunomodulatory agent; an antiviral agent; a second inhibitor of HCV protease; an inhibitor of another target in the HCV life cycle; or combinations thereof; wherein said additional agent is administered to said patient in the same dosage form as the serine protease inhibitor or as a separate dosage form. The immunomodulatory agent is α-, β-, or γ-interferon or thymosin; said antiviral agent is ribavarin or amantadine; or said inhibitor of another target in the HCV life cycle is an inhibitor of HCV helicase, polymerase, or metalloprotease.

In still other aspects, a method of eliminating or reducing HCV contamination of a biological sample or medical or laboratory equipment, includes the step of contacting said biological sample or medical or laboratory equipment with a compound of formula I. The sample or equipment may be selected from blood, other body fluids, biological tissue, a surgical instrument, a surgical garment, a laboratory instrument, a laboratory garment, a blood or other body fluid collection apparatus; a blood or other body fluid storage material.

The compounds of the invention, as described herein, also exhibit advantageous PK properties and/or increased potency.

The invention also relates to compositions that comprise the above compounds and the use thereof; methods of preparing compounds of formula I, and methods of assaying compounds for serine protease activity. Such compositions may be used to pre-treat devices that are to be inserted into a patient, to treat biological samples, or for direct administration to a patient. In each case, the composition will be used to lessen the risk of or the severity of the HCV infection.

In other aspects, the invention features certain compounds as described generically and specifically below. Such specific descriptions are illustrative only and are not meant to limit scope of the compounds or uses thereof.

DETAILED DESCRIPTION

I. Definitions

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention.

As used herein the term "aliphatic" encompasses the terms alkyl, alkenyl, alkynyl, each of which being optionally substituted as set forth below.

As used herein, an "alkyl" group refers to a saturated aliphatic hydrocarbon group containing 1-8 (e.g., 1-12, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, or heterocycloaliphaticamino], sulfonyl [e.g., aliphatic-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO$_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, phospho, cycloaliphatic [e.g., cycloalkyl or cycloalkenyl], heterocycloaliphatic [e.g., heterocycloalkyl or heterocycloalkenyl], aryl, heteroaryl, alkoxy, aroyl, heteroaroyl, acyl [e.g., (aliphatic)carbonyl, (cycloaliphatic)carbonyl, or (heterocycloaliphatic)carbonyl], nitro, cyano, amido [e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl], amino [e.g., aliphaticamino, cycloaliphaticamino, heterocycloaliphaticamino, or aliphaticsulfonylamino], sulfonyl [e.g., alkyl-SO$_2$—, cycloaliphatic-SO$_2$—, or aryl-SO$_2$—], sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO$_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl [e.g., aliphaticsulfanyl or cycloaliphaticsulfanyl], sulfinyl [e.g., aliphaticsulfinyl or cycloaliphaticsulfinyl], sulfonyl [e.g., aliphatic-SO$_2$—, aliphaticamino-SO$_2$—, or cycloaliphatic-SO$_2$—], amido [e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino or heteroarylaminocarbonyl], urea, thiourea, sulfamoyl, sulfamide, alkoxycarbonyl, alkylcarbonyloxy, cycloaliphatic, heterocycloaliphatic, aryl, heteroaryl, acyl [e.g., (cycloaliphatic)carbonyl or (heterocycloaliphatic)carbonyl], amino [e.g., aliphaticamino], sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino". These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ are defined below. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen, aliphatic, cycloaliphatic, (cycloaliphatic)aliphatic, aryl, araliphatic, heterocycloaliphatic, (heterocycloaliphatic)aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (araliphatic)carbonyl, (heterocycloaliphatic)carbonyl, ((heterocycloaliphatic)aliphatic)carbonyl, (heteroaryl)carbonyl, or (heteroaraliphatic) carbonyl, each of which being defined herein and being optionally substituted. Examples of amino groups include alkylamino, dialkylamino, or arylamino. When the term "amino" is not the terminal group (e.g., alkylcarbonylamino), it is represented by —$NR^X$—. $R^X$ has the same meaning as defined above.

As used herein, an "aryl" group used alone or as part of a larger moiety as in "aralkyl", "aralkoxy", or "aryloxyalkyl" refers to monocyclic (e.g., phenyl); bicyclic (e.g., indenyl, naphthalenyl, tetrahydronaphthyl, tetrahydroindenyl); and tricyclic (e.g., fluorenyl tetrahydrofluorenyl, or tetrahydroanthracenyl, anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more $C_{4-8}$ carbocyclic moieties. An aryl is optionally substituted with one or more substituents including aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic ring of a benzofused bicyclic or tricyclic aryl); nitro; carboxy; amido; acyl [e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic) carbonyl]; sulfonyl [e.g., aliphatic-$SO_2$— or amino-$SO_2$—]; sulfinyl [e.g., aliphatic-S(O)— or cycloaliphatic-S(O)—]; sulfanyl [e.g., aliphatic-S—]; cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl [e.g., mono-, di (such as p,m-dihaloaryl), and (trihalo)aryl]; (carboxy)aryl [e.g., (alkoxycarbonyl)aryl, ((aralkyl) carbonyloxy)aryl, and (alkoxycarbonyl)aryl]; (amido)aryl [e.g., (aminocarbonyl)aryl, (((alkylamino)alkyl)aminocarbonyl)aryl, (alkylcarbonyl)aminoaryl, (arylaminocarbonyl) aryl, and (((heteroaryl)amino)carbonyl)aryl]; aminoaryl [e.g., ((alkylsulfonyl)amino)aryl or ((dialkyl)amino)aryl]; (cyanoalkyl)aryl; (alkoxy)aryl; (sulfamoyl)aryl [e.g., (aminosulfonyl)aryl]; (alkylsulfonyl)aryl; (cyano)aryl; (hydroxyalkyl)aryl; ((alkoxy)alkyl)aryl; (hydroxy)aryl, ((carboxy) alkyl)aryl; (((dialkyl)amino)alkyl)aryl; (nitroalkyl)aryl; (((alkylsulfonyl)amino)alkyl)aryl; ((heterocycloaliphatic) carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "araliphatic" such as an "aralkyl" group refers to an aliphatic group (e.g., a $C_{1-4}$ alkyl group) that is substituted with an aryl group. "Aliphatic," "alkyl," and "aryl" are defined herein. An example of an araliphatic such as an aralkyl group is benzyl.

As used herein, an "aralkyl" group refers to an alkyl group (e.g., a $C_{1-4}$ alkyl group) that is substituted with an aryl group. Both "alkyl" and "aryl" have been defined above. An example of an aralkyl group is benzyl. An aralkyl is optionally substituted with one or more substituents such as aliphatic [e.g., alkyl, alkenyl, or alkynyl, including carboxyalkyl, hydroxyalkyl, or haloalkyl such as trifluoromethyl], cycloaliphatic [e.g., cycloalkyl or cycloalkenyl], (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido [e.g., aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, or heteroaralkylcarbonylamino], cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which being optionally substituted as set forth below. As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl. A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, or bicyclo[3.3.1]nonenyl. A cycloalkyl or cycloalkenyl group can be optionally substituted with one or more substituents such as phosphor, aliphatic [e.g., alkyl, alkenyl, or alkynyl], cycloaliphatic, (cycloaliphatic) aliphatic, heterocycloaliphatic, (heterocycloaliphatic) aliphatic, aryl, heteroaryl, alkoxy, (cycloaliphatic)oxy, (heterocycloaliphatic) oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl [e.g., alkyl-$SO_2$— and aryl-$SO_2$—], sulfinyl [e.g., alkyl-S(O)—], sulfanyl [e.g., alkyl-S—], sulfoxy, urea, thiourea, sulfamoyl, sulfamide, oxo, or carbamoyl.

As used herein, the term "heterocycloaliphatic" encompasses a heterocycloalkyl group and a heterocycloalkenyl group, each of which being optionally substituted as set forth below.

As used herein, a "heterocycloalkyl" group refers to a 3-10 membered mono- or bicylic (fused or bridged) (e.g., 5- to 10-membered mono- or bicyclic) saturated ring structure, in which one or more of the ring atoms is a heteroatom (e.g., N, O, S, or combinations thereof). Examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group can be fused with a phenyl moiety to form structures, such as tetrahydroisoquinoline, which would be categorized as heteroaryls. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phosphor, aliphatic [e.g., alkyl, alkenyl, or alkynyl], cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido [e.g., (aliphatic)carbonylamino, (cycloaliphatic)carbonylamino, ((cycloaliphatic) aliphatic)carbonylamino, (aryl)carbonylamino, (araliphatic) carbonylamino, (heterocycloaliphatic)carbonylamino, ((heterocycloaliphatic) aliphatic)carbonylamino, (heteroaryl)carbonylamino, or (heteroaraliphatic)carbonylamino], nitro, carboxy [e.g., HOOC—, alkoxycarbonyl, or alkylcarbonyloxy], acyl [e.g., (cycloaliphatic)carbonyl, ((cycloaliphatic) aliphatic)carbonyl, (araliphatic)carbonyl, (heterocycloaliphatic)carbonyl, ((heterocycloaliphatic)aliphatic) carbonyl, or (heteroaraliphatic)carbonyl], nitro, cyano, halo, hydroxy, mercapto, sulfonyl [e.g., alkylsulfonyl or arylsulfonyl], sulfinyl [e.g., alkylsulfinyl], sulfanyl [e.g., alkylsulfanyl], sulfoxy, urea, thiourea, sulfamoyl, sulfamide, oxo, or carbamoyl.

A "heteroaryl" group, as used herein, refers to a monocyclic, bicyclic, or tricyclic ring system having 4 to 15 ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having 2 to 3 rings. For example, a benzofused group includes benzo fused with one or two 4 to 8 membered heterocycloaliphatic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indolizyl, isoindolyl, indolyl, benzo[b]furyl, bexo[b]thiophenyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic [e.g., alkyl, alkenyl, or alkynyl]; cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl [e.g., aliphaticcarbonyl; (cycloaliphatic)carbonyl; ((cycloaliphatic)aliphatic) carbonyl; (araliphatic)carbonyl; (heterocycloaliphatic)carbonyl; ((heterocycloaliphatic)aliphatic)carbonyl; or (heteroaraliphatic)carbonyl]; sulfonyl [e.g., aliphaticsulfonyl or aminosulfonyl]; sulfinyl [e.g., aliphaticsulfinyl]; sulfanyl [e.g., aliphaticsulfanyl]; nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl [e.g., mono- and di-(halo)heteroaryl]; (carboxy)heteroaryl [e.g., (alkoxycarbonyl)heteroaryl]; cyanoheteroaryl; aminoheteroaryl [e.g., ((alkylsulfonyl)amino)heteroaryl and ((dialkyl)amino)heteroaryl]; (amido)heteroaryl [e.g., aminocarbonylheteroaryl, ((alkylcarbonyl)amino)heteroaryl, ((((alkyl)amino)alkyl)aminocarbonyl)heteroaryl, (((heteroaryl)amino)carbonyl)heteroaryl, ((heterocycloaliphatic)carbonyl)heteroaryl, and ((alkylcarbonyl)amino)heteroaryl]; (cyanoalkyl)heteroaryl; (alkoxy)heteroaryl; (sulfamoyl)heteroaryl [e.g., (aminosulfonyl)heteroaryl]; (sulfonyl)heteroaryl [e.g., (alkylsulfonyl)heteroaryl]; (hydroxyalkyl)heteroaryl; (alkoxyalkyl)heteroaryl; (hydroxy)heteroaryl; ((carboxy)alkyl)heteroaryl; (((dialkyl)amino)alkyl)heteroaryl; (heterocycloaliphatic)heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl)heteroaryl [e.g., (alkylcarbonyl)heteroaryl]; (alkyl)heteroaryl, and (haloalkyl)heteroaryl [e.g., trihaloalkylheteroaryl].

A "heteroaraliphatic (such as a heteroaralkyl group) as used herein, refers to an aliphatic group (e.g., a $C_{1-4}$ alkyl group) that is substituted with a heteroaryl group. "Aliphatic," "alkyl," and "heteroaryl" have been defined above.

A "heteroaralkyl" group, as used herein, refers to an alkyl group (e.g., a $C_{1-4}$ alkyl group) that is substituted with a heteroaryl group. Both "alkyl" and "heteroaryl" have been defined above. A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxabicyclo[2.2.2]octyl, 1-azabicyclo[2.2.2]octyl, 3-azabicyclo[3.2.1]octyl, and 2,6-dioxa-tricyclo[3.3.1.0$^{3,7}$] nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined.

As used herein, an "alkoxy" group refers to an alkyl-O— group where "alkyl" has been defined previously.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, aralphatic, heterocycloaliphatic, heteroaryl, or heteroaraliphatic.

As used herein, a "carboxy" group refers to —COOH, —COOR$^X$, —OC(O)H, —OC(O)R$^X$, when used as a terminal group; or —OC(O)— or —C(O)O— when used as an internal group.

As used herein, a "haloaliphatic" group refers to an aliphatic group substituted with 1-3 halogen. For instance, the term haloalkyl includes the group —CF$_3$.

As used herein, a "mercapto" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein Rx has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Exemplary sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, or the like.

As used herein, a "sulfonyl" group refers to —S(O)$_2$—R$^X$ when used terminally and —S(O)$_2$— when used internally, wherein R$^X$ has been defined above. Exemplary sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic(amido(aliphatic)))-S(O)$_2$— or the like.

As used herein, a "sulfoxy" group refers to —O—SO—R$^X$ or —SO—O—R$^X$, when used terminally and —O—S(O)— or —S(O)—O— when used internally, where R$^X$ has been defined above.

As used herein, a "halogen" or "halo" group refers to fluorine, chlorine, bromine or iodine.

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refer to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy aryl, heteroaryl, cycloaliphatic or amino.

As used herein, an "aminoalkyl" refers to the structure (R$^X$)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ when used terminally and —NR$^X$—CO—NR$^Y$— or —NR$^X$—CS—NR$^Y$— when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-6. A branched aliphatic chain is a straight aliphatic chain that is substituted with one or more aliphatic groups. A branched aliphatic chain has the structure —[CHQ]$_v$- where Q is hydrogen or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used interchangeably with the phrase "substituted or unsubstituted." As described herein, compounds of the invention can optionally be substituted with one or more substituents, such as are illustrated generally above, or as exemplified by particular classes, subclasses, and species of the invention. As described herein, the variables $R_1$, $R_2$, $R_3$, $R_4$, $R_5$, A and other variables contained in formulae described herein encompass specific groups, such as alkyl and aryl. Unless otherwise noted, each of the specific groups for the variables $R_1$, $R_2$, $R_3$, $R_4$, $R_5$, A, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl)carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

In general; the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as therapeutic agents.

II. Compounds

A. Generic Compounds

In some aspects, the invention provides compounds of formula I useful for inhibiting serine protease activity and methods of inhibiting serine protease activity. Compounds of formula I include:

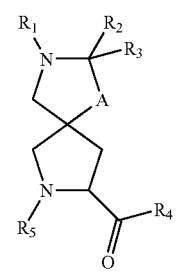

or a pharmaceutically acceptable salt thereof.

$R_1$ is —$Z^A R_8$, wherein each $Z^A$ is independently a bond or an optionally substituted branched or straight $C_{1-12}$ aliphatic chain wherein up to three carbon units of $Z^A$ are optionally and independently replaced by —C(O)—, —C(S)—, —C(O)NR$^A$—, —C(O)NR$^A$NR$^A$—, —C(O)O—, —NR$^A$C(O)O—, —O—, —NR$^A$C(O)NR$^A$—, —NR$^A$NR$^A$—, —S—, —SO—, —SO$_2$—, —NR$^A$—, —SO$_2$NR$^A$—, or —NR$^A$SO$_2$NR$^A$— provided that —O—, —NR$^A$NR$^A$—, —NR$^A$C(O)NR$^A$—, or —NR$^A$SO$_2$NR$^A$— is not directly bound to the nitrogen ring atom of formula I. Each $R_8$ is independently $R^A$, halo, —OH, —CN, —NO$_2$, —NH$_2$, or —OCF$_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

$R_2$ and $R_3$ are —$Z^B R_9$, wherein each $Z^B$ is independently a bond or an optionally substituted branched or straight $C_{1-6}$ aliphatic chain wherein up to three carbon units of $Z^B$ are optionally and independently replaced by —C(O)—, —C(O)NR$^B$—, —C(O)NR$^B$NR$^B$—, —C(O)O—, —NR$^B$C(O)O—, —NR$^B$C(O)NR$^B$—, —NR$^B$NR$^B$—, —S—, —SO—, —SO$_2$—, —NR$^B$—, —SO$_2$NR$^B$—, or —NR$^B$SO$_2$NR$^B$—. Each $R_9$ is independently $R^B$, halo, —OH, —CN, —NO$_2$, —NH$_2$, or —OCF$_3$. Each $R^B$ is independently hydrogen, an optionally substituted aliphatic, an optionally substituted cycloaliphatic, an optionally substituted aryl, or an optionally substituted heteroaryl.

Alternatively, $R_2$ and $R_3$, together form an oxo group.

A is —O—, or —$CR_6R_7$—, wherein each $R_6$ and $R_7$ is —$Z^C R_{10}$, wherein each $Z^C$ is independently a bond or an optionally substituted branched or straight $C_{1-6}$ aliphatic chain wherein up to three carbon units of $Z^C$ are optionally and independently replaced by —C(O)—, —C(S)—, —C(O)$NR^C$—, —C(O)$NR^C NR^C$—, —C(O)O—, —$NR^C$C(O)O—, —$NR^C$C(O)$NR^C$—, —$NR^C NR^C$—, —S—, —SO—, —$SO_2$—, —$NR^C$—, —$SO_2 NR^C$—, or —$NR^C SO_2 NR^C$—. Each $R^{10}$ is independently $R^C$, halo, —OH, —CN, —$NO_2$, —$NH_2$, or —$OCF_3$. Each $R^C$ is independently hydrogen, an optionally substituted aliphatic, an optionally substituted cycloaliphatic, an optionally substituted aryl, or an optionally substituted heteroaryl.

$R_4$ is —$Z^D R_{11}$, wherein each $Z^D$ is independently a bond or an optionally substituted branched or straight $C_{1-12}$ aliphatic chain wherein up to three carbon units of $Z^D$ are optionally and independently replaced by —C(O)—, —C(S)—, —C(O)$NR^D$—, —C(O)$NR^D NR^D$—, —C(O)O—, —$NR^D$C(O)O—, —O—, —$NR^D$C(O)$NR^D$—, —$NR^D NR^D$—, —S—, —SO—, —$SO_2$—, —$SO_2 NR^D$—, or —$NR^D SO_2 NR^D$—, provided that —SO—, —$SO_2$—, or —$SO_2 NR^D$— is not directly bound to the carbonyl adjacent to $R_4$. Each $R_{11}$ is independently $R^D$, halo, —OH, —CN, —$NO_2$, —$NH_2$, or —$OCF_3$. Each $R^D$ is independently hydrogen, an optionally substituted aliphatic, an optionally substituted cycloaliphatic, an optionally substituted heterocycloaliphatic, an optionally substituted aryl, or an optionally substituted heteroaryl.

$R_5$ is —$Z^E R_{12}$, wherein each $Z^E$ is independently a bond or an optionally substituted branched or straight $C_{1-12}$ aliphatic chain wherein up to three carbon units of $Z^E$ are optionally and independently replaced by —C(O)—, —C(S)—, —C(O)$NR^E$—, —C(O)$NR^E NR^E$—, —C(O)O—, —$NR^E$C(O)O—, —O—, —$NR^E$C(O)$NR^E$—, —$NR^E NR^E$—, —S—, —SO—, —$SO_2$—, —$NR^E$—, —$SO_2 NR^E$—, or —$NR^E SO_2 NR^E$—. Each $R_{12}$ is independently $R^E$, halo, —OH, —CN, —$NO_2$, —$NH_2$, or —$OCF_3$. Each $R^E$ is independently hydrogen, an optionally substituted aliphatic, an optionally substituted cycloaliphatic, an optionally substituted heterocycloaliphatic, an optionally substituted aryl, or an optionally substituted heteroaryl.

Or, $R_4$ and $R_5$ together with the atoms to which they are attached form an optionally substituted heterocycloaliphatic ring.

B. Specific Compounds

1. Substituent $R_1$ $R_1$ is —$Z^A R_8$, wherein each $Z^A$ is independently a bond or an optionally substituted branched or straight $C_{1-12}$ aliphatic chain wherein up to three carbon units of $Z^A$ are optionally and independently replaced by —C(O)—, —C(S)—, —C(O)$NR^A$—, —C(O)$NR^A NR^A$—, —C(O)O—, —$NR^A$C(O)O—, —O—, —$NR^A$C(O)$NR^A$—, —$NR^A NR^A$—, —S—, —SO—, —$SO_2$—, —$NR^A$—, —$SO_2 NR^A$—, or —$NR^A SO_2 NR^A$— provided that —O—, —$NR^A NR^A$—, —$NR^A$C(O)$NR^A$—, or —$NR^A SO_2 NR^A$— is not directly bound to the nitrogen ring atom of formula I Each $R_8$ is independently $R^A$, halo, —OH, —CN, —$NO_2$, —$NH_2$, or —$OCF_3$. Each $R^A$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments, $R_1$ is an optionally substituted aliphatic. For example, $R_1$ is an alkyl, alkenyl, or alkynyl, each of which is optionally substituted with 1-4 substituents independently selected from halo, aryl, heteroaryl, cycloaliphatic, and heterocycloaliphatic. Alternatively, $R_1$ is an optionally substituted alkyl. For example, $R_1$ is methyl, ethyl, propyl, or butyl, each of which is optionally substituted with 1-4 substituents independently selected from halo, aryl, heteroaryl, cycloaliphatic, and heterocycloaliphatic. In other examples, $R_1$ is an unsubstituted alkyl. Alternatively, $R_1$ is an optionally substituted aralkyl. In several examples, $R_1$ is an aryl-methyl, aryl-ethyl, or aryl-propyl, each of which is optionally substituted. Alternatively, $R_1$ is phenylmethyl, phenylethyl, or phenylpropyl, each of which is optionally substituted with 1-3 substituents independently selected from halo, aryl, hydroxy, aliphatic, cycloaliphatic, heterocycloaliphatic, aryl, or heteroaryl.

In several embodiments, $R_1$ is an optionally substituted aryl. For example, $R_1$ is a monocyclic or bicyclic aryl, each of which is optionally substituted. In other examples, $R_1$ is phenyl optionally substituted with 1-3 substituents selected from halo, hydroxy, aliphatic, aryl, heteroaryl, cycloaliphatic, or heterocycloaliphatic.

In other examples, $R_1$ is one selected from hydrogen, ethyl, phenyl, p-chloro-phenyl, and phenylmethyl.

2. Substituents $R_2$ and $R_3$ $R_2$ and $R_3$ are —$Z^B R_9$, wherein each $Z^B$ is independently a bond or an optionally substituted branched or straight $C_{1-6}$ aliphatic chain wherein up to three carbon units of $Z^B$ are optionally and independently replaced by —C(O)—, —C(S)—, —C(O)$NR^B$—, —C(O)$NR^B NR^B$—, —C(O)O—, —$NR^B$C(O)O—, —$NR^B$C(O)$NR^B$—, —$NR^B NR^B$—, —S—, —SO—, —$SO_2$—, —$SO_2 NR^B$—, or —$NR^B SO_2 NR^B$—. Each $R_9$ is independently $R^B$, halo, —OH, —CN, —$NO_2$, —$NH_2$, or —$OCF_3$. Each $R^B$ is independently hydrogen, an optionally substituted aliphatic, an optionally substituted cycloaliphatic, an optionally substituted aryl, or an optionally substituted heteroaryl.

Alternatively, $R_2$ and $R_3$, together form an oxo group.

In several embodiments, $R_2$ and $R_3$, together form an oxo group.

3. Group A

A is —O—, or —$CR_6R_7$—, wherein each $R_6$ and $R_7$ is —$Z^C R_{10}$, wherein each $Z^C$ is independently a bond or an optionally substituted branched or straight $C_{1-6}$ aliphatic chain wherein up to three carbon units of $Z^C$ are optionally and independently replaced by —C(O)—, —C(S)—, —C(O)$NR^C$—, —C(O)$NR^C NR^C$—, —C(O)O—, —$NR^C$C(O)O—, —$NR^C$C(O)$NR^C$—, —$NR^C NR^C$—, —S—, —SO—, —$SO_2$—, —$NR^C$—, —$SO_2 NR^C$—, or —$NR^C SO_2 NR^C$—. Each $R_{10}$ is independently $R^C$, halo, —OH, —CN, —$NO_2$, —$NH_2$, or —$OCF_3$. Each $R^C$ is independently hydrogen, an optionally substituted aliphatic, an optionally substituted cycloaliphatic, an optionally substituted aryl, or an optionally substituted heteroaryl.

In several embodiments, A is —O—.

In other embodiments, A is —$CR_6R_7$—. For example, in some embodiments, A is —$CR_6R_7$—, and one of $R_6$ or $R_7$ is hydrogen. In other examples, A is —$CR_6R_7$—, and one of $R_6$ or $R_7$ is hydrogen, and the other of $R_6$ or $R_7$ is optionally substituted $C_{1-6}$ aliphatic. In other examples, A is —$CR_6R_7$—, and one of $R_6$ or $R_7$ is hydrogen, and the other of $R_6$ or $R_7$ is unsubstituted $C_{1-6}$ aliphatic. Alternatively, A is —$CR_6R_7$—, and both of $R_6$ or $R_7$ are hydrogen.

4. Substituent $R_4$ $R_4$ is —$Z^D R_{11}$, wherein each $Z^D$ is independently a bond or an optionally substituted branched or straight $C_{1-12}$ aliphatic chain wherein up to three carbon units of $Z^D$ are optionally and independently replaced by —C(O)—, —C(S)—, —C(O)$NR^D$—, —C(O)$NR^D NR^D$—, —C(O)O—, —$NR^D$C(O)O—, —O—, —NR$^D$C(O)NR$^D$—, —NR$^D$NR$^D$—, —S—, —SO—, —NR$^D$—, —SO$_2$NR$^D$—, or —NR$^D$SO$_2$NR$^D$—, provided that —SO—, —SO$_2$—, or —SO$_2$NR$^D$— is not directly bound to the carbonyl adjacent to R$_4$. Each R$_{11}$ is independently R$^D$, halo, —OH, —CN, —NO$_2$, —NH$_2$, or —OCF$_3$. Each R$^D$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments, R$_4$ is —Z$^D$R$_{11}$, wherein each Z$^D$ is independently a bond or an optionally substituted branched or straight C$_{1-12}$ aliphatic chain wherein up to three carbon units of Z$^D$ are optionally and independently replaced by —C(O)—, —C(S)—, —C(O)NR$^D$—, —C(O)NR$^D$NR$^D$—, —C(O)O—, —NR$^D$C(O)O—, —NR$^D$C(O)NR$^D$—, —NR$^D$NR$^D$—, —S—, —SO—, —SO$_2$—, —NR$^D$—, —SO$_2$NR$^D$—, or —NR$^D$SO$_2$NR$^D$—, provided that —SO—, —SO$_2$—, or —SO$_2$NR$^D$— is not directly bound to the carbonyl of formula I. Each R$_{11}$ is independently R$^D$, halo, —OH, —CN, —NO$_2$, —NH$_2$, or —OCF$_3$. Each R$^D$ is independently hydrogen, an optionally substituted aliphatic, an optionally substituted cycloaliphatic, an optionally substituted aryl, or an optionally substituted heteroaryl.

In still further embodiments, R$_4$ is —Z$_1$-V$_1$-Z$_2$-V$_2$-Z$_3$-V$_3$ each of V$_1$, V$_2$, and V$_3$ is independently a bond, an optionally substituted aliphatic, an optionally substituted cycloaliphatic, an optionally substituted heterocycloaliphatic, an optionally substituted aryl, an optionally substituted heteroaryl, or a hydrogen when V$_1$, V$_2$, or V$_3$ is the terminal group of R$_4$; each of Z$_1$, Z$_2$, and Z$_3$ is independently a bond, —C(O)—, —C(O)C(O)—, —C(S)—, —C(O)N(Q$_6$)-, —N(Q$_6$)C(O)—, —C(O)C(O)N(Q$_6$)-, —O—, SO—, —SO$_2$—, —N(Q$_6$)SO$_2$—, —N(Q$_6$)C(O)N(Q$_6$)-, —N(Q$_6$)C(S)N(Q$_6$)-, —N(Q$_6$)-, —N(Q$_6$)SO$_2$—, —SO$_2$N(Q$_6$)-, —C(O)N(Q$_6$)SO$_2$—, —SO$_2$N(Q$_6$)C(O)—, or hydrogen when Z$_1$, Z$_2$, or Z$_3$ is the terminal group of R$_4$; and each Q$_6$ is independently hydrogen, or an optionally substituted aliphatic.

In other embodiments, R$_4$ is an optionally substituted (aliphatic)amino wherein the aliphatic portion of R$_4$ is —Z$_2$-V$_2$-Z$_3$-V$_3$ or —Z$_3$-V$_3$ wherein each of Z$_2$ and Z$_3$ is independently a bond, —C(O)—, —N(Q$_5$)-, —CH(OH)—, —C(O)N(Q$_6$)-, or —C(O)C(O)N(Q$_6$)-; V$_2$ is independently a bond, an optionally substituted aliphatic, or an optionally substituted cycloaliphatic; and V$_3$ is hydrogen, an optionally substituted aliphatic, or an optionally substituted cycloaliphatic.

In still further embodiments, Z$_2$ is —CH(OH)—, V$_2$ is a bond, and Z$_3$ is —C(O)N(Q$_6$)- such that R$_4$ is —N(Q$_6$)-CH(OH)—C(O)—N(V$_3$)(Q$_6$).

In certain embodiments, R$_4$ is an optionally substituted (aliphatic)amino, optionally substituted (cycloaliphatic)amino, an optionally substituted alkoxy, or hydroxy.

In still another embodiment, R$_4$ is an alkoxy optionally substituted with 1-3 of halo, hydroxy, aliphatic, cycloaliphatic, or heterocycloaliphatic.

In several embodiments, R$_4$ is amino. Examples of R$_4$ include a mono-substituted amino. Additional examples of R$_4$ include (cycloaliphatic(carbonyl(carbonyl(alkyl))))amino (amino(carbonyl(carbonyl(aliphatic))))amino, aliphatic(carbonyl(carbonyl(aliphatic))))amino, or (aryl(amino(carbonyl(carbonyl(aliphatic)))))amino, each of which is optionally substituted with 1 to 3 substituents.

In several embodiments, R$_4$ is —NR$_{4Z}$R'$_{4Z}$, —SR$_{4Y}$, or —NR$_{4Y}$—CR$_{4X}$R'$_{4X}$-L$_1$-NR$_{4Z}$—R$_{4W}$, wherein R$_{4Y}$ is independently hydrogen, an optionally substituted aliphatic, an optionally substituted cycloaliphatic, an optionally substituted heterocycloaliphatic, an optionally substituted aryl, or an optionally substituted heteroaryl; each R$_{4W}$ is independently hydrogen, optionally substituted aliphatic, optionally substituted aryl, optionally substituted heteroaryl, optionally substituted heterocycloaliphatic, or optionally substituted cycloaliphatic; each R$_{4X}$ and R'$_{4X}$ is independently hydrogen, an optionally substituted aliphatic, an optionally substituted heteroaryl, an optionally substituted phenyl, an optionally substituted cycloaliphatic, an optionally substituted heterocycloaliphatic; or R$_{4X}$ and R'$_{4X}$ together with the atom to which they are both attached form an optionally substituted 3 to 7 membered cycloaliphatic or heterocycloaliphatic ring; each L$_1$ is —CH$_2$—, —C(O)—, —CF$_2$—, —C(O)C(O)—, —C(O)O—, —S(O)—, or —SO$_2$—; each R$_{4Z}$ or R'$_{4Z}$ is hydrogen, an optionally substituted aliphatic, an optionally substituted cycloaliphatic, an optionally substituted heterocycloaliphatic, an optionally substituted aryl, or an optionally substituted heteroaryl; or R$_{4Z}$ and R'$_{4Z}$ together with the nitrogen to which they are both attached may form an optionally substituted 3 to 7 membered heterocycloaliphatic ring.

In several embodiments, each R$_{4X}$ and R'$_{4X}$ is independently hydrogen, or optionally substituted aliphatic, optionally substituted cycloaliphatic, or optionally substituted (cycloaliphatic)aliphatic.

In several embodiments, L$_1$ is —C(O)C(O)— or —SO$_2$—.

In several other embodiments, each R$_{4W}$ is hydrogen or optionally substituted cycloaliphatic.

In several embodiments, R$_4$ is —NH—CHR$_{4X}$—C(O)—C(O)—N(R$_{4Z}$)R$_{4W}$.

In several embodiments, R$_4$ is —NH—CHR$_{4X}$—CH(OH)—C(O)—N(R$_{4Z}$)R$_{4W}$.

In several embodiments, R$_4$ is —NH—CHR$_{4X}$—C(O)—C(O)—NHR$_{4Z}$ wherein —NHR$_{4Z}$ is NH-cyclopropyl, —NH-Me, —NH-Et, —NH-iPr, —NH-nPr.

In several embodiments R$_4$ is —NR$_{4Z}$R'$_{4Z}$, —SR$_{4Z}$ wherein each R$_{4Z}$ and R'$_{4Z}$ is independently hydrogen, alkyl, cycloalkyl or aralkyl. Non-limiting examples of R$_{4Z}$ include methyl, ethyl, t-butyl, cyclopentyl, cyclohexyl and benzyl.

In other embodiments R$_4$ is (—NH—CR$_{4X}$R'$_{4X}$-L$_1$-C(O))$_i$-M; wherein each M is independently —OH, —R$_{4X}$, —NR$_{4Z}$R'$_{4Z}$, or —OR$_{4X}$, each i is 1 or 2, and L$_1$, R$_{4Z}$, R$_{4X}$, and R'$_{4Z}$ are defined above.

In several embodiments R$_4$ is (—NH—CR$_{4Z}$R'$_{4Z}$-L$_1$-C(O))$_i$-M wherein L$_1$ is —C(O)—, i is 1 and M is independently —R$_{4X}$, —N(R$_{4X}$R'$_{4X}$), —OR$_{4X}$, —NHSO$_2$R$_{4X}$, or —SR$_{4X}$.

In some embodiments, R'$_{4Z}$ is H and R$_{4Z}$ is aliphatic, (aryl)aliphatic or cycloaliphatic. Non-limiting examples of R$_{4X}$ include hydrogen,

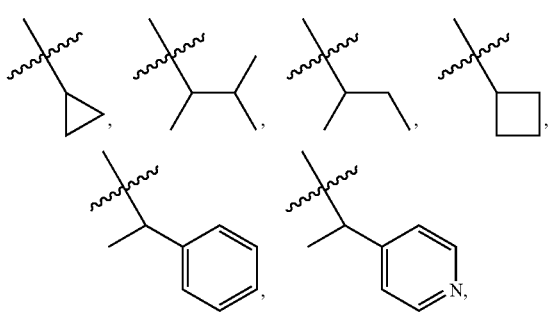

-continued

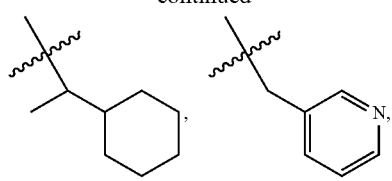

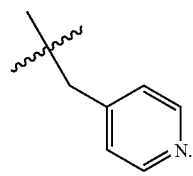

In some embodiments R'$_{4X}$ is H and R$_{4X}$ is optionally substituted aliphatic, optionally substituted aryl, optionally substituted aralkyl, optionally substituted heteroaliphatic or optionally substituted heteroaralkyl. Some non-limiting examples of R$_{4X}$ include:

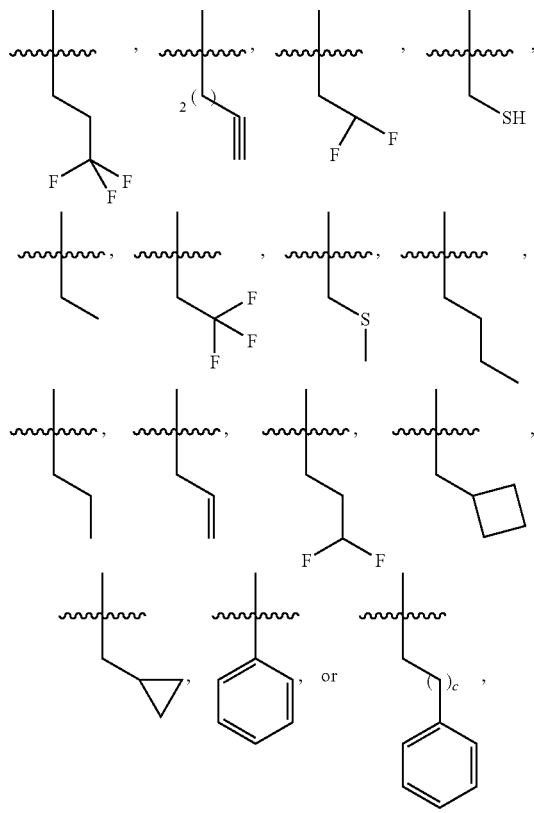

where c is 0-3.

In several embodiments, R$_4$ is:

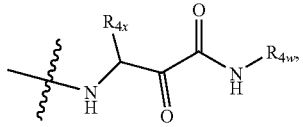

wherein R$_{4X}$ is

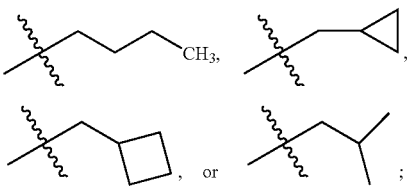

and R$_{4W}$ is

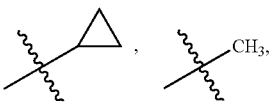

or hydrogen.

In some embodiments, R$_4$ is

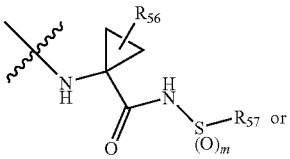

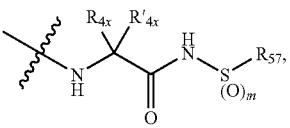

wherein each R$_{56}$ is independently optionally substituted C$_{1-6}$ aliphatic; optionally substituted aryl, optionally substituted heteroaryl, optionally substituted cycloaliphatic, or optionally substituted heterocycloaliphatic; each R$_{57}$ is independently optionally substituted aliphatic, optionally substituted aryl, optionally substituted aliphatic, optionally substituted heteroaryl, optionally substituted aliphatic, optionally substituted cycloaliphatic or optionally substituted amino; and m is 1 or 2; and each R$_{4X}$ and R'$_{4X}$ is independently hydrogen, an optionally substituted aliphatic, an optionally substituted cycloaliphatic, an optionally substituted heterocycloaliphatic, an optionally substituted aryl, or an optionally substituted heteroaryl; or R$_{4X}$ and R'$_{4X}$ (together with the atom to which they are both attached form an optionally substituted 3 to 7 membered cycloaliphatic or heterocycloaliphatic ring.

In some other embodiments, $R_4$ is:

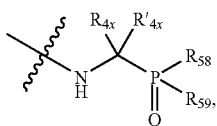

wherein $R_{58}$ and $R_{59}$ are each independently selected from optionally substituted aliphatic, optionally substituted alkoxy, optionally substituted aryloxy, optionally substituted heteroaryloxy, optionally substituted (cycloaliphatic)oxy, optionally substituted (heterocycloaliphatic)oxy optionally substituted aryl, optionally substituted heteroaryl, optionally substituted cycloaliphatic or optionally substituted amino; and each $R_{4X}$ and $R'_{4X}$ is independently hydrogen, an optionally substituted aliphatic, an optionally substituted cycloaliphatic, an optionally substituted heterocycloaliphatic, an optionally substituted aryl, or an optionally substituted heteroaryl; or $R_{4X}$ and $R'_{4X}$ together with the atom to which they are both attached form an optionally substituted 3 to 7 membered cycloaliphatic or heterocycloaliphatic ring.

In several embodiments, $R_4$ is one selected from:

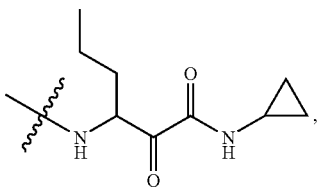

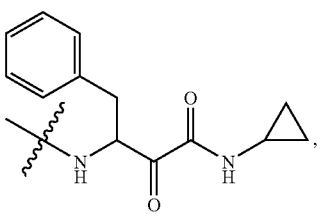

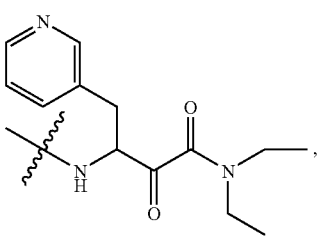

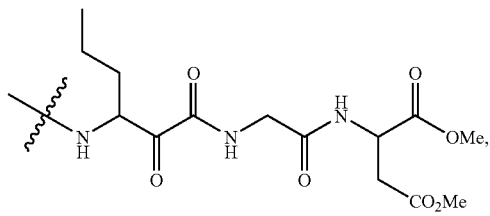

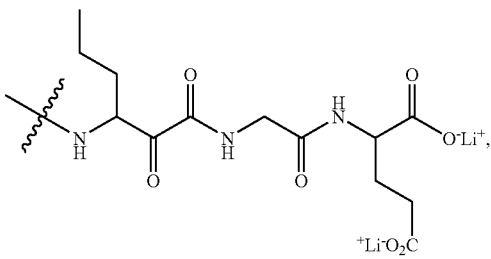

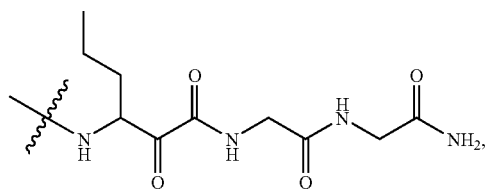

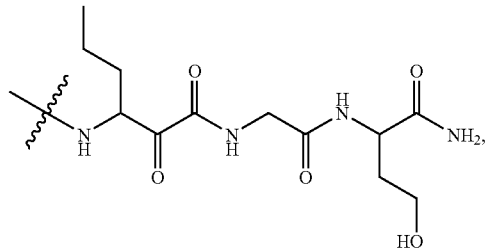

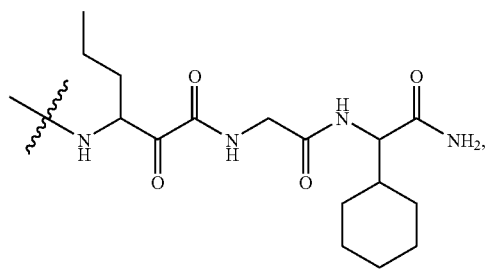

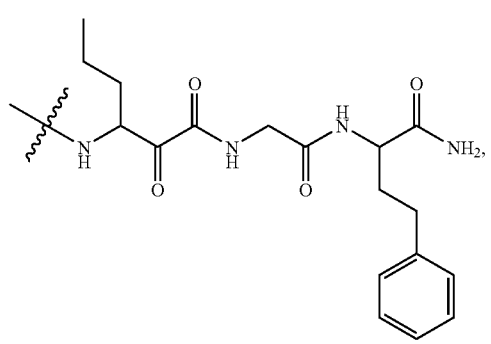

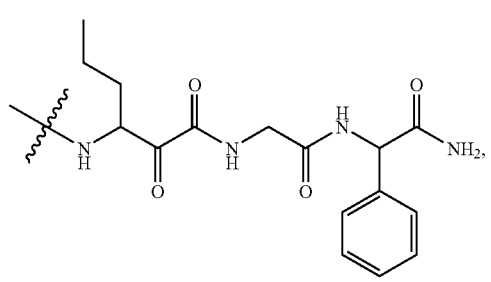

23
-continued
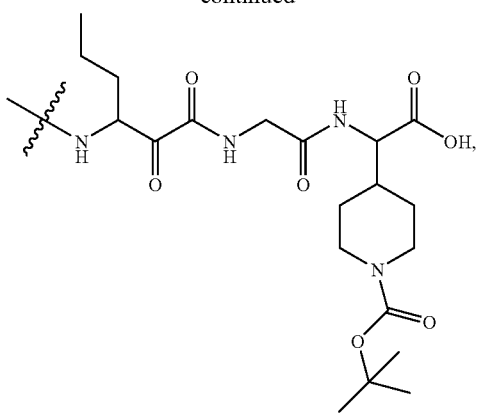
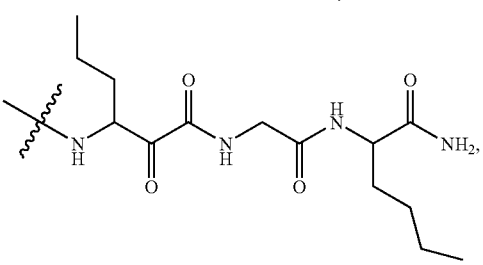
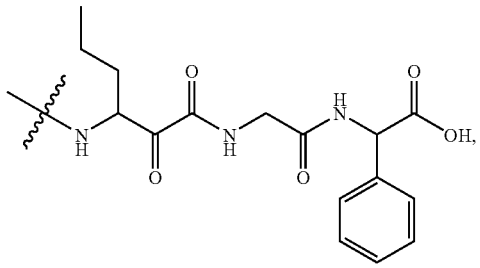
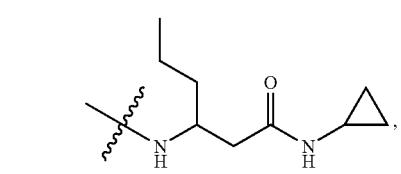
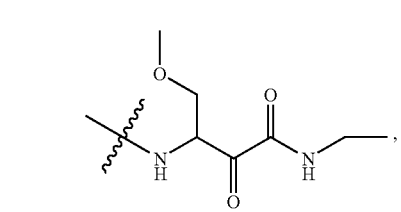
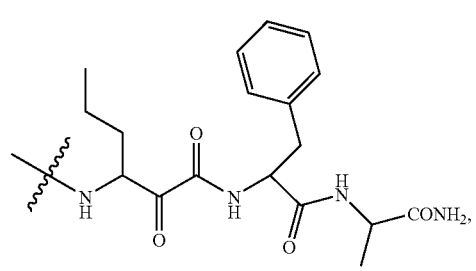
24
-continued
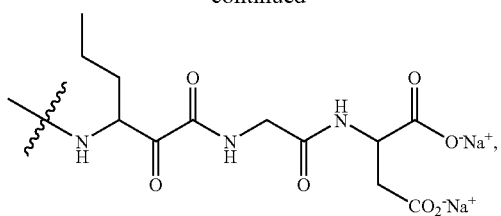
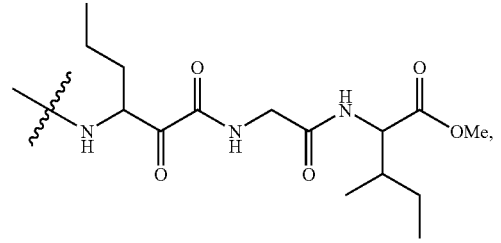
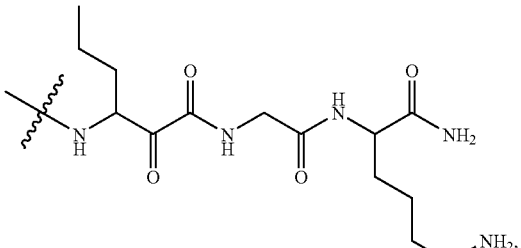
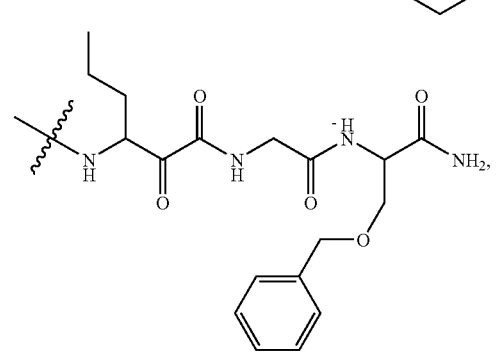
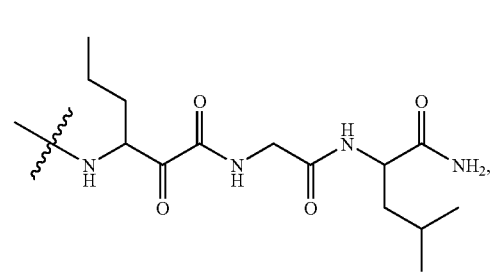
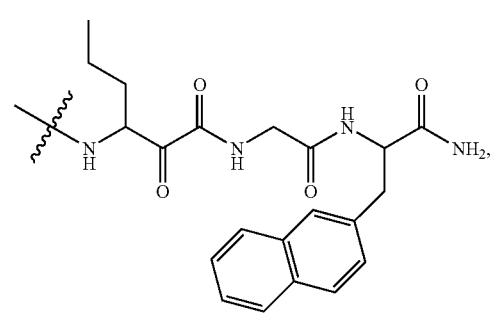

25
-continued
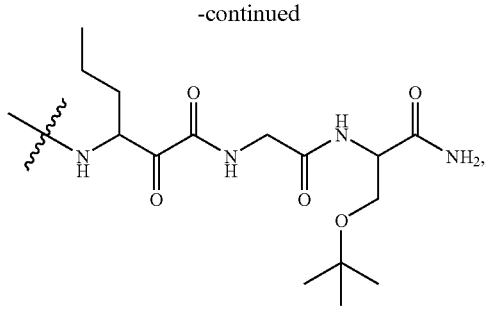
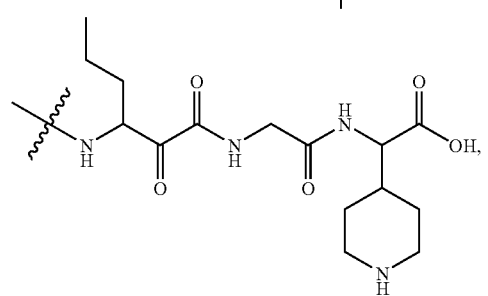
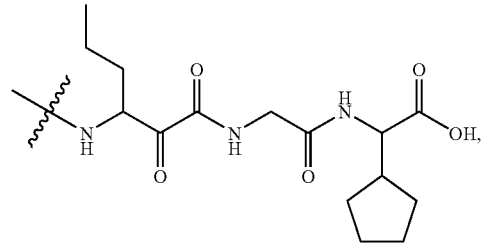
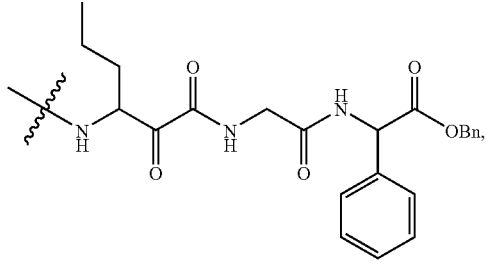
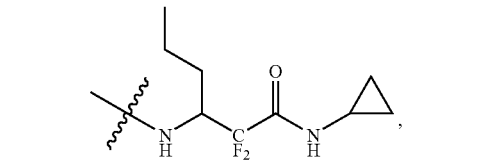
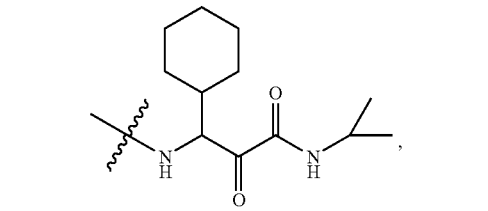
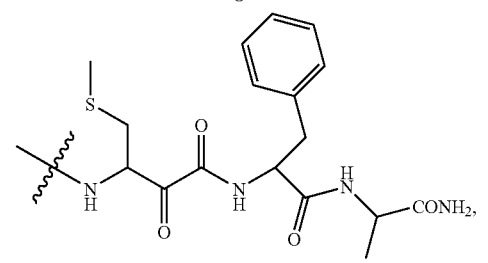
26
-continued
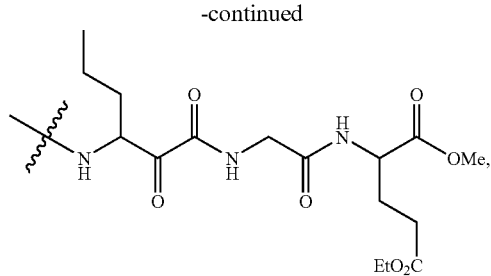
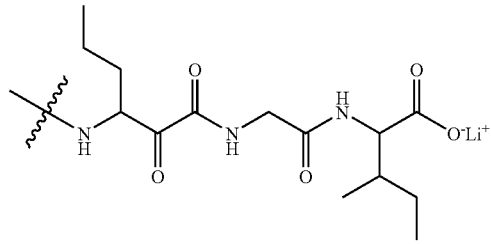
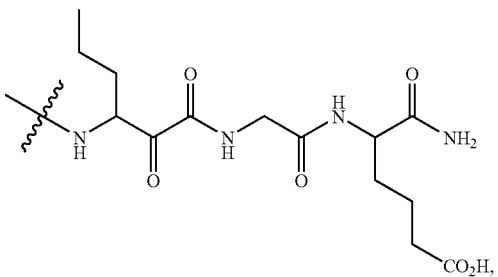
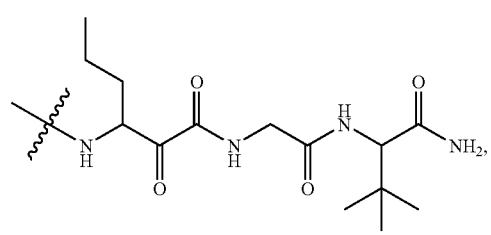
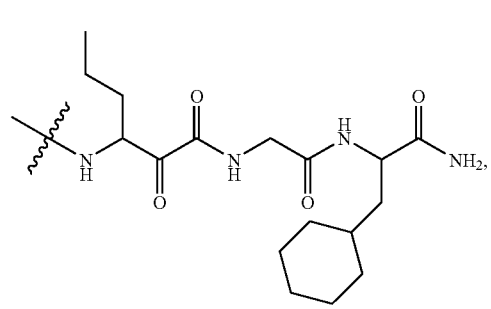
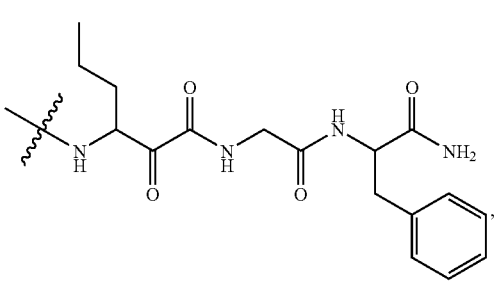

27
-continued
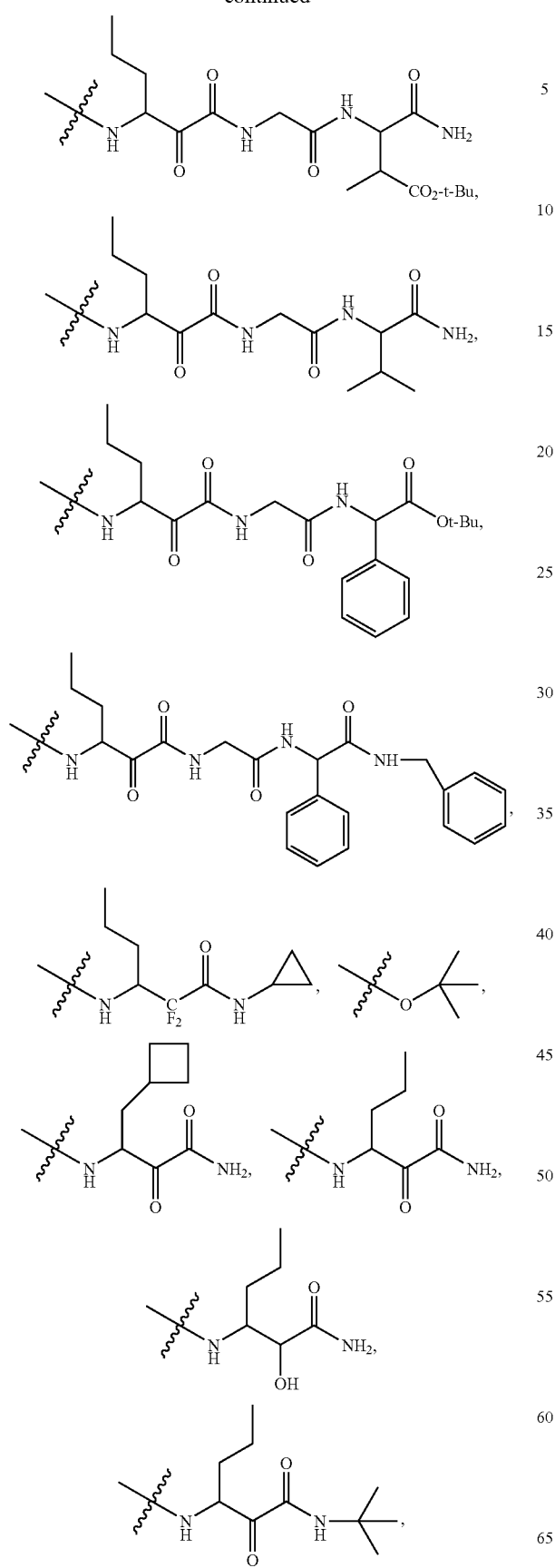
28
-continued
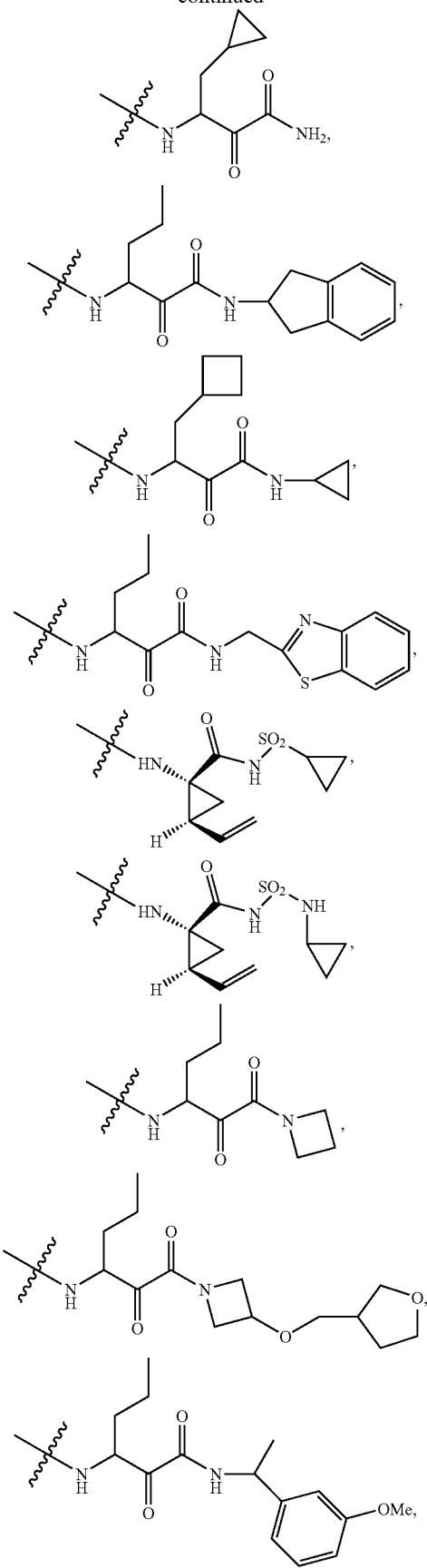

29
-continued
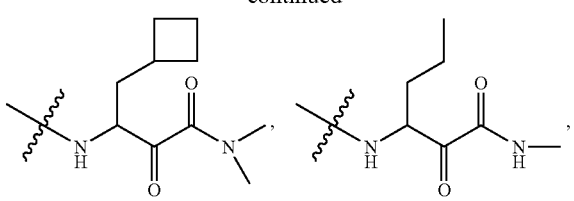
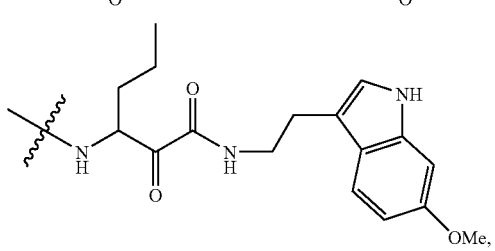
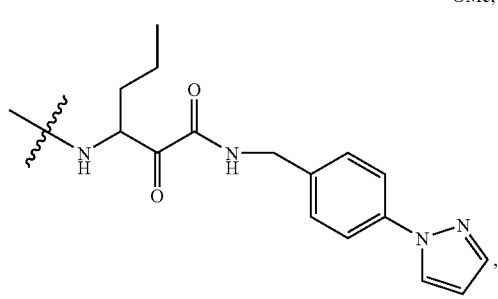
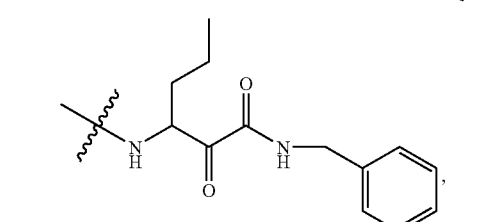
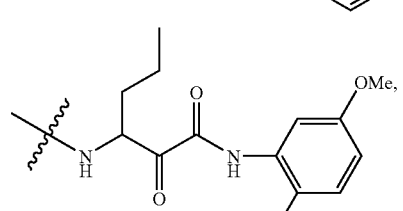
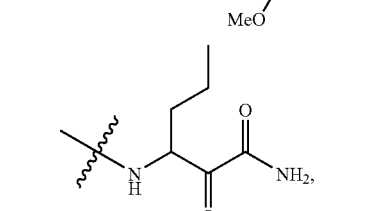
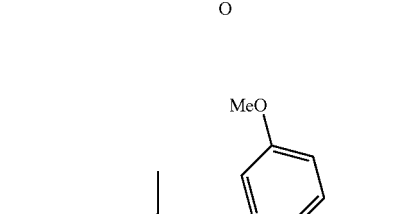
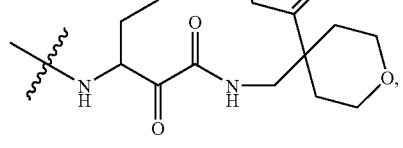
30
-continued
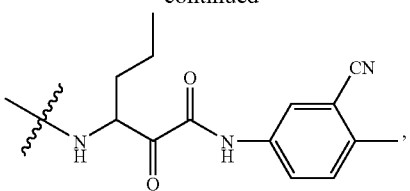
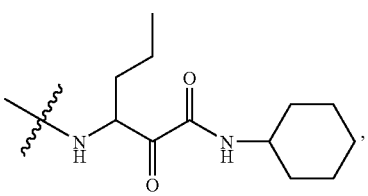
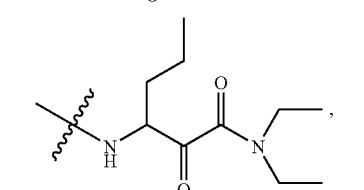
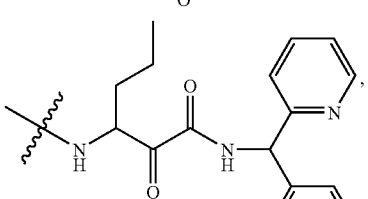
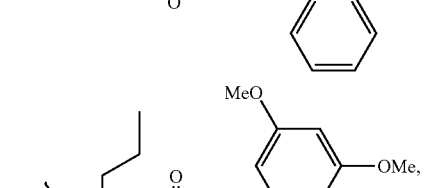
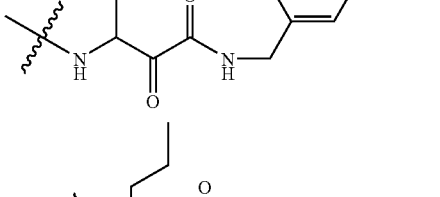
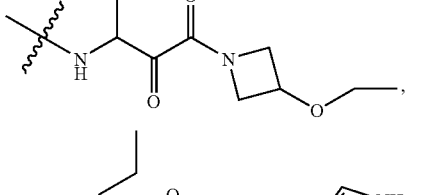
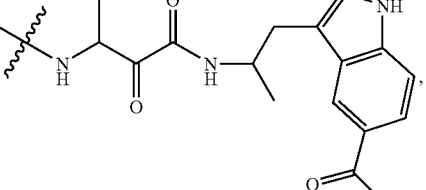
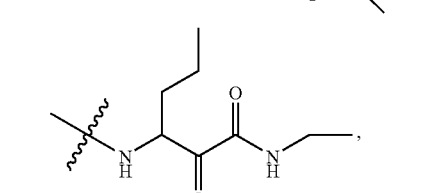

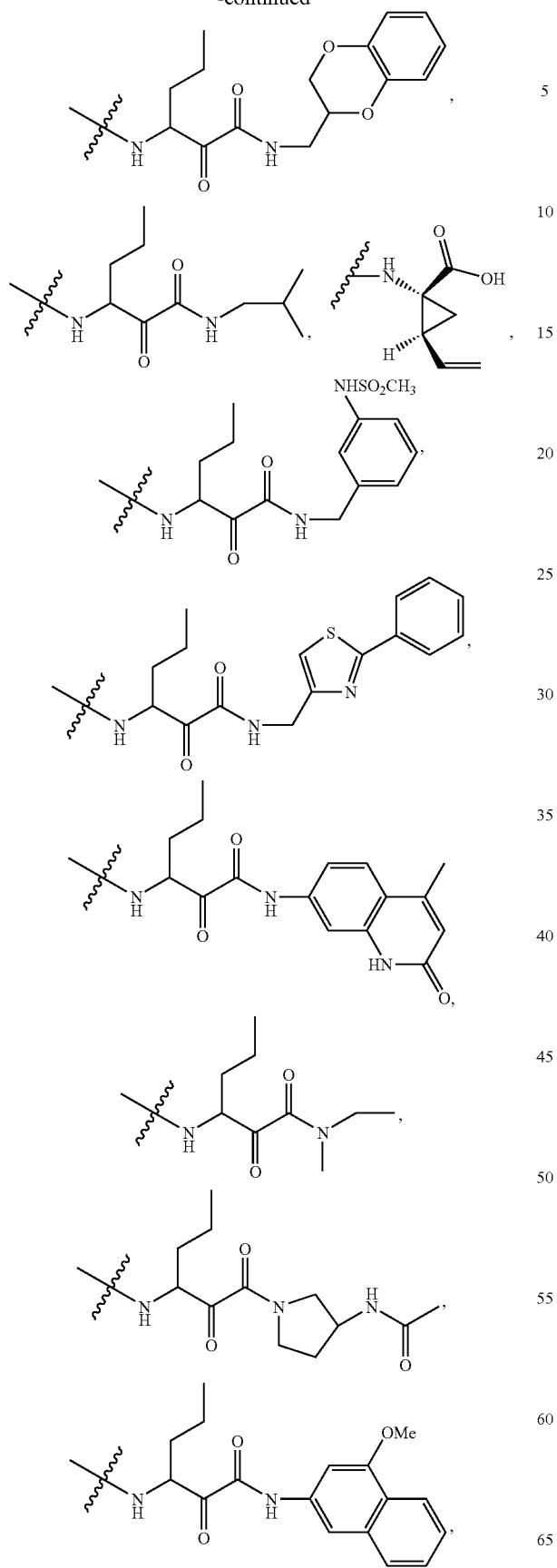
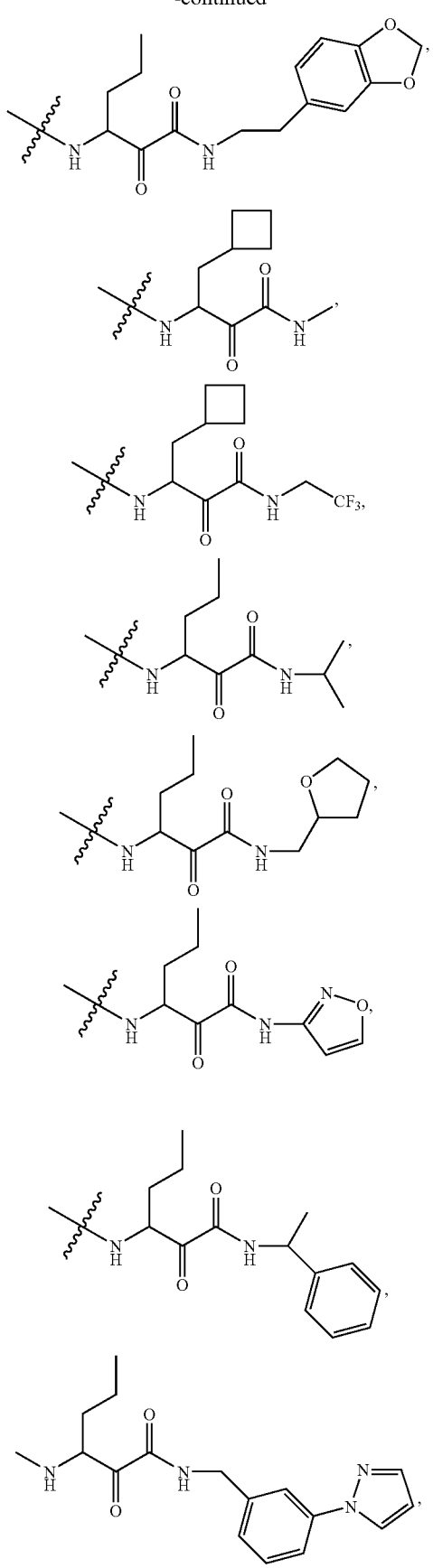

33
-continued
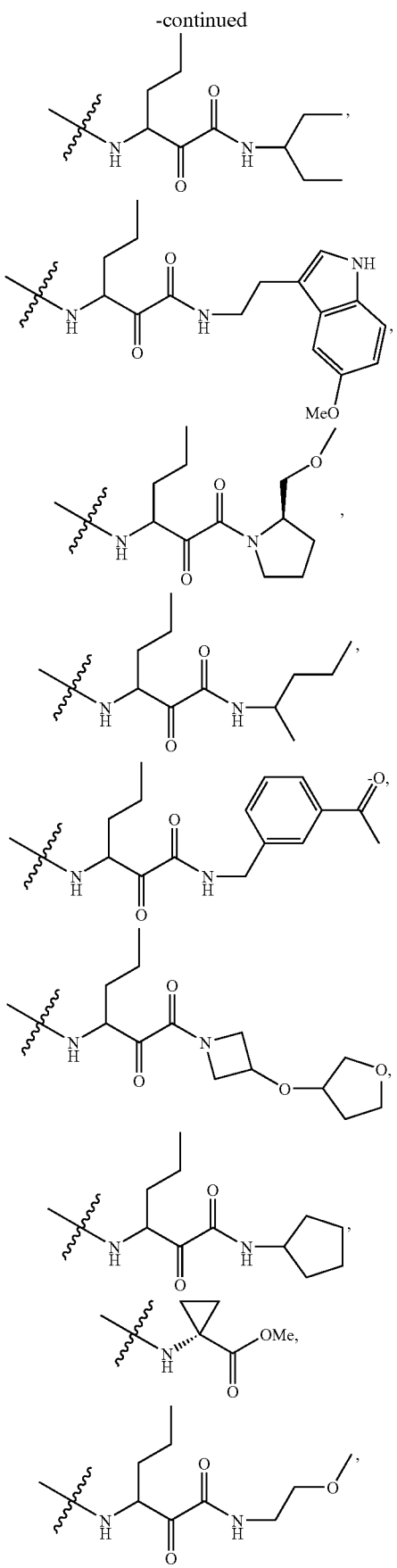
34
-continued
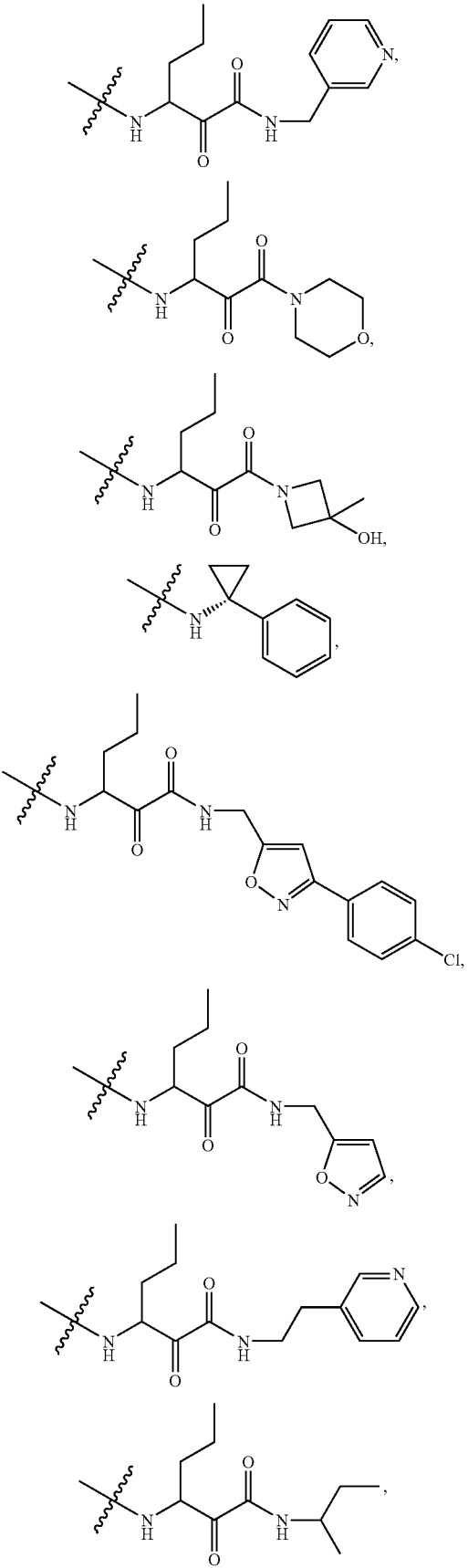

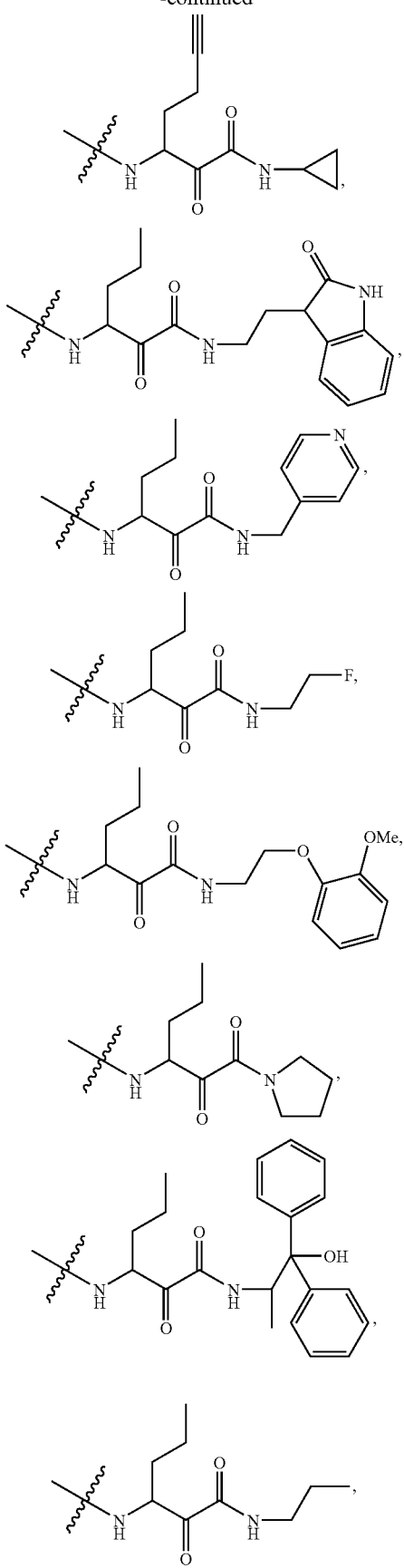
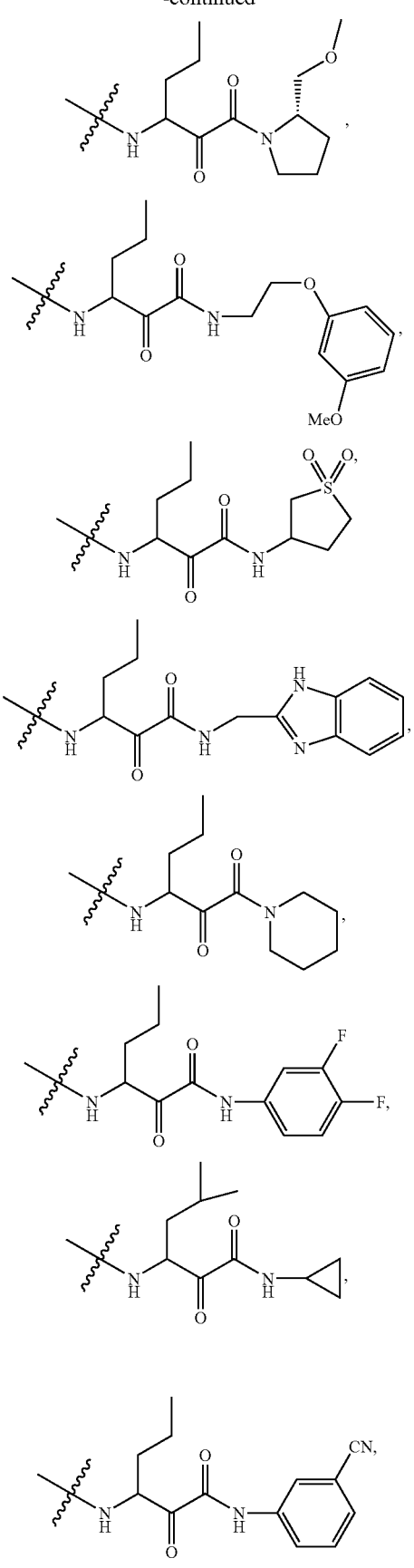

37
-continued
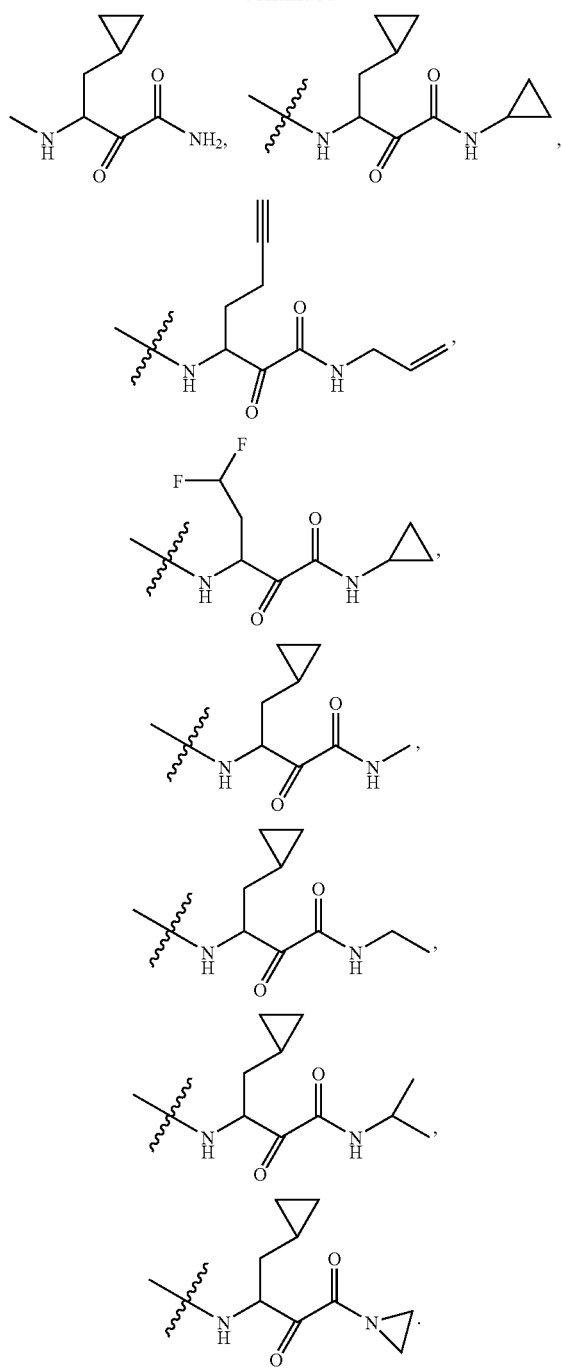
In some specific embodiments, R$_4$ is
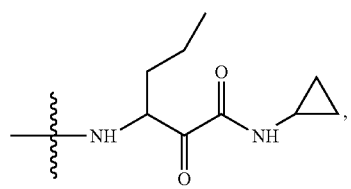
38
-continued
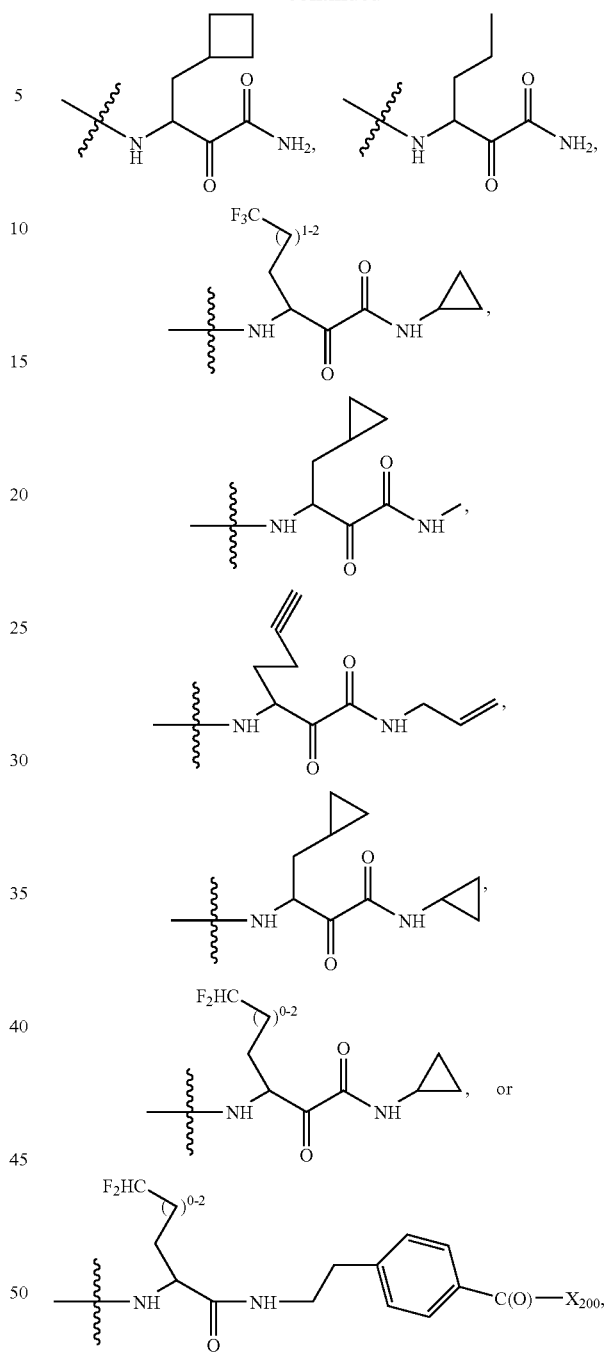
where X$_{200}$ is —OX$_{202}$ or —X$_{202}$, and X$_{202}$ is aliphatic, cycloaliphatic, heterocycloaliphatic, aryl, or heteroaryl.
In other embodiments, R$_4$ is
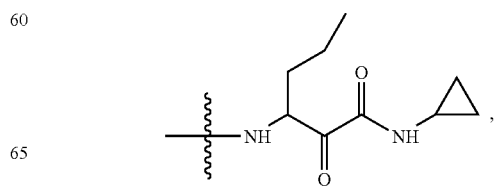

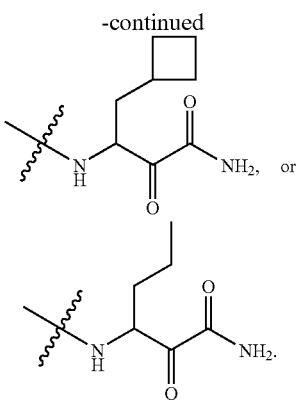

Additional examples of $R_4$ are illustrated in PCT publications WO 2004/103996 A1, WO 2004/72243 A2, WO 03/064456 A1, WO 03/64455 A2, WO 03/064416 A1, and U.S. Patent Publication US 2005/0090450, as well as those other publications referenced herein, each of which is incorporated in its entirety by reference.

5. Substituent $R_5$:

$R_5$ is —$Z^E R_{12}$, wherein each $Z^E$ is independently a bond or an optionally substituted branched or straight $C_{1-12}$ aliphatic chain wherein up to three carbon units of $Z^D$ are optionally and independently replaced by —C(O)—, —C(S)—, —C(O)$NR^E$—, —C(O)$NR^E NR^E$—, —C(O)O—, —$NR^E$C(O)O—, —O—, —$NR^E$C(O)$NR^E$—, —$NR^E NR^E$—, —S—, —SO—, —$SO_2$—, —$NR^E$—, —$SO_2 NR^E$—, or —$NR^E SO_2 NR^E$—. Each $R_{12}$ is independently $R^E$, halo, —OH, —CN, —$NO_2$, —$NH_2$, or —$OCF_3$. Each $R^E$ is independently hydrogen, an optionally substituted aliphatic, an optionally substituted cycloaliphatic, an optionally substituted heterocycloaliphatic, an optionally substituted aryl, or an optionally substituted heteroaryl.

In several embodiments $R_5$ is optionally substituted with 1 to 4 substituents.

In certain embodiments, $R_5$ is -$Q_4$-$W_4$-$Q_3$-$W_3$-$Q_2$-$W_2$-$Q_1$, wherein each of $W_2$, $W_3$, and $W_4$ is independently a bond, —C(O)—, —C(S)—, —C(O)N($Q_5$)-, —C(O)O—, —O—, —N($Q_5$)C(O)N($Q_5$)-, —$SO_2$—, —N($Q_5$)$SO_2$—, —S—, —N($Q_5$)-, —SO—, —OC(O)—, —N($Q_5$)C(O)O—, or —$SO_2$N($Q_5$)-; each of $Q_1$, $Q_2$, $Q_3$ and $Q_4$ is independently a bond, an optionally substituted $C_{1-4}$ aliphatic, an optionally substituted cycloaliphatic, an optionally substituted heterocycloaliphatic, an optionally substituted aryl, an optionally substituted heteroaryl, or a hydrogen when $Q_1$, $Q_2$, $Q_3$, or $Q_4$ is the terminal group of $R_5$; and each $Q_5$ is independently hydrogen or an optionally substituted aliphatic. In some specific embodiments, $Q_4$ is a bond.

In several embodiments, $R_5$ is an optionally substituted acyl group. In several examples, $R_5$ is an optionally substituted alkylcarbonyl. Additional examples of $R_5$ include (amino)alkylcarbonyl, (halo)alkylcarbonyl, (aryl)alkylcarbonyl, (cycloaliphatic)alkylcarbonyl, or (heterocycloaliphatic)alkylcarbonyl. Included in these examples are embodiments where $R_5$ is (heterocycloalkyl(oxy(carbonyl(amino))))alkylcarbonyl, (heteroaryl(carbonyl(amino(alkyl(carbonyl(amino)))))alkylcarbonyl, (bicycloaryl(sulfonyl(amino)))alkylcarbonyl, (aryl(alkoxy(carbonyl(amino))))alkylcarbonyl, (alkyl(carbonyl(amino)))alkylcarbonyl, (alkenyl(alkoxy(carbonyl(amino))))alkylcarbonyl, (cycloaliphatic(alkyl(amino(carbonyl(amino)))))alkylcarbonyl, (heteroaryl(carbonyl(amino(alkyl(carbonyl(amino))))))alkylcarbonyl, (alkyl(amino(carbonyl(amino))))alkylcarbonyl, or (bicycloaryl(amino(carbonyl(amino))))alkylcarbonyl, each of which is optionally substituted with 1-3 substituents.

In several embodiments, $R_5$ is an optionally substituted carboxy group. In one example, $R_5$ is optionally substituted alkoxycarbonyl. Another example of $R_5$ includes $C_{1-4}$ alkoxycarbonyl, or (tricyclic aryl)alkoxycarbonyl, each of which is optionally substituted with 1-3 substituents. Other carboxy groups include (aliphatic(oxy))carbonyl, a (heteroaralkyl(oxy))carbonyl, (heterocycloaliphatic(oxy)carbonyl, (aralkyl(oxy))carbonyl, each of which is optionally substituted with 1-3 of halo, alkoxy, aliphatic, cycloaliphatic, heterocycloaliphatic, aryl, heteroaryl, or combinations thereof.

In several embodiments, $R_5$ is optionally substituted aminocarbonyl. Examples of $R_5$ include (alkoxy(aryl(alkyl)))aminocarbonyl, (alkyl)aminocarbonyl, or (aryl(alkoxy(carbonyl(alkyl(amino(carbonyl)alkyl))))))aminocarbonyl, each of which is optionally substituted with 1-3 substituents.

In several embodiments, $R_5$ is optionally substituted heteroaryl. In one example, $R_5$ is an optionally substituted oxazolyl, pyrrolyl, furyl, thiophenyl, triazinyl, pyridinyl, pyrazinyl, pyrimidinyl, or pyridazinyl.

In several embodiments, $R_5$ is an alkylsulfonyl, aminosulfonyl, arylsulfonyl, heteroarylsulfonyl, cycloaliphaticsulfonyl, or heterocycloaliphaticsulfonyl, each of which is optionally substituted with 1-4 substituents.

In several embodiments, $R_5$ is an optionally substituted alkylsulfonyl. Examples of $R_5$ include (aryl)alkylsulfonyl, or (alkyl(amino))alkylsulfonyl, each of which is optionally substituted with 1-3 substituents. alkylsulfonyl, aminosulfonyl, arylsulfonyl, heteroarylsulfonyl, cycloaliphaticsulfonyl, or heterocycloaliphaticsulfonyl, each of which is optionally substituted. In certain embodiments, $R_5$ is an optionally substituted alkylsulfonyl.

In other certain embodiments, $R_5$ is (aryl)alkylsulfonyl, or (alkyl(amino))alkylsulfonyl, each of which is optionally substituted.

In some specific embodiments, $R_5$ is (amino)alkylcarbonyl, (halo)alkylcarbonyl, (aryl)alkylcarbonyl, (cycloaliphatic)alkylcarbonyl, or (heterocycloaliphatic)alkylcarbonyl, (heterocycloalkyl(oxy(carbonyl(amino))))alkylcarbonyl, (heteroaryl(carbonyl(amino(alkyl(carbonyl(amino)))))alkylcarbonyl, (bicycloaryl(sulfonyl(amino)))alkylcarbonyl, (aryl(alkoxy(carbonyl(amino))))alkylcarbonyl, (alkyl(carbonyl(amino)))alkylcarbonyl, (alkenyl(alkoxy(carbonyl(amino))))alkylcarbonyl, (cycloaliphatic(alkyl(amino(carbonyl(amino)))))alkylcarbonyl, (heteroaryl(carbonyl(amino(alkyl(carbonyl(amino))))))alkylcarbonyl, (alkyl(amino(carbonyl(amino))))alkylcarbonyl, or (bicycloaryl(amino(carbonyl(amino))))alkylcarbonyl, each of which is optionally substituted.

In other specific embodiments, $R_5$ is a heteroarylcarbonyl, a (cycloaliphatic(alkyl(amido(alkyl))))carbonyl, a (heterocycloaliphatic(oxy(amido(alkyl))))carbonyl, an (aryl(sulfonyl(amino(alkyl))))carbonyl, an (aralkyl(oxy(amido(alkyl))))carbonyl, an (aliphatic(oxy(amido(alkyl))))carbonyl, a (cycloaliphatic(alkyl(amido(alkyl))))carbonyl, a (heterocycloaliphatic)carbonyl, or a (heteroaryl(amido(alkyl(amido(alkyl))))carbonyl, each of which is optionally substituted with 1-4 of halo, aliphatic, cycloaliphatic, acyl, alkoxy, or combinations thereof.

In still other embodiments, $R_5$ is amido. For example, $R_5$ is (alkoxy(aryl(alkyl)))aminocarbonyl, (alkyl)aminocarbonyl, or (aryl(alkoxy(carbonyl(alkyl(amino(carbonyl(alkyl)))))))aminocarbonyl, each of which is optionally substituted.

In several embodiments, $R_5$ is

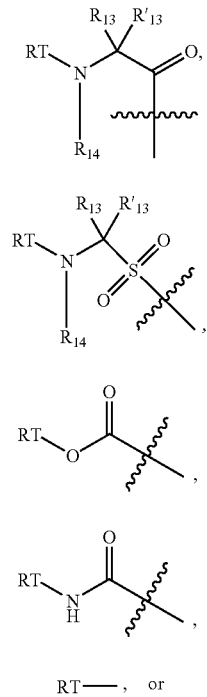

QI

QII

QIII

QIV

RT—, or QV

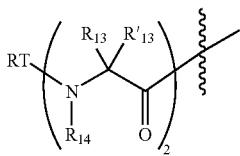

QVI wherein T is a bond, —C(O)—, —OC(O)—, —NHC(O)—, —S(O)$_2$N(H)—, —C(O)C(O)— or —SO$_2$—; each R is independently hydrogen, amino, an optionally substituted aliphatic, an optionally substituted cycloaliphatic, an optionally substituted heterocycloaliphatic, an optionally substituted aryl, or an optionally substituted heteroaryl; each $R_{13}$ and $R'_{13}$ is independently hydrogen, an optionally substituted aliphatic, an optionally substituted cycloaliphatic, an optionally substituted heterocycloaliphatic, an optionally substituted aryl, or an optionally substituted heteroaryl; and each $R_{14}$ is independently hydrogen, an optionally substituted aliphatic, an optionally substituted heteroaryl, an optionally substituted phenyl, or $R_{13}$ and $R_{14}$, bound on adjacent atoms, taken together with the atoms to which they are attached form a 5 to 7 membered, optionally substituted monocyclic heterocycloaliphatic, or a 6 to 12 membered, optionally substituted bicyclic heterocycloaliphatic; or $R_{13}$ and $R'_{13}$, taken together with the atoms to which they are attached form an optionally substituted cycloaliphatic or an optionally substituted heterocycloaliphatic. For clarity, when $R_5$ is QVI, each of $R_{13}$, $R'_{13}$ and $R_{14}$ in each subunit can be independently selected as described above. The set of $R_{13}$, $R'_{13}$ and $R_{14}$ variables in one subunit need not necessarily be identical to the same set of $R_{13}$, $R'_{13}$ and $R_{14}$ variables in the other subunit.

In other embodiments, $R_5$ is QI or QII.

In some embodiments, R in the substituent in QI, QII, QIII, QIV, QV, or QVI is

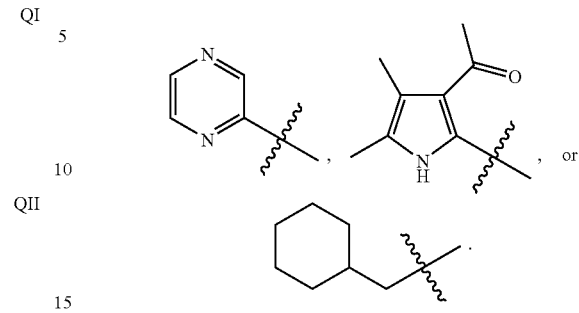

In other embodiments, $R_5$ is QVI and R is

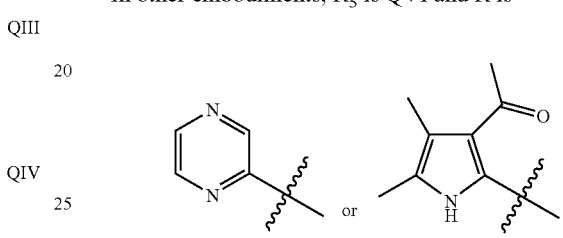

In other embodiments, R in the substituent in QI, QII, QIII, QIV, QV, or QVI is

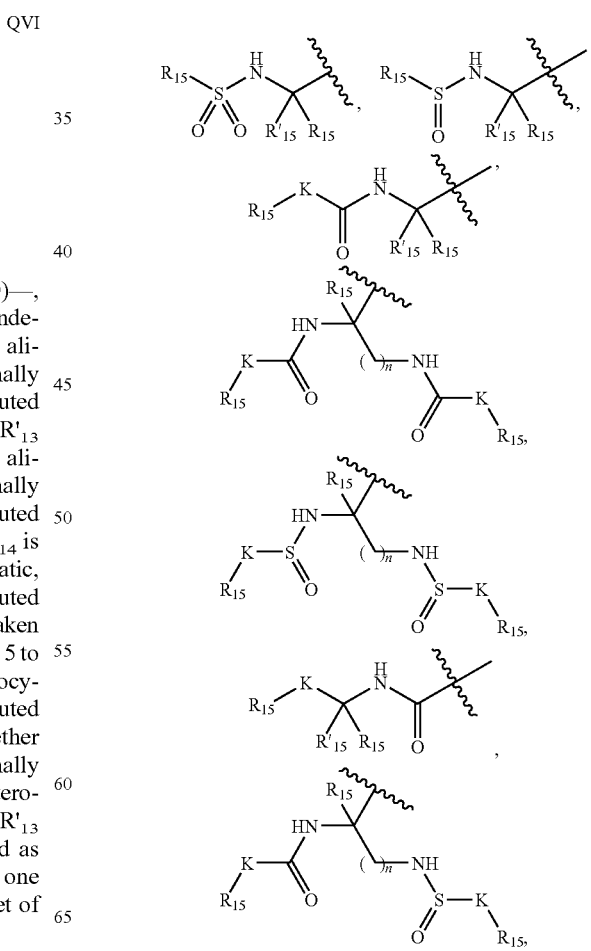

-continued

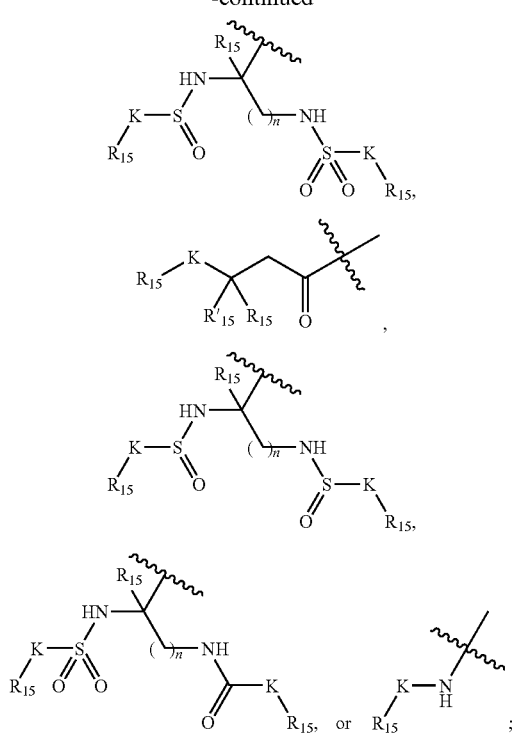

wherein each $R_{15}$ and $R'_{15}$ is independently hydrogen, optionally substituted aliphatic, optionally substituted aryl, optionally substituted heteroaryl, optionally substituted heterocycloaliphatic, or optionally substituted cycloaliphatic, or $R_{15}$ and $R'_{15}$ together with the atom to which they are both bound form an optionally substituted cycloaliphatic or an optionally substituted heterocycloaliphatic; and each K is independently a bond, $C_{1-12}$ aliphatic, —O—, —S—, —S(O)$_2$—, —NR$_{16}$—, —C(O)—, or —C(O)NR$_{16}$—, wherein $R_{16}$ is hydrogen or an optionally substituted $C_{1-12}$ aliphatic; and n is 1-3. For clarity, when more than one $R_{15}$ is present in QI, QII, QIII, QIV, QV, or QVI, each $R_{15}$ can be the same or different. In several embodiments, $R_{15}$ or $R'_{15}$ is [$C_{3-10}$ cycloalkyl or $C_{3-10}$ cycloalkenyl]-$C_{1-12}$ aliphatic, (3 to 10 membered)-heterocycloaliphatic, (3 to 10 membered)-heterocycloaliphatic-$C_{1-12}$ aliphatic, (5 to 10 membered)-heteroaryl, or (5 to 10 membered)-heteroaryl-$C_{1-12}$ aliphatic-.

In still other embodiments, R in the substituent in QI, QII, QIII, QIV, QV, or QVI is

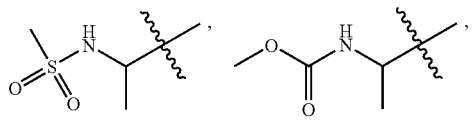

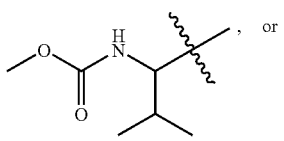, or

-continued

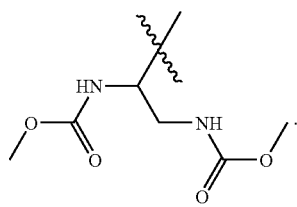

In further embodiments, R in the substituent in QI, QII, QIII, QIV, QV, or QVI is

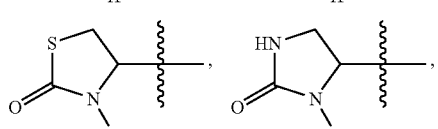

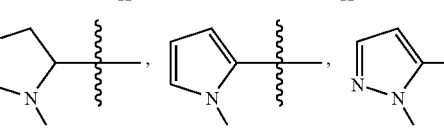

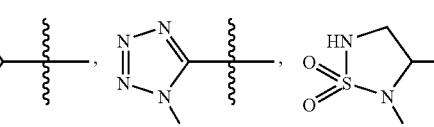

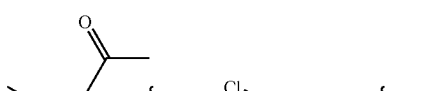

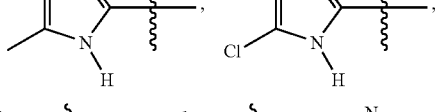

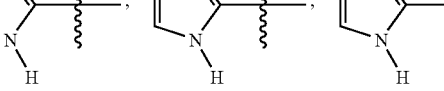

-continued

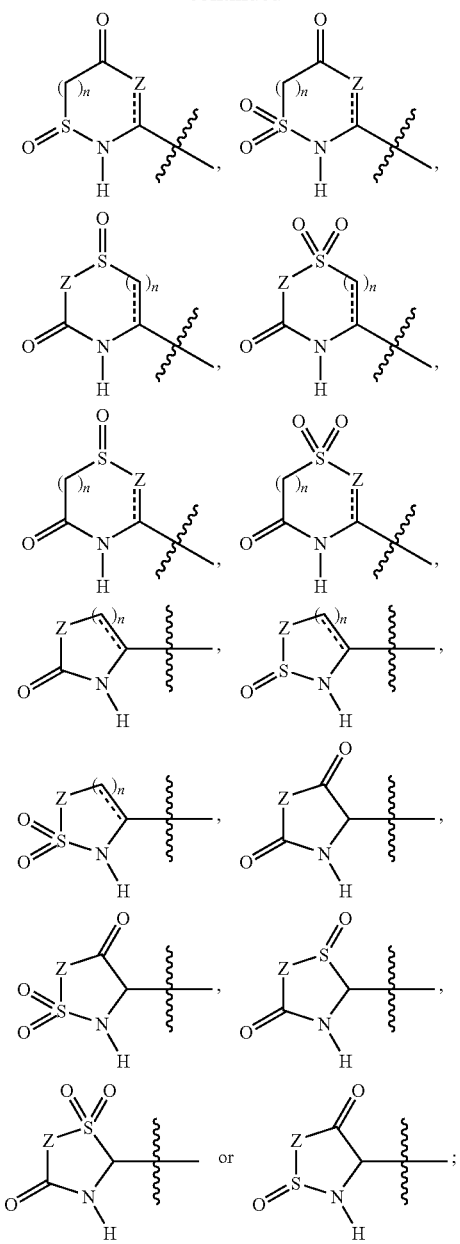

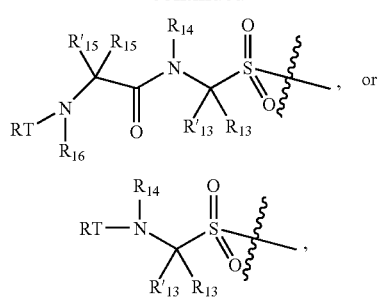

wherein each Z is independently —O—, —S—, —NR$_{50}$—, or —C(R$_{50}$)$_2$—, ---- is independently a single bond or a double bond, and each R$_{50}$ is independently hydrogen, optionally substituted aliphatic, optionally substituted aryl, optionally substituted heteroaryl, optionally substituted heterocycloaliphatic, or optionally substituted cycloaliphatic; and n is 1 or 2.

In several embodiments, R$_5$ is

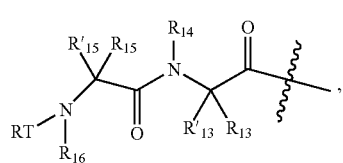

-continued

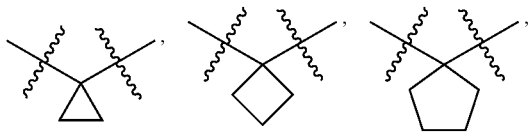

wherein T is a bond, —C(O)—, —OC(O)—, —NHC(O)—, —S(O)$_2$N(H)—, —C(O)C(O)— or —SO$_2$—; each R is independently hydrogen, amino, an optionally substituted aliphatic, an optionally substituted cycloaliphatic, an optionally substituted heterocycloaliphatic, an optionally substituted aryl, or an optionally substituted heteroaryl; each R$_{13}$ and R'$_{13}$ is independently hydrogen, an optionally substituted aliphatic, an optionally substituted cycloaliphatic, an optionally substituted heterocycloaliphatic, an optionally substituted aryl, or an optionally substituted heteroaryl; and each R$_{13}$ is independently hydrogen, an optionally substituted aliphatic, an optionally substituted heteroaryl, an optionally substituted phenyl, or R$_{13}$ and R$_{14}$, bound on adjacent atoms, taken together with the atoms to which they are attached form a 5 to 7 membered, optionally substituted monocyclic heterocycloaliphatic, or a 6 to 12 membered, optionally substituted bicyclic heterocycloaliphatic, in which each heterocycloaliphatic ring; or R$_{13}$ and R'$_{13}$, taken together with the atoms to which they are attached form an optionally substituted cycloaliphatic or an optionally substituted heterocycloaliphatic; each R$_{15}$ and R'$_{15}$ is independently hydrogen, an optionally substituted aliphatic, an optionally substituted heteroaryl, an optionally substituted phenyl, an optionally substituted cycloaliphatic, an optionally substituted heterocycloaliphatic; or R$_{15}$ and R'$_{15}$ together with the atom to which they are both attached form an optionally substituted 3 to 7 membered cycloaliphatic or heterocycloaliphatic ring; and each R$_{16}$ is independently hydrogen or a protecting group.

In some embodiments, R$_{15}$ and R'$_{15}$ together with the atom to which they are attached form a 3 to 7 membered ring. Non-limiting examples include:

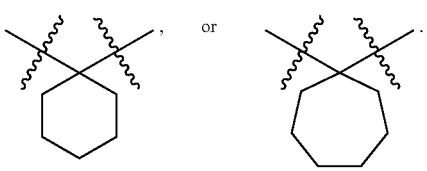

Non-limiting examples of $R_{11}$ and $R_{13}$ include:

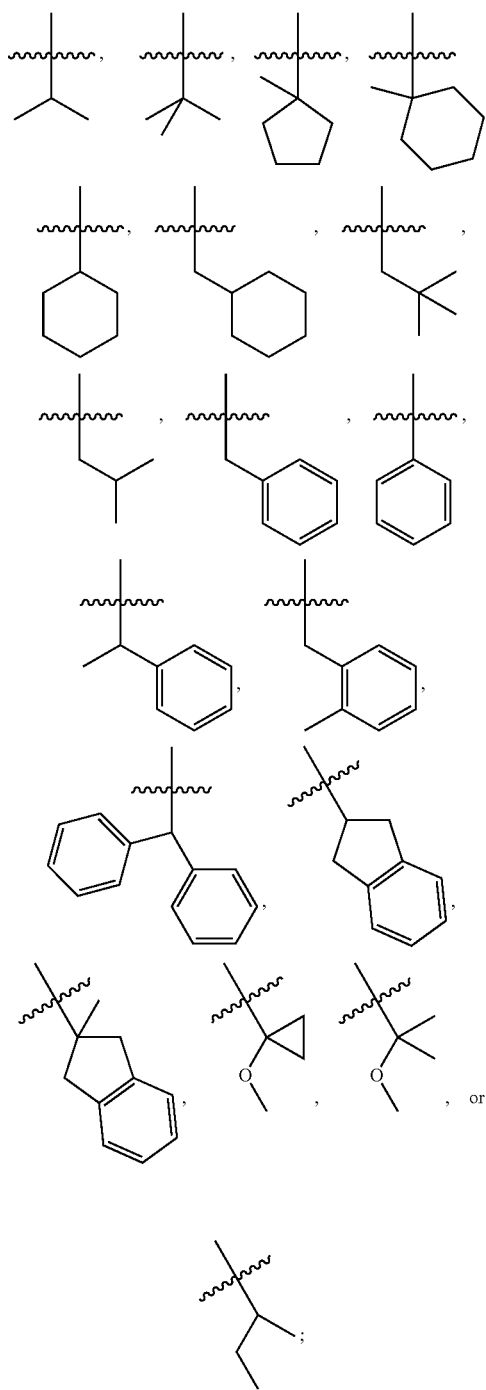

Alternatively, $R_{13}$ and $R_{15}$ together with the atoms to which they are attached may form an optionally substituted 5 to 7 membered monocyclic heterocycloaliphatic or an optionally substituted 6 to 12 membered bicyclic heterocycloaliphatic, in which each heterocycloaliphatic or aryl ring optionally contains an additional heteroatom selected from O, S and N.

Also, $R_{15}$ and $R_{16}$ together to with the atoms to which they are attached can form a ring.

In several embodiments, $R_5$ is:

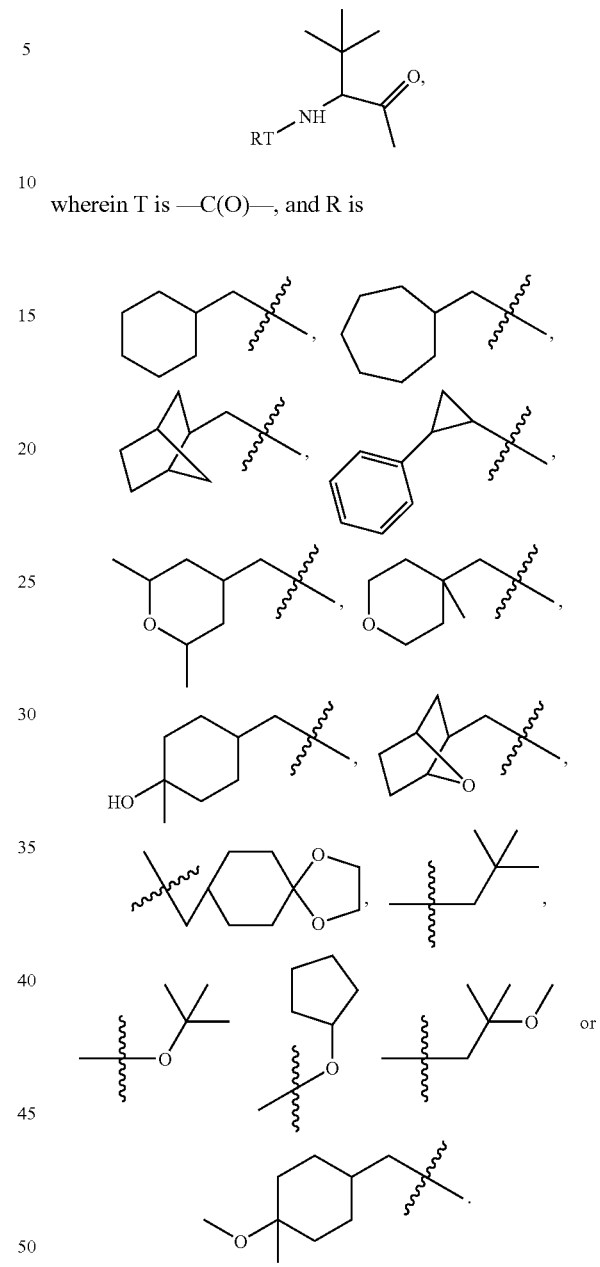

wherein T is —C(O)—, and R is

In several embodiments, $R_5$ is a group selected from:

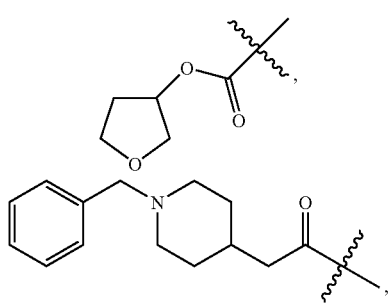

-continued
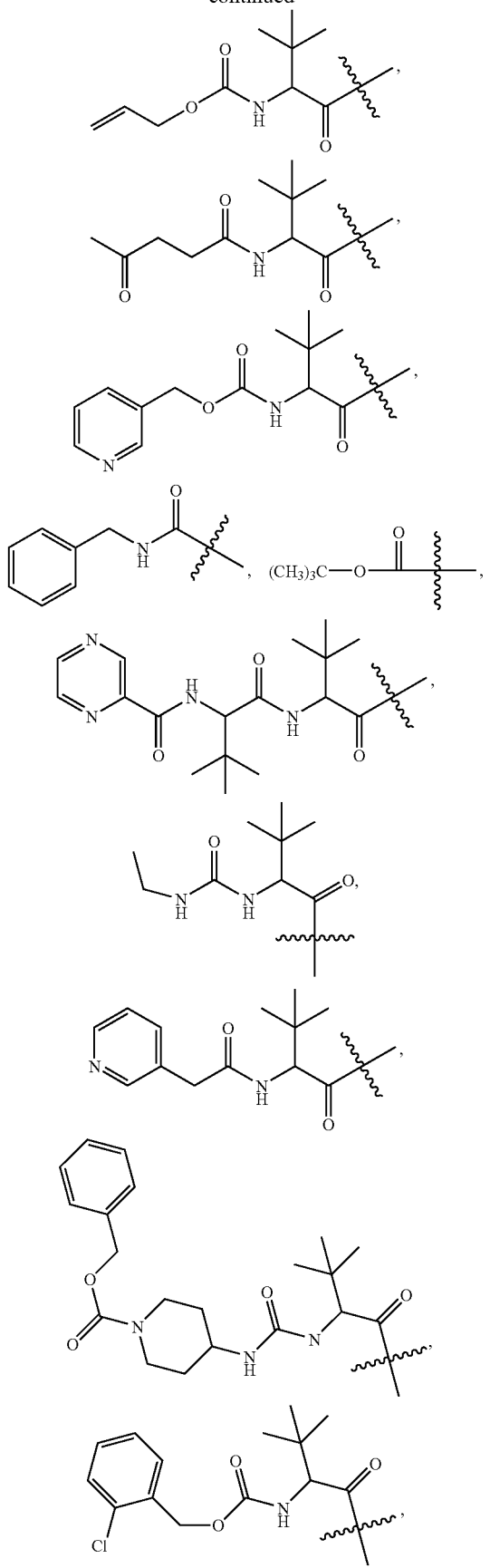
-continued
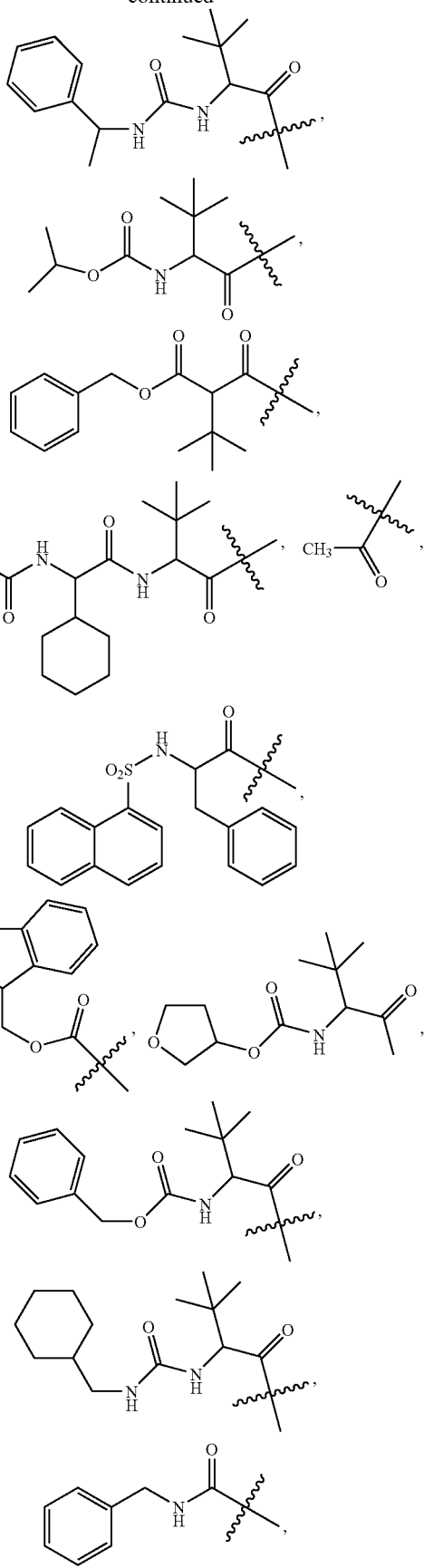

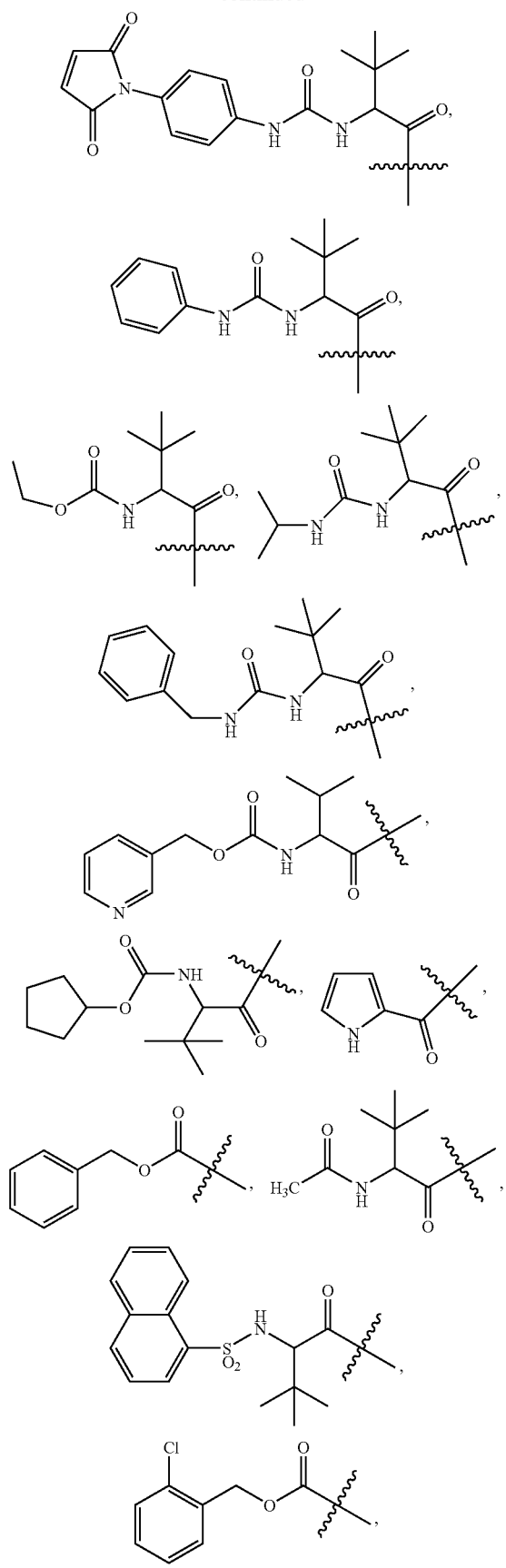
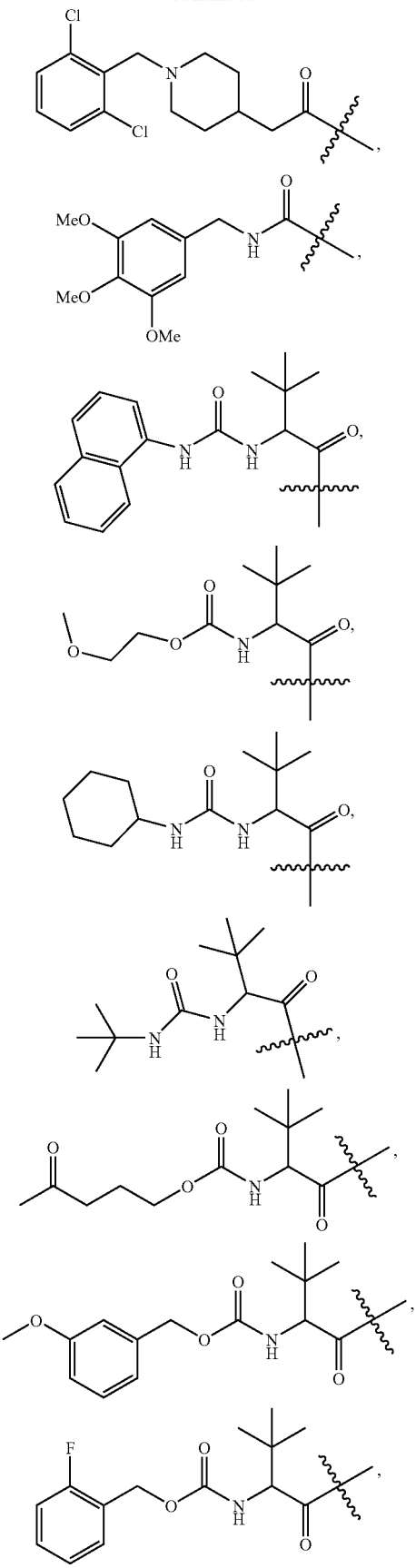

53
-continued
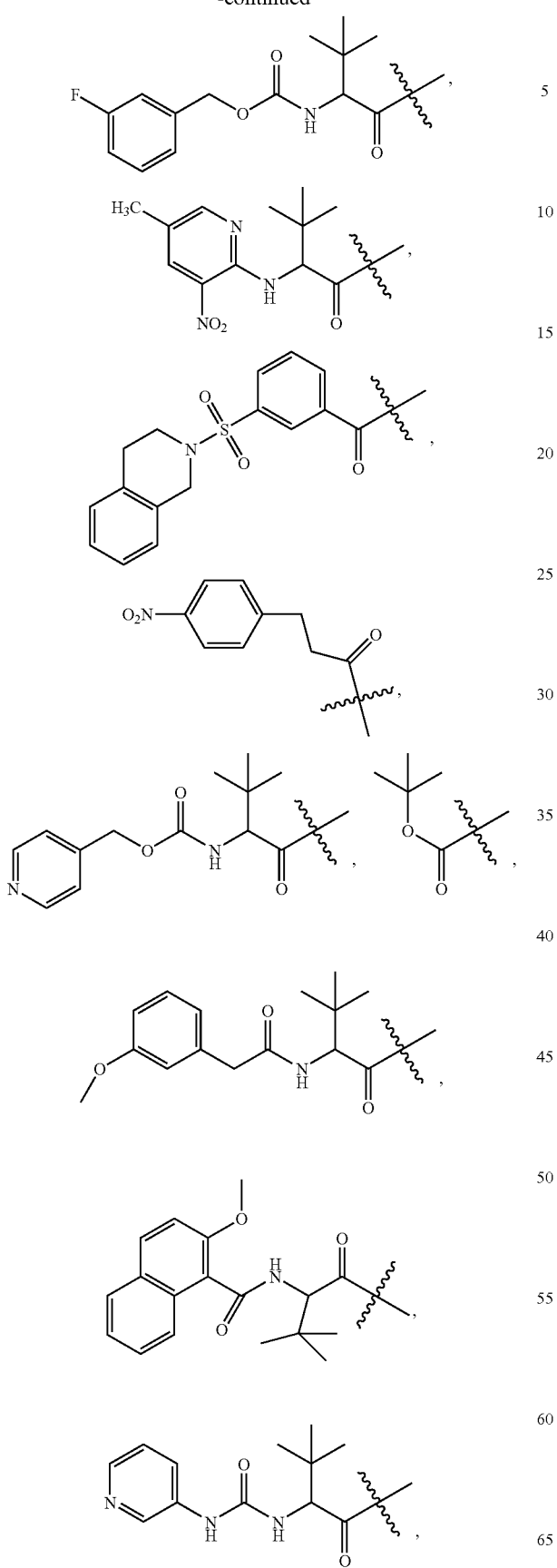
54
-continued
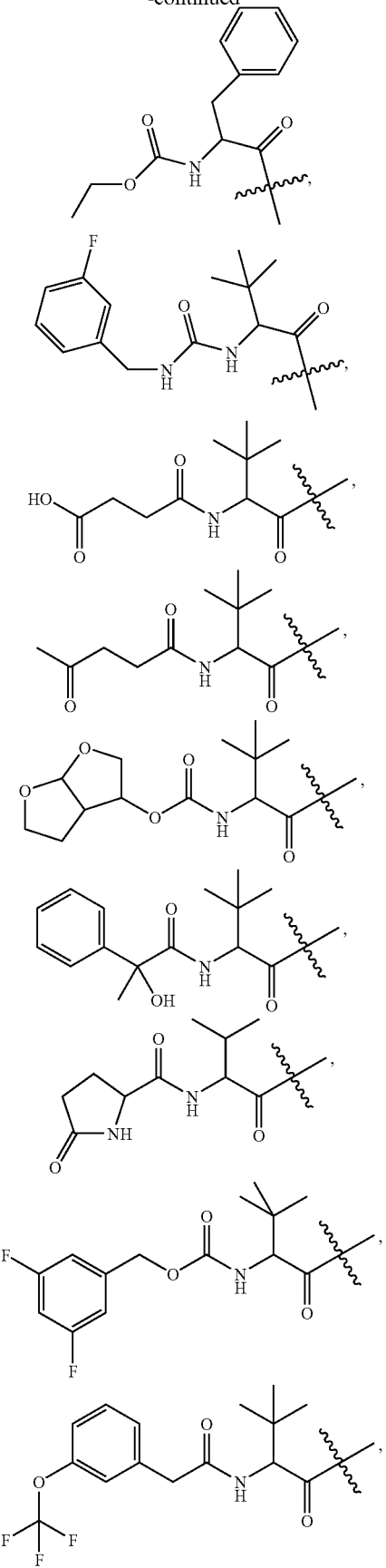

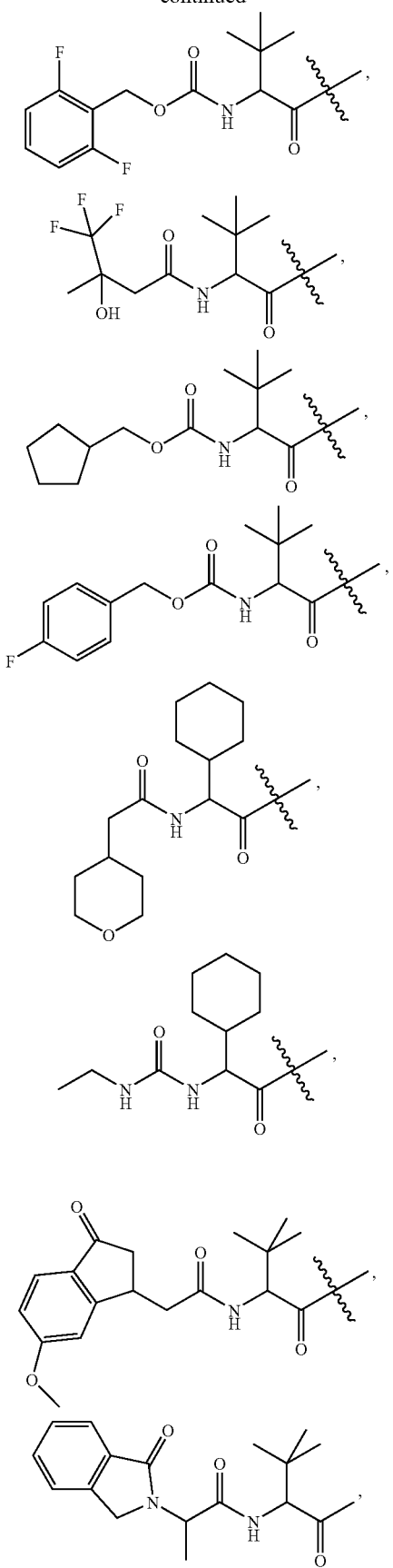
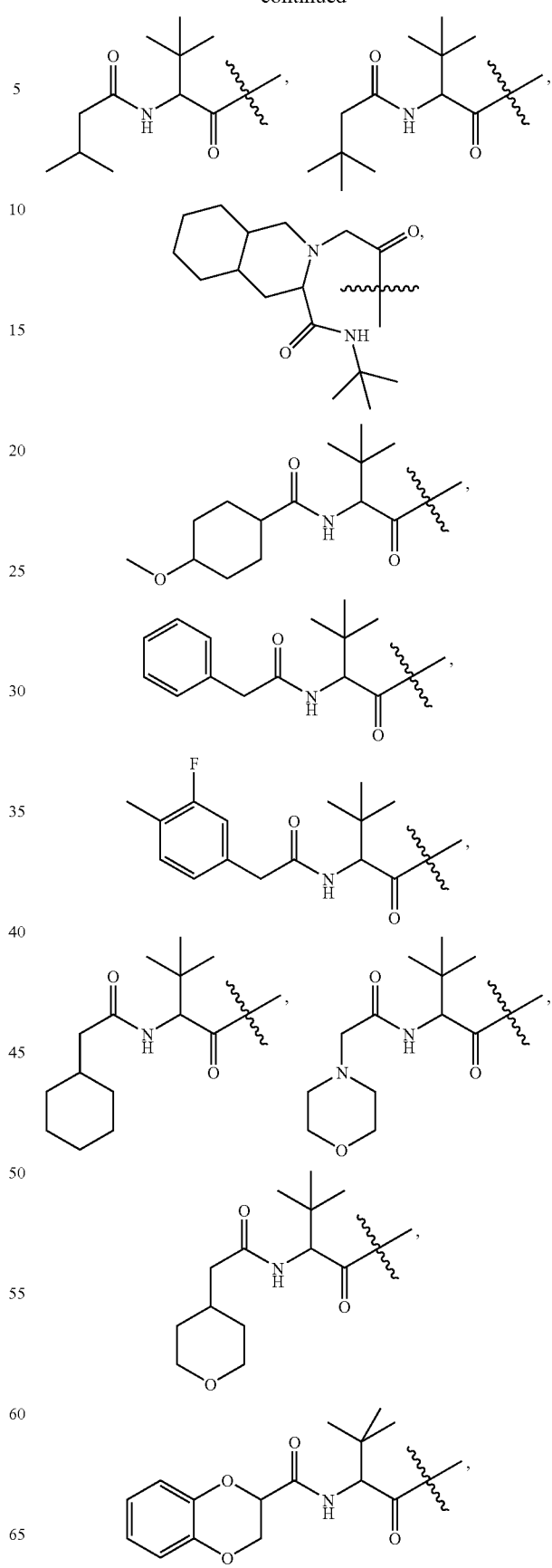

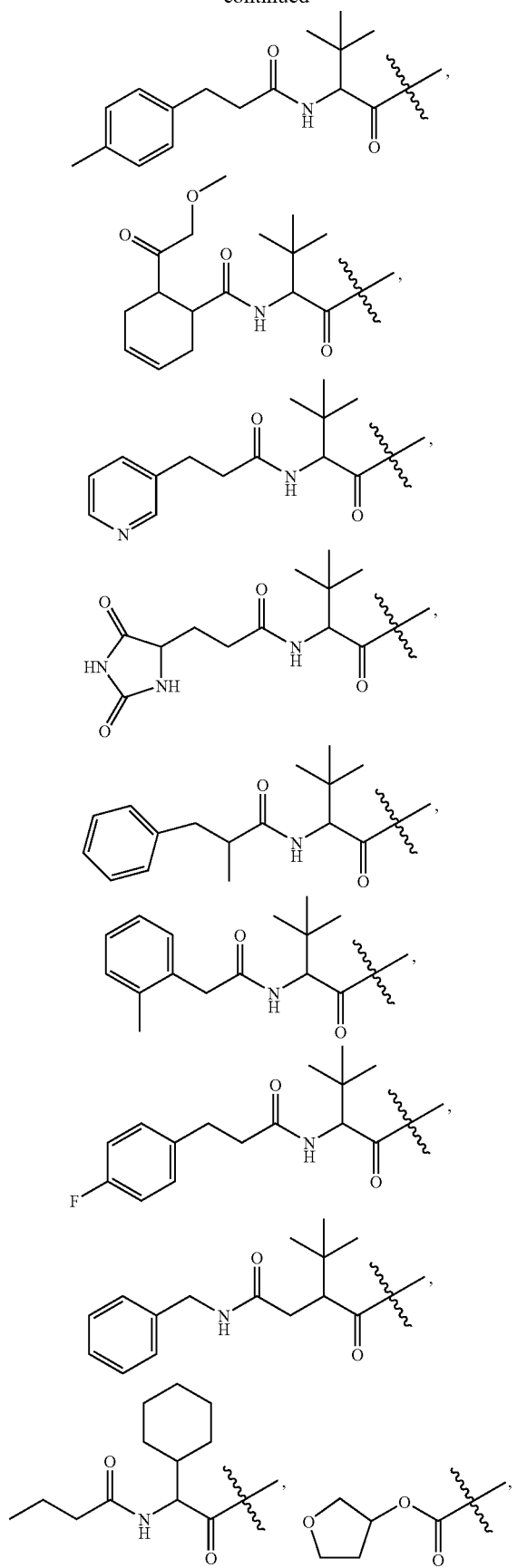
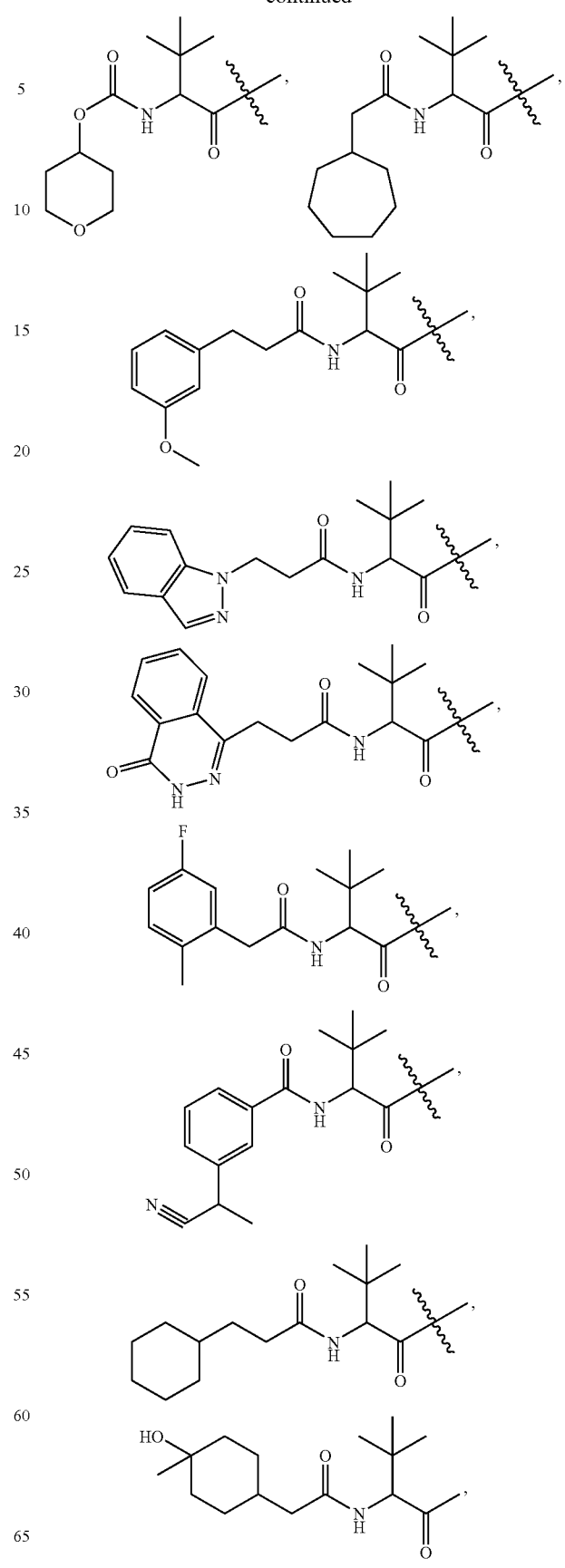

59
-continued
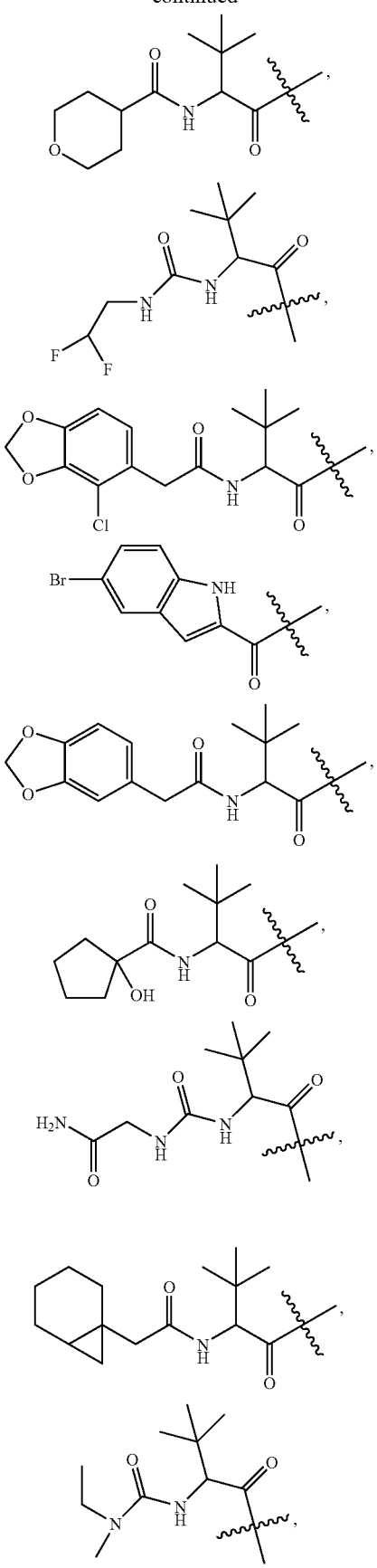
60
-continued
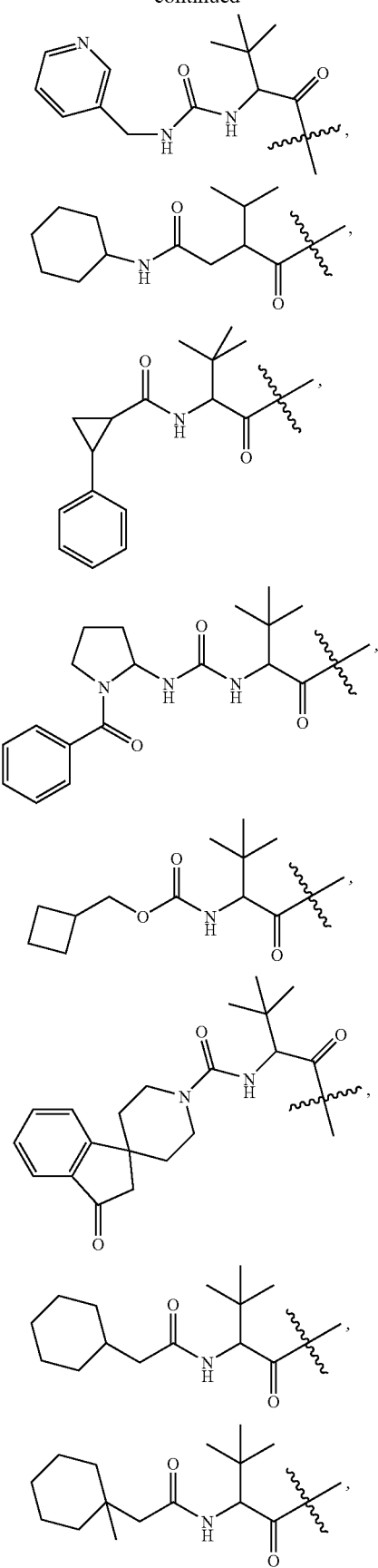

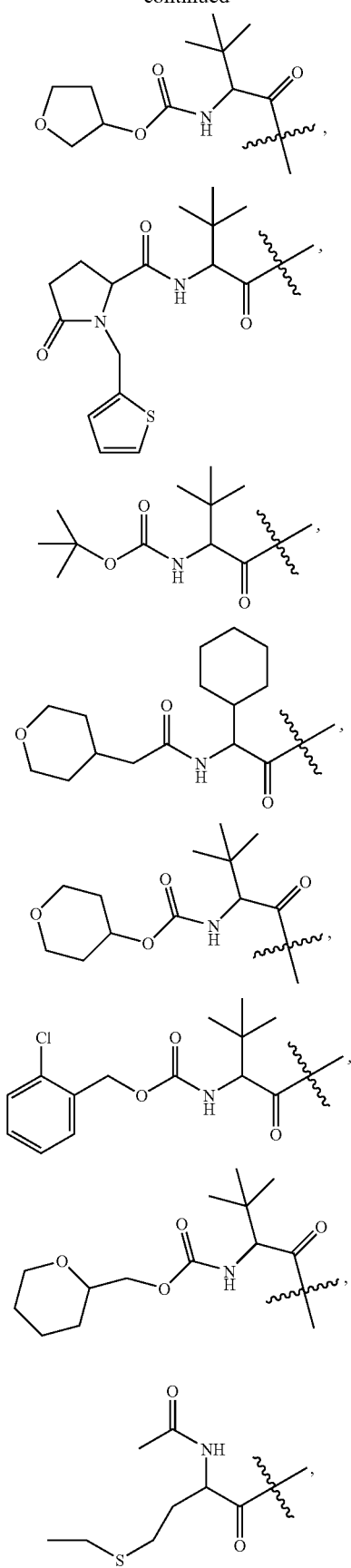
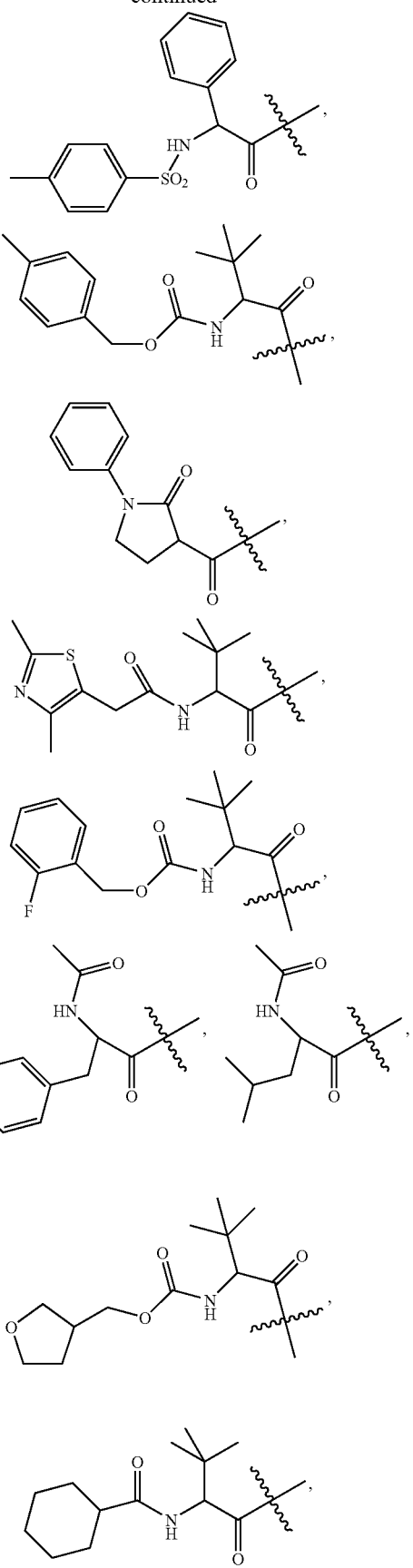

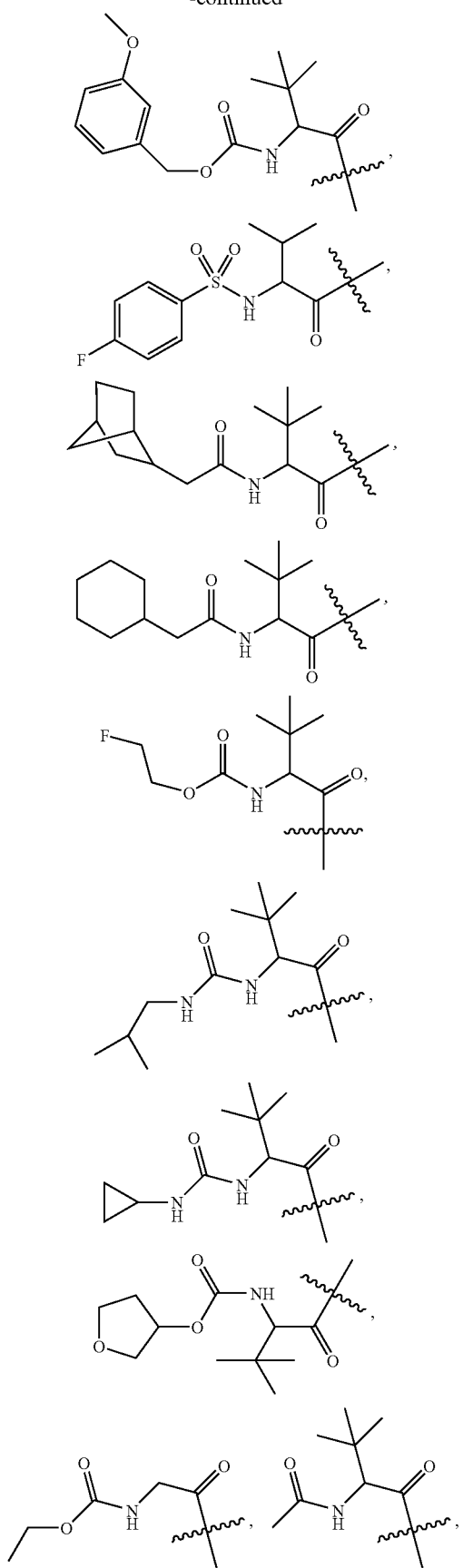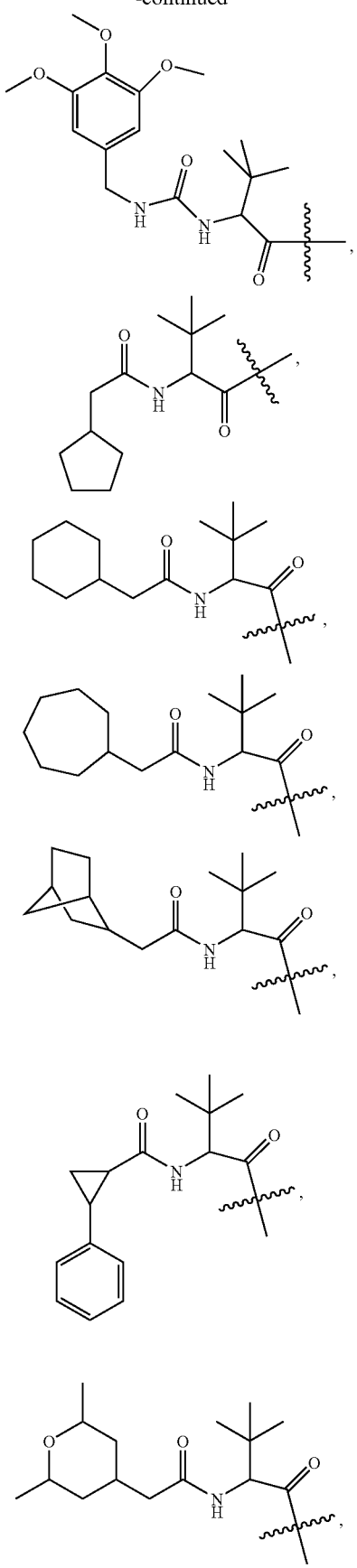

-continued

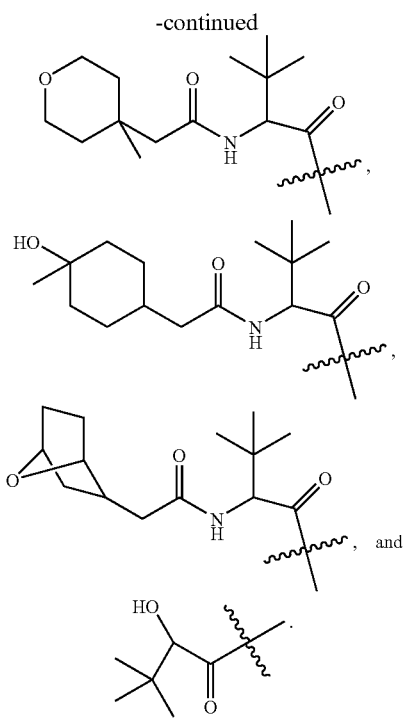

In some embodiments, $R_5$ is

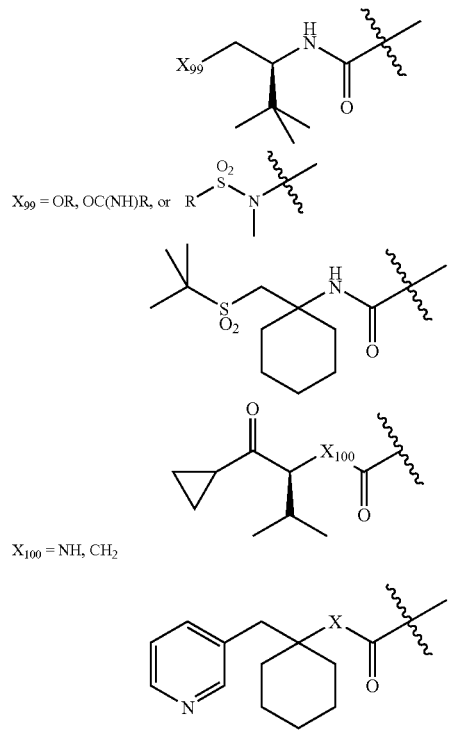

where R is defined above.

Additional examples of $R_5$ are illustrated in PCT publications WO 2004/103996 A1, WO 2004/72243 A2, WO 03/064456 A1, WO 03/64455 A2, WO 03/064416 A1, and U.S. Patent Publication US 2005/0090450, as well as those other publications referenced herein, each of which is incorporated in its entirety by reference.

C. Sub-Generic Compounds:

Another aspect of the present invention provides compounds of formula Ia useful for inhibiting serine protease activity and methods inhibiting serine protease activity. Compounds of formula Ia include:

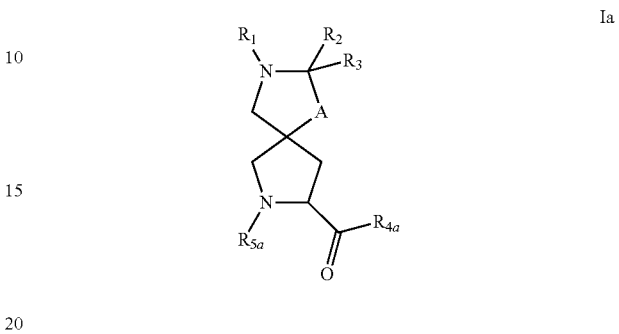

Ia or a pharmaceutically acceptable salt thereof wherein $R_1$, $R_2$, $R_3$, and A are defined above in formula I.

Each $R_{4a}$ is —$Z_1$-$V_1$-$Z_2$-$V_2$-$Z_3$-$V_3$ each of $V_1$, $V_2$, and $V_3$ is independently a bond, an optionally substituted aliphatic, an optionally substituted cycloaliphatic, an optionally substituted heterocycloaliphatic, an optionally substituted aryl, an optionally substituted heteroaryl, or a hydrogen when $V_1$, $V_2$, $V_3$ is the terminal group of $R_2$; each of $Z_1$, $Z_2$, and $Z_3$ is independently a bond, —C(O)—, —C(O)C(O)—, —C(S)—, —C(O)N($Q_5$)-, —N($Q_5$)C(O)—, —C(O)C(O)N($Q_5$)-, —O—, SO—, —$SO_2$—, —N($Q_5$)$SO_2$—, —N($Q_5$)C(O)N($Q_5$)-, —N($Q_5$)C(S)N($Q_5$)-, —N($Q_5$)-, —N($Q_5$)$SO_2$—, —$SO_2$N($Q_5$)-, —C(O)N($Q_5$)$SO_2$—, —$SO_2$N($Q_5$)C(O)—, or hydrogen when $Z_1$, $Z_2$, or $Z_3$ is the terminal group of $R_2$; and each $Q_5$ is independently hydrogen, or an optionally substituted aliphatic.

Each $R_{5a}$ is -$Q_4$-$W_4$-$Q_3$-$W_3$-$Q_2$-$W_2$-$Q_1$; wherein each of $W_2$, $W_3$, and $W_4$ is independently a bond, —C(O)—, —C(S)—, —C(O)N($Q_5$)-, —C(O)O—, —O—, —N($Q_5$)C(O)N($Q_5$)-, —$SO_2$—, —N($Q_5$)$SO_2$—, —S—, —N($Q_5$)-, —SO—, —N($Q_5$)C(O)—, —OC(O)—, —N($Q_5$)C(O)O—, or —$SO_2$N($Q_5$)-; each of $Q_1$, $Q_2$, $Q_3$ and $Q_4$ is independently a bond, an optionally substituted $C_{1-4}$ aliphatic, an optionally substituted cycloaliphatic, an optionally substituted heterocycloaliphatic, an optionally substituted aryl, an optionally substituted heteroaryl, or a hydrogen when $Q_1$, $Q_2$, $Q_3$, or $Q_4$ is the terminal group of $R_{5a}$; and each $Q_5$ is independently hydrogen or an optionally substituted aliphatic.

In several examples, $R_{4a}$ is an optionally substituted (aliphatic)amino, an optionally substituted alkoxy, or hydroxy.

In several examples, $R_{4a}$ is an (aliphatic)amino wherein the nitrogen atom is optionally substituted with —$Z_2$-$V_2$-$Z_3$-$V_3$ or —$Z_3$-$V_3$ wherein each of $Z_2$ and $Z_3$ is independently a bond, —C(O)—, —N($Q_5$)-, or —C(O)C(O)N($Q_5$)-; and each of $V_2$ and $V_3$ is independently a bond, an optionally substituted aliphatic, or an optionally substituted cycloaliphatic.

Another aspect of the present invention provides compounds of formula Ib useful for inhibiting serine protease activity and methods inhibiting serine protease activity. Compounds of formula Ib include:

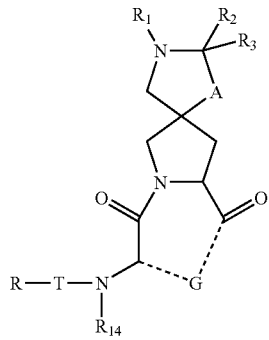

Ib or a pharmaceutically acceptable salt thereof, wherein $R_1$, $R_2$, $R_3$, $R_{14}$, R, T, and A are defined above in formula I.

Each G is a 2 to 15 atom optionally substituted aliphatic chain optionally containing 1 to 3 heteroatoms selected from O, S and N.

Examples of compounds of formula Ib include:

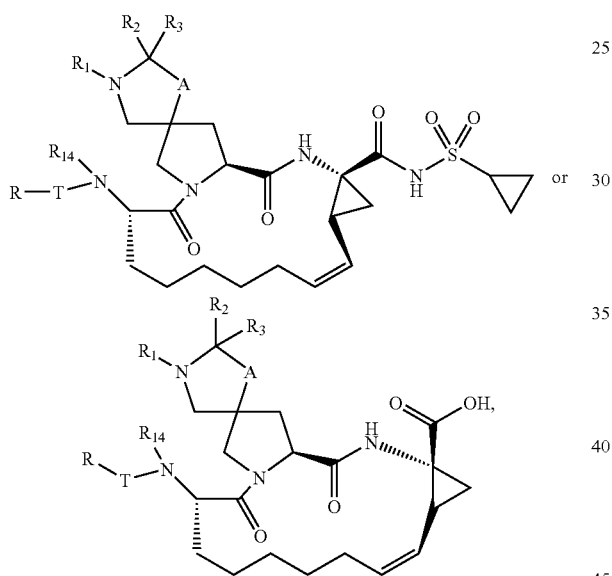

wherein $R_1$, $R_2$, $R_3$, $R_8$, R, T, and A are defined above in formula I.

Still other examples of formula Ib are

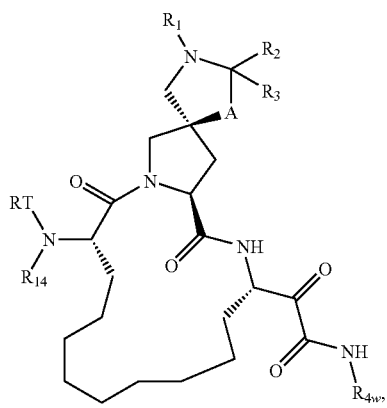

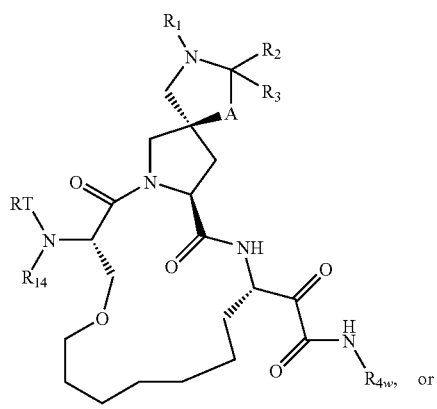

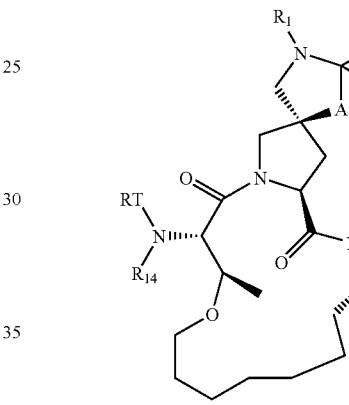

wherein $R_1$, $R_2$, $R_3$, and A are defined in formula I above, and each $R_{4W}$ is independently

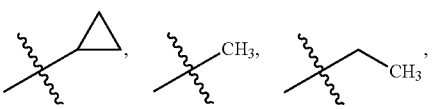

or hydrogen; each T is independently a bond, —C(O)—, —OC(O)—, —NHC(O)—, —S(O)$_2$N(H)—, —C(O)C(O)—, or —SO$_2$—; each R is independently hydrogen, an optionally substituted aliphatic, an optionally substituted cycloaliphatic, an optionally substituted heterocycloaliphatic, an optionally substituted aryl, or an optionally substituted heteroaryl; and each $R_{14}$ is independently hydrogen, an optionally substituted aliphatic, an optionally substituted heteroaryl, an optionally substituted phenyl.

Further specific examples of compounds of formula Ib are
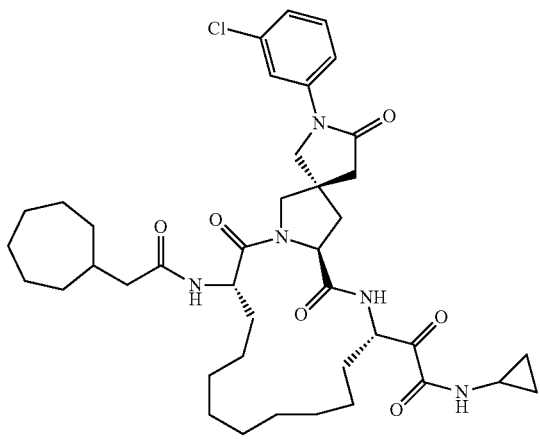
or
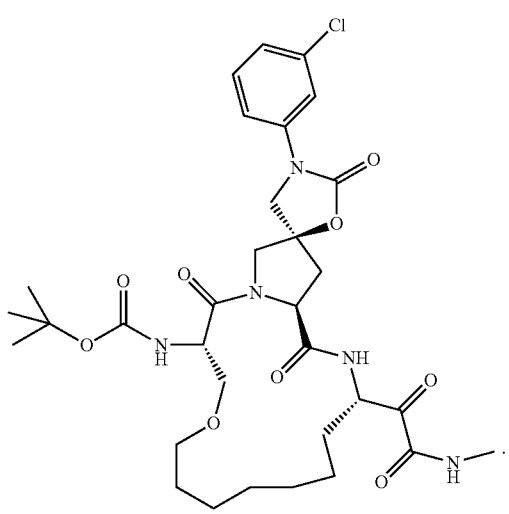
Other examples of compounds of formula Ib include:
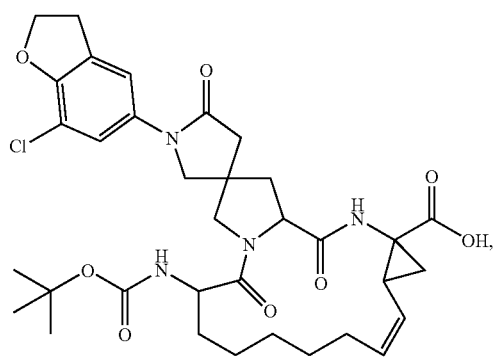
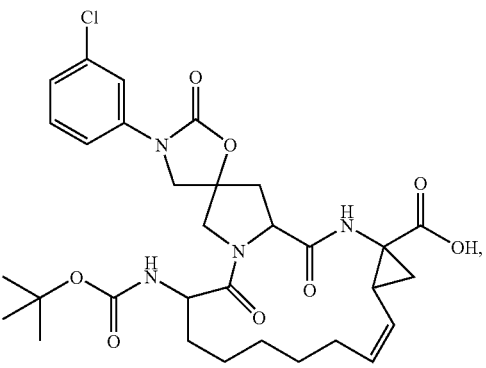

Another aspect of the present invention provides compounds of formula II useful for inhibiting serine protease activity and methods inhibiting serine protease activity. Compounds of formula II include:

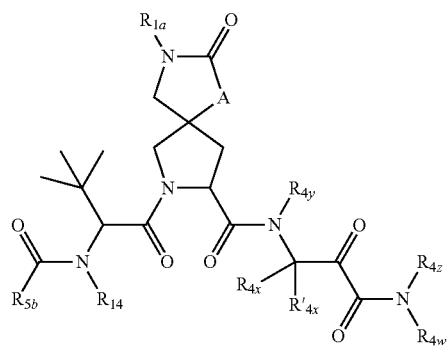

or a pharmaceutically acceptable salt thereof, wherein $R_{4X}$, $R'_{4X}$, $R_{4Z}$, $R_{4W}$, and A are defined above.

Each $R_{1a}$ is an optionally substituted aryl or an optionally substituted heteroaryl.

Each $R_{4Y}$ is independently hydrogen, an optionally substituted aliphatic, an optionally substituted cycloaliphatic, an optionally substituted heterocycloaliphatic, an optionally substituted aryl, or an optionally substituted heteroaryl.

Each $R_{14}$ is independently hydrogen, optionally substituted aliphatic, optionally substituted aryl, optionally substituted heteroaryl, optionally substituted heterocycloaliphatic, or optionally substituted cycloaliphatic.

Each $R_{4X}$ and $R'_{4X}$ is independently hydrogen, an optionally substituted aliphatic, an optionally substituted heteroaryl, an optionally substituted phenyl, an optionally substituted cycloaliphatic, an optionally substituted heterocycloaliphatic; or $R_{4X}$ and $R'_{4X}$ together with the atom to which they are both attached form an optionally substituted 3 to 7 membered cycloaliphatic or heterocycloaliphatic ring, or $R_{4X}$ and $R_{4Y}$ together with the atoms to which they are attached form an optionally substituted 5 to 7 membered heterocycloaliphatic ring.

Each $R_{5b}$ is $-Z^F R_{21}$, wherein $Z^F$ is $-CH_2-$, $-NH-$, $-CH(R_{22})-$, or $-O-$, and $R_{21}$ is optionally substituted 6-7 membered cycloaliphatic or optionally substituted tert-butyl; and $R_{22}$ is optionally substituted aliphatic, optionally substituted cycloaliphatic, optionally substituted heterocycloaliphatic, optionally substituted aryl, or optionally substituted heteroaryl.

Each $R_{4Z}$ is independently hydrogen, optionally substituted cycloaliphatic, optionally substituted heterocycloaliphatic, or optionally substituted aliphatic.

Additionally, each $R_{4W}$ is independently hydrogen, optionally substituted cycloaliphatic, optionally substituted heterocycloaliphatic, or optionally substituted aliphatic, or $R_{4Z}$ and $R_{4W}$ together with the nitrogen atom to which they are attached form an optionally substituted heterocycloaliphatic.

Another aspect of the present invention provides compounds of formula III useful for inhibiting serine protease activity and methods inhibiting serine protease activity. Compounds of formula III include:

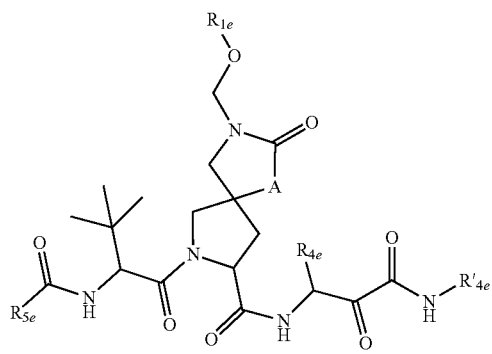

or a pharmaceutically acceptable salt thereof, wherein A is defined above in formula I and $R_{5e}$ is

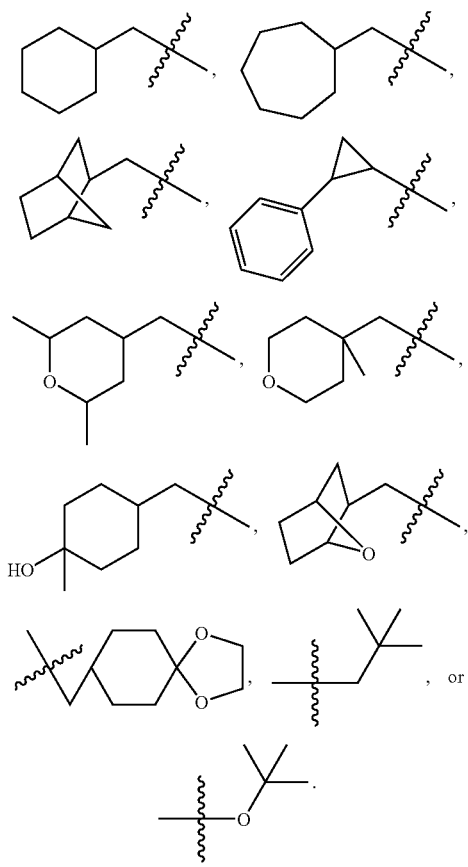

$R_{4e}$ is:

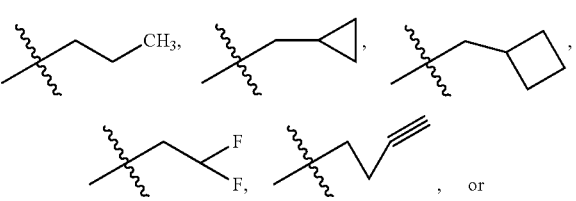

R'$_{4e}$ is:

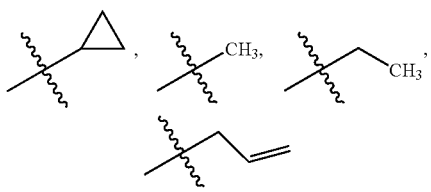

or hydrogen; and R$_{1e}$ is optionally substituted aryl or optionally substituted heteroaryl.

Another aspect of the present invention provides compounds of formula IV useful for inhibiting serine protease activity and methods inhibiting serine protease activity. Compounds of formula IV include:

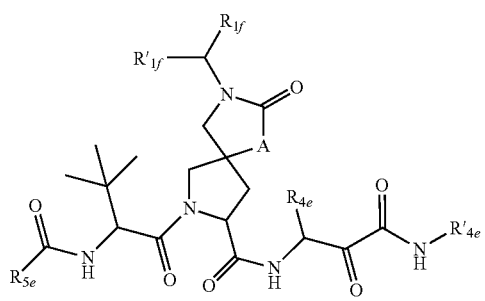

or a pharmaceutically acceptable salt thereof, wherein R$_{5e}$ is:

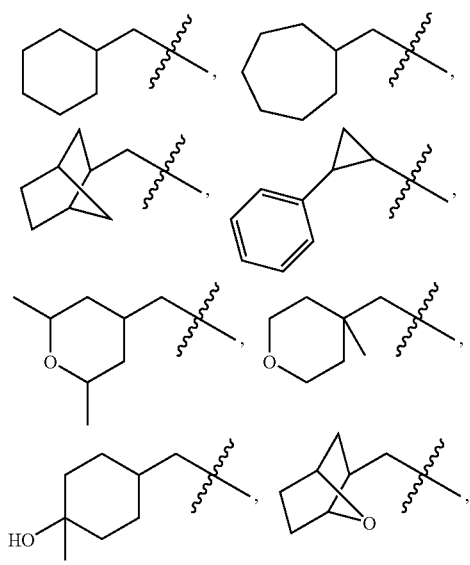

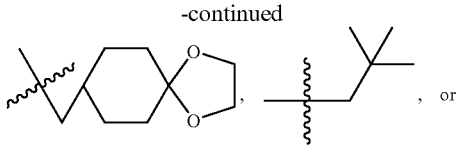

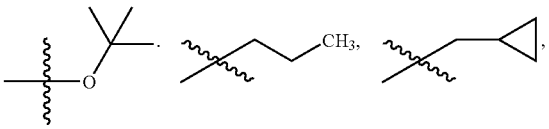

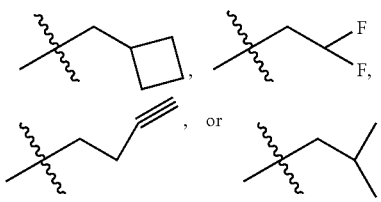

R$_{4e}$ is
R'$_{4e}$ is

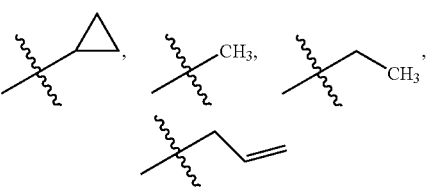

or hydrogen.

Additionally, each of R$_{1f}$ and R'$_{1f}$ is independently hydrogen, sulfonamide, sulfonyl, sulfinyl, optionally substituted acyl, optionally substituted aliphatic, optionally substituted cycloaliphatic, optionally substituted heterocycloaliphatic, optionally substituted aryl, or optionally substituted heteroaryl, or R$_{1f}$ and R'$_{1f}$ together with the nitrogen atom to which they are attached form an optionally substituted, saturated, partially unsaturated, or full unsaturated, 5-8 membered heterocycloaliphatic or heteroaryl.

Another aspect of the present invention provides compounds of formula V useful for inhibiting serine protease activity and methods inhibiting serine protease activity. Compounds of formula V include:

V

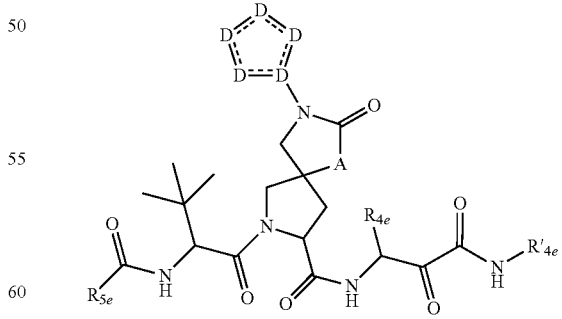

or a pharmaceutically acceptable salt thereof, wherein R$_{5e}$, R$_{4e}$, and R'$_{4e}$ are defined above in formula III.

Each D is independently —CR$_{14}$—, N, S, or O, provided that no more than two D are independently, S, or O; and R$_{14}$ is defined above in formula I.

Another aspect of the present invention provides compounds of formula VI useful for inhibiting serine protease activity and methods inhibiting serine protease activity. Compounds of formula VI include:

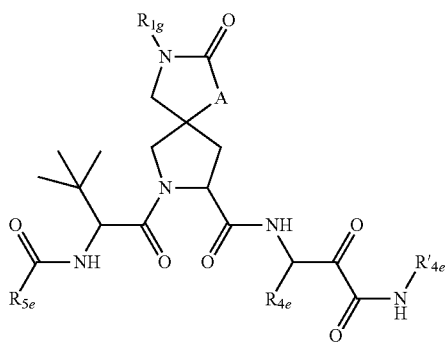

VI or a pharmaceutically acceptable salt thereof, wherein $R_{5e}$, $R_{4e}$, and $R'_{4e}$ are defined above in formula III.

Each $R_{1g}$ is a substituted aryl or a substituted heteroaryl. In some embodiments, $R_{1g}$ is

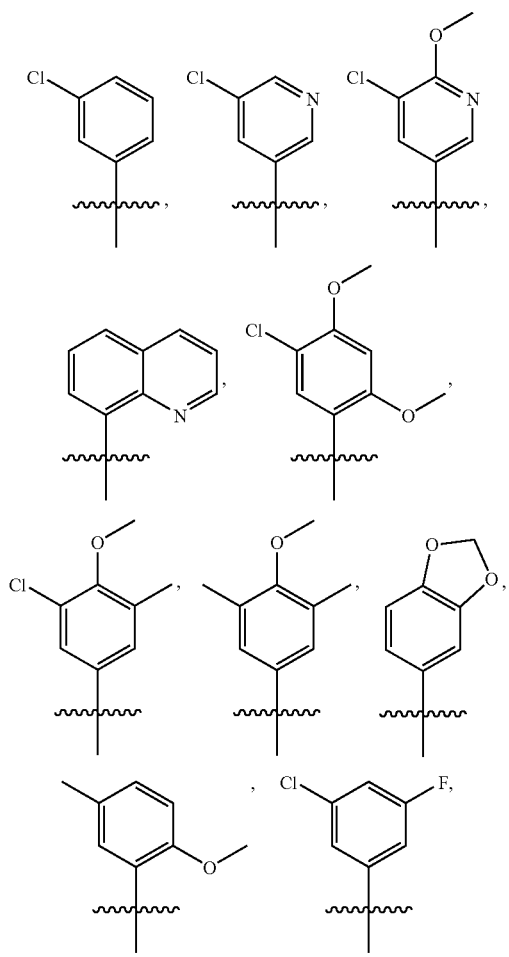

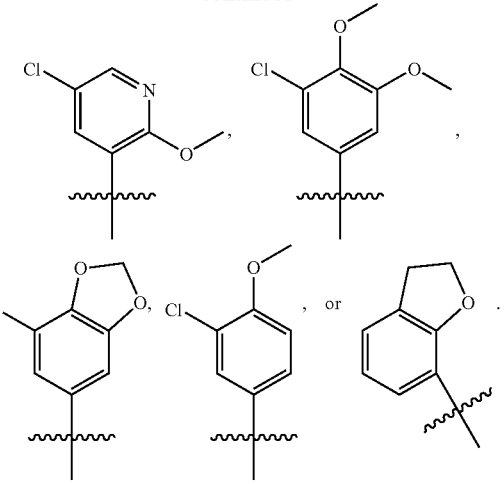

D. Combinations of Embodiments

Other embodiments include any combination of the aforementioned substituents $R_1$, $R_2$, $R_3$, $R_4$, $R_5$, and A.

E. Exemplary Compounds

The invention is intended to include compounds wherein $R_1$ and $R_2$ contain structural elements of a serine protease inhibitor. Compounds having the structural elements of a serine protease inhibitor equivalent to substituents $R_1$ and $R_2$ include, but are not limited to, the compounds of the following publications: WO 97/43310, US 20020016294, WO 01/81325, WO 01/58929, WO 01/32691, WO 02/08198, WO 01/77113, WO 02/08187, WO 02/08256, WO 02/08244, WO 03/006490, WO 01/74768, WO 99/50230, WO 98/17679, WO 02/48157, WO 02/08251, WO 02/07761, WO 02/48172, WO 02/08256, US 20020177725, WO 02/060926, US 20030008828, WO 02/48116, WO 01/64678, WO 01/07407, WO 98/46630, WO 00/59929, WO 99/07733, WO 00/09588, US 20020016442, WO 00/09543, WO 99/07734, U.S. Pat. No. 6,018,020, U.S. Pat. No. 6,265,380, U.S. Pat. No. 6,608, 027, US 20020032175, US 20050080017, WO 98/22496, WO 05/028502, U.S. Pat. No. 5,866,684, WO 02/079234, WO 00/31129, WO 99/38888, WO 99/64442, WO 2004072243, WO 02/18369, US2006046956, US2005197301, WO2005058821, WO2005051980, WO2005030796, WO2005021584, WO2005113581, WO2005087731, WO2005087725, WO2005087721, WO2005085275, WO2005085242, US2003216325, WO2003062265, WO2003062228, WO2002008256, WO 2002008198, WO2002008187, WO 2002048172, WO 2001081325, WO 2001077113, U.S. Pat. No. 6,251,583, U.S. Pat. No. 5,990,276, US20040224900, US20040229818, WO2004037855, WO2004039833, WO200489974, WO2004103996, WO2004030670, WO2005028501, WO2006007700, WO2005070955, WO2006007708, WO2006000085, WO2005073195, WO2005073216, WO2004026896, WO2004072243, WO2004113365, WO2005010029, US20050153877, WO2004093798, WO2004094452, WO2005046712, WO2005051410, WO2005054430, WO2004032827, WO2005095403, WO2005077969, WO2005037860, WO2004092161, WO2005028502, WO2003087092, and WO2005037214, each of which is incorporated herein by reference.

Specific exemplary compounds of the invention are shown below in Table 1.
TABLE 1
Exemplary compounds of the present invention.
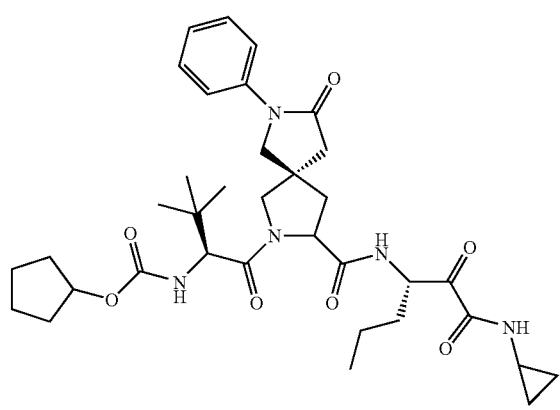 [SMILES: CCC[C@H](NC(=O)C1C[C@@]2(CC(=O)N(c3ccccc3)C2)CN1C(=O)[C@@H](NC(=O)OC1CCCC1)C(C)(C)C)C(=O)C(=O)NC1CC1]
1
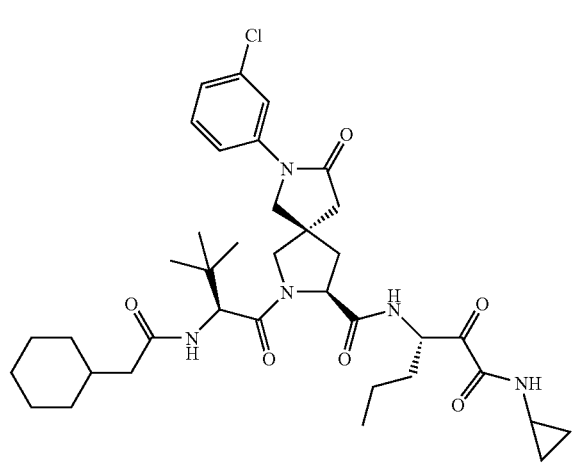
2
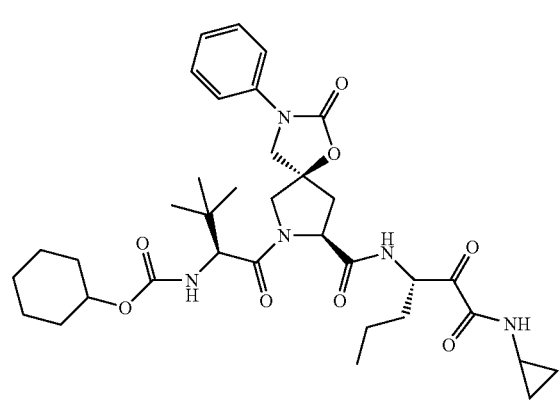 [SMILES: CCC[C@H](NC(=O)[C@@H]1C[C@@]2(CN(c3ccccc3)C(=O)O2)CN1C(=O)[C@@H](NC(=O)OC1CCCCC1)C(C)(C)C)C(=O)C(=O)NC1CC1]
3
TABLE 1-continued
Exemplary compounds of the present invention.
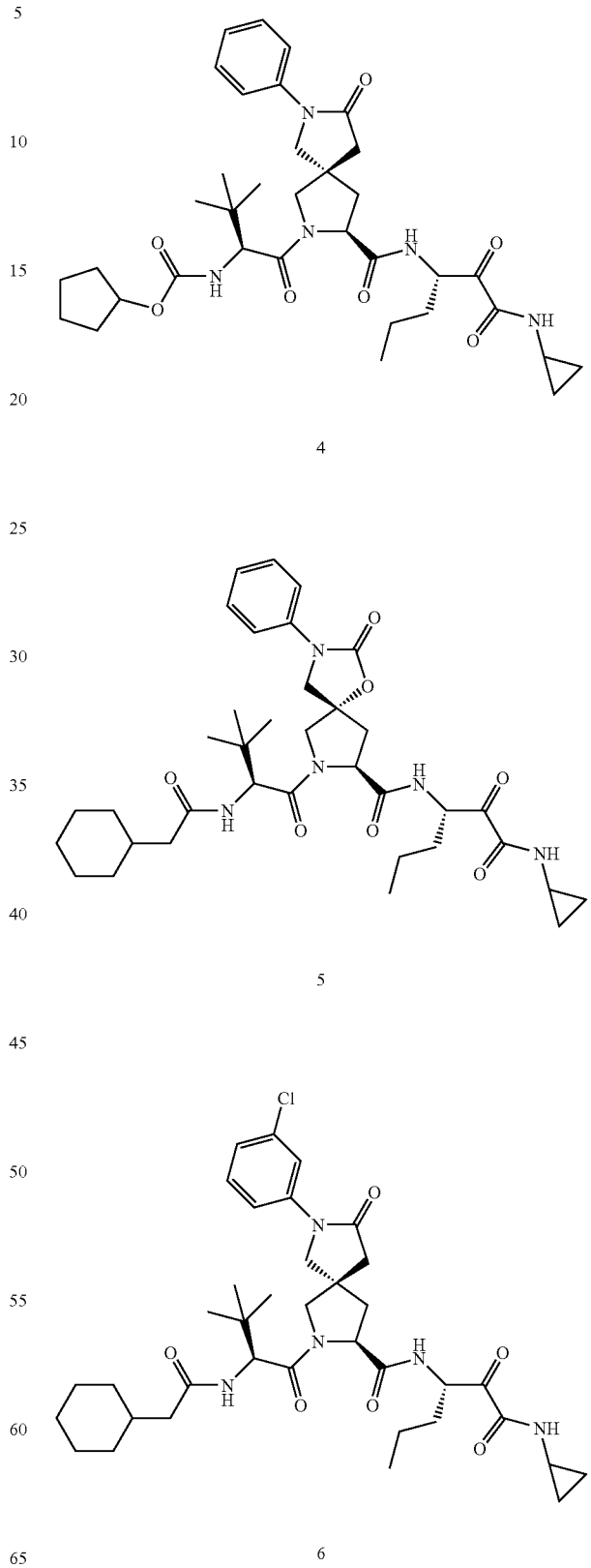
4
5
6

TABLE 1-continued

Exemplary compounds of the present invention.

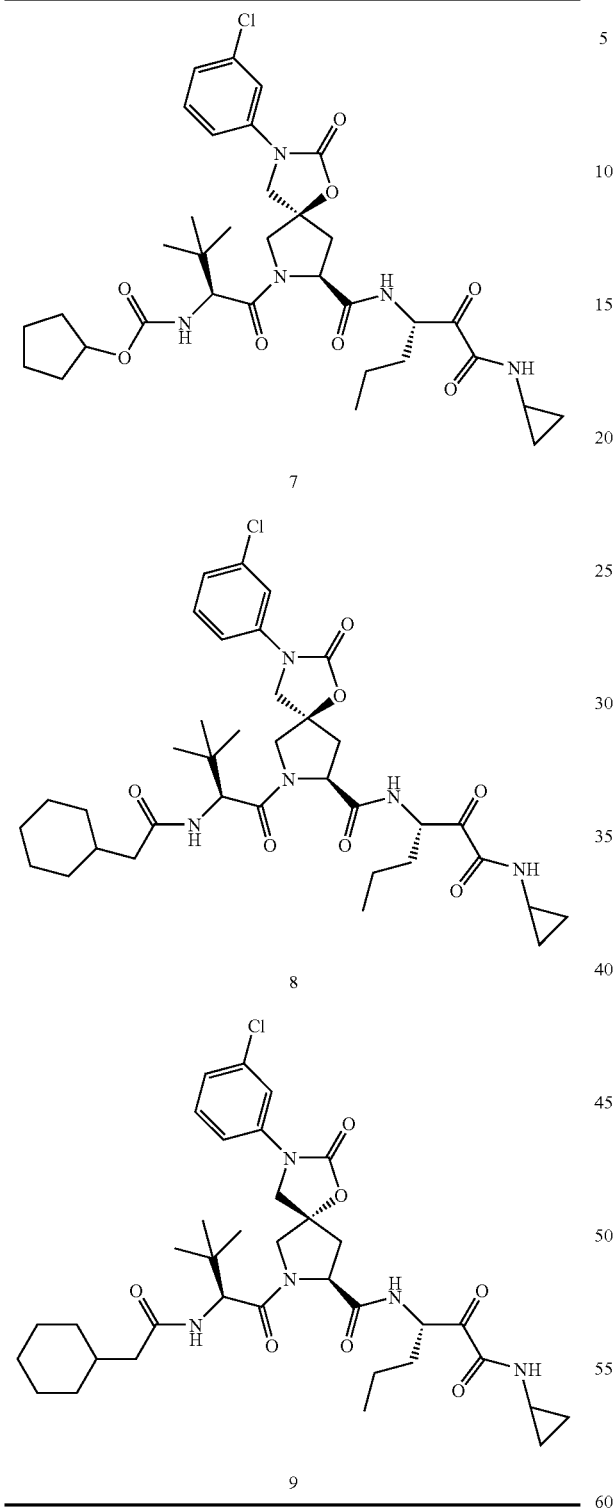

7

8

9

III. Synthetic Schemes

Compounds of Formula I may be readily synthesized from commercially available starting materials using the exemplary synthetic routes provided below. Exemplary synthetic routes to produce compounds of Formula I are provided below in the Preparations, Methods, Examples, and Schemes.

A method for preparing compounds of formula I, wherein A is O, is illustrated in Scheme 1.

Scheme 1:

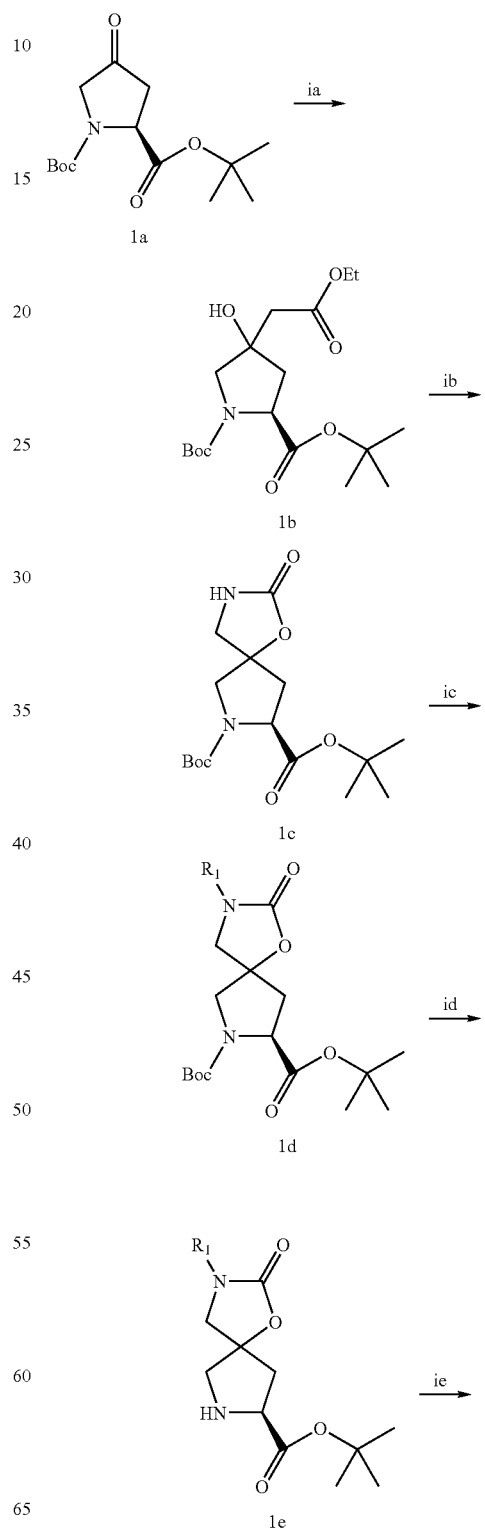

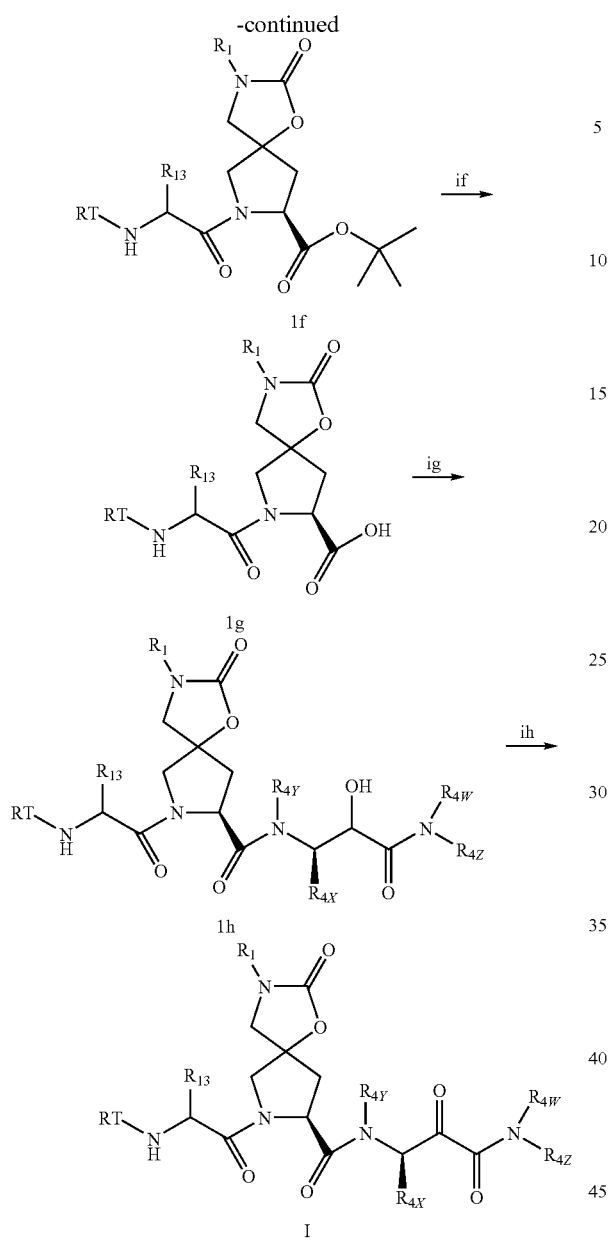

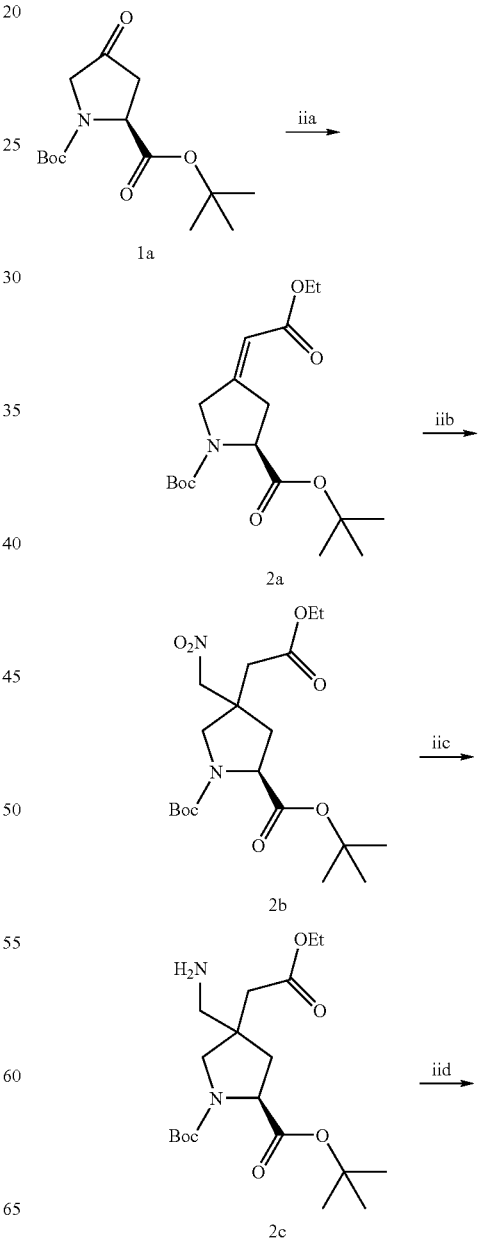

Selective removal of the N protecting group from 1d to provide 1e may be accomplished with HCl in ethyl acetate. The intermediates 1e are further converted to the intermediate 1f by reaction of 1e with $R_{12}$—C(O)—OH in the presence of a coupling reagent such as, for example, EDC, HOBT and DIEA. Removal of the ester protecting group from 1f using, for example, TFA in methylene chloride, provides the acid intermediate 1g. Reaction of 1 g with $R_{11}$—N($R^D$)NH in the presence of a coupling reagent such as, for example, EDC, HOBT and DIEA provides compounds of the invention wherein A is O. In certain embodiments, $R_{11}$ may contain the hydroxy moiety —CH(OH)C(O)—, oxidation of which with, for example, Des-Martin periodinane or sodium hypochlorite in the presence of TEMPO provides compounds of formula I wherein $R_{12}$ contains the moiety —C(O)C(O)—.

Scheme 2:

The diprotected prolineone 1a reacts with ethyl bromoacetate in the presence of zinc and trimethylsilyl chloride to produce the ester intermediate 1b as a 4:1 diastereomeric mixture. The ester intermediate 1b reacts with hydrazine to form an intermediate hydrazide (not shown) which in turn is oxidized with, for example, sodium nitrite followed by cyclization to produce the substituted spiropyrrolidine intermediate 1c. The substituted spiropyrrolidine intermediate 1c can be converted to the substituted intermediate 1d by two methods. Reaction of 1c with an aryl halide such as, for example, a substituted bromobenzene in the presence of a palladium catalyst such as, for example, $Pd_2(dba)_3$, Xantphos and potassium carbonate provides intermediates 1d wherein $R_1$ is aryl. Alternatively, intermediate 1c may be alkylated with an appropriate alkyl halide such as, for example, benzyl bromide or ethyl iodide in the presence of a base such as, for example, sodium hydride to provide intermediates 1d wherein $R_1$ is an optionally substituted alkyl. The diastereomers of 1d may be separated using chromatography.

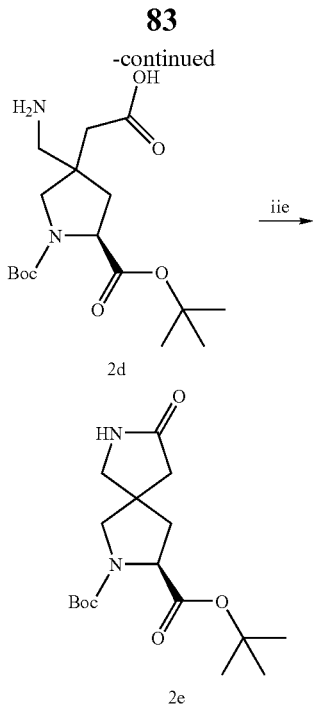

Referring to Scheme 2, the diprotected prolineone 1a reacts with (carboethoxy-methylene)triphenylphosphorane to provide the unsaturated ester 2a. Reaction of 2a with nitro methane in the presence of tetramethylguanidine (TMG) provides the intermediate nitro compound 2b. Catalytic hydrogenation of 2b in the presence of 10% Pd/C provides the amino compound 2c. Hydrolysis of 2c with lithium hydroxide in water provides the acid 2d which is cyclized in the presence of EDC, HOBT and DIEA to provide the lactam intermediate 2e. Conversion of the intermediate 2e to compounds of formula I wherein A is $CH_2$ is achieved as previously described under Scheme I for 1c.

IV. Formulations, Administrations, and Uses

Another embodiment of this invention provides a pharmaceutical composition comprising a compound of Formula I or pharmaceutically acceptable salts or mixtures of salts thereof. According to another embodiment, the compound of Formula I is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2 hydroxyethanesulfonate, lactate, maleate, methanesulfonate, 2 naphthalenesulfonate, nicotinate, oxalate, pamoate, pectinate, persulfate, 3 phenyl propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N methyl D glucamine, and salts with amino acids such as arginine, lysine, and so forth.

Also, the basic nitrogen containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose based substances, polyethylene glycol, sodium carboxymethylcellulose, polyacrylates, waxes, polyethylene polyoxypropylene block polymers, polyethylene glycol and wool fat.

According to another embodiment, the compositions of this invention are formulated for pharmaceutical administration to a mammal. In one embodiment said mammal is a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra articular, intra synovial, intrasternal, intrathecal, intrahepatic, intralesional and intracranial injection or infusion techniques. Preferably, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non toxic parenterally acceptable diluent or solvent, for example as a solution in 1,3 butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, dosage levels of between about 0.01 and about 100 mg/kg body weight per day of the protease inhibitor compounds described herein are useful in a monotherapy for the prevention and treatment of antiviral, particularly anti-HCV mediated disease. In another embodiment, dosage levels of between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). In one embodiment, such preparations contain from about 20% to about 80% active compound.

When the compositions of this invention comprise a combination of a compound of formula I and one or more additional therapeutic or prophylactic agents, both the compound and the additional agent should be present at dosage levels of between about 10 to 100% of the dosage normally administered in a monotherapy regimen. In another embodiment, the additional agent should be present at dosage levels of between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the pharmaceutical compositions are formulated for oral administration.

In another embodiment, the compositions of this invention additionally comprise another anti-viral agent, preferably an anti-HCV agent. Such anti-viral agents include, but are not limited to, immunomodulatory agents, such as α, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807, 876, 6,498,178, 6,344,465, and 6,054,472, WO 97/40028, WO 98/40381, WO 00/56331, and mycophenolic acid and derivatives thereof, and including, but not limited to VX-497, VX-148, and/or VX-944; or combinations of any of the above. See also W. Markland et al., Antimicrobial & Antiviral Chemotherapy, 44, p. 859 (2000) and U.S. Pat. No. 6,541, 496.

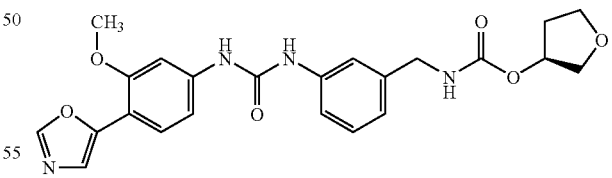

The following definitions are used herein (with trademarks referring to products available as of this application's filing date).

"Peg-Intron" means PEG-INTRON®, peginteferon alfa-2b, available from Schering Corporation, Kenilworth, N.J.

"Intron" means INTRON-A®, interferon alfa-2b available from Schering Corporation, Kenilworth, N.J.

"Ribavirin" means ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition; also available as REBETROL® from Schering Corporation, Kenilworth, N.J., or as COPEGASUS® from Hoffmann-La Roche, Nutley, N.J.

"Pagasys" means PEGASYS®, peginterferon alfa-2a available Hoffmann-La Roche, Nutley, N.J.

"Roferon" mean ROFERON®, recombinant interferon alfa-2a available from Hoffmann-La Roche, Nutley, N.J.

"Berefor" means BEREFOR®, interferon alfa 2 available from Boehringer Ingelheim. Pharmaceutical, Inc., Ridgefield, Conn.

SUMIFERON®, a purified blend of natural alpha interferons such as Sumiferon available from Sumitomo, Japan.

WELLFERON®, interferon alpha n1 available from Glaxo_Wellcome LTd., Great Britain.

ALFERON®, a mixture of natural alpha interferons made by Interferon Sciences, and available from Purdue Frederick Co., CT.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

According to one embodiment of the present invention, the interferon is α-interferon. According to another embodiment, a therapeutic combination of the present invention utilizes natural alpha interferon 2a. Or, the therapeutic combination of the present invention utilizes natural alpha interferon 2b. In another embodiment, the therapeutic combination of the present invention utilizes recombinant alpha interferon 2a or 2b. In yet another embodiment, the interferon is pegylated alpha interferon 2a or 2b. Interferons suitable for the present invention include:

(a) INTRON-A® (interferon-alpha 2B, Schering Plough),
(b) PEG-INTRON®,
(c) PEGASYS®,
(d) ROFERON®,
(e) BEREFOR®,
(f) SUMIFERON®,
(g) WELLFERON®,
(h) consensus alpha interferon available from Amgen, Inc., Newbury Park, Calif.,
(i) ALFERON®;
(j) VIRAFERON®;
(k) INFERGEN®;
(l) ALBUFERON™.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In one embodiment, the protease inhibitor and interferon are administered in separate dosage forms. In one embodiment, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, Albuferon™ (albumin-Interferon alpha) available from Human Genome Sciences; PEG-INTRON® (peginterferon alfa-2b, available from Schering Corporation, Kenilworth, N.J.); INTRON-A®, (interferon alfa-2b available from Schering Corporation, Kenilworth, N.J.); ribavirin (1-beta-D-ribofuranosyl-1H-1,2,4-triazole-3-carboxamide, available from ICN Pharmaceuticals, Inc., Costa Mesa, Calif.; described in the Merck Index, entry 8365, Twelfth Edition); REBETROL® (Schering Corporation, Kenilworth, N.J.), COPEGUS® (Hoffmann-La Roche, Nutley, N.J.); PEGASYS® (peginterferon alfa-2a available Hoffmann-La Roche, Nutley, N.J.); ROFERON® (recombinant interferon alfa-2a available from Hoffmann-La Roche, Nutley, N.J.); BEREFOR® (interferon alfa 2 available from Boehringer Ingelheim Pharmaceutical, Inc., Ridgefield, Conn.); SUMIFERON® (a purified blend of natural alpha interferons such as Sumiferon available from Sumitomo, Japan); WELLFERON® (interferon alpha n1 available from Glaxo Wellcome Ltd., Great Britain); ALFERON® (a mixture of natural alpha interferons made by Interferon Sciences, and available from Purdue Frederick Co., CT); α-interferon; natural alpha interferon 2a; natural alpha interferon 2b; pegylated alpha interferon 2a or 2b; consensus alpha interferon (Amgen, Inc., Newbury Park, Calif.); VIRAFERON®; INFERGEN®; REBETRON® (Schering Plough, Interferon-alpha 2B+Ribavirin); pegylated interferon alpha (Reddy, K. R. et al. "Efficacy and Safety of Pegylated (40-kd) Interferon alpha-2a Compared with Interferon alpha-2a in Noncirrhotic Patients with Chronic Hepatitis C (Hepatology, 33, pp. 433-438 (2001); consensus interferon (Kao, J. H., et al., "Efficacy of Consensus Interferon in the Treatment of Chronic Hepatitis" J. Gastroenterol. Hepatol. 15, pp. 1418-1423 (2000); lymphoblastoid or "natural" interferon; interferon tau (Clayette, P. et al., "IFN-tau, A New Interferon Type I with Antiretroviral activity" Pathol. Biol. (Paris) 47, pp. 553-559 (1999); interleukin-2 (Davis, G. L. et al., "Future Options for the Management of Hepatitis C." Seminars in Liver Disease, 19, pp. 103-112 (1999); Interleukin-6 (Davis et al. "Future Options for the Management of Hepatitis C." Seminars in Liver Disease, 19, pp. 103-112 (1999); interleukin-12 (Davis, G. L. et al., "Future Options for the Management of Hepatitis C." Seminars in Liver Disease, 19, pp. 103-112 (1999); and compounds that enhance the development of type 1 helper T cell response (Davis et al., "Future Options for the Management of Hepatitis C." Seminars in Liver Disease, 19, pp. 103-112 (1999)). Also included are compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) including, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Compounds that stimulate the synthesis of interferon in cells (Tazulakhova, E. B. et al., "Russian Experience in Screening, analysis, and Clinical Application of Novel Interferon Inducers" J. Interferon Cytokine Res., 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" J. Am. Acad. Dermatol., 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

Still other agents include those described in various published U.S. patent applications. These publications provide additional teachings of compounds and methods that could be used in combination with N-(3-(3-(3-methoxy-4-(oxazol-5-yl)phenyl)ureido)benzyl)tetrahydrofuran-3-carboxamide (VX950) in the methods of this invention, particularly for the treatment of hepatitis. It is contemplated that any such methods and compositions may be used in combination with the methods and compositions of the present invention. For brevity, the disclosure the disclosures from those publications is referred to be reference to the publication number but it should be noted that the disclosure of the compounds in particular is specifically incorporated herein by reference. Exemplary such publications include U.S. Patent Publication No. 20040058982; U.S. Patent Publication No. 20050192212; U.S. Patent Publication No. 20050080005; U.S. Patent Publication No. 20050062522; U.S. Patent Publication No. 20050020503; U.S. Patent Publication No. 20040229818; U.S. Patent Publication No. 20040229817; U.S. Patent Publication No. 20040224900; U.S. Patent Publication No. 20040186125; U.S. Patent Publication No. 20040171626; U.S. Patent Publication No. 20040110747; U.S. Patent Publication No. 20040072788; U.S. Patent Publication No. 20040067901; U.S. Patent Publication No. 20030191067; U.S. Patent Publication No. 20030187018; U.S. Patent Publication No. 20030186895; U.S. Patent Publication No. 20030181363; U.S. Patent Publication No. 20020147160; U.S. Patent Publication No. 20040082574; U.S. Patent Publication No. 20050192212; U.S. Patent Publication No. 20050187192; U.S. Patent Publication No. 20050187165; U.S. Patent Publication No. 20050049220; and U.S. Patent Publication No. US2005/0222236.

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methylpyrazole, cyclosporin, and clomethiazole. For preferred dosage forms of ritonavir, see U.S. Pat. No. 6,037,157, and the documents cited therein: U.S. Pat. No. 5,484,801, U.S. application Ser. No. 08/402,690, WO 95/07696 and WO 95/09614.

Methods for measuring the ability of a compound to inhibit cytochrome P450 monooxygenase activity are known. See, e.g., U.S. Pat. No. 6,037,157, and Yun, et al. Drug Metabolism & Disposition, vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

According to another embodiment, the invention provides a method for treating a patient infected with a virus characterized by a virally encoded serine protease that is necessary for the life cycle of the virus by administering to said patient a pharmaceutically acceptable composition of this invention. In one embodiment, the methods of this invention are used to treat a patient suffering from a HCV infection. Such treatment may completely eradicate the viral infection or reduce the severity thereof. In another embodiment, the patient is a human being.

In an alternate embodiment, the methods of this invention additionally comprise the step of administering to said patient an anti-viral agent preferably an anti-HCV agent. Such anti-viral agents include, but are not limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498,178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

Pharmaceutical compositions may also be prescribed to the patient in "patient packs" containing the whole course of treatment in a single package, usually a blister pack. Patient packs have an advantage over traditional prescriptions, where a pharmacist divides a patients supply of a pharmaceutical from a bulk supply, in that the patient always has access to the package insert contained in the patient pack, normally missing in traditional prescriptions. The inclusion of a package insert has been shown to improve patient compliance with the physician's instructions.

It will be understood that the administration of the combination of the invention by means of a single patient pack, or patient packs of each formulation, containing within a package insert instructing the patient to the correct use of the invention is a desirable additional feature of this invention.

According to a further aspect of the invention is a pack comprising at least one compound of formula I (in dosages according to this invention) and an information insert containing directions on the use of the combination of the invention. Any composition, dosage form, therapeutic regimen or other embodiment of this invention may be presented in a pharmaceutical pack. In an alternative embodiment of this invention, the pharmaceutical pack further comprises one or more of additional agent as described herein. The additional agent or agents may be provided in the same pack or in separate packs.

Another aspect of this involves a packaged kit for a patient to use in the treatment of HCV infection or in the prevention of HCV infection (or for use in another method of this invention), comprising: a single or a plurality of pharmaceutical formulation of each pharmaceutical component; a container housing the pharmaceutical formulation(s) during storage and prior to administration; and instructions for carrying out drug administration in a manner effective to treat or prevent HCV infection.

Accordingly, this invention provides kits for the simultaneous or sequential administration of a dose of at least one compound of formula I (and optionally an additional agent). Typically, such a kit will comprise, e.g. a composition of each compound and optional additional agent(s) in a pharmaceutically acceptable carrier (and in one or in a plurality of pharmaceutical formulations) and written instructions for the simultaneous or sequential administration.

In another embodiment, a packaged kit is provided that contains one or more dosage forms for self administration; a container means, preferably sealed, for housing the dosage forms during storage and prior to use; and instructions for a patient to carry out drug administration. The instructions will typically be written instructions on a package insert, a label, and/or on other components of the kit, and the dosage form or forms are as described herein. Each dosage form may be individually housed, as in a sheet of a metal foil-plastic laminate with each dosage form isolated from the others in individual cells or bubbles, or the dosage forms may be housed in a single container, as in a plastic bottle. The present kits will also typically include means for packaging the individual kit components, i.e., the dosage forms, the container means, and the written instructions for use. Such packaging means may take the form of a cardboard or paper box, a plastic or foil pouch, etc.

A kit according to this invention could embody any aspect of this invention such as any composition, dosage form, therapeutic regimen, or pharmaceutical pack. The packs and kits according to this invention optionally comprise a plurality of compositions or dosage forms. Accordingly, included within this invention would be packs and kits containing one composition or more than one composition.

In yet another embodiment the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

According to another embodiment the invention provides methods of treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as, for example, shunts and stents.

In another embodiment, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support.

In one embodiment, the viral serine protease isolated by this method is HCV NS3-NS4A protease.

All references cited within this document are incorporated herein by reference.

V. PREPARATIONS AND EXAMPLES

In order that the invention described herein may be more fully understood, the following preparations and examples are provided. It should be understood that these methods and examples are for illustrative purposes only and are not to be construed as limiting this invention in any manner.

A. Preparation of Intermediates for Compounds of Formula I

Set forth below are various methods for preparing intermediates that can be used to synthesize the compound of Formula I.

Set forth below are various methods for preparing intermediates that can be used to synthesize the compound of Formula I.

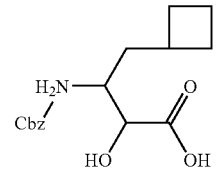 [SMILES: O=C(NC(CC1CCC1)C(O)C(=O)O)OCc1ccccc1]

Preparation of 3-(benzyloxycarbonylamino)-4-cyclobutyl-2-hydroxybutanoic acid

A solution of the cyanohydrin prepared according to methods described in WO 04/113294 (1 g, 3.65 mmol) in conc. HCl (12 mL) was heated to reflux for 18 hrs. The reaction was concentrated in vacuo to afford the desired amino acid as an HCl salt (1.7 g) which was used in the next step without further purification. A solution of the above HCl salt in THF was treated with DIPEA (2.68 g) and Z—OSu (5.16 g). The reaction mixture was stirred at room temperature for 8 hrs. The reaction mixture was diluted with toluene and HCl (12 N, until pH=1). After separation, the organic layer was extracted with sat. NaHCO₃ (50 mL, twice). The aqueous layer was made acidic with HCl (6 N) until pH=1 and extracted with EtOAc (200 mL). The combined organic layer was dried and concentrated in vacuo to afford the title compound (0.6 g). (M+1) 308.

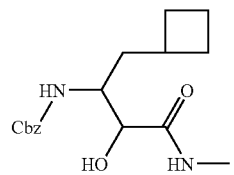 [SMILES: CNC(=O)C(O)C(CC1CCC1)NC(=O)OCc1ccccc1]

Preparation of benzyl 1-cyclobutyl-3-hydroxy-4-(methylamino)-4-oxobutan-2-ylcarbamate To a solution of 3-(benzyloxycarbonylamino)-4-cyclobutyl-2-hydroxybutanoic acid (250 mg, 0.81 mmol) in DCM (20 mL) was added HOSu (140 mg, 1.22 mmol), EDC (234 mg, 1.22 mmol). After stirring for 1 hr, methylamine in THF (2 N, 0.81 mL) was added to the above mixture. The reaction mixture was stirred for 18 hrs and then concentrated in vacuo. The residue was purified by Gilson Prep to afford the title compound (135 mg). $^1$H-NMR (CDCl$_3$): δ 7.54-7.28 (m, 5H), 6.67 (NH, 1H), 5.03 (dd, 2H), 3.68 (m, 1H), 2.73 (m, 3H), 2.26 (m, 1H), 1.97-1.31 (m, 9H). (M+1) 321.

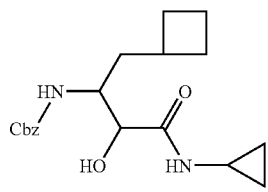 [SMILES: O=C(NC(CC1CCC1)C(O)C(=O)NC1CC1)OCc1ccccc1]

Preparation of benzyl 1-cyclobutyl-4-(cyclopropylamino)-3-hydroxy-4-oxobutan-2-ylcarbamate To a solution of 3-(benzyloxycarbonylamino)-4-cyclobutyl-2-hydroxybutanoic acid (600 mg, 1.95 mmol) in DCM (20 mL) was added HOSu (337 mg, 2.93 mmol), EDC (562 mg, 2.93 mmol). After stirring for 1 hr, cyclopropylamine (223 mg, 3.9 mmol) was added to the above mixture. The product was extracted with EtOAc. The combined organic layer was then washed with HCl (1N), water, NaHCO$_3$, and brine and then concentrated in vacuo to afford benzyl 1-cyclobutyl-4-(cyclopropylamino)-3-hydroxy-4-oxobutan-2-yl carbamate (530 mg). (M+1) 347.

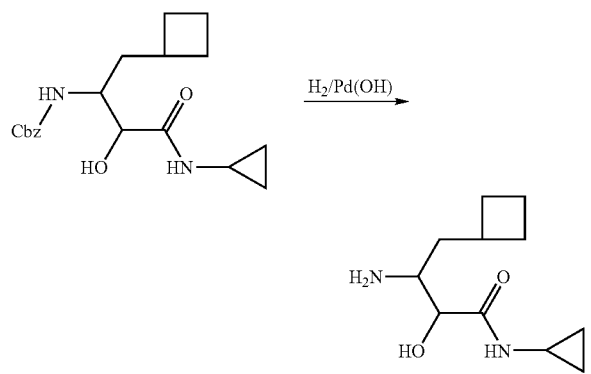

Preparation of 3-amino-4-cyclobutyl-N-cyclopropyl-2-hydroxybutanamide

To a solution of the CBz amide (530 mg, 1.53 mmol) in MeOH (30 mL) was added Pd(OH)$_2$/C (106 mg). The mixture was stirred under H$_2$ (1 atm) for 18 hrs. After filtration, the filtrate was concentrated in vacuo to afford the title compound (300 mg). $^1$H-NMR (CDCl$_3$): δ 3.29 (m, 1H), 2.74 (m, 1H), 2.37-1.66 (m, 9H), 1.40 (m, 1H), 0.78 (m, 2H), 0.51 (m, 2H). (M+1) 213.

The following compounds were prepared in a similar fashion to preparing 3-amino-4-cyclobutyl-N-cyclopropyl-2-hydroxybutanamide by using the appropriate amine:

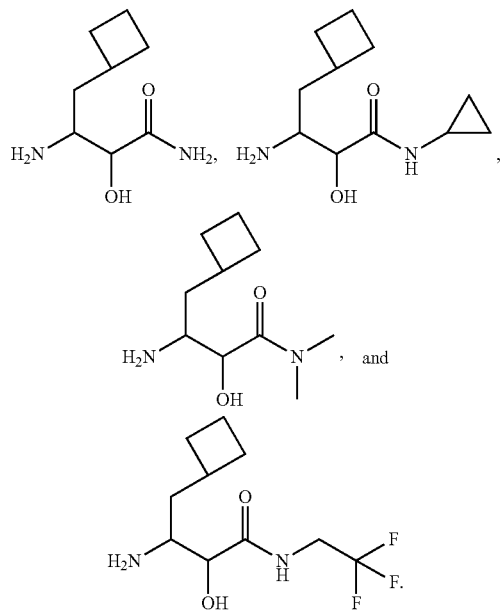

Preparation of 3-amino-N-cyclopropyl-2-hydroxyhept-6-ynamide

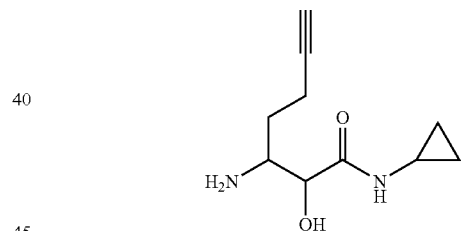

3-Amino-N-cyclopropyl-2-hydroxyhept-6-ynamide was prepared as described by N. Kobayashi, et al. in US 2003/0153788, which is incorporated herein by reference in its entirety. $^1$H-NMR (500 MHz, DMSO-d$_o$): 8.18 (s), 6.34 (s), 4.22 (s), 3.45 (s), 3.17 (s), 2.84 (s), 2.69 (d, J=3.2 Hz), 2.30 (m), 2.24 (m), 1.70 (m), 1.59 (m), 0.62 (d, J=5.0 Hz), 0.53 (s) ppm; FIA m/z 197.01 ES$^+$.

Preparation of Cbz-Protected (3S)-3-amino-4-cyclopropyl-2-hydroxy-N-methylbutanamide

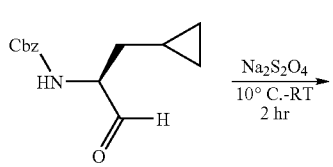

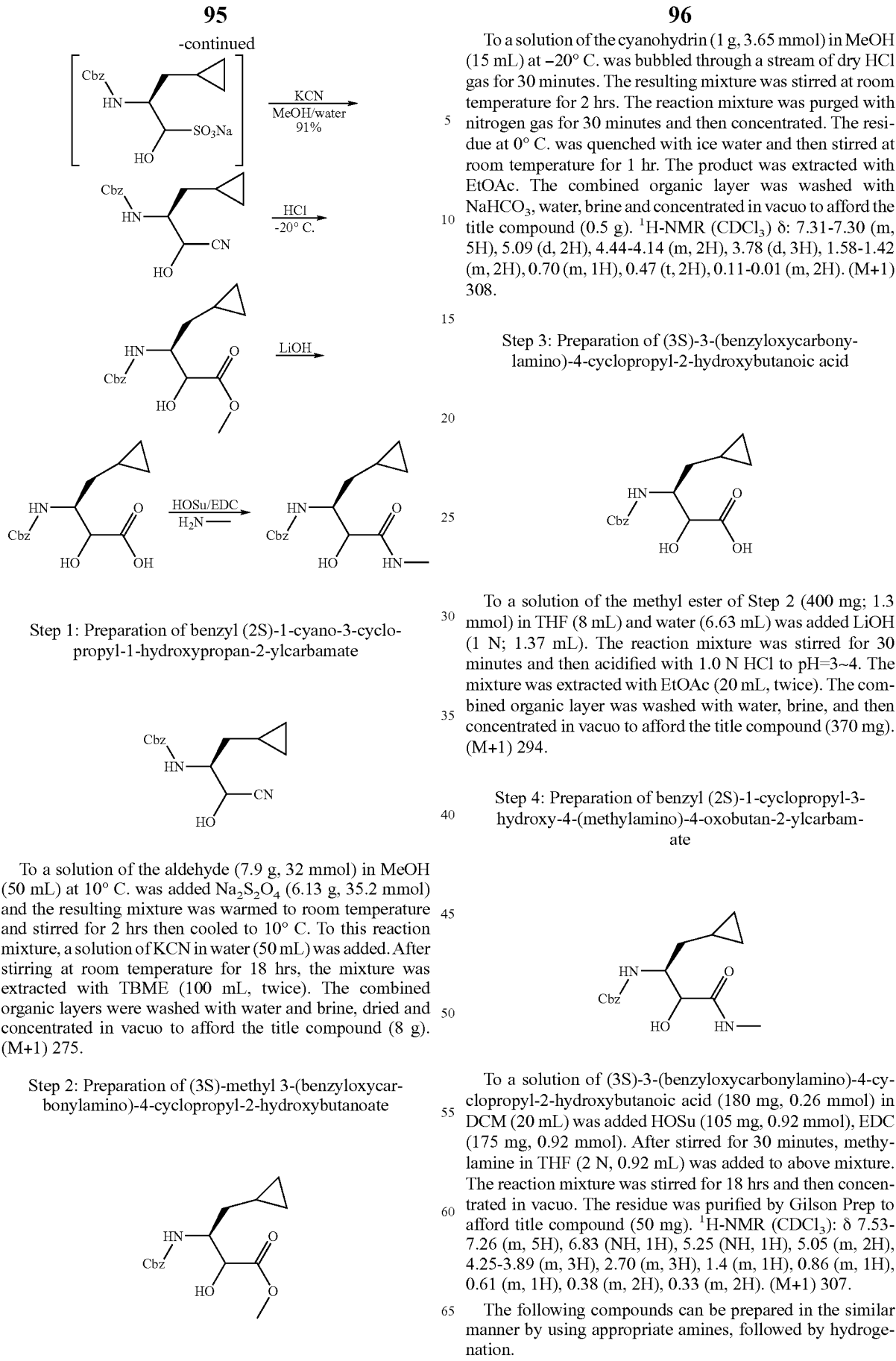

Step 1: Preparation of benzyl (2S)-1-cyano-3-cyclopropyl-1-hydroxypropan-2-ylcarbamate To a solution of the aldehyde (7.9 g, 32 mmol) in MeOH (50 mL) at 10° C. was added $Na_2S_2O_4$ (6.13 g, 35.2 mmol) and the resulting mixture was warmed to room temperature and stirred for 2 hrs then cooled to 10° C. To this reaction mixture, a solution of KCN in water (50 mL) was added. After stirring at room temperature for 18 hrs, the mixture was extracted with TBME (100 mL, twice). The combined organic layers were washed with water and brine, dried and concentrated in vacuo to afford the title compound (8 g). (M+1) 275.

Step 2: Preparation of (3S)-methyl 3-(benzyloxycarbonylamino)-4-cyclopropyl-2-hydroxybutanoate To a solution of the cyanohydrin (1 g, 3.65 mmol) in MeOH (15 mL) at −20° C. was bubbled through a stream of dry HCl gas for 30 minutes. The resulting mixture was stirred at room temperature for 2 hrs. The reaction mixture was purged with nitrogen gas for 30 minutes and then concentrated. The residue at 0° C. was quenched with ice water and then stirred at room temperature for 1 hr. The product was extracted with EtOAc. The combined organic layer was washed with $NaHCO_3$, water, brine and concentrated in vacuo to afford the title compound (0.5 g). $^1$H-NMR ($CDCl_3$) δ: 7.31-7.30 (m, 5H), 5.09 (d, 2H), 4.44-4.14 (m, 2H), 3.78 (d, 3H), 1.58-1.42 (m, 2H), 0.70 (m, 1H), 0.47 (t, 2H), 0.11-0.01 (m, 2H). (M+1) 308.

Step 3: Preparation of (3S)-3-(benzyloxycarbonylamino)-4-cyclopropyl-2-hydroxybutanoic acid To a solution of the methyl ester of Step 2 (400 mg; 1.3 mmol) in THF (8 mL) and water (6.63 mL) was added LiOH (1 N; 1.37 mL). The reaction mixture was stirred for 30 minutes and then acidified with 1.0 N HCl to pH=3~4. The mixture was extracted with EtOAc (20 mL, twice). The combined organic layer was washed with water, brine, and then concentrated in vacuo to afford the title compound (370 mg). (M+1) 294.

Step 4: Preparation of benzyl (2S)-1-cyclopropyl-3-hydroxy-4-(methylamino)-4-oxobutan-2-ylcarbamate To a solution of (3S)-3-(benzyloxycarbonylamino)-4-cyclopropyl-2-hydroxybutanoic acid (180 mg, 0.26 mmol) in DCM (20 mL) was added HOSu (105 mg, 0.92 mmol), EDC (175 mg, 0.92 mmol). After stirred for 30 minutes, methylamine in THF (2 N, 0.92 mL) was added to above mixture. The reaction mixture was stirred for 18 hrs and then concentrated in vacuo. The residue was purified by Gilson Prep to afford title compound (50 mg). $^1$H-NMR ($CDCl_3$): δ 7.53-7.26 (m, 5H), 6.83 (NH, 1H), 5.25 (NH, 1H), 5.05 (m, 2H), 4.25-3.89 (m, 3H), 2.70 (m, 3H), 1.4 (m, 1H), 0.86 (m, 1H), 0.61 (m, 1H), 0.38 (m, 2H), 0.33 (m, 2H). (M+1) 307.

The following compounds can be prepared in the similar manner by using appropriate amines, followed by hydrogenation.

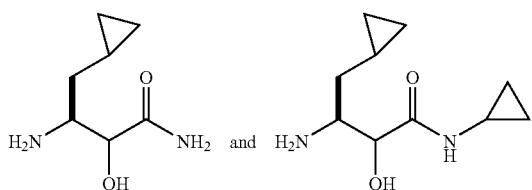 [SMILES: NC(=O)C(O)[C@@H](N)CC1CC1 ; "and" ; N[C@@H](CC1CC1)C(O)C(=O)NC1CC1]

The following compounds can be prepared in the methods described by Perni, R. et al. in WO 01/74768, which is incorporated herein by reference in its entirety.

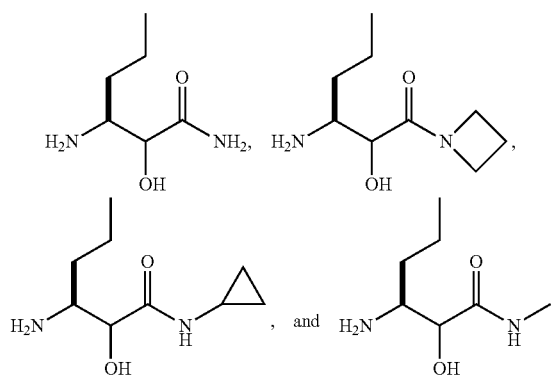

Preparation of (S)-2-(cyclopentyloxycarbonylamino)-3,3-dimethylbutanoic acid

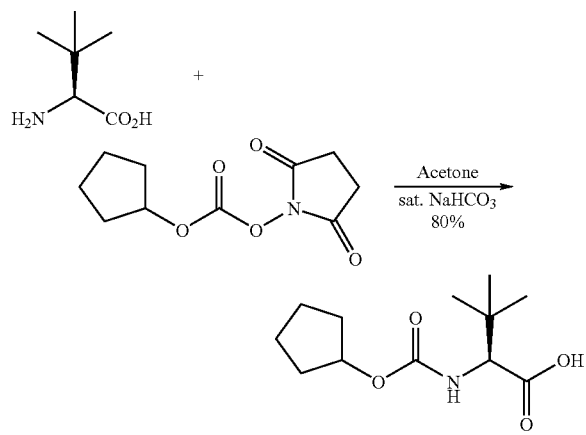

In a 5 L RB flask dissolved t-butyl glycine (74 g, 0.56 mol, 1.02 eq.) in saturated sodium bicarbonate (11 vol). Cyclopentyl 2,5-dioxopyrrolidin-1-yl carbonate (126 g, 0.55 mol, 1 eq.) was dissolved in acetone (5.5 vol) and the solution slowly added via addition funnel at room temperature to the solution of the glycine. The reaction mixture was stirred at room temperature until complete (approximately 4 hrs). The acetone was removed under reduced pressure and the remaining aqueous solution was extracted with 30% ethyl acetate in hexanes (thrice, 5.5 vol each). The organic layers were discarded. The pH of the aqueous layer was adjusted to 2 with 2 N HCl and then extracted with ethyl acetate (thrice, 5.5 vol). The combined organic layers were dried ($Na_2SO_4$), filtered, and the solvent removed under reduced pressure to provide a clear oil the slowly crystallized. The crude product was crystallized from hexanes/ethyl acetate to provide (S)-2-(cyclopentyloxycarbonylamino)-3,3-dimethylbutanoic acid as a white solid (82 g). The mother liquid was stripped and a second crop of crystals obtained (combined yield 105.54 g).

Preparation of Sulfonyl Compounds

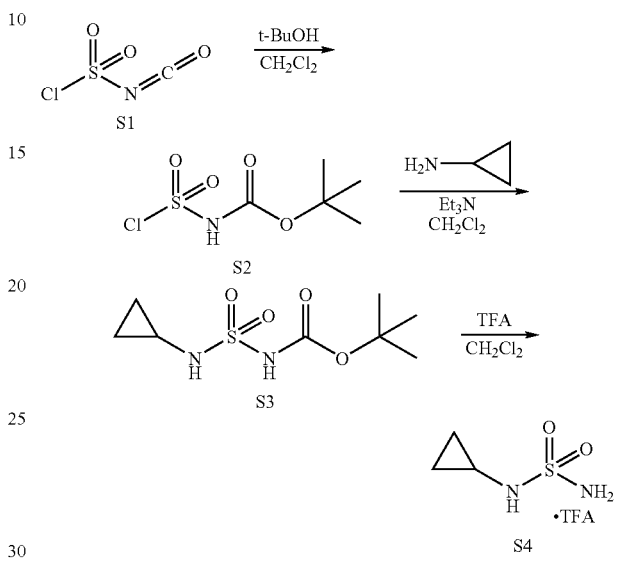

Compounds S1, S2, S3, and S4, shown above, were prepared according to procedures described in WO 2005/095403 and PCT/US2005/010494, hereby incorporated by references by their entireties. Specifically, to a solution of chlorosulfonylisocyanate (10 mL, 115 mmol) in $CH_2Cl_2$ (200 mL) at 0° C. was added t-BuOH (11 mL, 1 eq.). The mixture was stirred for 60 minutes, then added via cannula into a solution of cyclopropylamine (6.6 g) in $CH_2Cl_2$ (200 mL) with triethylamine (30 mL) at 0° C. concurrently with a solution of triethylamine (50 mL) in $CH_2Cl_2$ (100 mL) via addition funnel. Internal temperature was maintained below 8° C. Stirred at room temperature after completion of addition for 4 hrs. The reaction was then diluted with $CH_2Cl_2$ and transferred to a separatory funnel, washed with 1 N HCl (twice, 400 mL each), brine (300 mL), dried ($MgSO_4$), filtered and concentrated. The product was recrystallized from ethyl acetate/hexanes to yield 16.8 g (71.3 mmol, 62%) of S3. Compound S3 was deprotected with trifluoroacetic acid in $CH_2Cl_2$ to give compound S4 in quantitative yield.

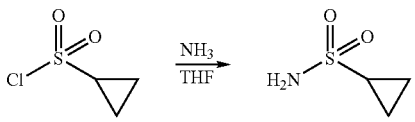

Ammonia gas was bubbled through a gas dispersion tube into THF (40 mL) cooled to 0° C. for 5 minutes. To this solution at 0° C. was added cyclopropylsulfonylchloride (1 gram, 7.1 mmol). The reaction was stirred at room temperature overnight, then filtered through a plug of silica gel, followed by elution with EtOAc to yield 750 mg (6.19 mmol, 87%) of cyclopropylsulfonamide. $^1$H-NMR (500 MHz, Methanol-$d_4$): 4.79 (s, 2H), 2.59-2.54 (m, 1H), 1.06-0.96 (m, 4H).

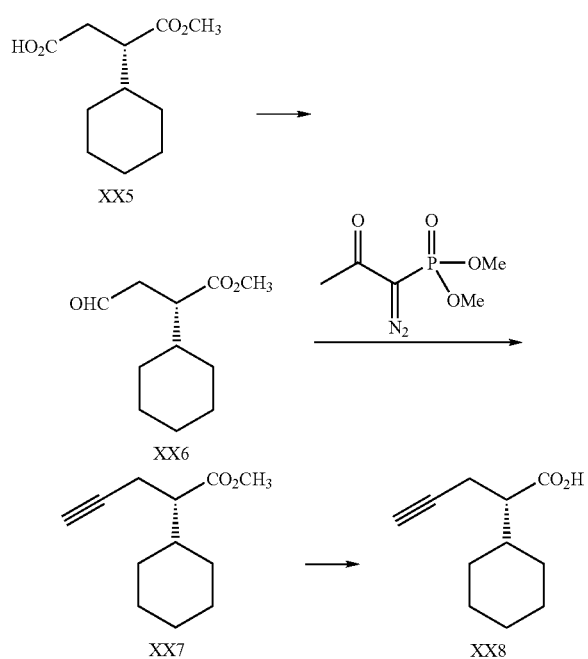

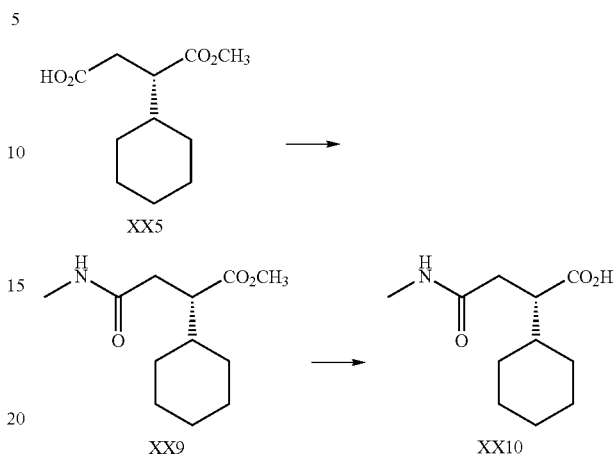

To a solution of compound XX5 (1.37 g, 6.41 mmol) in THF (30 mL) at 0° C. was added dropwise borane-dimethylsulfide (3.85 mL, 7.8 mmol, 2.0 M in toluene). The reaction mixture was stirred for 1 h with gradual warming to room temperature, quenched with H₂O (20 mL), and extracted with ethyl acetate (thrice, 30 mL each). The combined organics were dried and concentrated under reduced pressure to provide 1.3 g of a colorless oil which was used without further purification. To oxalyl chloride (2.24 mL, 25.6 mmol) in CH₂Cl₂ (15 mL, anhydrous) at −78° C. under inert atmosphere was added dropwise a solution of DMSO (2.73 mL, 38.5 mmol) in CH₂Cl₂ (8 mL). After stirring for 10 min, a solution of the alcohol (1.3 g, 6.41 mmol) in CH₂Cl₂ (6 mL) was added dropwise. After an additional 10 min, triethylamine (7.15 mL, 51.3 mmol) in CH₂Cl₂ was added and the reaction was stirred another 30 min with gradual warming to 0° C. The reaction mixture was washed with 1 M HCl (20 mL) followed by brine (20 mL). The organic layer was dried over MgSO₄ and concentrated under reduced pressure. The resulting oil was purified via silica gel chromatography to afford 748 mg (59% over 2 steps) of aldehyde XX6. ¹H-NMR (500 MHz, CDCl₃): 9.75 (s, 1H), 3.67 (s, 3H), 2.91-2.85 (m, 1H), 2.78-2.74 (m, 1H), 2.56-2.52 (m, 1H), 1.74-1.71 (m, 2H), 1.66-1.58 (m, 4H), 1.27-0.95 (m, 5H).

To a solution of compound XX6 (581 mg, 2.9 mmol) and K₂CO₃ (811 mg, 5.9 mmol) in MeOH (15 mL) was added dimethyl 1-diazo-2-oxopropylphosphonate (676 mg, 3.5 mmol, Synlett 1996, p. 521). The reaction was stirred 1 h at room temperature, diluted with Et₂O (20 mL), and washed with saturated NaHCO₃ solution (10 mL, aqueous). The organic layer was dried over MgSO₄ and concentrated under reduced pressure to give 600 mg (100%) of alkyne XX7 which was used without further purification. ¹H-NMR (500 MHz, CDCl₃): 3.69 (s, 3H), 2.48-2.37 (m), 1.95 (s, H), 1.73-1.60 (m), 1.30-0.94 (m).

To a solution of compound XX7 (600 mg, 2.9 mmol) in a solution of THF/H₂O/MeOH (25 mL, 2:1:2) was added LiOH monohydrate (850 mg, 20.3 mmol). The reaction mixture was stirred 2 h at room temperature, acidified using 1 N HCl (25 mL), and extracted with EtOAc (thrice, 15 mL each). The combined organics were dried over MgSO₄ and concentrated to yield 533 mg (99%) of carboxylic acid XX8, which was used without further purification.

To a solution of compound XX5 (100 mg, 0.5 mmol) in CH₂Cl₂ (2.5 mL) was added EDC (107 mg, 0.6 mmol), HOBt (76 mg, 0.6 mmol) and triethylamine (195 μL, 1.4 mmol). To the activated acid solution was added methylamine hydrochloride (38 mg, 0.6 mmol) and the reaction was stirred at room temperature for 12 h. The reaction mixture was washed with H₂O (2 mL), 1 N HCl (2 mL) and saturated NaHCO₃ solution (2 mL). The organic layer was dried over MgSO₄ and concentrated to give 100 mg of amide XX9, which was used without further purification. ¹H-NMR (500 MHz, CDCl₃) 3.61 (s, 3H), 2.75-2.70 (m, 4H), 2.48-2.42 (m, 1H), 2.28-2.24 (m, 1H), 1.66-1.48 (m, 6H), 1.35-0.90 (m, 5H).

To a solution of compound XX9 (100 mg, 0.5 mmol) in a solution of THF/H₂O/MeOH (3 mL, 2:1:2) was added LiOH monohydrate (124 mg, 3 mmol). The reaction mixture was stirred 2 h at room temperature, acidified using 1 N HCl (4 mL), and extracted with EtOAc (3×5 mL). The combined organics were dried over MgSO₄ and concentrated to yield 87 mg of carboxylic acid XX10, which was used without further purification. ¹H-NMR (500 MHz, CDCl₃) 11.32 (s, H), 2.75-2.64 (m, H), 2.52-2.46 (m, H), 2.37-2.33 (m, H), 2.25 (td, J=8.7, 2.9 Hz, H), 1.97 (s, H), 1.79 (s, H), 1.74-1.62 (m, H), 1.59-1.49 (m, H), 1.23-1.12 (m, H), 1.08-0.81 (m, H).

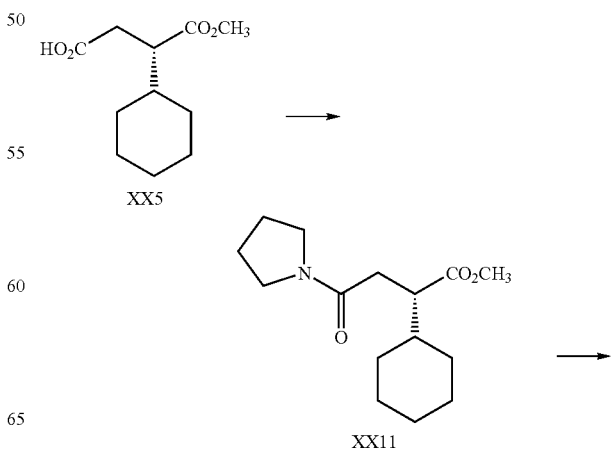

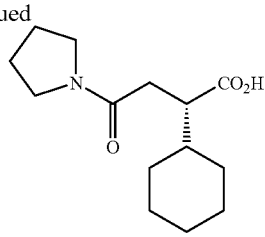

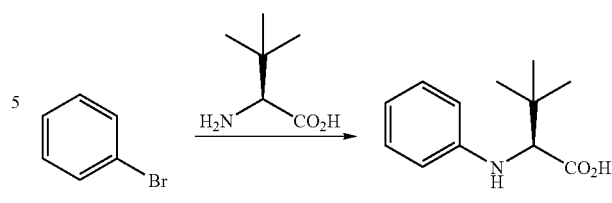

Intermediate XX12 was prepared according to the procedure for preparing intermediate XX10 described above, except for using pyrrolidine as a reagent instead of methylamine hydrochloride. ¹H-NMR (500 MHz, CDCl₃) 11.47 (s, 1H), 3.45-3.32 (m, 4H), 2.76-2.72 (m, 1H), 2.64-2.59 (m, 1H), 2.37-2.33 (m, 1H), 1.92-1.76 (m, 4H), 1.71-1.57 (m), 1.22-0.84 (m).

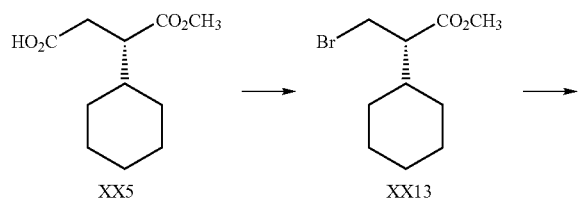

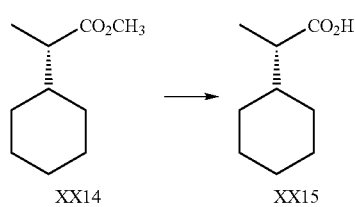

To a solution of compound XX5 (1 g, 4.7 mmol) and HgO yellow (1.01 g, 4.7 mmol) in CCl₄ (23 mL) at reflux was added dropwise over 30 min a solution of bromine (264 μL, 5.1 mmol) in CCl₄ (5 mL). The reaction was stirred at reflux for 1 h, cooled to room temperature, diluted with CH₂Cl₂ (20 mL), washed with 1 N HCl (10 mL), H₂O (10 mL), and brine (10 mL). The organic layer was dried over MgSO₄ and concentrated under reduced pressure to yield 1.3 g of compound XX13 as a colorless oil that was used without further purification. ¹H-NMR (500 MHz, CDCl₃): 3.67 (s, 3H), 3.52-3.44 (m, 2H), 2.63-2.58 (m, 1H), 1.70-1.64 (m, 3H), 1.60-1.54 (m, 3H), 1.24-0.92 (m, 5H).

To a solution of compound XX13 (578 mg, 2.3 mmol) in DMSO (12 mL) was added sodium borohydride (177 mg, 4.7 mmol). The reaction mixture was stirred at 90° C. for 1 h, diluted with H₂O (10 mL), and extracted with hexanes (3×15 mL). The combined organics were dried over MgSO₄ and concentrated under reduced pressure. Purification via silica gel chromatography, eluting with EtOAc/petroleum ether, afforded 204 mg of compound XX14. ¹H-NMR (500 MHz, CDCl₃): 3.59 (s, 3H), 2.18 (m, 1H), 1.69-1.43 (m, 6H), 1.21-0.83 (m, 8H).

Intermediate XX15 was prepared according to the procedure for preparing intermediate XX10, step b, except for using substrate XX14 instead of XX9.

To a solution of (S)-2-amino-3,3-dimethylbutanoic acid (787 mg, 6.0 mmol), bromobenzene (632 μL, 6.0 mmol), K₂CO₃ (1.24 g, 9.0 mmol) and CuI (114 mg, 0.6 mmol) was added N,N-dimethylacetamide (7.5 mL). The contents were stirred for 16 h at 90° C. in a sealed pressure vessel. The reaction mixture was diluted with H₂O (15 mL), cooled to 0° C., and acidified to pH~5 using 1 N HCl. The mixture was extracted with EtOAc (3×20 mL), and the combined organics were washed with brine (1×15 mL), dried over MgSO₄, and concentrated under reduced pressure. The resulting residue was purified via silica gel chromatography to provide 150 mg (12%) of compound XX16. ¹H-NMR (500 MHz, CDCl3): 7.11-7.09 (m, 2H), 6.69 (t, J=7.3 Hz, 1H), 6.60-6.59 (m, 2H), 3.69 (s, 1H), 1.02 (s, 9H).

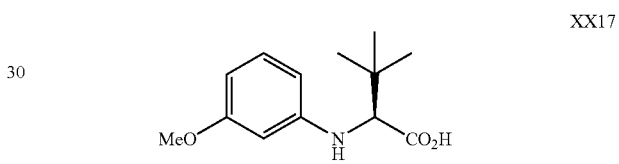

Intermediate XX17 was prepared according to the procedure for preparing XX16, except for using 1-bromo-3-methoxybenzene as a reagent instead of bromobenzene. ¹H-NMR (500 MHz, CDCl₃): 6.98 (t, J=8.1 Hz, 1H), 6.24-6.18 (m, 2H), 6.14 (s, 1H), 3.69 (s, 1H), 3.66 (s, 3H), 1.00 (s, 9H).

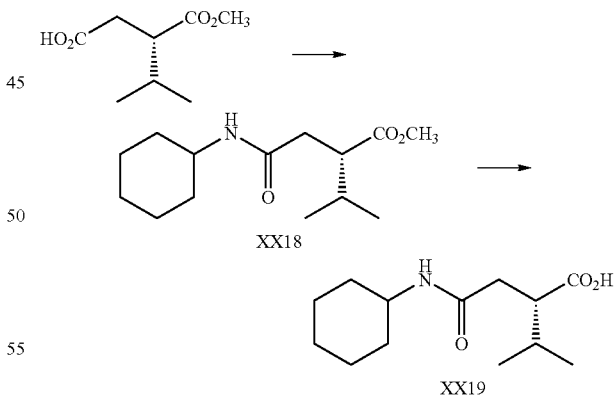

To a solution of (S)-3-(methoxycarbonyl)-4-methylpentanoic acid (200 mg, 1.2 mmol) in CH₂Cl₂ (6 mL) was added EDC (264 mg, 1.4 mmol), HOBt (186 mg, 1.4 mmol) and triethylamine (481 μL, 3.5 mmol). To the activated acid solution was added cyclohexylamine (158 μL, 1.4 mmol) and the reaction was stirred 4 hrs. The reaction mixture was washed with H₂O (3 mL), 1 N HCl (3 mL), and saturated NaHCO₃ solution (3 mL). The organic layer was dried over MgSO₄, and concentrated under reduced pressure to afford 290 mg of compound XX18 which was used without further purification. $^1$H-NMR (500 MHz, CDCl$_3$): 5.78 (d, J=7.5 Hz, 1H), 3.69-3.61 (m, 4H), 2.73-2.69 (m, 1H), 2.45-2.40 (m, 1H), 2.24-2.20 (m, 1H), 1.85 (m, 1H), 1.82-1.76 (m, 2H), 1.63-1.60 (m, 2H), 1.54-1.50 (m, 1H), 1.31-1.22 (m, 2H), 1.12-1.00 (m, 3H), 0.90-0.85 (m, 6H).

Intermediate XX19 was prepared according to the procedure for preparing compound XX10 described above, except for using substrate XX18 as a reagent instead of compound XX9. ES (+) MS: m/e 256 (M+H)$^+$.

XX20

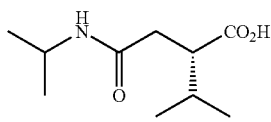

Intermediate XX20 was prepared according to the procedure for preparing compound XX18 or XX19 described above, except for using isopropylamine as a reagent instead of cyclohexylamine. ES (+) MS: m/e 216 (M+H)$^+$.

XX21

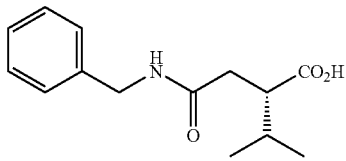

Intermediate XX21 was prepared according to the procedure for preparing XX18 or XX19 described above, except for using benzylamine as a reagent instead of cyclohexylamine. ES (+) MS: m/e 264 (M+H)$^+$.

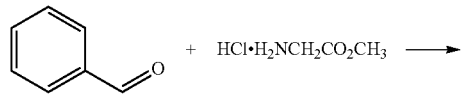

Glycine methyl ester hydrochloride (50.0 g) was suspended in MTBE (300 mL) at RT. To this was added benzaldehyde (40.5 mL) and anhydrous Na$_2$SO$_4$ (33.9 g). The suspension was cooled in an ice-water bath for 20 minutes, then triethylamine (80 mL) was added dropwise over 15 minutes. After 5 minutes, the reaction was removed from the ice-water bath, and stirred at RT for 24 hrs. The reaction was quenched with 200 mL ice-water mixture and the organic layer was separated. The aqueous layer was extracted with MTBE (200 mL). The organic layers were combined, washed with a 1:1 mixture of brine and saturated NaHCO$_3$ (aq.), dried (MgSO$_4$), and concentrated to yield 62.83 grams of the N-benzyl imine as a yellow oil. $^1$H-NMR (500 MHz, CDCl$_3$): 8.30 (s, 1H), 7.78-7.77 (m, 2H), 7.45-7.40 (m, 3H), 4.42 (s, 2H), 3.78 (s, 3H).

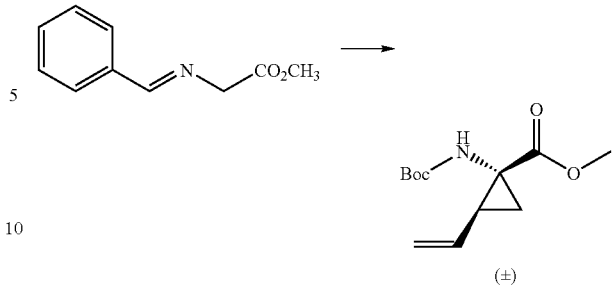

Lithium tert-butoxide (15.13 g) was suspended in dry toluene (200 mL) at room temperature. To this was added dropwise a solution of the N-benzyl imine of glycine methyl ester (16.89 g) and 1,4-dibromo-2-butene (19.28 g) in toluene (100 mL) over 40 minutes. The red solution was stirred for 100 minutes, then quenched with H$_2$O (200 mL). The contents were transferred to a separatory funnel and diluted with MTBE (200 mL). The layers were separated and the aqueous layer was extracted with MTBE. The combined organic layers were stirred with 1 N HCl (aq.) (500 mL) for 3 hrs. The layers were separated and the organic layer was extracted with H$_2$O (100 mL). The aqueous layers were combined, NaCl (250 g) and MTBE (700 mL) were added and the pH was brought to ~13 with 10 N NaOH (aq). The organic layer was separated and the aqueous layer was extracted with MTBE (twice, 300 mL each). The organic layers were combined, dried (MgSO$_4$), and concentrated to a volume of ≈ 400 mL. To the solution was added di-tert-butyl dicarbonate (25.0 g) and the reaction was stirred for 3 days. Additional di-tert-butyl dicarbonate (5.6 g) was added, followed by heating of the reaction in a 60° C. bath for 1 hr. The reaction was purified by flash silica gel column chromatography with EtOAc/hexane (1:9) as eluent to yield 10.89 g of racemic N-Boc-(1R,2S)/(1S,2R)-1-amino-2-vinylcyclopropane carboxylic acid methyl ester. See, e.g., WO00/09558 and Beaulieu, P. L. et al., J. Org. Chem., 70 (15), 5869-5879, 2005. $^1$H-NMR (500 MHz, CDCl$_3$): 5.78-5.71 (m, 1H), 5.29-5.26 (m, 1H), 5.11 (dd, J=1.2, 10.3 Hz, 1H), 3.71 (s, 3H), 2.14 (q, J=8.8 Hz, 1H), 1.79 (s, 1H), 1.53-1.45 (m, 10H).

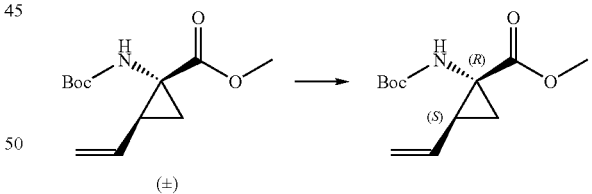

Racemic N-Boc-(1R,2S)/(1S,2R)-1-amino-2-vinylcyclopropane carboxylic acid methyl ester (4.2 g) was dissolved in acetone (80 mL) and then diluted with water (160 mL). The pH was adjusted to 7.8 with 0.2N NaOH (aq). Subtilisin A (product P-5380 from Sigma, St. Louis, Mo., USA) (4.5 g) was added to the solution. Its pH was maintained between 7.4 and 8.7 for 3 days by the dropwise addition of 0.1 N NaOH (aq.). When HPLC analysis (Chiralpak AD from Daicel Chemical Industries, Tokyo, 4.6 mm×250 mm, 0.5 mL/min, 10-85% 2-propanol/hexanes over 10 minutes, monitor 215.4 nm) of the reaction indicated the presence of only the (1R, 2S)-enantiomer (retention time of (1R,2S)=6.2 min, (1S,2R)=5.9 min) the pH was brought to 8.5 with 2 N NaOH (aq). The contents of the reaction were transferred to a separatory funnel and extracted with MTBE (3×400 mL). The extracts were washed with saturated NaHCO₃ (aq) solution (3×150 mL), water (2×200 mL), and dried (MgSO₄). The solution was filtered, concentrated, diluted with CH₂Cl₂, dried (MgSO₄), filtered, and concentrated to yield 1.95 g of N-Boc-(1R,2S)-1-amino-2-vinylcyclopropane carboxylic acid methyl ester.

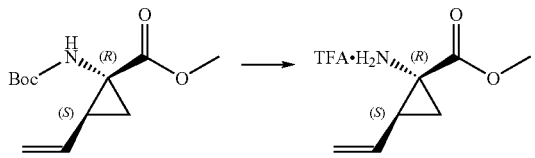

N-Boc-(1R,2S)-1-amino-2-vinylcyclopropane carboxylic acid methyl ester (125 mg, 0.52 mmol) stirred in CH₂Cl₂/TFA (1:1, 2 mL) at RT for 90 minutes. Solvents removed under vacuum to yield (1R,2S)-1-amino-2-vinylcyclopropane carboxylic acid methyl ester trifluoroacetic acid salt.

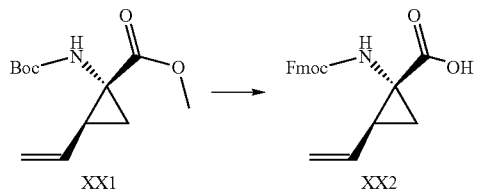

Compound XX1 (2.34 g, 9.71 mmol) was stirred with LiOH.H₂O (0.45 g, 10.7 mmol) in THF/H₂O/THF (3:1:0.5, 22 mL) at room temperature overnight. The solvents were evaporated and the remaining solids were taken up in CH₂Cl₂/EtOAc and 1N HCl (aq). The aqueous layer was extracted with CH₂Cl₂ and the combined organic extracts were dried (MgSO₄), filtered, and concentrated. This material was dissolved in CH₂Cl₂ (10 mL) at room temperature and treated with trifluoroacetic acid (10 mL). HPLC analysis at 70 minutes showed no starting material was present. The solvents were removed in vacuo to yield a viscous light colored oil. This was taken up in additional CH₂Cl₂ (30 mL) and evaporated on a rotary evaporator to yield a tan solid. This solid was dissolved in saturated NaHCO₃ (aq) and acetone (1:1, 50 mL) and treated with Fmoc-Cl (2.65 g, 10.2 mmol). After 4 hrs, the contents of the flask were transferred to a separatory funnel with CH₂Cl₂ and acidified with 2N HCl (aq). The aqueous layer was extracted with CH₂Cl₂, the combined organic layers were dried (MgSO₄), filtered, and concentrated to yield 1.86 g (5.3 mmol) of XX2 as a light yellow solid. (M+1)=350.1

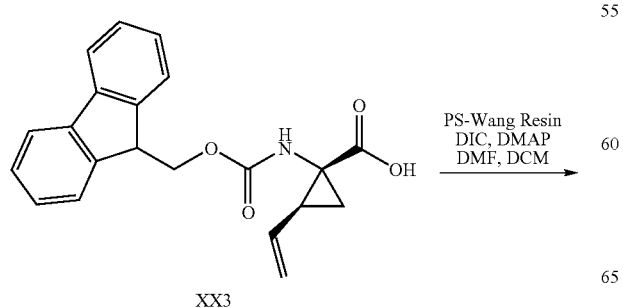

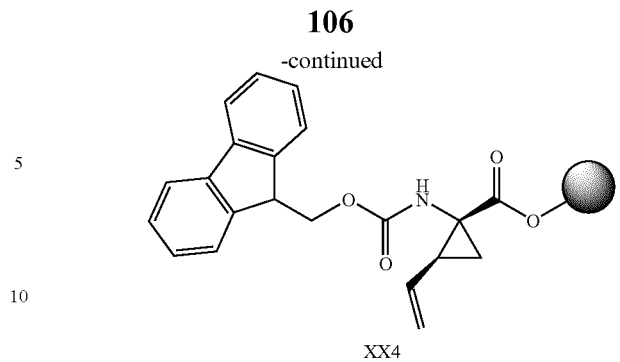

PS-Wang resin (2.0 g, 1.0 eq.) swelled in DMF (enough to cover). (1R,2S)-1-((((9H-fluoren-9-yl)methoxy)carbonyl)amino)-2-vinylcyclopropanecarboxylic acid (XX3) (922 mg, 1.1 eq.) was stirred in DCM. Diisopropylcarbodiimide (409 uL, 1.1 eq.) was added to the DCM solution and stirred at 4° C. for 2 hrs, then added to resin and DMF. Dimethylaminopyridine (29 mg, 0.1 eq.) in DMF was added to resin solution and shaken for 5 hrs. Drained and washed with DMF (thrice) and DCM (thrice) to yield Compound XX4.

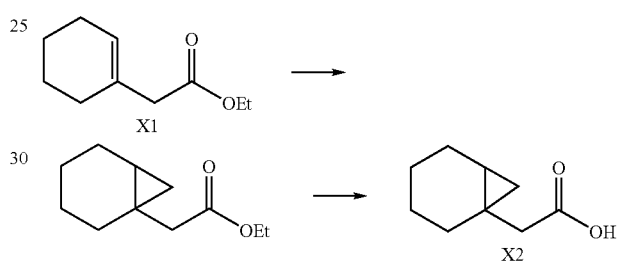

Preparation of 2-(bicyclo[4.1.0]heptan-1-yl)acetic acid X2

Commercially available compound X1 (Aldrich Chemical Co., Milwaukee, Wis., USA) was converted to X2 according to method described by E. J. Kantorowski et al. in J. Org. Chem., 1999, 64, 570-580. ¹H-NMR (CDCl₃, 500 MHz): 9.2 (br s, 1H), 2.23 (m, 2H), 1.92 (m, 1H), 1.76 (m, 2H), 1.58 (m, 1H), 1.34 (m, 1H), 1.18 (m, 4H), 0.85 (m, 1H), 0.52 (dd, 1H), 0.31 (t, 1H) ppm.

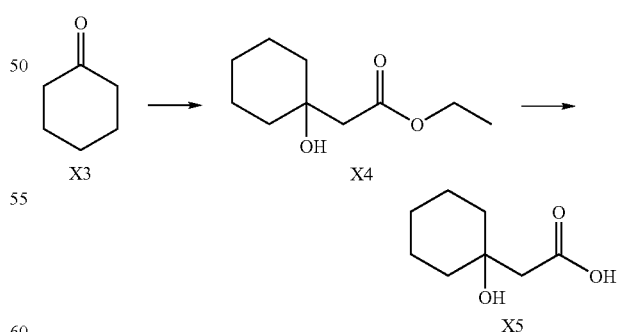

Preparation of 2-(1-hydroxycyclohexyl)acetic acid X5

Compound X4 was prepared using essentially the procedure described in Bull. Chem. Soc. Jpn., 1971, 44, 1090.

Specifically, A solution of ethylbromoacetate (8.3 mL) (Aldrich Chemical Co., Milwaukee, Wis., USA) in toluene was added dropewise at 80° C. over 30 min. to a thoroughly stirred mixture of cyclohexanone X3 (4.9 g) and zinc powder (4.9 g) in toluene. The addition was carefully monitored and the temperature was kept at 80° C. After the addition was completed, the mixture was refluxed for 90 min., cooled, decomposed with 1N aqueous HCl, and extracted with Et$_2$O. The organics were washed with water, aq. NaHCO$_3$, dried (MgSO$_4$) and concentrated in vacuo to yield X4 (5.9 g): $^1$H-NMR (CDCl$_3$, 500 MHz) 4.16 (t, 2H), 3.0 (br s, 1H), 2.46 (s, 2H), 1.40-1.69 (m, 10H), 1.27 (t, 3H) ppm; FIA m/z 187.1 ES$^+$.

To a solution of X4 (510 mg) in MeOH was added 1N aqueous NaOH. The reaction mixture was stirred at 60° C. for 1 h, and then concentrated in vacuo. The residue was diluted with water, washed with Et$_2$O and the aqueous layer acidified with 1N aqueous citric acid and extracted with EtOAc. The organics were dried (MgSO$_4$) and concentrated in vacuo to yield after recrystallization compound X5 (220 mg): $^1$H-NMR (CDCl$_3$, 500 MHz) 3.63 (s, 1H), 2.45 (s, 2H), 1.22-1.64 (m, 10H) ppm; FIA m/z 157.2 ES$^-$.

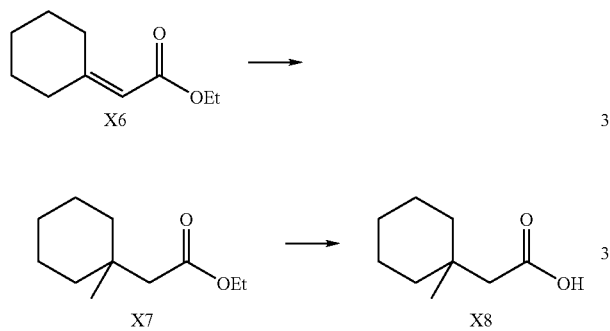

Preparation of 2-(1-methylcyclohexyl)acetic acid (X8)

Commercially available compound X6 (Aldrich Chemical Co., Milwaukee, Wis., USA) was converted to compound X7 according to the method described by N. Asao et al. in Tetrahedron Lett., 2003, 44, 4265. $^1$H-NMR (CDCl$_3$, 500 MHz): 4.12 (q, 2H), 2.22 (s, 2H), 1.30-1.48 (m, 10H), 1.25 (t, 3H), 1.01 (s, 3H) ppm.

To a solution of compound X7 in EtOH was added 1 N aqueous NaOH. The reaction mixture was stirred at 50° C. for 3 hrs, and then concentrated in vacuo. The residue was diluted with water, washed with Et$_2$O and the aqueous layer acidified with 1 N aqueous citric acid and extracted with CH$_2$Cl$_2$. The organics were dried (MgSO$_4$) and concentrated in vacuo to yield compound X8. $^1$H-NMR (CDCl$_3$, 500 MHz): 11.7 (s, 1H), 2.26 (s, 2H), 1.32-1.49 (m, 10H), 1.05 (s, 3H) ppm.

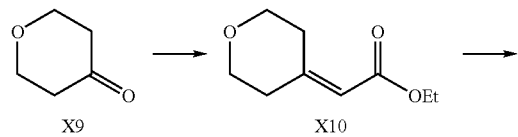

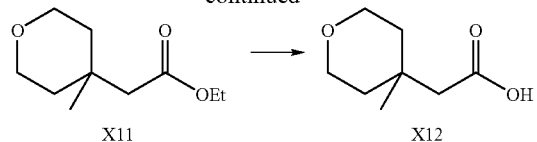

Preparation of 2-(4-methyltetrahydro-2H-pyran-4-yl)acetic acid (X12)

To a solution of dihydro-2H-pyran-4(3H)-one (X9) (3.13 g, from Aldrich) in toluene was added (carbethoxymethylene)-triphenylphosphorane (12.0 g, Aldrich). The solution was stirred at 110° C. for 3 days. The resulting dark solution was concentrated in vacuo and the residue directly purified by column over silica gel to yield compound X10 (4.54 g) as a clear liquid. $^1$H-NMR (CDCl$_3$, 500 MHz): 5.66 (s, 1H), 4.16 (q, 2H), 3.98 (s, 4H), 3.00 (t, 2H), 2.38 (m, 2H), 1.77 (m, 4H), 1.27 (t, 3H) ppm.

Compounds X11 and X12 were obtained in a similar manner as described for compounds X7 and X8. $^1$H-NMR (CDCl$_3$, 500 MHz): 3.64-3.73 (m, 4H), 2.35 (s, 2H), 1.65 (ddd, 2H), 1.50 (ddt, 2H), 1.17 (s, 3H) ppm.

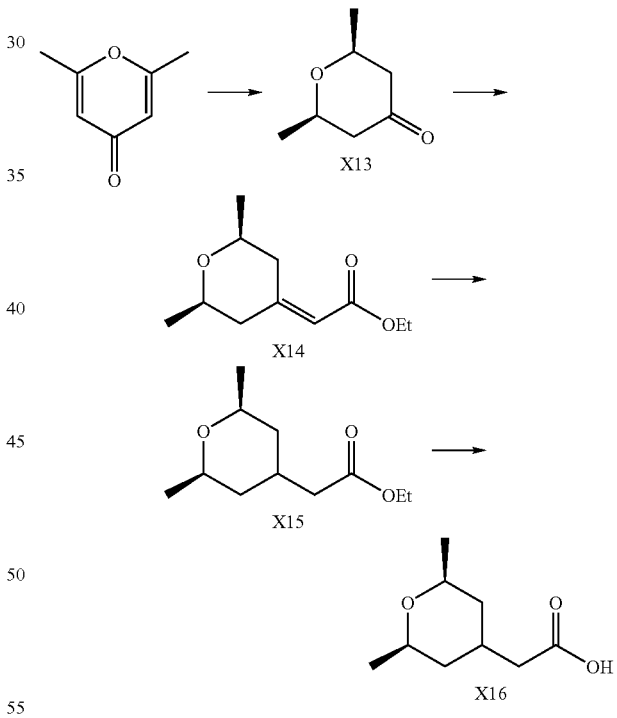

Preparation of 2-(cis-2,6-dimethyltetrahydro-2H-pyran-4-yl)acetic acid (X16)

Intermediate X13 was prepared from commercially available 2,6-dimethyl-g-pyrone (Aldrich Chemical Co., Milwaukee, Wis., USA). A solution of the g-pyrone was dissolved in EtOH and hydrogenated (2 atm. H$_2$) with 10% Pd/C over 2 h. The catalyst was subsequently filtered off and the solution was concentrated in vacuo to yield crude X13 which was purified by column chromatography to yield pure compound X13. $^1$H-NMR (CDCl$_3$, 500 MHz): 3.72 (m, 2H), 2.35 (m, 2H), 2.21 (dd, 2H), 1.32 (d, 6H) ppm.

Compound X14 was then obtained from compound X13 in a similar manner as described for compound X10. $^1$H-NMR (CDCl$_3$, 500 MHz): 5.65 (s, 1H), 4.15 (q, 2H), 3.80 (dt, 1H), 3.49 (m, 2H), 2.17 (dt, 1H), 2.07 (dd, 1H), 1.79 (dt, 1H), 1.28 (m, 9H) ppm. LC-MS m/z 199.126 ES$^+$.

A solution of compound X14 in EtOAc was then hydrogenated (1 atm. H$_2$) with 10% wet Pd/C over 1 hr. The catalyst was subsequently filtered off and the solution was concentrated in vacuo to yield crude compound X15 which was used without further purification for the next step. Compound X16 was then prepared from compound X15 in a similar manner as described for compound X8. $^1$H-NMR (CDCl$_3$, 500 MHz) major diastereomer: 3.50 (m, 2H), 2.27 (d, 2H), 2.07 (m, 1H), 1.71 (m, 2H), 1.19 (d, 6H) 0.92 (m, 2H) ppm; major diastereomer: 3.64 (m, 2H), 2.56 (d, 2H), 2.47 (m, 1H), 1.49 (m, 2H), 1.15 (d, 6H), 0.86 (m, 2H) ppm.

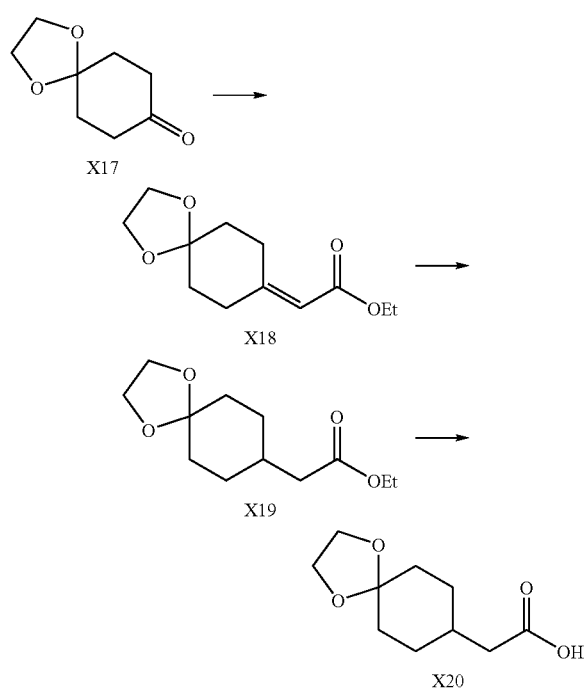

Preparation of 2-(1,4-dioxaspiro[4.5]decan-8-yl)acetic acid X20

Compound X20 was prepared from compound X17 (from Aldrich) according to the procedures described above for preparing compound X16.

Compound X18: $^1$H-NMR (CDCl$_3$, 500 MHz): 5.66 (s, 1H), 4.15 (q, 2H), 3.98 (s, 4H), 3.00 (m, 2H), 2.38 (m, 2H), 1.77 (m, 4H), 1.27 (t, 3H) ppm.

Compound X19: $^1$H-NMR (CDCl$_3$, 500 MHz): 4.12 (q, 2H), 3.93 (s, 4H), (d, 2H), 1.83 (m, 1H), 1.72 (m, 4H), 1.56 (dt, 2H), 1.33 (m, 2H), 1.30 (m, 3H) ppm.

Compound X20: $^1$H-NMR (CDCl$_3$, 500 MHz): 3.93 (s, 4H), 2.28 (d, 2H), 1.73-1.86 (m, 4H), 1.57 (dt, 2H), 1.35 (m, 2H) ppm.

Preparation of 2-(trans-2,6-dimethyltetrahydro-2H-pyran-4-yl)acetic acid 25

Compounds X21 and X22 were prepared according to the method described by S. Danishefsky et al. in J. Org. Chem. 1982, 47, 1597-1598 and D. S. Reddy et al. in J. Org. Chem. 2004, 69, 1716-1719, respectively. Compound X25 was prepared from compound X22 according to the method described above for preparing compound X16.

Compound X23. $^1$H-NMR (CDCl$_3$, 500 MHz): 5.72 (s, 1H), 4.16 (q, 2H), 4.08 (q, 2H), 3.06 (dd, 1H), 2.75 (dd, 1H), 2.39 (dd, 1H), 2.05 (dd, 1H), 1.28 (t, 3H), 1.19 (m, 6H) ppm.

X25: $^1$H-NMR (CDCl$_3$, 500 MHz) 4.24 (m, 1H), 3.78 (m, 1H), 2.25 (m, 3H), 1.71 (m, 1H), 1.53 (m, 1H), 1.46 (m, 1H), 1.29 (d, 3H), 1.13 (d, 3H), 0.90 (m, 1H) ppm.

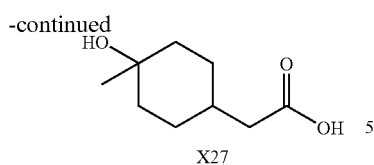

Preparation of
2-(4-hydroxy-4-methylcyclohexyl)acetic acid X27

A solution of compound X20 in dioxane was treated with 4N HCl in dioxane. The reaction solution was stirred at room temperature for 4 hrs and concentrated in vacuo to give crude compound X26 which was used without further purification for the next step. To a stirred solution of compound X26 in THF was slowly added MeMgBr (3 N in THF). The resulting mixture was stirred at 40° C. for 3 hrs, quenched with 1 N aqueous citric acid and diluted with EtOAc. The phase were separated and the organics were dried (MgSO$_4$), concentrated in vacuo and purified by chromatography over silica gel to give compound X27 as a mixture of two diastereomers: isomer 1: $^1$H-NMR (CDCl$_3$, 500 MHz): 4.50 (br s), 2.27 (m, 2H), 1.75 (m, 1H), 1.65 (m, 4H), 1.39 (m, 4H), 1.22 (s, 3H) ppm; isomer 2: $^1$H-NMR (CDCl$_3$, 500 MHz): 2.12 (m, 2H), 1.69 (m, 3H), 1.56 (m, 2H), 1.39 (m, 2H), 1.12 (s, 3H), 1.05 (m, 2H) ppm.

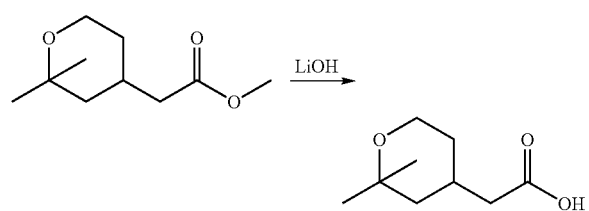

Preparation of
2-(2,2-dimethyltetrahydro-2H-pyran-4-yl)acetic acid

To a solution of the methyl ester (500 mg; 2.69 mmol) in THF (21.5 mL), MeOH (21.5 mL) and water (10.75 mL) was added LiOH (1 N; 10.75 mL). The reaction mixture was stirred for 3 hrs. The reaction was acidified with HCl (1 N, pH=5). The product was extracted with EtOAc (twice, 20 mL each). The combined organic layer was then wash with water, brine and concentrated in vacuo to afford 420 mg of 2-(2,2-dimethyltetrahydro-2H-pyran-4-yl)acetic acid. $^1$H-NMR (CDCl$_3$): δ 3.76-3.67 (m, 2H), 2.56-2.19 (m, 3H), 1.63 (m, 2H), 1.26-1.10 (m, 8H). (M+1) 173.

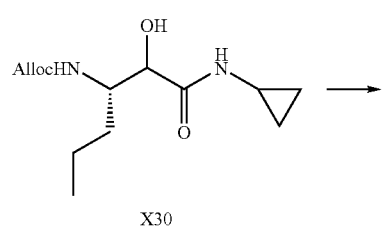

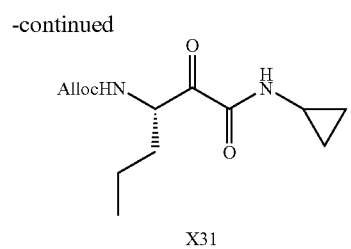

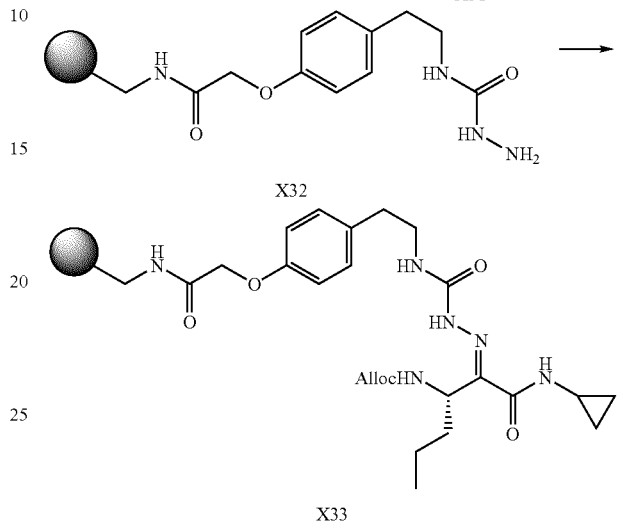

To a solution of compound X30 (64 g, 237 mmol) and EDC (226 g, 1.19 mol) in EtOAc (1.5 L) was added DMSO (400 mL), and the resulting suspension was cooled to 0° C. To this mixture was added a solution of dichloroacetic acid in EtOAc (1:1 v/v, 130 mL) keeping the internal reaction temperature below 25° C. The reaction was warmed to room temperature, stirred for 15 minutes, cooled to 0° C., and quenched with 1 N HCl (1 L). The organic layer was separated, washed with H$_2$O (2×500 mL), dried over MgSO$_4$, and concentrated under reduced pressure. The resulting oil was filtered through a plug of silica eluting with EtOAc/hexanes to afford 48 g (76%) of compound X31 as a white solid.

To resin X32 (prepared according to the procedure described in WO 00/23421) (100 g, 0.88 mmol/g) was added a solution of X31 (48 g, 179 mmol) in THF (650 mL), followed by AcOH (30 mL). The mixture was shaken for 16 hrs, and the resin was filtered, washed with THF (4 times, 400 mL each) and CH$_2$Cl$_2$ (4 times, 400 mL each) and dried in vacuo. The filtrate and washes were combined and concentrated, and the above procedure was repeated to afford resin X33 with a loading of approximately 0.4 mmol/g.

Preparation of Aldehyde Compounds 5-chloronicotinaldehyde was prepared according to methods described by D. L. Comins et al. in Hetereocycles, 1987, 26 (8), pp. 2159-2164.

Some other aldehydes such as 2-fluoro-5-chlorobenzaldehyde, 2-methoxy-3-methyl benzaldehyde, 2-methoxynicotinaldehyde, 2,3-dihydrobenofuran-7-carbaldehyde can be made from corresponding acid based on following procedure:

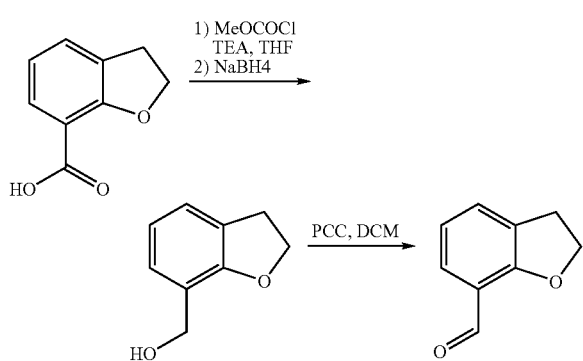

Preparation of 2,3-dihydrobenzofuran-7-carbaldehyde 2,3-Dihydrobenzofuran-7-carboxylic acid (820 mg, 5 mmol) was dissolved in THF (10 mL). To the solution was added TEA (0.7 mL, 5 mmol) and methylchloroformate (0.43 mL, 5 mmol). The solution was stirred for 0.5 hr. The white precipitates were removed by filtration, the filtrate was added to a solution of NaBH$_4$ (437 mg, 12.5 mmol) in H$_2$O (5 mL). The resulting solution was stirred overnight. The reaction mixture was neutralized with 2 M aqueous HCl solution and then extracted with EtOAc. The organic layer was washed with brine, dried over anhydrous Na$_2$SO$_4$ and concentrated in vacuo. The crude alcohol was dissolved in DGM. To the solution was added PCC (1.83 g, 7.5 mmol). The mixture was stirred for 2 hrs at room temperature and diluted with diethyl ether, then ether layers were decanted. Combined organic layer was filtered though a layer of Celite®. The filtrate was concentrated to give crude product. The crude was purified from column with 10% EtOAc/hexane to afford 450 mg of 2,3-dihydrobenzofuran-7-carbaldehyde as a slightly yellow solid. HPLC 4.3 min.

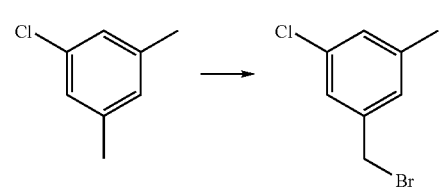

Preparation of 4-chloropicolinaldehyde

A suspension of MnO$_2$ (7.3 g, 84 mmol) and (4-chloropyrindin-2-yl)methanol (1 g, 7 mmol) in CHCl$_3$ was heated to refulx for 90 minutes. The mixture was filtered though a layer of Celite® and concentrated in vacuo to afford 520 mg of 4-chloropicolinaldehyde as a white solid. HPLC 1.8 minutes and MS 142 as M=1 peak.

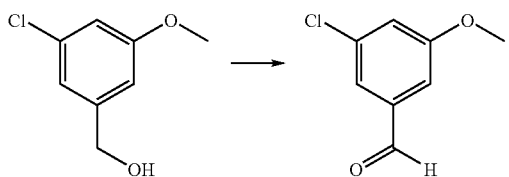

Preparation of 3-chloro-5-methoxybenzaldehyde

A mixture of 3-chloro-5-methoxybenzyl alcohol (5.0 g, 28.9 mmol) and pyridinium chlorochromate (20% on alumina, 40 g, 37.8 mmol) was allowed to stir for 1.25 hr. Diethyl ether (200 ml) was then added followed by filtration of precipitate. The filtrate was concentrated under reduced pressure and the resulting residue was purified via silica gel chromatography using 40% dichloromethane, 60% petroleum ether as eluant, to give 3.8 g of 3-chloro-5-methoxybenzaldehyde (78%). $^1$H-NMR (CDCl$_3$): 3.84 (s, 3H) 7.13 (s, 1H), 7.28 (s, 1H), 7.41 (s, 1H), 9.89 (s, 1H).

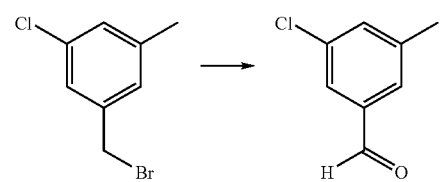

Preparation of 1-(bromomethyl)-3-chloro-5-methylbenzene

To a solution of m-chloroxylene (0.96 g, 6.8 mmol) in carbon tetrachloride at reflux was added N-bromosuccinimide (1.4 g, 7.5 mmol) followed by benzoyl peroxide (1.6 g, 6.8 mmol). The reaction was allowed to stir for 20 minutes and cooled to room temperature, filtered off precipitate and the filtrate was concentrated under reduced pressure and the resulting residue was purified via silica gel chromatography using petroleum ether as eluant to give 0.89 g of 1-(bromomethyl)-3-chloro-5-methylbenzene (60%). NMR (CDCl$_3$): 2.31 (s, 3H) 4.37 (s, 2H) 7.09 (s, 1H) 7.12 (s, 1H) 7.20 (s, 1H).

Preparation of 3-chloro-5-methylbenzaldehyde

To a solution of sodium metal (52 mg, 2.3 mmol) in ethanol was added 2-nitropropane (0.23 g, 2.4 mmole) followed by the addition of 3-chloro-5-methybenzylbromide (0.5 g, 2.3 mmol). The reaction was allowed to stir for 3 hrs and the precipitate formed was filtered off. The filtrate was concentrated under reduced pressure, redissolved in diethylether and washed with 1N sodium hydroxide (twice), water, and dried over sodium sulfate, filtered and the filtrate was concentrated under reduced pressure. The resulting residue was purified via silica gel chromatography using 10% dichloromethane and 90% petroleum ether, to give 0.15 g of 3-chloro-5-methylbenzaldehyde (42%). $^1$H-NMR (CDCl$_3$): 2.46 (s, 3H) 7.43 (s, 1H) 7.56 (s, 1H) 7.68 (s, 1H), 9.92 (s, 1H).

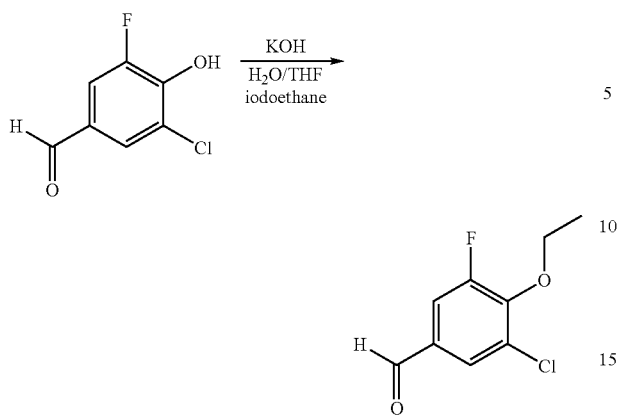

3-Chloro-5-fluoro-4-hydroxybenzaldehyde (1.0 gram, 5.7 mmol) in THF (40 mL) was heated at reflux for 17 hrs with KOH (534 mg, 9.5 mmol, 1.7 eq) in water (5 mL) and iodoethane (1 mL, 2.2 eq). The reaction was then transferred to a separatory funnel with water and extracted with methylene chloride (thrice, 150 mL each). The combined organic layers were washed with 10% aqueous HCl (40 mL), dried (MgSO$_4$), and concentrated to a viscous orange liquid to yield 1.13 g of 3-chloro-4-ethoxy-5-fluorobenzaldehyde (98%). $^1$H-NMR (500 MHz, CDCl$_3$): 9.84 (d, J=1.9 Hz, 1H), 7.71 (t, J=1.6 Hz, 1H), 7.53 (dd, J=1.9, 10.7 Hz, 1H), 4.37-4.32 (m, 2H), 1.47-1.40 (m, 3H).

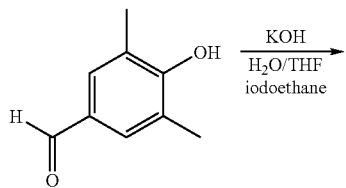

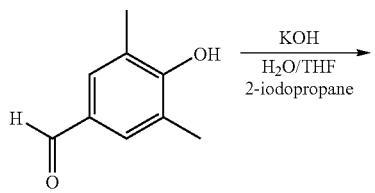

4-Ethoxy-3,5-dimethylbenzaldehyde was prepared in a manner similar to that of 3-chloro-4-ethoxy-5-fluorobenzaldehyde. $^1$H-NMR (300 MHz, CDCl$_3$): 9.89 (s, 1H), 7.56 (s, 2H), 3.91 (q, 7 Hz, 1H), 2.34 (s, 6H), 1.44 (t, J=7 Hz, 6H).

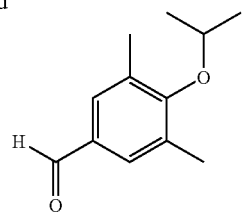

4-Isopropoxy-3,5-dimethylbenzaldehyde was prepared in a manner similar to that of 4-Ethoxy-3,5-dimethylbenzaldehyde. $^1$H-NMR (300 MHz, CDCl$_3$): 9.88 (s, 1H), 7.55 (s, 2H), 4.31 (q, J=6 Hz, 1H), 2.32 (s, 6H), 1.32 (d, J=6 Hz, 6H).

4-(Cyclopropylmethoxy)-3,5-dimethylbenzaldehyde was prepared in a manner similar to that of 4-Ethoxy-3,5-dimethylbenzaldehyde. $^1$H-NMR (300 MHz, CDCl$_3$): 9.87 (s, 1H), 7.55 (s, 2H), 3.69 (d, J=7 Hz, 2H), 2.35 (s, 6H), 1.35-1.23 (m, 1H), 0.67-0.060 (m, 2H), 0.35-0.30 (m, 2H).

Preparation of (S)-1-(tert-butoxycarbonyl)-4-oxopyrrolidine-2-carboxylic acid

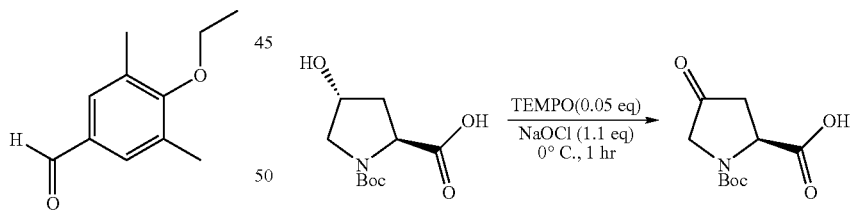

A solution of (2S,4R)-1-(tert-butoxycarbonyl)-4-hydroxypyrrolidine-2-carboxylic acid (1.0 eq.) in isopropyl acetate (5 vol) was cooled to 0° C. and TEMPO (0.05 eq.) was added. A solution of bleach (12.5 wt %, 1.2 eq., 2.6 vol) was then slowly added over 1 hr while maintaining the temperature at 0-5° C. The mixture was stirred and monitored by HPLC for completion, then aqueous 10% KHSO$_4$ (2.5 vol) was added, stirred for 10 minutes, and then the phases were separated. The organic phase was washed with aqueous 5% Na$_2$SO$_3$ (2 vol) then brine (1 vol) then dried azeotropically and concentrated to afford the title compound as a solid. The solid was triturated with acetonitrile (1.0 vol) to remove residual color and impurities. $^1$H-NMR (400 MHz, DMSO): δ 4.54 (m, 1H), 3.82 (m, 1H), 3.67 (m, 1H); 3.15 (m, 1H); ≈2.50 (m, 1H, coincides with DMSO); 1.42 and 1.39 (2s rotamers, 9H).

Preparation of (S)-1-(tert-butoxycarbonyl)-4-methyl-enepyrrolidine-2-carboxylic acid

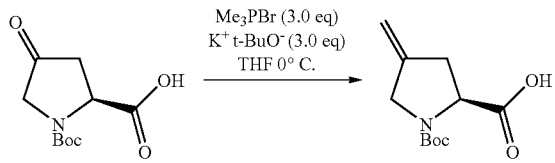 [SMILES: CC(C)(C)OC(=O)N1CC(=O)C[C@H]1C(=O)O ; C=C1C[C@@H](C(=O)O)N(C(=O)OC(C)(C)C)C1]

To a suspension of methyltriphenylphosphonium bromide (2.2 eq.) in 2-methyl tetrahydrofuran (3 vol) was added rapidly solid potassium tert-butoxide (2.3 eq.) maintaining the temperature around 0° C. The temperature was kept at +20° C. for 2 hrs (a suspension remained) and re-cooled to 0° C. Keeping the temperature below 6° C., (S)-1-(tert-butoxycarbonyl)-4-oxopyrrolidine-2-carboxylic acid (1 eq.) was added over 40 minutes. The reaction was warmed to room temperature and stirred for 16 h and then cooled to 0° C. The reaction was quenched with saturated NaHCO$_3$ (5 vol) and water (2 vol) and the aqueous layer was separated. The organic layer was extracted with saturated NaHCO$_3$/water (1.8 vol/1.8 vol) and the combined aqueous layers were filtered through Celite®. The aqueous layer was acidified with 6 N HCl (2.6 vol) at ambient temperature and extracted twice with isopropyl acetate (16 vol, then 8 vol). The organic phase was dried (MgSO$_4$) and the solvent removed. The crude product was dissolved in isopropyl acetate (10 vol) and extracted with 0.5 M NaOH (10 vol, then 1 vol). The combined aqueous layers were acidified at ambient temperature with 6 N HCl to pH=3, and extracted twice with ethyl acetate (10 vol, then 8 vol). The combined extracts were dried (Na$_2$SO$_4$), the solvent removed and the crude product was recrystallized from cyclohexane (5 vol) to afford the title compound. $^1$H-NMR (400 MHz, DMSO): δ 12.9, (broad, 1H); 5.00 (m, 2H); 4.24 (dt, J=1.9H, J=7.3 Hz, 1H), 3.91 (m, 2H); 2.98 (m, 1H); ≈2.50 (m, 1H, coincides with DMSO); 1.41 and 1.36 (2s rotamers, 9H).

B. Synthesis of Exemplary Compounds of Formula I

Certain exemplary compounds of Formula I may be prepared by Method 1 as illustrated below.

All of the following reactions were performed under nitrogen and used anhydrous solvents unless otherwise noted.

Example 1

(5S,8S)-7-((S)-2-(2-cyclohexylacetamido)-3,3-dimethylbutanoyl)-N-((S)-1-(cyclopropylamino)-1,2-dioxohexan-3-yl)-2-oxo-3-phenyl-1-oxa-3,7-diazaspiro[4.4]nonane-8-carboxamide (Cmpd No. 8)

Step A: (2S)-di-tert-butyl 4-(2-ethoxy-2-oxoethyl)-4-hydroxypyrrolidine-1,2-dicarboxylate (A1)

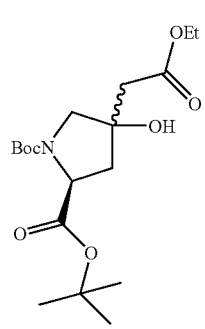

A1

Zinc dust (1.05 g, 16 mmol, 1.6 eq.) in a flask was heated with a heat gun two times. Dry THF (10 mL) and chlorotrimethylsilane (0.405 mL, 3.2 mmol, 0.32 eq.) were added to this flask. The suspension was stirred for 15 min at room temp., heated to reflux, and then removed from the heat. (S)-di-tert-butyl 4-oxopyrrolidine-1,2-dicarboxylate (2.85 g, 10 mmol, 1 eq.) and ethyl 2-bromoacetate (1.77 mL, 16 mmol, 1.6 eq.) were combined with dry THF (10 mL), and added slowly to the Zinc suspension at a rate that at which a gentle reflux was observed. The reaction was refluxed for 2 hrs and monitored by TLC. Upon completion, the reaction was concentrated. Chromatography using hexanes and ethyl acetate gave 2.64 g (7.3 mmol) of (2S)-di-tert-butyl 4-(2-ethoxy-2-oxoethyl)-4-hydroxypyrrolidine-1,2-dicarboxylate (A1) as a 4:1 (2S,4S:2S,4R) mixture of the diastereomers. $^1$H NMR (300 MHz, DMSO) 4.97 (m, 1H), 4.14-4.01 (m, 3H), 3.48-3.33 (m, 2H), 2.56 (m, 2H), 2.35-2.19 (m, 1H), 2.03 (dd, 1H), 1.40-1.35 (m, 18H), 1.18 (t, 3H).

Step B: (8S)-di-tert-butyl 2-oxo-1-oxa-3,7-diazaspiro[4.4]nonane-7,8-dicarboxylate (B1)

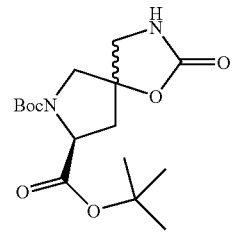

(2S)-di-tert-butyl 4-(2-ethoxy-2-oxoethyl)-4-hydroxypyrrolidine-1,2-dicarboxylate (A1) (1.58 g, 4.42 mmol, 1 eq.) was diluted in methanol (6 mL). To this mixture, hydrazine (0.417 mL, 13.26 mmol, 3 eq.) was added. The reaction was stirred at room temp. overnight then concentrated. To the residue, 0.5 N HCl (22.1 mL, 11.05 mmol, 2.5 eq.) was added and the mixture was sonnicated until the residue dissolved in the acid. The solution was cooled in an icewater bath. A 1.0 M solution of NaNO$_2$ (5.3 mL, 5.3 mmol, 1.2 eq.) was added slowly and stirred for 15 min. A 1:1 benzene:chloroform mixture was added, the organic layer was separated and added slowly to refluxing benzene (2×). The reaction was refluxed for 1 hr then concentrated. Chromatography using DCM and 20% MeOH in DCM gave 0.978 g (2.86 mmol) of (8S)-di-tert-butyl 2-oxo-1-oxa-3,7-diazaspiro[4.4]nonane-7,8-dicarboxylate (B1) as a 4:1 (5S,8S:5S,8R) mixture of the diastereomers. $^1$H NMR (300 MHz, DMSO) 7.63 (m, 1H), 4.29-4.09 (m, 1H), 3.65-3.39 (m, 4H), 2.5-2.0 (m, 2H), 1.43-1.18 (m, 18H).

Step C: (5S,8S)-di-tert-butyl-2-oxo-3-phenyl-1-oxa-3,7-diazaspiro[4.4]nonane-7,8-dicarboxylate (C1)

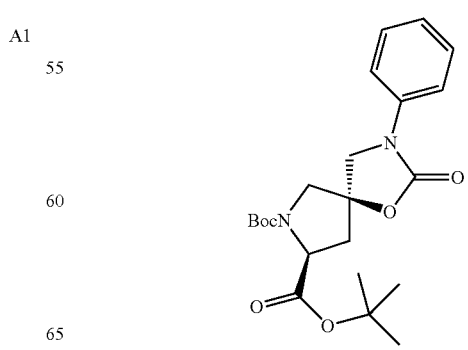

(8S)-di-tert-butyl 2-oxo-1-oxa-3,7-diazaspiro[4.4]nonane-7,8-dicarboxylate (B1) (0.189 g, 0.55 mmol, 1 eq.), Xantphos (4,5-Bis(diphenylphosphino)-9,9-dimethylxanthene) (17.4 mg, 0.03 mmol, 0.06 eq.), K₃PO₄ (148.6 mg, 0.7 mmol, 1.4 eq.) were combined in a sealable tube, evacuated, and purged with nitrogen 3 times. Dry 1,4-dioxane (20 mL) was added and the suspension was degassed for 0.5 hrs. Pd₂(dba)₃ (9.1 mg g, 0.01 mmol, 0.02 eq.) was added and the sealable tube was degassed for an additional 15 min. Bromobenzene (53 µL, 0.5 mmol, 1 eq.) was added, the reaction was sealed and heated at 95° C. for 72 hrs (later optimization showed that 24 hrs were sufficient and additional equivalents of bromobenzene, up to 3 eq., gave higher yields). The reaction was cooled, filtered and flushed with DCM. Chromatography on the organic layer using hexanes and ethyl acetate with a conservative gradient separated the diastereomers to give 50 mg (0.12 mmol) of (5S,8S)-di-tert-butyl-2-oxo-3-phenyl-1-oxa-3,7-diazaspiro[4.4]nonane-7,8-dicarboxylate (C1). ¹H NMR (300 MHz, DMSO) 7.52 (d, 2H), 7.43-7.37 (m, 2H), 7.14 (t, 1H), 4.22-4.07 (m, 3H), 3.85 (d, 1H), 3.60-3.46 (m, 1H), 2.8-2.65 (m, 1H), 2.27-2.19 (m, 1H), 1.42 (m, 18H).

Step D: (5S,8S)-tert-butyl 2-oxo-3-phenyl-1-oxa-3,7-diazaspiro[4.4]nonane-8-carboxylate (D1)

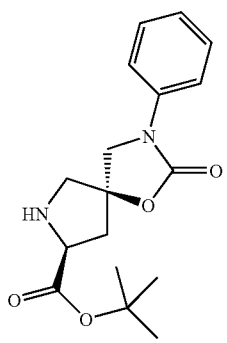

D1

(5S,8S)-di-tert-butyl-2-oxo-3-phenyl-1-oxa-3,7-diazaspiro[4.4]nonane-7,8-dicarboxylate (C1) (0.262 g, 0.626 mmol, 1 eq.) was added to a flask and cooled in an ice water bath. 1.0 M HCl in anhydrous ethyl acetate (6.26 mL, 6.26 mmol, 10 eq.) was added to the cooled intermediate, and the mixture was stirred at room temp. overnight. The solvent was evaporated while the mixture was cold. Chromatography using DCM and 20% MeOH in DCM gave 148 mg (466 µmol) of (5S,8S)-tert-butyl 2-oxo-3-phenyl-1-oxa-3,7-diazaspiro[4.4]nonane-8-carboxylate (D1). LC MS+: 319.17 at 1.76 min (10-90%, 3-5 min, Formic Acid).

Step E: (5S,8S)-tert-butyl 7-((S)-2-(benzyloxycarbonylamino)-3,3-dimethylbutanoyl)-2-oxo-3-phenyl-1-oxa-3,7-diazaspiro[4.4]nonane-8-carboxylate (E1)

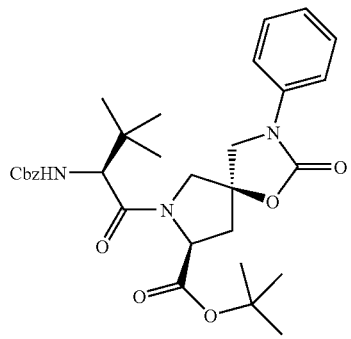

E1

L-Cbz-t-leu-OH (284 mg, 0.642 mmol, 1.4 eq.), EDC (123 mg, 0.642 mmol, 1.4 eq.) and HOBt (98 mg, 0.642 mmol, 1.4 eq.) were combined in DMF (0.9 mL) and stirred for 0.5 hrs at room temp. (5S,8S)-tert-butyl 2-oxo-3-phenyl-1-oxa-3,7-diazaspiro[4.4]nonane-8-carboxylate (D1) (146 mg, 0.459 mmol, 1 eq.) and DIEA (240 µL, 1.377 mmol, 3 eq.) were added to the room temp. mixture, and the resulting mixture was stirred for 24 hrs at room temp. 1.0 M histamine (aq., 230µL, 0.5 eq.) was added to this mixture, and the resulting mixture stirred for 0.5 hrs. Ethyl acetate was added and the mixture was washed first with 1N HCl then 1M K₂CO₃. Ethyl acetate was used for extraction, and this extraction process was repeated once. The combined organic layers were dried on Na₂SO₄ and concentrated. Chromatography using hexanes and ethyl acetate gave (5S,8S)-tert-butyl 7-((S)-2-(benzyloxycarbonylamino)-3,3-dimethylbutanoyl)-2-oxo-3-phenyl-1-oxa-3,7-diazaspiro[4.4]nonane-8-carboxylate (E1). LC MS+: 566.44 at 3.61 min (10-90%, 3-5 min, Formic Acid).

Step F: (5S,8S)-tert-butyl 7-((S)-2-amino-3,3-dimethylbutanoyl)-2-oxo-3-phenyl-1-oxa-3,7-diazaspiro[4.4]nonane-8-carboxylate (F1)

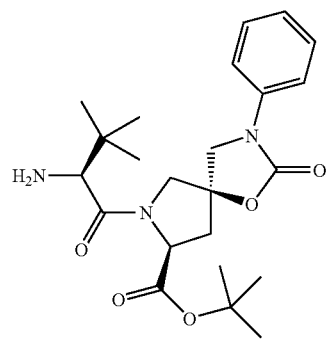

F1

Palladium (10%) on carbon (100 mg) was wetted with MeOH (2.5 mL) and added to (5S,8S)-tert-butyl 7-((S)-2-

(benzyloxycarbonylamino)-3,3-dimethylbutanoyl)-2-oxo-3-phenyl-1-oxa-3,7-diazaspiro[4.4]nonane-8-carboxylate (E1) (323 mg, 411 mot, 1 eq.). The reaction was hydrogenated at 50 psi overnight at room temp., then filtered and concentrated to give (5S,8S)-tert-butyl 7-((S)-2-amino-3,3-dimethylbutanoyl)-2-oxo-3-phenyl-1-oxa-3,7-diazaspiro[4.4]nonane-8-carboxylate (F1) in quantitative yield. LC MS+: 432.39 at 1.94 min (10-90%, 3-5 min, Formic Acid).

Step G: (5S,8S)-tert-butyl 7-((S)-2-(2-cyclohexylacetamido)-3,3-dimethylbutanoyl)-2-oxo-3-phenyl-1-oxa-3,7-diazaspiro[4.4]nonane-8-carboxylate (G1)

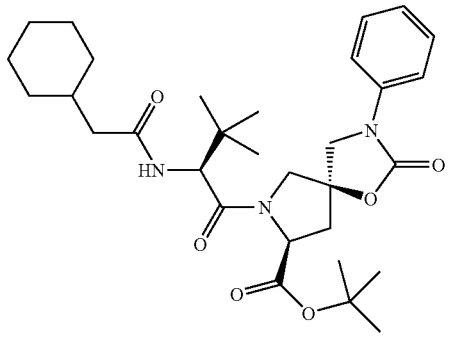

G1

Cyclohexylacetic acid (48 mg, 337 µmol, 1.4 eq.), EDC (65 mg, 337 µmol, 1.4 eq.) and HOBt (52 mg, 337 µmol, 1.4 eq.) were combined in DMF (0.3 mL) and stirred for 0.5 hrs. at room temp. (5S,8S)-tert-butyl 7-((S)-2-amino-3-dimethylbutanoyl)-2-oxo-3-phenyl-1-oxa-3,7-diazaspiro[4.4]nonane-8-carboxylate (F1) (105 mg, 243 µmol, 1 eq.) and DIEA (118 µL 675 µmol, 2.8 eq.) were added to this mixture and the resulting mixture was stirred for 24 hrs at room temp. 1.0 M histamine (aq., 120 µL, 0.5 eq.) was added and the mixture was stirred for 0.5 h. Ethyl acetate was added and the mixture was washed with 1N HCl then 1M K$_2$CO$_3$ and extracted with ethyl acetate (2×). The combined organic layers were concentrated and chromatography using hexanes and ethyl acetate gave 50 mg of (5S,8S)-tert-butyl 7-((S)-2-(2-cyclohexylacetamido)-3,3-dimethylbutanoyl)-2-oxo-3-phenyl-1-oxa-3,7-diazaspiro[4.4]nonane-8-carboxylate (G1). $^1$H NMR (300 MHz, DMSO) 7.90 (d, 1 H), 7.53 (d, 2 H), 7.44-7.37 (m, 2H), 7.14 (m, 1H), 4.47 (d, 1H), 4.30-3.99 (m, 3H), 3.89-3.83 (m, 1H), 3.18 (d, 1H), 2.79-2.67 (m, 1H), 2.27-2.00 (m, 3H), 1.7-1.55 (m, 5H), 1.45-1.39 (m, 11H), 1.2-1.1 (m, 4H), 0.98-0.91 (m, 9H). Later optimization showed that steps E to G could be replaced by doing a single coupling on E1 with (S)-2-(2-cyclohexylacetamido)-3,3-dimethylbutanoic acid. NMR confirmed that epimerization was not occurring.

Step H: (5S,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (H1)

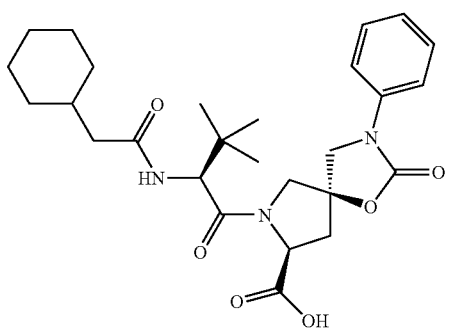

H1

(5S,8S)-tert-butyl 7-((S)-2-(2-cyclohexylacetamido)-3,3-dimethylbutanoyl)-2-oxo-3-phenyl-1-oxa-3,7-diazaspiro[4.4]nonane-8-carboxylate (G1) (70 mg, 126 µmol, 1 eq.) was diluted in 1:1 DCM:TFA (2 mL) and stirred overnight at room temp. then concentrated to give (5S,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (H1) in quantitative yield. LC MS+/−: 500.41/498.55 at 3.09 min (10-90%, 3-5 min, Formic Acid).

Step I: (5S,8S)-7-((S)-2-(2-cyclohexylacetamido)-3,3-dimethylbutanoyl)-N-((3S)-1-(cyclopropylamino)-2-hydroxy-1-oxohexan-3-yl)-2-oxo-3-phenyl-1-oxa-3,7-diazaspiro[4.4]nonane-8-carboxamide (I1)

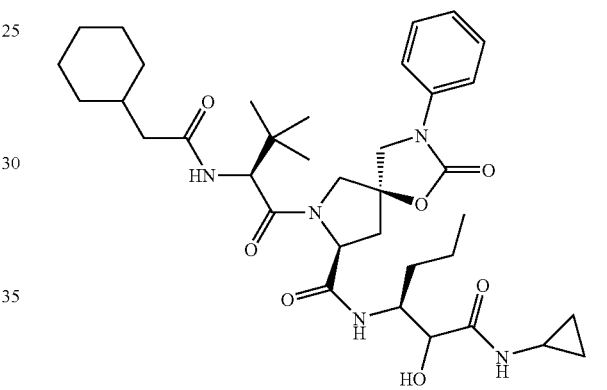

I1

(3S)-3-amino-N-cyclopropyl-2-hydroxyhexanamide (20 mg, 87 µmol, 1.4 eq.), EDC (17 mg, 87 µmol, 1.4 eq.) and HOBt (13 mg, 87 µmol, 1.4 eq.) were combined in DMF (0.3 mL) and stirred at room temp. for 0.5 hrs. (5S,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (H1) (31 mg 62 µmol, 1 eq.) and DIEA (33 µL, 186 mol, 3 eq.) were added to the mixture and stirred at room temp. overnight. 1.0 M histamine (aq., 31 µL, 0.5 eq.) was added and the resulting mixture was stirred for 0.5 hrs. Ethyl acetate was added and the mixture was washed first with 1N HCl then with 1M K$_2$CO$_3$; and then extracted with ethyl acetate. The combined organic layers concentrated and chromatography using DCM and 20% MeOH in DCM gave 20 mg (30 µmol) of (5S,8S)-7-((S)-2-(2-cyclohexylacetamido)-3,3-dimethylbutanoyl)-N-((3S)-1-(cyclopropylamino)-2-hydroxy-1-oxohexan-3-yl)-2-oxo-3-phenyl-1-oxa-3,7-diazaspiro[4.4]nonane-8-carboxamide (I1). LC MS+/−: 668.56/666.64 at 3.24 min (10-90%, 3-5 min, Formic Acid).

Step J: (5S,8S)-7-((S)-2-(2-cyclohexylacetamido)-3,3-dimethylbutanoyl)-N-((S)-1-(cyclopropylamino)-1,2-dioxohexan-3-yl)-2-oxo-3-phenyl-1-oxa-3,7-diazaspiro[4.4]nonane-8-carboxamide (Cmpd. No. 3)

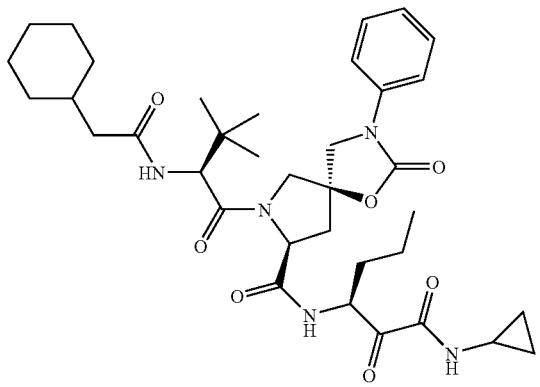

Cmpd No. 3

(5S,8S)-7-((S)-2-(2-cyclohexylacetamido)-3,3-dimethylbutanoyl)-N-((3S)-1-(cyclopropylamino)-2-hydroxy-1-oxohexan-3-yl)-2-oxo-3-phenyl-1-oxa-3,7-diazaspiro[4.4]nonane-8-carboxamide (I1) (20 mg, 30 µmol, 1 eq.) was diluted in DCM. Dess Martin reagent (38 mg, 90 µmol, 3 eq.) was added and the mixture was stirred for 3 hrs at room temp. Na$_2$S$_2$O$_3$ (aq., 5 eq.) was added and the mixture was stirred for another 0.5 hrs. The product was extracted with DCM. Chromatography on the combined organic layers using hexanes and ethyl acetate gave 15.9 mg (24 mot) (5S,8S)-7-((S)-2-(2-cyclohexylacetamido)-3,3-dimethylbutanoyl)-N-((S)-1-(cyclopropylamino)-1,2-dioxohexan-3-yl)-2-oxo-3-phenyl-1-oxa-3,7-diazaspiro[4.4]nonane-8-carboxamide (compound no. 3). $^1$H NMR (300 MHz, CDCl$_3$) 7.5 (d, 2H), 7.4-7.32 (m, 2H), 7.2-7.12 (m, 2H), 6.9 (m, 1H), 6.17 (d, 1H), 5.4-5.3 (m, 1H), 4.77 (t, 1H), 4.65 (d, 1H), 4.42 (d, 1H), 4.15-3.98 (m, 2H), 3.76 (d, 1H), 2.83-2.75 (m, 1H), 2.6 (m, 2H), 2.2-0.8 (m, 31H), 0.6 (m, 2H).

Example 2

(5R,8S)-7-((S)-2-(2-cyclohexylacetamido)-3,3-dimethylbutanoyl)-N-((S)-1-(cyclopropylamino)-1,2-dioxohexan-3-yl)-2-oxo-3-phenyl-1-oxa-3,7-diazaspiro[4.4]nonane-8-carboxamide (Cmpd No. 5)

Step A: (5R,8S)-di-tert-butyl-2-oxo-3-phenyl-1-oxa-3,7-diazaspiro[4.4]nonane-7,8-dicarboxylate (A2)

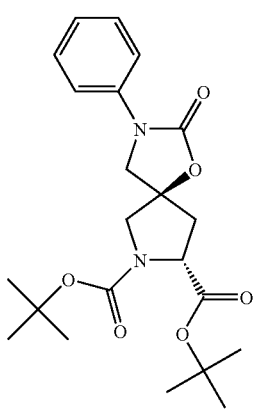

A2

Following the same procedure as Example 1 step C using (8S)-di-tert-butyl 2-oxo-1-oxa-3,7-diazaspiro[4.4]nonane-7,8-dicarboxylate (B1) (1.044 g, 3.05 mmol) gave 475 mg of (5R,8S)-di-tert-butyl-2-oxo-3-phenyl-1-oxa-3,7-diazaspiro[4.4]nonane-7,8-dicarboxylate (A2). $^1$H NMR (300 MHz, DMSO) 7.52 (d, 2H), 7.43-7.37 (m, 2H), 7.14 (t, 1H), 4.37-4.3 (m, 1H), 4.18-4.07 (m, 2H), 3.77-3.6 (m, 2H), 2.6-2.55 (m, 1H), 2.45-2.35 (m, 1H), 1.42 (m, 18H).

Step B: (5R,8S)-tert-butyl 2-oxo-3-phenyl-1-oxa-3,7-diazaspiro[4.4]nonane-8-carboxylate (B2)

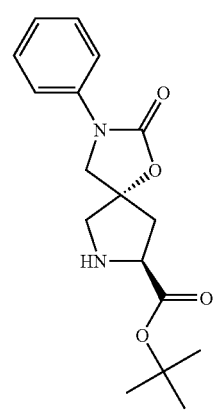

B2

Following the same procedure as Example 1 step D using (5R,8S)-di-tert-butyl-2-oxo-3-phenyl-1-oxa-3,7-diazaspiro[4.4]nonane-7,8-dicarboxylate (A2) (145 mg, 0.346 mmol) gave 92 mg (0.289 mmol) of (5R,8S)-tert-butyl 2-oxo-3-phenyl-1-oxa-3,7-diazaspiro[4.4]nonane-8-carboxylate (B2). $^1$H NMR (300 MHz, DMSO) 7.54 (d, 2H), 7.41-7.36 (m, 2H), 7.15-7.10 (m, 1H), 4.08 (dd, 2H), 3.75-3.70 (m, 1H), 2.90 (m, 1H), 2.31-2.26 (m, 1H), 1.44-1.39 (m, 9H).

Step C: (5R,8S)-tert-butyl 7-((S)-2-(benzyloxycarbonylamino)-3,3-dimethylbutanoyl)-2-oxo-3-phenyl-1-oxa-3,7-diazaspiro[4.4]nonane-8-carboxylate (C2)

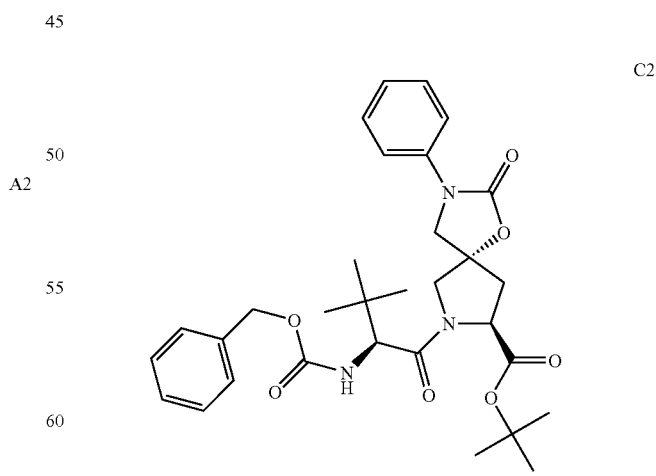

C2

Following the same procedure as Example 1 step E using (5R,8S)-tert-butyl 2-oxo-3-phenyl-1-oxa-3,7-diazaspiro[4.4]nonane-8-carboxylate (B2) (130 mg, 411 µmol) gave (5R,8S)-tert-butyl 7-((S)-2-(benzyloxycarbonylamino)-3,3- dimethylbutanoyl)-2-oxo-3-phenyl-1-oxa-3,7-diazaspiro [4.4]nonane-8-carboxylate (C2). LC MS+: 566.44 at 3.61 min (10-90%, 3-5 min, Formic Acid).

Step D: (5R,8S)-tert-butyl 7-((S)-2-amino-3,3-dimethylbutanoyl)-2-oxo-3-phenyl-1-oxa-3,7-diazaspiro [4.4]nonane-8-carboxylate (D2)

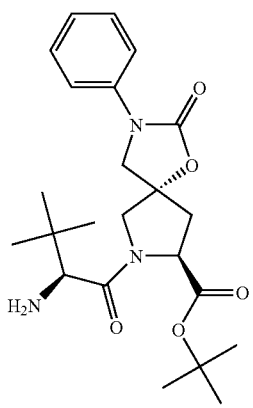

D2

Following the same procedure as Example 1 step F, (5R, 8S)-tert-butyl 7-((S)-2-(benzyloxycarbonylamino)-3,3-dimethylbutanoyl)-2-oxo-3-phenyl-1-oxa-3,7-diazaspiro[4.4] nonane-8-carboxylate (C2) gave (5R,8S)-tert-butyl 7-((S)-2-amino-3,3-dimethylbutanoyl)-2-oxo-3-phenyl-1-oxa-3,7-diazaspiro[4.4]nonane-8-carboxylate (D2). LC MS+: 432.39 at 1.94 min (10-90%, 3-5 min, Formic Acid).

Step E: (5R,8S)-tert-butyl 7-((S)-2-(2-cyclohexylacetamido)-3,3-dimethylbutanoyl)-2-oxo-3-phenyl-1-oxa-3,7-diazaspiro[4.4]nonane-8-carboxylate (E2)

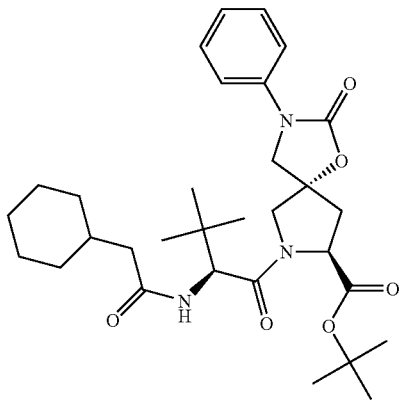

E2

Following the same procedure as Example 1 step G using (5R,8S)-tert-butyl 7-((S)-2-amino-3,3-dimethylbutanoyl)-2-oxo-3-phenyl-1-oxa-3,7-diazaspiro[4.4]nonane-8-carboxylate (94 mg, 218 µmol) gave 70 mg (126 µmol) of (5R,8S)-tert-butyl 7-((S)-2-(2-cyclohexylacetamido)-3,3-dimethylbutanoyl)-2-oxo-3-phenyl-1-oxa-3,7-diazaspiro [4.4]nonane-8-carboxylate (E2). $^1$H NMR (300 MHz, DMSO) 7.85 (d, 1H), 7.55 (d, 2H), 7.44-7.37 (m, 2H), 7.13 (m, 1H), 4.52 (m, 1H), 4.38 (d, 1H), 4.2-3.99 (m, 2H), 3.18 (d, 1H), 2.6 (m, 1H), 2.4 (m, 1H), 2.2-1.94 (m, 3H), 1.7-0.8 (m, 29H).

Step F: (5R,8S)-7-((S)-2-(2-cyclohexylacetamido)-3, 3-dimethylbutanoyl)-2-oxo-3-phenyl-1-oxa-3,7-diazaspiro[4.4]nonane-8-carboxylic acid (F2)

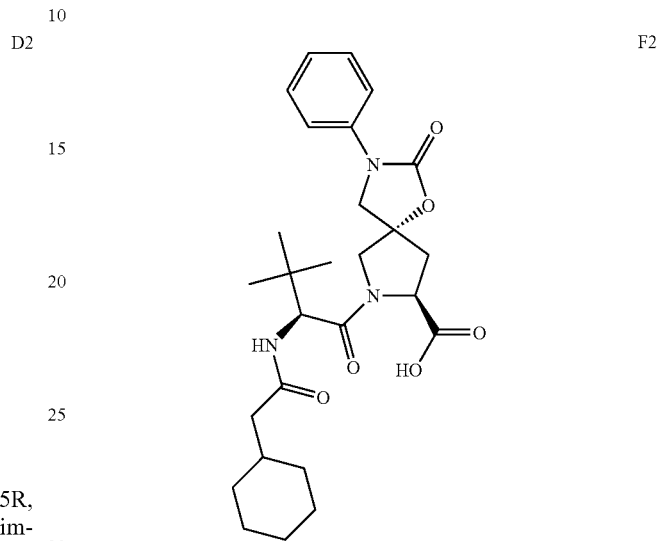

F2

Following the same procedure as Example 1 step H using (5R,8S)-tert-butyl 7-((S)-2-amino-3,3-dimethylbutanoyl)-2-oxo-3-phenyl-1-oxa-3,7-diazaspiro[4.4]nonane-8-carboxylate (70 mg, 126 µmol) gave (5R,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (F2). LC MS+/−: 500.41/498.55 at 3.09 min (10-90%, 3-5 min, Formic Acid).

Step G: (5R,8S)-7-((S)-2-(2-cyclohexylacetamido)-3,3-dimethylbutanoyl)-N-((3S)-1-(cyclopropylamino)-2-hydroxy-1-oxohexan-3-yl)-2-oxo-3-phenyl-1-oxa-3,7-diazaspiro[4.4]nonane-8-carboxamide (G2)

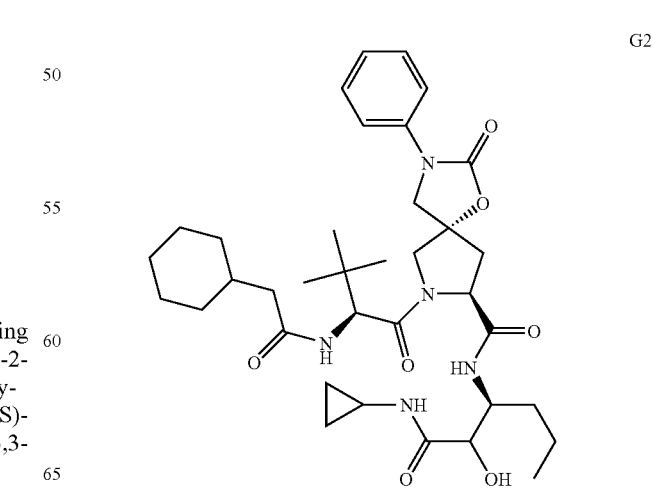

G2

Following the same procedure as Example 1 step 9 using (5R,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (49 mg, 98 μmol) and (3S)-3-amino-N-cyclopropyl-2-hydroxyhexanamide (31 mg, 137 μmol, 1.4 eq.) gave 20 mg (30 μmol) of (5R,8S)-7-((S)-2-(2-cyclohexylacetamido)-3,3-dimethylbutanoyl)-N-((3S)-1-(cyclopropylamino)-2-hydroxy-1-oxohexan-3-yl)-2-oxo-3-phenyl-1-oxa-3,7-diazaspiro[4.4]nonane-8-carboxamide (G2). LC MS+/−: 668.56/666.64 at 3.24 min (10-90%, 3-5 min, Formic Acid).

Step H: (5R,8S)-7-((S)-2-(2-cyclohexylacetamido)-3,3-dimethylbutanoyl)-N-((S)-1-(cyclopropylamino)-1,2-dioxohexan-3-yl)-2-oxo-3-phenyl-1-oxa-3,7-diazaspiro[4.4]nonane-8-carboxamide (Cmpd No. 5)

Cmpd No. 5

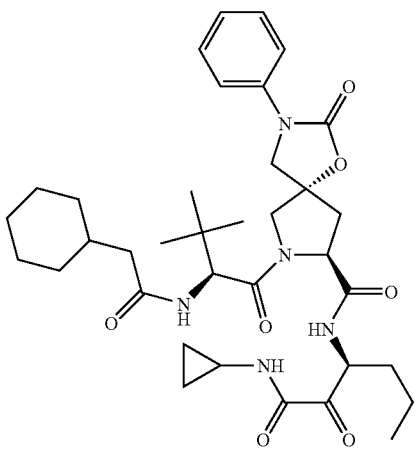

Following the same procedure as Example 1 step 10 using (5R,8S)-7-((S)-2-(2-cyclohexylacetamido)-3,3-dimethylbutanoyl)-2-oxo-3-phenyl-1-oxa-3,7-diazaspiro[4.4]nonane-8-carboxylic acid (20 mg, 30 μmol) gave 14.4 mg (22 μmol) of (5R,8S)-7-((S)-2-(2-cyclohexylacetamido)-3,3-dimethylbutanoyl)-N—((S)-1-(cyclopropylamino)-1,2-dioxohexan-3-yl)-2-oxo-3-phenyl-1-oxa-3,7-diazaspiro[4.4]nonane-8-carboxamide (compound no. 5). $^1$H NMR (300 MHz, CDCl$_3$) 7.6-7.37 (m, 4H), 7.2-7.12 (m, 2H), 6.95 (m, 1H), 6.17 (d, 1H), 5.45-5.35 (m, 1H), 4.75 (m, 1H), 4.45 (d, 1H), 4.35 (d, 1H), 4.25 (d, 1H), 4.15-3.98 (m, 2H), 3.05-2.97 (m, 1H), 2.85-2.73 (m, 1H), 2.3 (m, 1H), 2.15-0.8 (m, 31H), 0.6 (m, 2H).

Example 3

Cyclopentyl (S)-1-((5S,8S)-3-(3-chlorophenyl)-8-((S)-1-(cyclopropylamino)-1,2-dioxohexan-3-ylcarbamoyl)-2-oxo-1-oxa-3,7-diazaspiro[4.4]nonan-7-yl)-3,3-dimethyl-1-oxobutan-2-ylcarbamate (Cmpd No. 7)

Step A: (5S,8S)-di-tert-butyl 3-(3-chlorophenyl)-2-oxo-1-oxa-3,7-diazaspiro[4.4]nonane-7,8-dicarboxylate (A3)

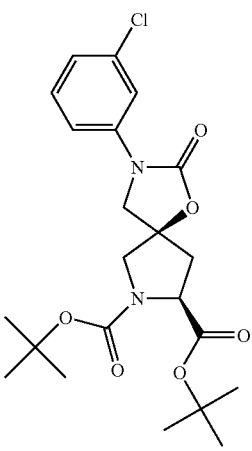

A3

Following the same procedure as Example 1 step 3 using (8S)-di-tert-butyl 2-oxo-1-oxa-3,7-diazaspiro[4.4]nonane-7,8-dicarboxylate (8S)-di-tert-butyl 2-oxo-1-oxa-3,7-diazaspiro[4.4]nonane-7,8-dicarboxylate (B1) (224 mg, 0.654 mmol) and 3-chloro bromobenzene (230 μL, 1.962 mmol, 3 eq.) gave 107 mg (0.236 mmol) of (5S,8S)-di-tert-butyl 3-(3-chlorophenyl)-2-oxo-1-oxa-3,7-diazaspiro[4.4]nonane-7,8-dicarboxylate (A3). $^1$H NMR (300 MHz, DMSO) 7.68 (m, 1H), 7.55-7.38 (m, 2H), 7.2 (m, 1H), 4.23-4.05 (m, 3H), 3.8-3.7 (m, 1H), 3.5 (m, 1H), 2.7-2.6 (m, 1H), 2.25-2.1 (m, 1H), 1.4 (m, 18H).

Step B: (5S,8S)-methyl-3-(3-chlorophenyl)-2-oxo-1-oxa-3,7-diazaspiro[4.4]nonane-8-carboxylate (B3)

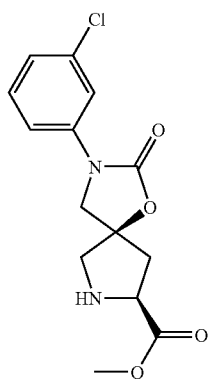

B3

Saturated HCl in MeOH (5 mL) was added to (5S,8S)-di-tert-butyl 3-(3-chlorophenyl)-2-oxo-1-oxa-3,7-diazaspiro[4.4]nonane-7,8-dicarboxylate (107 mg, 0.236 mmol) and stirred at room temp. overnight. The solution was concentrated and chromatography using DCM and 20% MeOH in DCM gave 60 mg (0.193 mmol) of (5S,8S)-methyl-3-(3-chlorophenyl)-2-oxo-1-oxa-3,7-diazaspiro[4.4]nonane-8-carboxylate (B3). $^1$H NMR (300 MHz, DMSO) 7.68 (s, 1H), 7.6-7.4 (m, 2H), 7.23 (m, 1H), 4.62 (m, 1H), 4.22 (m, 2H), 3.85-3.68 (m, 4H), 3.6-3.5 (m, 1H), 2.9-2.7 (m, 2H). LC MS+: 311.14 at 1.65 min (10-90%, 3-5 min, Formic Acid).

Step C: (5S,8S)-methyl-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylate (C3)

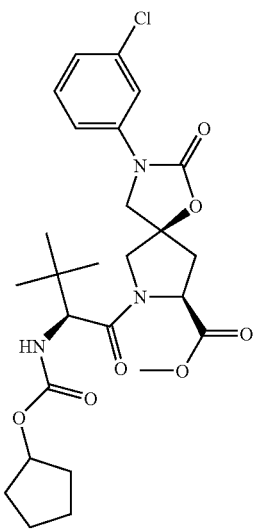

C3

Following the same procedure as Example 1 step G using (5S,8S)-methyl-3-(3-chlorophenyl)-2-oxo-1-oxa-3,7-diazaspiro[4.4]nonane-8-carboxylate (30 mg, 97 µmol) and (S)-2-(cyclopentyloxycarbonylamino)-3,3-dimethylbutanoic acid (28 mg, 116 µmol, 1.2 eq.) gave 22 mg (41 µmol) of (5S,8S)-methyl-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylate (C3). $^1$H NMR (300 MHz, CDCl$_3$) 7.35-6.8 (m, 4H), 5.21-5.06 (m, 1H), 4.86 (m, 1H), 4.55-3.56 (m, 8H), 2.65-2.48 (m, 1H), 2.0 (m, 1H), 1.7-1.1 (m, 9H), 0.9-0.7 (m, 9H).

Step D: (5S,8S)-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylic acid (D3).

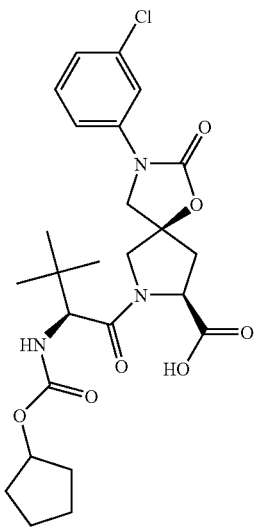

D3

(5S,8S)-methyl-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylate (C3) (22 mg, 41 µmol, 1 eq.) was diluted with dry THF (0.5 mL) then 1 M LiOH (82 µL, 82 µmol, 2 eq.) and MeOH (20 µL) was added. The reaction was stirred overnight at room temp. and concentrated to give 10 mg (19 µmol) of (5S,8S)-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylic acid (D3). LC MS+: 522.35 at 3.14 min (10-90%, 3-5 min, Formic Acid).

Step E: Cyclopentyl 2-((5S,8S)-3-(3-chlorophenyl)-8-((3S)-1-(cyclopropylamino)-2-hydroxy-1-oxohexan-3-ylcarbamoyl)-2-oxo-1-oxa-3,7-diazaspiro[4.4]nonan-7-yl)-2-oxoethylcarbamate (D4).

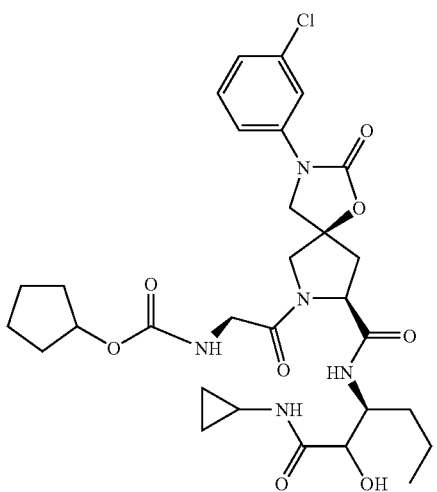

E3

Following the same procedure as Example 1 step 1 using (5S,8S)-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylic acid (D3) (10 mg, 20 μmol) and (3S)-3-amino-N-cyclopropyl-2-hydroxyhexanamide (7 mg, 28 μmol) gave 5 mg (7.2 μmol) of Cyclopentyl-(2S)-1-((5S,8S)-3-(3-chlorophenyl)-8-((3S)-1-(cyclopropylamino)-2-hydroxy-1-oxohexan-3-ylcarbamoyl)-2-oxo-1-oxa-3,7-diazaspiro[4.4]nonan-7-yl)-3,3-dimethyl-1-oxobutan-2-ylcarbamate (E3). LC MS+: 690.38 at 3.31 min (10-90%, 3-5 min, Formic Acid).

Step F: Cyclopentyl 2-((5S,8S)-3-(3-chlorophenyl)-8-((S)-1-(cyclopropylamino)-1,2-dioxohexan-3-ylcarbamoyl)-2-oxo-1-oxa-3,7-diazaspiro[4.4]nonan-7-yl)-2-oxoethylcarbamate (Compound No. 7)

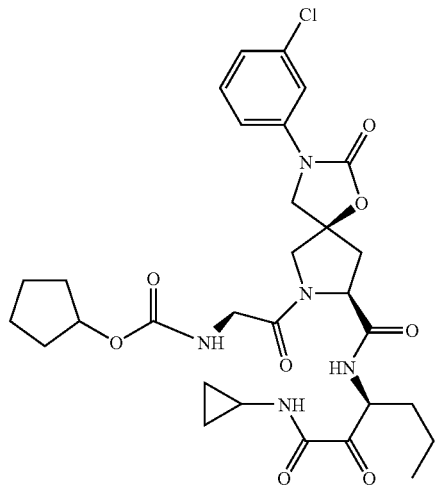

Cmpd No. 7

Following the same procedure as Example 1 step 10 using cyclopentyl 2-((5S,8S)-3-(3-chlorophenyl)-8-((3S)-1-(cyclopropylamino)-2-hydroxy-1-oxohexan-3-ylcarbamoyl)-2-oxo-1-oxa-3,7-diazaspiro[4.4]nonan-7-yl)-2-oxoethylcarbamate (D4) (5 mg, 7.2 μmol) gave 0.9 mg (1.3 μmol) of cyclopentyl-2-((5S,8S)-3-(3-chlorophenyl)-8-((S)-1-(cyclopropylamino)-1,2-dioxohexan-3-ylcarbamoyl)-2-oxo-1-oxa-3,7-diazaspiro[4.4]nonan-7-yl)-2-oxoethylcarbamate (compound no. 7). LC MS+/−: 688.4/686.6 at 3.6 min (10-90%, 3-5 min, Formic Acid).

Example 4

(5R,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (Cmpd No. 9)

Step A: (5R,8S)-di-tert-butyl 3-(3-chlorophenyl)-2-oxo-1-oxa-3,7-diazaspiro[4.4]nonane-7,8-dicarboxylate (A4)

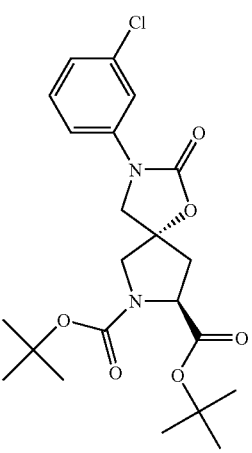

A4

Following the procedure from Example 1 step C using (8S)-di-tert-butyl 2-oxo-1-oxa-3,7-diazaspiro[4.4]nonane-7,8-dicarboxylate (2) (189 mg, 0.55 mmol, 1 eq.) and 3-chloro bromobenzene (60 μl, 0.55 mmol, 1 eq.) gave 54 mg (119) of (5R,8S)-di-tert-butyl 3-(3-chlorophenyl)-2-oxo-1-oxa-3,7-diazaspiro[4.4]nonane-7,8-dicarboxylate (A4). ¹H NMR (300 MHz, DMSO) 7.68 (m, 1H), 7.55-7.38 (m, 2H), 7.2 (m, 1H), 4.38-4.28 (m, 1H), 4.2-4.05 (m, 2H), 3.75-3.6 (m, 2H), 2.7-2.4 (m, 2H), 1.4 (m, 18H).

Step B: (5R,8S)-tert-butyl-3-(3-chlorophenyl)-2-oxo-1-oxa-3,7-diazaspiro[4.4]nonane-8-carboxylate (B4)

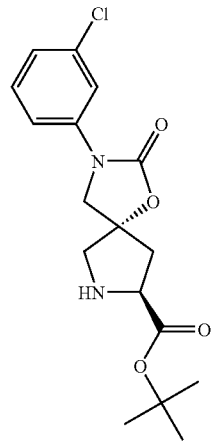

B4

Following the procedure from Example 1 step D using (5R,8S)-di-tert-butyl 3-(3-chlorophenyl)-2-oxo-1-oxa-3,7-diazaspiro[4.4]nonane-7,8-dicarboxylate (A4) (54 mg, 120 µmol) gave 20 mg (57 µmol) of (5R,8S)-tert-butyl-3-(3-chlorophenyl)-2-oxo-1-oxa-3,7-diazaspiro[4.4]nonane-8-carboxylate (B4).

Step C: (5R,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (C4)

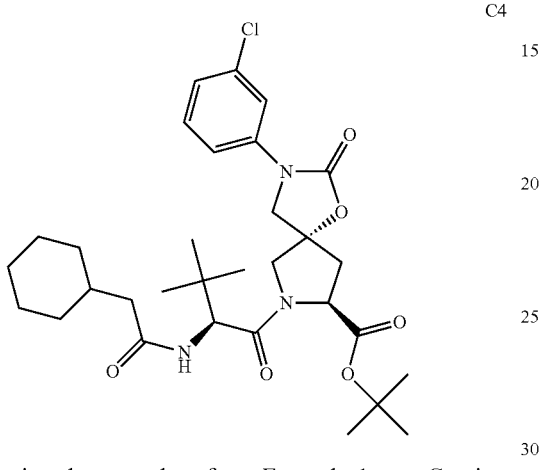

C4

Following the procedure from Example 1 step G using (5R,8S)-tert-butyl-3-(3-chlorophenyl)-2-oxo-1-oxa-3,7-diazaspiro[4.4]nonane-8-carboxylate (B4) (20 mg, 54 µmol, 1 eq.) and (S)-2-(2-cyclohexylacetamido)-3,3-dimethylbutanoic acid (16 mg, 63 µmol, 1.2 eq.) gave 16 mg (27 µmol) of (5R,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (C4). LC MS+/−: 590.31/589.47 at 3.95 min (10-90%, 3-5 min, Formic Acid).

Step D: (5R,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D4)

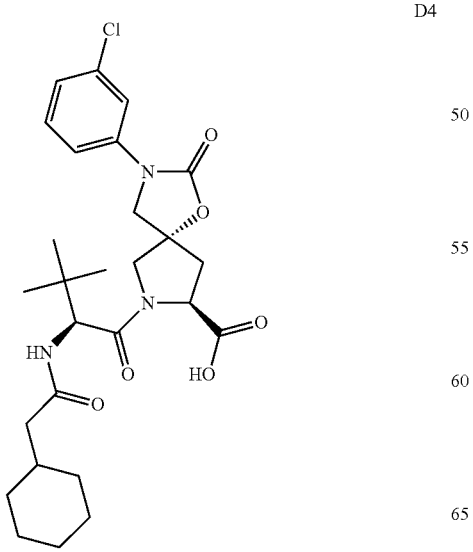

D4

Following the procedure from Example 1 step H using (5R,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (C4) (16 mg, 27 µmol) gave (5R,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D4). LC MS+/−: 534.32/532.53 at 3.35 min (10-90%, 3-5 min, Formic Acid).

Step E: (5R,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E4)

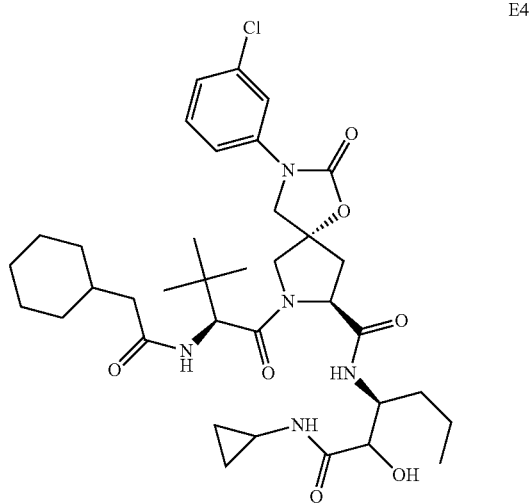 [SMILES: CCC[C@H](NC(=O)[C@@H]1C[C@]2(CN(c3cccc(Cl)c3)C(=O)O2)CN1C(=O)[C@@H](NC(=O)CC1CCCCC1)C(C)(C)C)C(O)C(=O)NC1CC1]

E4

Following the procedure from Example 1 step I using (5R,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D4) (12 mg, 22 µmol) and (3S)-3-amino-N-cyclopropyl-2-hydroxyhexanamide (7.3 mg, 33 µmol) gave 10 mg (14 µmol) of (5R,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E4). LC MS+/−: 702.54/700.74 at 3.68 min (10-90%, 3-5 min, Formic Acid).

Step F: (5R,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (F4)

Cmpd No. 9

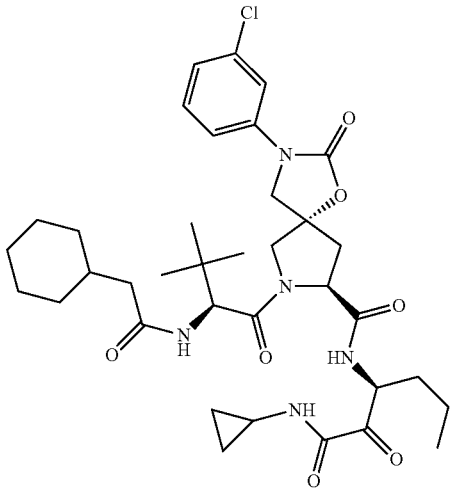

Following the procedure from Example 1 step J using (5R,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E4) (10 mg, 14 µmol) gave 2 mg (2.9 µmol) of (5R,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (compound no. 9). $^1$H NMR (300 MHz, CDCl$_3$) 7.62 (m, 1H), 7.55-7.35 (m, 2H), 7.14 (m, 1H), 6.9 (m, 1H), 5.98 (m, 1H), 5.4 (m, 1H), 4.75 (m, 1H), 4.5-4.25 (m, 3H), 4.0-3.8 (m, 2H), 3.05 (m, 1H), 2.8 (m, 1H), 2.3 (m, 1H), 2.15-1.9 (m, 2H) 1.7-0.8 (m, 30H), 0.6 (m, 2H).

Example 5

(5S,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (Cmpd. No. 8)

Step A: (5S,8S)-di-tert-butyl 3-(3-chlorophenyl)-2-oxo-1-oxa-3,7-diazaspiro[4.4]nonane-7,8-dicarboxylate (A5)

A5

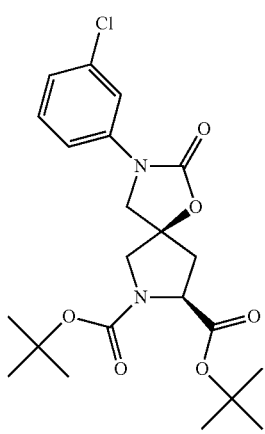

Following the procedure from Example 1 step C using (8S)-di-tert-butyl 2-oxo-1-oxa-3,7-diazaspiro[4.4]nonane-7,8-dicarboxylate (B2) (189 mg, 0.55 mmol, 1 eq.) and 3-chloro bromobenzene (60 µl, 0.55 mmol, 1 eq.) gave 48 mg (0.106 mmol) of (5S,8S)-di-tert-butyl 3-(3-chlorophenyl)-2-oxo-1-oxa-3,7-diazaspiro[4.4]nonane-7,8-dicarboxylate (A5). $^1$H NMR (300 MHz, DMSO) 7.68 (m, 1H), 7.55-7.38 (m, 2H), 7.2 (m, 1H), 4.23-4.05 (m, 3H), 3.8-3.7 (m, 1H), 3.5 (m, 1H), 2.7-2.6 (m, 1H), 2.25-2.1 (m, 1H), 1.4 (m, 18H).

Step B: (5S,8S)-tert-butyl-3-(3-chlorophenyl)-2-oxo-1-oxa-3,7-diazaspiro[4.4]nonane-8-carboxylate (32)

B5

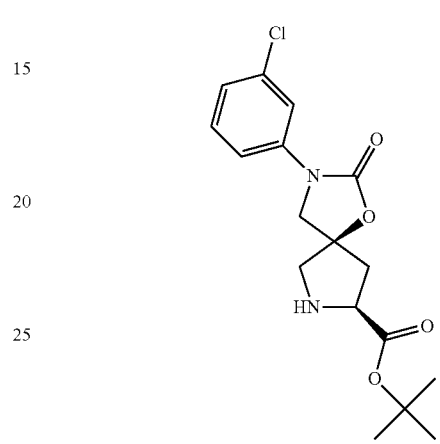

Following the procedure from Example 1 step 4 on (5S,8S)-di-tert-butyl 3-(3-chlorophenyl)-2-oxo-1-oxa-3,7-diazaspiro[4.4]nonane-7,8-dicarboxylate (A5) (48 mg, 106 µmol) gave 34 mg (96 µmol) of (5S,8S)-tert-butyl-3-(3-chlorophenyl)-2-oxo-1-oxa-3,7-diazaspiro[4.4]nonane-8-carboxylate (B5).

Step C: (5S,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (33).

C5

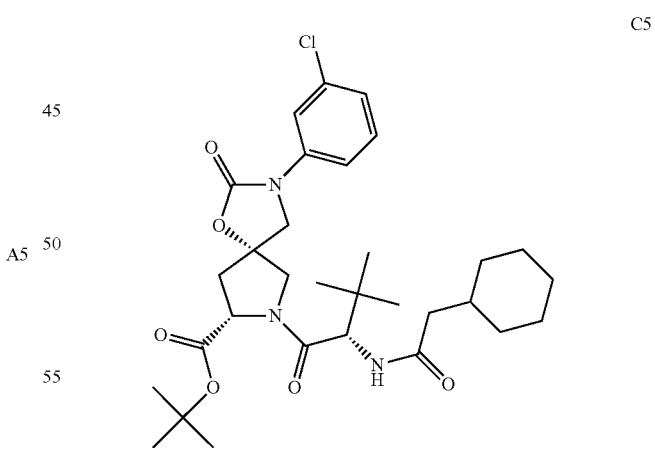

Following the procedure from Example 1 step G using (5S,8S)-tert-butyl-3-(3-chlorophenyl)-2-oxo-1-oxa-3,7-diazaspiro[4.4]nonane-8-carboxylate (B5) (32 mg, 91 µmol, 1 eq.) and (S)-2-(2-cyclohexylacetamido)-3,3-dimethylbutanoic acid (25 mg, 100 µmol, 1.2 eq.) gave 25 mg (42 µmol) of (5S,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (C5). LC MS+/-: 590.31/589.47 at 3.95 min (10-90%, 3-5 min, Formic Acid).

Step D: (5S,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D5)

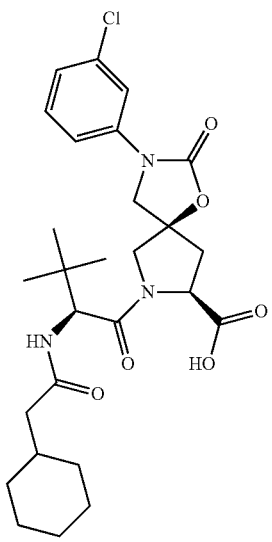

Following the procedure from Example 1 step H using (5S,8S)-tert-butyl-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylate (C5) (25 mg, 42 μmol) gave (5S,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D5). LC MS+/−: 534.32/532.53 at 3.39 min (10-90%, 3-5 min, Formic Acid).

Step E: (5S,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E5)

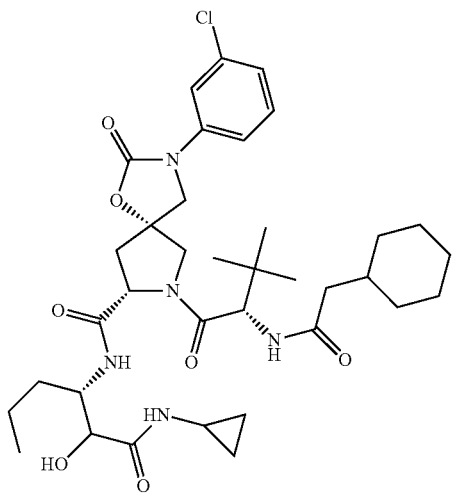

Following the procedure from Example 1 step 1 using (5S,8S)-3-(3-chlorophenyl)-7-((S)-2-(2-cyclohexylacetamido)-3,3-dimethylbutanoyl)-2-oxo-1-oxa-3,7-diazaspiro[4.4]nonane-8-carboxylic acid (D5) (23 mg, 43 μmol) and (3S)-3-amino-N-cyclopropyl-2-hydroxyhexanamide (15 mg, 65 μmol) gave 10 mg (14 μmol) of (5S,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E5). LC MS+/−: 702.54/700.62 at 3.63 min (10-90%, 3-5 min, Formic Acid).

Step F: (5S,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (Cmpd. No. 8)

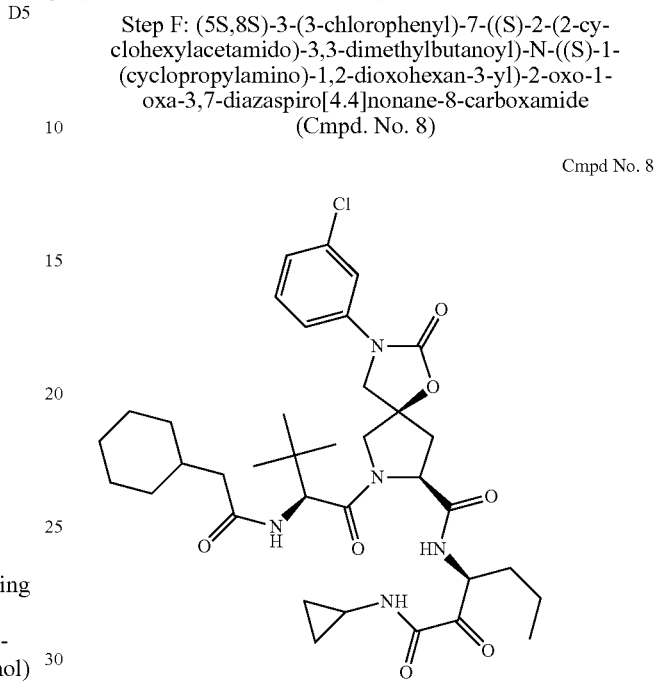

Following the procedure from Example 1 step J using (5S,8S)-3-(3-chlorophenyl)-7-((S)-2-(2-cyclohexylacetamido)-3,3-dimethylbutanoyl)-N-((3S)-1-(cyclopropylamino)-2-hydroxy-1-oxohexan-3-yl)-2-oxo-1-oxa-3,7-diazaspiro[4.4]nonane-8-carboxamide (E5) (10 mg, 14 μmol) gave 1.3 mg (1.9 μmol) of (5S,8S)-3-(3-chlorophenyl)-7-((S)-2-(2-cyclohexylacetamido)-3,3-dimethylbutanoyl)-N-((S)-1-(cyclopropylamino)-1,2-dioxohexan-3-yl)-2-oxo-1-oxa-3,7-diazaspiro[4.4]nonane-8-carboxamide (compound no. 8). $^1$H NMR (300 MHz, CDCl$_3$) 7.6-7.28 (m, 3H), 7.13 (m, 2H), 6.9 (m, 1H), 6.03 (m, 1H), 5.33 (m, 1H), 4.8-4.75 (m, 1H), 4.61 (m, 1H), 4.46-4.4 (m, 1H), 4.25-3.7 (m, 3H), 2.8 (m, 1H), 2.68-2.52 (m, 1H), 2.2-1.9 (m, 2H), 1.9-0.8 (m, 30H), 0.6 (m, 2H).

Example 6

Cyclopentyl-(S)-1-((3S,5R)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (Cmpd No. 1) and cyclopentyl (S)-1-((3S,5S)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (Cmpd No. 4)

Step A: (S)-di-tert-butyl-4-(2-ethoxy-2-oxoethylidene)pyrrolidine-1,2-dicarboxylate (A6)

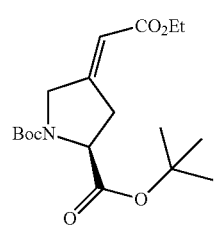

To a solution of ((S)-di-tert-butyl 4-oxopyrrolidine-1,2-dicarboxylate (A1), 2.43 g, 8.5 mmol) in Toluene (20 ml) was added (carboethoxy-methylene)triphenylphosphorane (4.52 g, 13 mmol, 1.5 eq). The reaction was refluxed overnight, and concentrated to an oil. The oil was purified on silica (120 g, hexane/ethyl acetate gradient) to afford (S)-di-tert-butyl-4-(2-ethoxy-2-oxoethylidene)pyrrolidine-1,2-dicarboxylate (A6) (1.00 g, 2.8 mmol) as a colorless oil. $^1$H NMR (DMSO) δ 1.20 (t, 3H), 1.40 (m, 18H), 2.54 (m, 2H), 3.30 (m, 2H), 4.10 (m, 3H), 4.71 (m, 0.5H), 5.62 (m, 0.5H).

Step B: (2S)-di-tert-butyl-4-(2-ethoxy-2-oxoethyl)-4-(nitromethyl)pyrrolidine-1,2-dicarboxylate (B6)

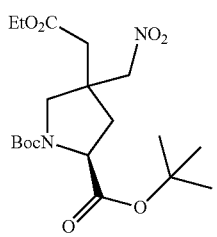

B6

A solution of (S)-di-tert-butyl-4-(2-ethoxy-2-oxoethylidene)pyrrolidine-1,2-dicarboxylate (A6) (1.00 g, 2.8 mmol) in nitromethane (5 ml) was treated with tetramethylguanidine (TMG, 0.35 g, 3.0 mmol, 1.1 eq). The reaction was refluxed for 3 hrs and concentrated to a yellow oil. The oil was purified on silica (hexane/ether gradient) to give (2S)-di-tert-butyl-4-(2-ethoxy-2-oxoethyl)-4-(nitromethyl)pyrrolidine-1,2-dicarboxylate (B6) (0.46 g, 1.1 mmol) as a mixture of diastereomers. $^1$H NMR (DMSO) δ 1.15 (t, 3H), 1.35 (m, 18H), 1.95 (m, 1H), 2.40 (m, 1H), 2.54 (m, 8H), 2.70 (s, 1.5H), 3.30 (s, 8.6H), 3.5-3.6 (m, 1H), 4.0-4.2 (m, 3H), 4.7-4.85 (m, 2H).

Step C: (2S)-di-tert-butyl 4-(aminomethyl)-4-(2-ethoxy-2-oxoethyl)pyrrolidine-1,2-dicarboxylate (C6)

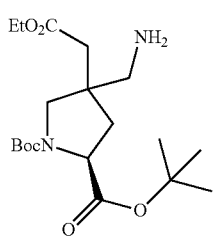

C6

The nitromethane adduct (2S)-di-tert-butyl-4-(2-ethoxy-2-oxoethyl)-4-(nitromethyl)pyrrolidine-1,2-dicarboxylate (B6) (1.24 g, 3.0 mmol) was dissolved in ethyl acetate (20 ml), and to this was added 10% Pd/C (75 mg, cat). The reaction was stirred under hydrogen atmosphere 2 days. The solution was filtered through celite and concentrated to an oil. The crude was purified on silica (1% to 20% MeOH/CH$_2$Cl$_2$ gradient) to give (2S)-di-tert-butyl 4-(aminomethyl)-4-(2-ethoxy-2-oxoethyl)pyrrolidine-1,2-dicarboxylate (C6) (566 mg, 1.5 mmol) as a white foam. $^1$H NMR (DMSO) δ 1.20 (t, 1H), 1.4 (m, 18H), 1.8-1.9 (m, 1H), 2.1-2.6 (m, 11H), 3.0-3.5 (m, 5H), 3.9-4.2 (m, 214), 7.61 (m, 0.5H).

Step D: 2-((5S)-3-(aminomethyl)-1,5-bis(tert-butoxycarbonyl)pyrrolidin-3-yl)acetic acid (D6)

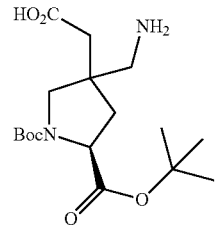

D6

Ester (2S)-di-tert-butyl 4-(aminomethyl)-4-(2-ethoxy-2-oxoethyl)pyrrolidine-1,2-dicarboxylate (C6) (560 mg, 1.45 mmol) was dissolved in THF (12 ml). To this was added 1N lithium hydroxide in water (2.9 ml, 2.9 mmol, 2.0 eq). The mixture was stirred at room temperature overnight. The reaction was cooled to 0° C. and quenched with 1N hydrochloric acid in water. The mixture was blown to dryness with N$_2$ gas and stripped from acetonitrile several times to give 2-((5S)-3-(aminomethyl)-1,5-bis(tert-butoxycarbonyl)pyrrolidin-3-yl)acetic acid (D6) (1.45 mmol) as a glassy solid. $^1$H NMR (DMSO) δ 1.35 (m, 18H), 2.00 (m, 2H), 2.35 (m, 2H), 2.80 (m, 1H), 3.65 (m, 1H), 4.00 (m, 1H); LCMS for C$_{17}$H$_{30}$N$_2$O$_6$ 358.21 [M], found ES+ 359.21 [M+H]$^+$ and ES− 357.17 [M−H]$^-$ at 1.8 minutes retention time, using 10-90% acetonitrile/water (with 0.1% formic acid buffer) gradient over 5 minutes.

Step E: (3S)-di-tert-butyl 8-oxo-2,7-diazaspiro[4.4]nonane-2,3-dicarboxylate (E6)

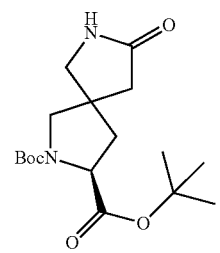

E6

To a solution of amino acid 2-((5S)-3-(aminomethyl)-1,5-bis(tert-butoxycarbonyl)pyrrolidin-3-yl)acetic acid (D6) (1.45 mmol) in CH$_2$Cl$_2$ (32 ml) was added 1-hydroxybenzotriazole (HOBT, 196 mg, 1.45 mmol, 1 eq), 1-ethyl-(3-dimethylaminopropyl)carbodiimide hydrochloride (EDC, 418 mg, 2.2 mmol, 1.5 eq), and N,N-Diisopropylethylamine (DIEA, 756 μl, 4.4 mmol, 3.0 eq). The reaction was aged at room temp. overnight. The solution was diluted with CH$_2$Cl$_2$ (100 ml) and washed with water (100 ml), 1N sodium hydroxide in water (100 ml) and brine (100 ml). The organics were dried over sodium sulfate, filtered, and concentrated with a second extract, to give crude product. This was purified on silica (1% to 20% MeOH/CH$_2$Cl$_2$ gradient) to give spirolactam (3S)-di-tert-butyl 8-oxo-2,7-diazaspiro[4.4]nonane-2,3-dicarboxylate (E6) (295 mg, 868 μmol). $^1$H NMR (CDCl$_3$) δ1.35 (m, 18H), 1.91 (m, 2H), 2.3 (m, 3H), 3.2 (m, 2H), 3.3-3.5 (m, 2H), 4.10 (m, 1H), 6.21 (m, 1H); LCMS for C$_{17}$H$_{28}$N$_2$O$_5$ 340.20 [M], found ES+ 341.2 [M+H]$^+$, 285.2 [M+H, minus t-butyl]$^+$, 285.2 [M+H, minus t-butyl, minus BOC]$^+$ at 2.6 minutes retention time, using 10-90% acetonitrile/water (with 0.1% formic acid buffer) gradient over 5 minutes.

141

Step F: (3S,5S)-di-tert-butyl-8-oxo-7-phenyl-2,7-diazaspiro[4.4]nonane-2,3-dicarboxylate (F6)

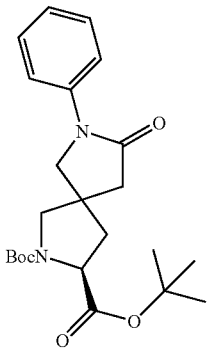

Spirolactam (3S)-di-tert-butyl 8-oxo-2,7-diazaspiro[4.4]nonane-2,3-dicarboxylate (E6) (34 mg, 100 µmol) was placed in a tube with $CsCO_3$ (56 mg, 172 µmol, 1.7 eq), $Pd_2dba_3$ (3.0 mg, 3.2 µmol, 3.2%) and xanthphos ligand (5.7 mg, 9.8 µmol, 9.8%). Dioxane (1.0 ml) was added via syringe, followed by addition of bromobenzene (21 mg, 134 µmol, 1.3 eq). The sealed reaction was heated to 100° C. for 16 hrs with efficient magnetic stirring. The reaction was diluted with $CH_2Cl_2$ (10 ml), filtered through celite and concentrated. The crude was purified on silica (1% to 6% $MeOH/CH_2Cl_2$ gradient) to give phenylated lactam (3S,5S)-di-tert-butyl-8-oxo-7-phenyl-2,7-diazaspiro[4.4]nonane-2,3-dicarboxylate (F6) (32 mg, 77 µmol) as a white foam. $^1H$ NMR ($CDCl_3$) δ1.45 (m, 18H), 2.10 (m, 1H), 2.45 (m, 1H), 2.6-2.8 (m, 2H), 3.55 (m, 1H), 3.75 (m, 2H), 4.25 (m, 1H), 7.15 (m, 1H), 7.35 (m, 2H), 7.55 (m, 2H); LCMS for $C_{23}H_{32}N_2O_5$ 416.23 [M], found ES+ 417.23 $[M+H]^+$ at 3.5 minutes retention time, using 10-90% acetonitrile/water (with 0.1% formic acid buffer) gradient over 5 minutes.

Step G: (3S,5R)-tert-butyl-8-oxo-7-phenyl-2,7-diazaspiro[4.4]nonane-3-carboxylate (G1a) and (3S,5S)-tert-butyl 8-oxo-7-phenyl-2,7-diazaspiro[4.4]nonane-3-carboxylate (G1b)

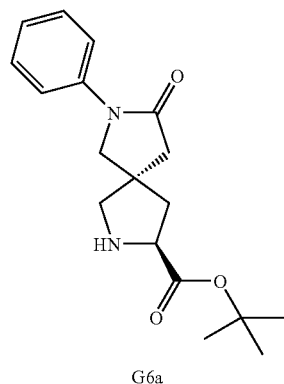

G6a

+

142

-continued

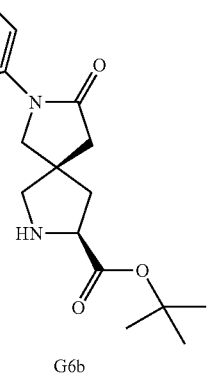

G6b

The phenylated lactam (3S,5S)-di-tert-butyl-8-oxo-7-phenyl-2,7-diazaspiro[4.4]nonane-2,3-dicarboxylate (F6) (29 mg, 70 µmol) was taken up in dry ethyl acetate (1.0 ml) and treated with 1M hydrochloric acid in ethyl acetate (1.0 ml, 1000 µmol, 14 eq). The reaction was aged at room temperature for 24 hrs. The reaction was purged by bubbling $N_2$ gas through it, until dry. The product was extracted with ethyl acetate and saturated sodium bicarbonate in water. The organics were washed with brine, dried over sodium sulfate, filtered and concentrated with a second extract to give crude product. The crude was purified on silica (1% to 20% $MeOH/CH_2Cl_2$ gradient) to give (3S,5R)-tert-butyl-8-oxo-7-phenyl-2,7-diazaspiro[4.4]nonane-3-carboxylate (G6a) (6.1 mg, 19 µmol, 27%). $^1H$ NMR ($CDCl_3$) δ1.45 (s, 9H), 2.00 (m, 1H), 2.40 (m, 1H), 2.5-2.8 (m, 4H), 3.0-3.2 (m, 2H), 3.88 (m, 3H), 7.20 (m, 1H), 7.38 (m, 2H), 7.6 (m, 2H). The minor diastereomer (3S,5S)-tert-butyl 8-oxo-7-phenyl-2,7-diazaspiro[4.4]nonane-3-carboxylate (G6b) (0.5 mg, 1.6 µmol, 2.2%) was also obtained from the column. $^1H$ NMR ($CDCl_3$) δ 1.45 (s, 9H), 2.25 (m, 1H), 2.45 (m, 1H), 2.6-2.9 (m, 2H), 3.37 (m, 1H), 3.5-3.8 (m, 2H), 3.91 (m, 1H), 4.25 (m, 1H), 7.15 (m, 1H), 7.32 (m, 2H), 7.55 (m, 2H).

Step H: (3S,5R)-tert-butyl-2-((S)-2-(cyclopentyloxycarbonylamino)-3,3-dimethylbutanoyl)-8-oxo-7-phenyl-2,7-diazaspiro[4.4]nonane-3-carboxylate (H6a) and (3S,5S)-tert-butyl 2-((S)-2-(cyclopentyloxycarbonylamino)-3,3-dimethylbutanoyl)-8-oxo-7-phenyl-2,7-diazaspiro[4.4]nonane-3-carboxylate (H6b)

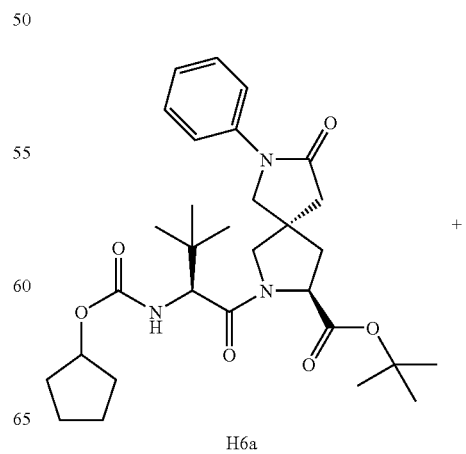

H6a

+

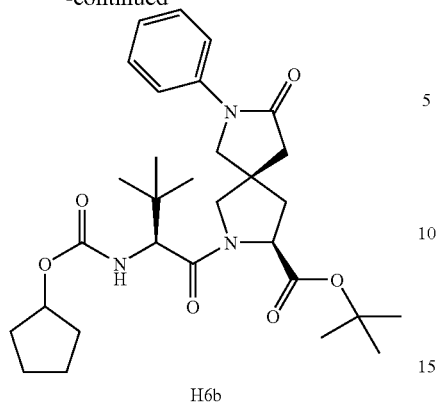

H6b

The amine (3S,5R)-tert-butyl-8-oxo-7-phenyl-2,7-diazaspiro[4.4]nonane-3-carboxylate (6.1 mg, 19 μmol) in DMF (200 μl) was treated with (5S,8S)-methyl-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylate (C3) (40 μmol, 2 eq), 1-hydroxybenzotriazole (HOBT, 25 μmol, 1 eq), 1-ethyl-(3-dimethylaminopropyl) carbodiimide hydrochloride (EDC, 40 μmol, 2 eq), and N,N-Diisopropylethylamine (DIEA, 80 μmol, 4 eq). The reaction was aged at room temp. overnight, quenched with 1M histamine in water (40 μl, 2 eq), and blown to dryness with nitrogen gas. The residue was extracted with ethyl acetate (2×5 ml) and 0.5N hydrochloric acid in water (2×2 ml), dried over sodium sulfate, filtered and concentrated to give (3S,5R)-tert-butyl-2-((S)-2-(cyclopentyloxycarbonylamino)-3,3-dimethylbutanoyl)-8-oxo-7-phenyl-2,7-diazaspiro[4.4]nonane-3-carboxylate (H6a) (9.2 mg, 17 μmol). $^1$H NMR (CDCl$_3$) δ1.08 (s, 9H), 1.4-1.9 (m, 20H), 2.09 (m, 1H), 2.40 (m, 1H), 2.70 (s, 2H), 3.61 (m, 2H), 3.91 (m, 1H), 4.20 (m, 2H), 4.45 (m, 1H), 5.00 (m, 1H), 5.20 (m, 1H), 7.15 (m, 1H), 7.35 (m, 2H), 7.60 (m, 2H); LCMS for C$_{30}$H$_{43}$N$_3$O$_6$ 541.32 [M], found ES+ 564.3 [M+Na]$^+$, 542.32 [M+H]$^+$ at 3.7 minutes retention time, using 10-90% acetonitrile/water (with 0.1% formic acid buffer) gradient over 5 minutes. The minor diastereomer (3S,5S)-tert-butyl 2-((S)-2-(cyclopentyloxycarbonylamino)-3,3-dimethylbutanoyl)-8-oxo-7-phenyl-2,7-diazaspiro[4.4]nonane-3-carboxylate (H6b) (5 μmol) was obtained in similar fashion. LCMS for C$_{30}$H$_{43}$N$_3$O$_6$ 541.32 [M], found 542.32 [M+H]$^+$ at 3.7 minutes retention time, using 10-90% acetonitrile/water (with 0.1% formic acid buffer) gradient over 5 minutes.

Step I: (3S,5R)-2-((S)-2-(cyclopentyloxycarbonylamino)-3,3-dimethylbutanoyl)-8-oxo-7-phenyl-2,7-diazaspiro[4.4]nonane-3-carboxylic acid (I6a) and (3S,5S)-2-((S)-2-(cyclopentyloxycarbonylamino)-3,3-dimethylbutanoyl)-8-oxo-7-phenyl-2,7-diazaspiro[4.4]nonane-3-carboxylic acid (I6b)

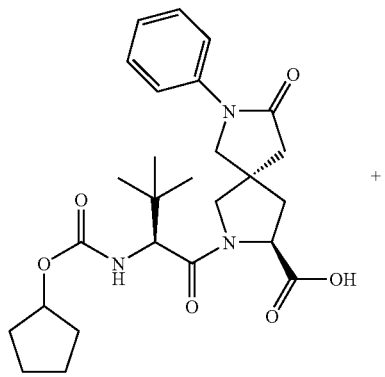

I6a

+

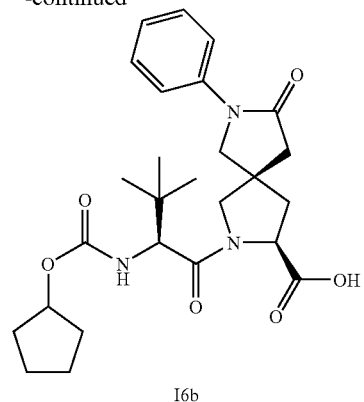

I6b

The protected proline (3S,5R)-tert-butyl-2-((S)-2-(cyclopentyloxycarbonylamino)-3,3-dimethylbutanoyl)-8-oxo-7-phenyl-2,7-diazaspiro[4.4]nonane-3-carboxylate (H6a) (9.2 mg, 17 μmol) was dissolved in CH$_2$Cl$_2$ (1.0 ml) and treated with trifluoroacetic acid (0.3 ml) for 4 hrs at room temperature. The reaction was concentrated to dryness under high vacuum to give (3S,5R)-2-((S)-2-(cyclopentyloxycarbonylamino)-3,3-dimethylbutanoyl)-8-oxo-7-phenyl-2,7-diazaspiro[4.4]nonane-3-carboxylic acid (I6a) (17 μmol). The minor diastereomer (3S,5S)-2-((S)-2-(cyclopentyloxycarbonylamino)-3,3-dimethylbutanoyl)-8-oxo-7-phenyl-2,7-diazaspiro[4.4]nonane-3-carboxylic acid (I6b) (5 μmol) was obtained in similar fashion.

Step J: Cyclopentyl-(S)-1-((3S,5R)-3-((S)-1-(cyclopropylamino)-2-hydroxy-1-oxohexan-3-ylcarbamoyl)-8-oxo-7-phenyl-2,7-diazaspiro[4.4]nonan-2-yl)-3,3-dimethyl-1-oxobutan-2-ylcarbamate (J6a) and cyclopentyl (S)-1-((3S,5S)-3-((S)-1-(cyclopropylamino)-2-hydroxy-1-oxohexan-3-ylcarbamoyl)-8-oxo-7-phenyl-2,7-diazaspiro[4.4]nonan-2-yl)-3,3-dimethyl-1-oxobutan-2-ylcarbamate (J6b)

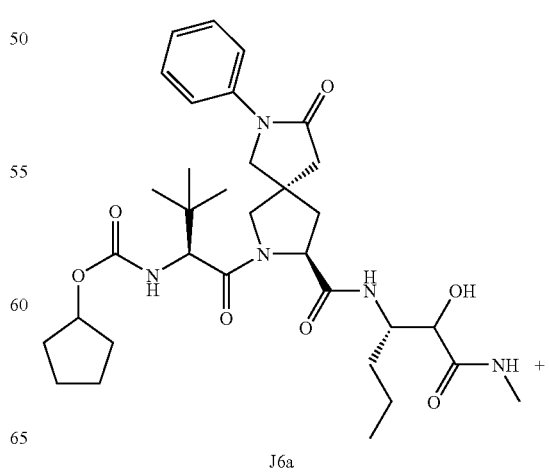

J6a

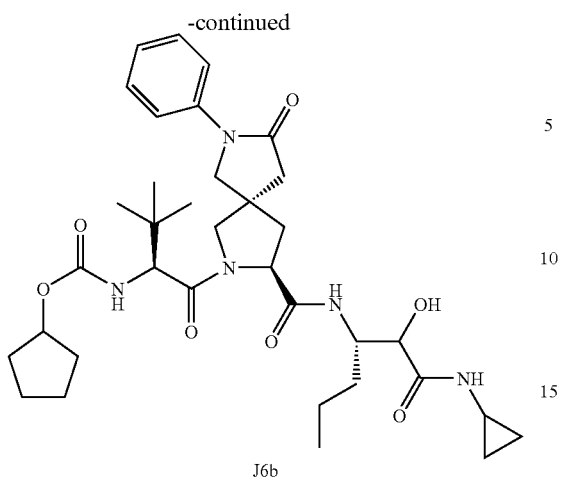

J6b

Step K: Cyclopentyl-(S)-1-((3S,5R)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (Cmpd No. 1) and cyclopentyl (S)-1-((3S,5S)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (Cmpd No. 4)

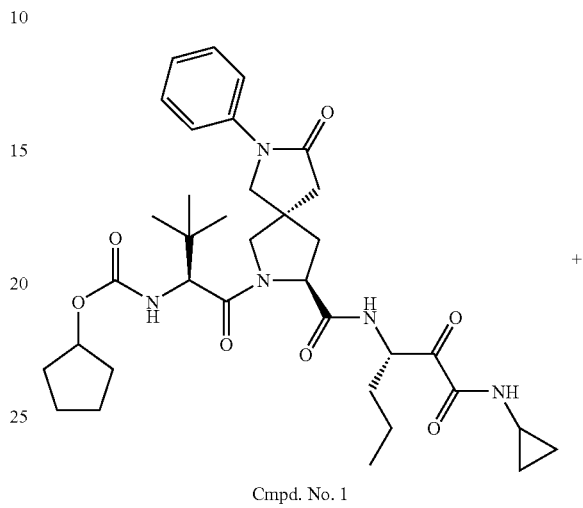

Cmpd. No. 1

The carboxylic acid (3S,5R)-2-((S)-2-(cyclopentyloxycarbonylamino)-3,3-dimethylbutanoyl)-8-oxo-7-phenyl-2,7-diazaspiro[4.4]nonane-3-carboxylic acid (I6a) (17 µmol) and (2R,3S)-3-amino-N-cyclopropyl-2-hydroxyhexanamide hydrochloride salt (warhead (5S,8S)-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylic acid (D3), 7.6 mg, 34 µmol, 2 eq) were dissolved in DMF (1.0 ml). To this was added 1-hydroxybenzotriazole (HOBT, 4.6 mg, 34 µmol, 2 eq), 1-ethyl-(3-dimethylaminopropyl) carbodiimide hydrochloride (EDC, 6.5 mg, 34 µmol, 2 eq), and N,N-Diisopropylethylamine (DIEA, 12 µl, 68 µmol, 4 eq). The reaction was aged at room temperature overnight, concentrated to dryness and extracted with $CH_2Cl_2$ (2×5 ml) and water (2 ml). The organics were dried over sodium sulfate, filtered and concentrated to crude. The crude was purified on silica (1% MeOH/$CH_2Cl_2$ to 20% MeOH/$CH_2Cl_2$ gradient) to give cyclopentyl-(S)-1-((3S,5R)-3-((S)-1-(cyclopropylamino)-2-hydroxy-1-oxohexan-3-ylcarbamoyl)-8-oxo-7-phenyl-2,7-diazaspiro[4.4]nonan-2-yl)-3,3-dimethyl-1-oxobutan-2-ylcarbamate (J6a) (4.1 mg, 6.3 µmol). LCMS for $C_{35}H_{51}N_5O_7$ 653.38 [M], found ES⁺ 654.5 [M+H]⁺ and ES⁻ 652.6 [M–H]⁻, at 3.0 minutes retention time, using 10-90% acetonitrile/water (with 0.1% formic acid buffer) gradient over 5 minutes. The minor diastereomer cyclopentyl (S)-1-((3S,5S)-3-((S)-1-(cyclopropylamino)-2-hydroxy-1-oxohexan-3-ylcarbamoyl)-8-oxo-7-phenyl-2,7-diazaspiro[4.4]nonan-2-yl)-3,3-dimethyl-1-oxobutan-2-ylcarbamate (J6b) (3 µmol) was obtained in similar fashion. LCMS for $C_{35}H_{51}N_5O_7$ 653.38 [M], found ES⁺ 654.5 [M+H]⁺ and ES⁻ 652.6 [M–H]⁻, at 3.0 minutes retention time, using 10-90% acetonitrile/water (with 0.1% formic acid buffer) gradient over 5 minutes.

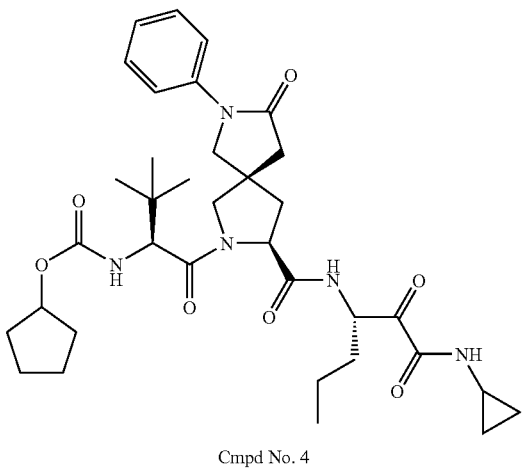

Cmpd No. 4

The hydroxy amide cyclopentyl-(S)-1-((3S,5R)-3-((S)-1-(cyclopropylamino)-2-hydroxy-1-oxohexan-3-ylcarbamoyl)-8-oxo-7-phenyl-2,7-diazaspiro[4.4]nonan-2-yl)-3,3-dimethyl-1-oxobutan-2-ylcarbamate (J6a) (4.1 mg, 6.3 µmol) was dissolved in $CH_2Cl_2$ (1.0 ml) and treated with Dess-Martin periodinane (DMP, 8.0 mg, 18.9 µmol, 3 eq) for 3 hrs at room temp. The reaction was quenched with 1M sodium thiosulfate in water (32 µl, 5 eq). The reaction was loaded onto silica (eluted with ethyl acetate/hexane gradient) to give cyclopentyl-(S)-1-((3S,5R)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (compound no. 1) (3.1 mg, 4.8 µmol) as a white solid. NMR (CDCl₃) δ5.95m, 46H), 1.96 (m, 1H), 2.25 (m, 1H), 2.61 (m, 2H), 2.80 (s, 2H), 3.60 (dd, 2H), 4.00 (d, 1H), 4.22

(m, 2H), 4.70 (m, 1H), 4.90 (m, 1H), 5.20 (d, 1H), 5.35 (m, 1H), 6.90 (s, 1H), 7.19 (m, 1H), 7.38 (m, 2H), 7.65 (d, 1H). LCMS for $C_{35}H_{49}N_5O_7$ 651.36 [M], found $ES^+$ 652.5 $[M+H]^+$ and $ES^-$ 650.6 $[M-H]^-$, at 3.2 minutes retention time, using 10-90% acetonitrile/water (with 0.1% formic acid buffer) gradient over 5 minutes. The minor diastereomer cyclopentyl (S)-1-((3S,5S)-3-((S)-1-(cyclopropylamino)-1,2-dioxohexan-3-ylcarbamoyl)-8-oxo-7-phenyl-2,7-diazaspiro[4.4]nonan-2-yl)-3,3-dimethyl-1-oxobutan-2-ylcarbamate (compound no. 4) (1.4 mg, 2 pimp was obtained in similar fashion. $^1$H NMR (CDCl$_3$) δ0.52 (m, 2H), 7$_1$m, 14H), 1.0-2.0 (m, 22H), 2.10 (m, 1H), 2.45-2.75 (m, 4H), 3.64 (t, 2H), 3.90 (d, 2H), 4.15 (d, 1H), 4.60 (m, 1H), 5.00 (m, 1H), 5.13 (d, 1H), 5.25 (m, 1H), 6.80 (m, 1H), 7.10 (m, 2H), 7.30 (m, 4H), 7.50 (m, 2H), 7.90 (m, 1H); LCMS for $C_{35}H_{49}N_5O_7$ 651.36 [M], found $ES^+$652.5 $[M+H]^+$ and $ES^-$ 650.6 $[M-H]^-$, at 3.2 minutes retention time, using 10-90% acetonitrile/water (with 0.1% formic acid buffer) gradient over 5 minutes.

Example 7

(3S,5R)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 2) and (3S,5S)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 6)

Step A: (3S,5S)-di-tert-butyl-7-(3-chlorophenyl)-8-oxo-2,7-diazaspiro[4.4]nonane-2,3-dicarboxylate (A7a) and (3S,5R)-di-tert-butyl 7-(3-chlorophenyl)-8-oxo-2,7-diazaspiro[4.4]nonane-2,3-dicarboxylate (A7b)

Spirolactam (5S,8S)-tert-butyl 7-((S)-2-amino-3,3-dimethylbutanoyl)-2-oxo-3-phenyl-1-oxa-3,7-diazaspiro[4.4]nonane-8-carboxylate (F1) (51 mg, 150 μmol) was placed in a tube with CsCO$_3$ (70 mg, 215 μmol, 1.4 eq), Pd$_2$ dba$_3$ (6.6 mg, 7.2 μmol, 4.8%) and xanthphos ligand (13.5 mg, 23.3 μmol, 15.5%). Dioxane (1.5 ml) was added via syringe, followed by addition of 1-bromo-3-chlorobenzene (46 mg, 240 μmol, 1.6 eq). The sealed reaction was heated to 100° C. for 17 hrs with efficient magnetic stirring. The reaction was diluted with CH$_2$Cl$_2$ (10 ml), filtered through celite and concentrated. The crude was purified on silica (1% to 6% MeOH/CH$_2$Cl$_2$ gradient) to give the product as a mixture of diastereomers. The diastereomers were separated on silica (10% to 50% ether/hexane) to give (3S,5S)-di-tert-butyl-7-(3-chlorophenyl)-8-oxo-2,7-diazaspiro[4.4]nonane-2,3-dicarboxylate (A7a) (45.7 mg, 101 μmol). $^1$H NMR (CDCl$_3$) δ 1.48 (m, 18H), 2.09 (m, 1H), 2.45 (m, 1H), 2.70 (q, 2H), 3.50 (m, 1H), 3.70 (m, 3H), 4.28 (m, 1H), 7.15 (d, 1H), 7.30 (m, 1H), 7.50 (d, 1H), 7.65 (d, 1H); LCMS for $C_{23}H_{31}N_2O_5Cl$ 450.19 [M], found ES+ 451.19 $[M+H]^+$ at 3.7 minutes retention time, using 10-90% acetonitrile/water (with 0.1% formic acid buffer) gradient over 5 minutes. The minor diastereomer, (3S,5R)-di-tert-butyl 7-(3-chlorophenyl)-8-oxo-2,7-diazaspiro[4.4]nonane-2,3-dicarboxylate (A7b) (15.2 mg, 34 μmol) was also obtained. NMR (CDCl$_3$) δ 1.48 (m, 18H), 2.09 (m, 1H), 2.45 (m, 1H), 2.65 (s, 2H), 3.4-3.95 (m, 4H), 4.25 (m, 1H), 7.15 (d, 1H), 7.1-7.7 (m, 4H); LCMS for $C_{23}H_{31}N_2O_5Cl$ 450.19 [M], found ES+ 451.19 $[M+H]^+$ at 3.8 minutes retention time, using 10-90% acetonitrile/water (with 0.1% formic acid buffer) gradient over 5 minutes.

Step B: (3S,5R) methyl-7-(3-chlorophenyl)-8-oxo-2,7-diazaspiro[4.4]nonane-3-carboxylate (B7a) and (3S,5S)-methyl 7-(3-chlorophenyl)-8-oxo-2,7-diazaspiro[4.4]nonane-3-carboxylate (B7b)

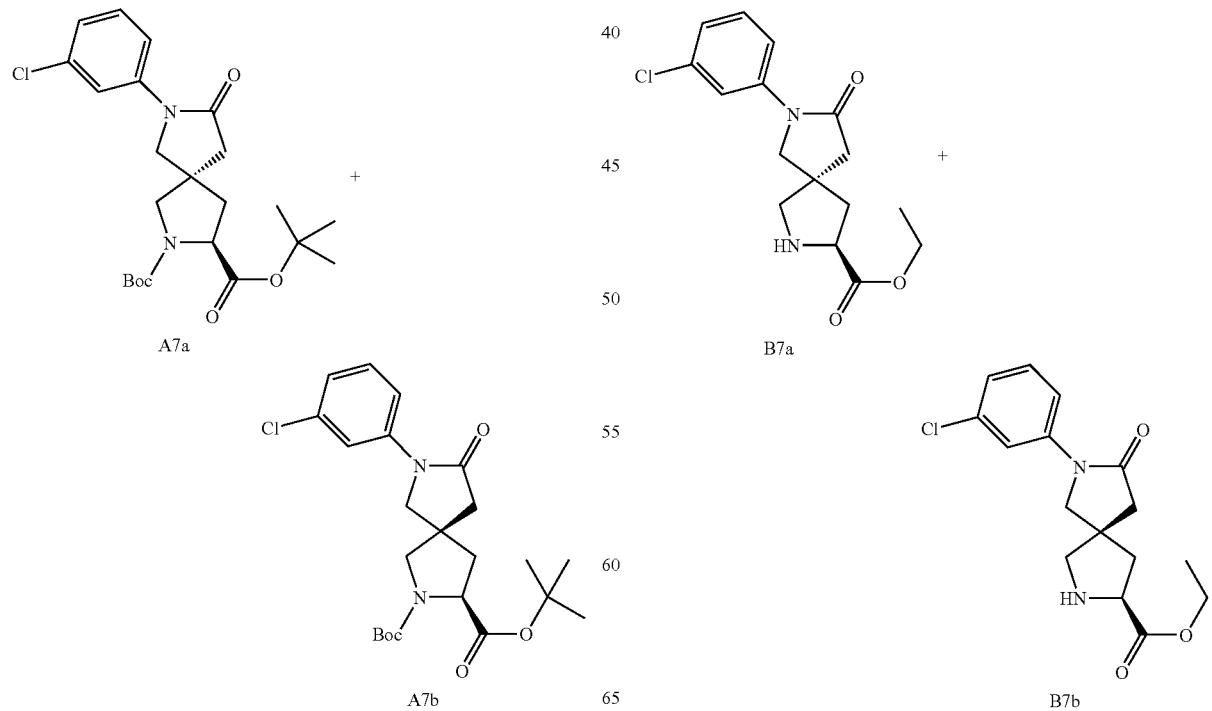

The arylated lactam (3S,5S)-di-tert-butyl-7-(3-chlorophenyl)-8-oxo-2,7-diazaspiro[4.4]nonane-2,3-dicarboxylate (A7a) (45.7 mg, 101 μmol) was taken up in 1M HCl in ethyl acetate (1.0 ml, 10 eq). The reaction was aged at room temperature overnight. The reaction was purged by bubbling $N_2$ gas through it, until dry. The product was then taken up in a saturated solution of hydrochloric acid in methanol (2 ml), and aged at room temperature overnight. The reaction was blown dry with nitrogen gas and dried in-vacuo to give (3S, 5R) methyl-7-(3-chlorophenyl)-8-oxo-2,7-diazaspiro[4.4]nonane-3-carboxylate (B7a) (35.2 mg, 102 μmol). LCMS for $C_{15}H_{17}N_2O_3Cl$ 308.09 [M], found ES+ 309.2 [M+H]$^+$ and 311.1 [M+H]$^+$ (for the chlorine isotope) at 2.0 minutes retention time, using 5-45% acetonitrile/water (with 0.1% formic acid buffer) gradient over 7 minutes. The minor diastereomer (3S,5R)-di-tert-butyl 7-(3-chlorophenyl)-8-oxo-2,7-diazaspiro[4.4]nonane-2,3-dicarboxylate (A7b) (15.2 mg, 34 μmol) was treated similarly to give (3S,5S)-methyl 7-(3-chlorophenyl)-8-oxo-2,7-diazaspiro[4.4]nonane-3-carboxylate (B7b) (12.4 mg, 36 μmol). LCMS for $C_{15}H_{17}N_2O_3Cl$ 308.09 [M], found ES+ 309.2 [M+H]$^+$ and 311.1 [M+H]$^+$ (for the chlorine isotope) at 2.2 minutes retention time, using 5-45% acetonitrile/water (with 0.1% formic acid buffer) gradient over 7 minutes.

Step C: (3S,5R)-methyl-2-((S)-2-(tert-butoxycarbonylamino)-3,3-dimethylbutanoyl)-7-(3-chlorophenyl)-8-oxo-2,7-diazaspiro[4.4]nonane-3-carboxylate (C7a) and (3S,5S)-methyl-2-((S)-2-(tert-butoxycarbonylamino)-3,3-dimethylbutanoyl)-7-(3-chloro phenyl)-8-oxo-2,7-diazaspiro[4.4]nonane-3-carboxylate (C7b)

Proline (3S,5R) methyl-7-(3-chlorophenyl)-8-oxo-2,7-diazaspiro[4.4]nonane-3-carboxylate (B7a) (35.2 mg, 102 μmol) in DMF (0.7 ml) was treated with (S)-2-(tert-butoxycarbonylamino)-3,3-dimethylbutanoic acid (33.3 mg, 144 μmol, 1.2 eq), 1-hydroxybenzotriazole (HOBT, 16.5 mg, 122 μmol, 1.2 eq), 1-ethyl-(3-dimethylaminopropyl)carbodiimide hydrochloride (EDC, 63.3 mg, 330 μmol, 3.2 eq), and N,N-Diisopropylethylamine (DIEA, 86 μA, 68 μmol, 4 eq) for three days at room temp. The reaction was quenched with 1M histamine in water (381 μl, 3.7 eq) and blown to dryness with $N_2$ gas. The residue was extracted with ethyl acetate (2×10 ml) and 0.5 N hydrochloric acid (2×5 ml). The organics were washed with 1M potassium carbonate in water (2×2 ml), dried over sodium sulfate, filtered and concentrated. The product was purified on silica (ethyl acetate/hexane gradient) to give (3S,5R)-methyl-2-((S)-2-(tert-butoxycarbonylamino)-3,3-dimethylbutanoyl)-7-(3-chlorophenyl)-8-oxo-2,7-diazaspiro[4.4]nonane-3-carboxylate (C7a) (36.9 mg, 70.6 μmol). $^1$H NMR (CDCl$_3$) δ 1.07 (s, 9H), 1.39 (s, 9H), 1.60 (s, 1H), 2.10 (m, 1H), 2.45 (m, 1H), 2.71 (s, 2H), 3.60 (m, 2H), 3.75 (s, 3H), 3.99 (d, 1H), 4.13 (d, 1H), 4.30 (d, 1H), 4.60 (t, 1H), 5.08 (d, 1H), 7.15 (m, 1H), 7.29 (m, 2H), 7.60 (m, 2H); LCMS for $C_{26}H_{36}N_3O_6Cl$ 521.23 [M], found ES+ 522.23 [M+H]$^+$ and 422.23 [M+H-Boc]$^+$ at 3.5 minutes retention time, using 10-90% acetonitrile/water (with 0.1% formic acid buffer) gradient over 5 minutes. The minor diastereomer (3S,5S)-methyl 7-(3-chlorophenyl)-8-oxo-2,7-diazaspiro[4.4]nonane-3-carboxylate (B7b) (12.4 mg, 36 μmol) was reacted similarly to give (3S,5S)-methyl-2-((S)-2-(tert-butoxycarbonylamino)-3,3-dimethylbutanoyl)-7-(3-chloro phenyl)-8-oxo-2,7-diazaspiro[4.4]nonane-3-carboxylate (C7b) (9.4 mg, 18 μmol, 50%). LCMS for $C_{26}H_{36}N_3O_6Cl$ 521.23 [M], found ES$^+$ 522.23 [M+H]$^+$ and 422.23 [M+H-Boc]$^+$ at 3.5 minutes retention time, using 10-90% acetonitrile/water (with 0.1% formic acid buffer) gradient over 5 minutes.

Step D: (3S,5R)-methyl 2-((S)-2-amino-3,3-dimethylbutanoyl)-7-(3-chlorophenyl)-8-oxo-2,7-diazaspiro[4.4]nonane-3-carboxylate (D7a) and (3S,5S)-methyl 2-((S)-2-amino-3,3-dimethylbutanoyl)-7-(3-chlorophenyl)-8-oxo-2,7-diazaspiro[4.4]nonane-3-carboxylate (D7b)

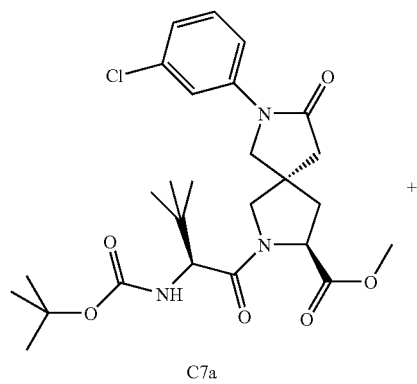

C7a

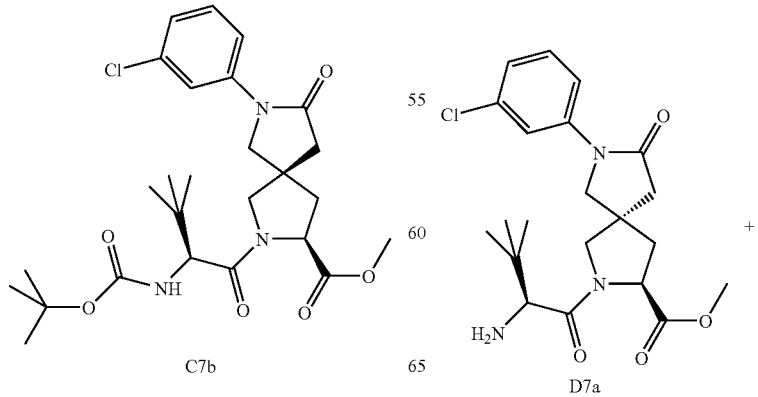

C7b

D7a

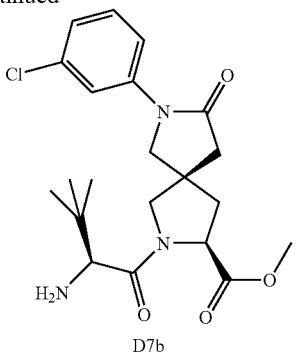

D7b

The compound (3S,5R)-methyl-2-((S)-2-(tert-butoxycarbonylamino)-3,3-dimethylbutanoyl)-7-(3-chlorophenyl)-8-oxo-2,7-diazaspiro[4.4]nonane-3-carboxylate (C7a) (36.9 mg, 70.6 pimp was dissolved in CH₂Cl₂ (1.0 ml) and treated with trifluoroacetic acid (0.3 ml) for 6 hrs at room temperature. The reaction was concentrated to dryness to give (3S,5R)-methyl 2-((S)-2-amino-3,3-dimethylbutanoyl)-7-(3-chlorophenyl)-8-oxo-2,7-diazaspiro[4.4]nonane-3-carboxylate (D7a) (70.6 μmol). The minor diastereomer (3S,5S)-methyl-2-((S)-2-(tert-butoxycarbonylamino)-3,3-dimethylbutanoyl)-7-(3-chloro phenyl)-8-oxo-2,7-diazaspiro[4.4]nonane-3-carboxylate (C7b) (9.4 mg, 18 μmol) was treated similarly to give (3S,5S)-methyl 2-((S)-2-amino-3,3-dimethylbutanoyl)-7-(3-chlorophenyl)-8-oxo-2,7-diazaspiro[4.4]nonane-3-carboxylate (D7b) (18 μmol, 100%).

Step E: (3S,5R)-methyl-7-(3-chlorophenyl)-2-((S)-2-(2-cyclohexylacetamido)-3,3-dimethyl butanoyl)-8-oxo-2,7-diazaspiro[4.4]nonane-3-carboxylate (E7a) and (3S,5S)-methyl 7-(3-chlorophenyl)-2-((S)-2-(2-cyclohexylacetamido)-3,3-dimethylbutanoyl)-8-oxo-2,7-diazaspiro[4.4]nonane-3-carboxylate (E7b)

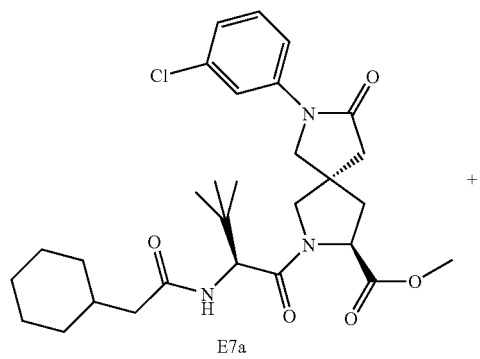

E7a

The amine (3S,5R)-methyl 2-((S)-2-amino-3,3-dimethylbutanoyl)-7-(3-chlorophenyl)-8-oxo-2,7-diazaspiro[4.4]nonane-3-carboxylate (D7a) (70.6 μmol) was taken up in CH₂Cl₂ (2.0 ml) and treated with 2-cyclohexylacetic acid (20.0 mg, 141 μmol, 2.0 eq), 1-hydroxybenzotriazole (HOBT, 9.5 mg, 70 μmol, 1.0 eq), 1-ethyl-(3-dimethylaminopropyl)carbodiimide hydrochloride (EDC, 27.1 mg, 141 μmol, 2.0 eq), and N,N-diisopropylethylamine (DIEA, 74 μl, 424 μmol, 6 eq) at room temp. overnight. The reaction was extracted with CH₂Cl₂ (2×10 ml) and water (5 ml). The organics were washed with brine, dried over sodium sulfate, filtered and concentrated to give crude. The product was purified on silica (ethyl acetate/hexane gradient) to give (3S,5R)-methyl-7-(3-chlorophenyl)-2-((S)-2-(2-cyclohexylacetamido)-3,3-dimethyl butanoyl)-8-oxo-2,7-diazaspiro[4.4]nonane-3-carboxylate (E7a) (12.8 mg, 23 μmol). ¹H NMR (CDCl₃) δ0.85-1.4 (m, 17H), 1.67 (m, 8H), 2.10 (m, 4H), 2.45 (m, 1H), 2.70 (d, 2H), 3.65 dd, 2H), 3.79 (s, 3H), 3.92 (d, 1H), 4.30 (d, 1H), 4.50 (d, 1H), 4.60 (t, 1H), 6.00 (d, 1H), 7.15 (d, 1H), 7.30 (m, 2H), 7.50 (m, 1H), 7.70 (s, 1H); LCMS for C₂₉H₄₀N₃O₅Cl 545.26 [M], found ES+ 546.3 [M+H]⁺ and 548.4 [M+H]⁺ (for the chlorine isotope) and ES– 544.3 [M–H]⁻ at 3.6 minutes retention time, using 10-90% acetonitrile/water (with 0.1% formic acid buffer) gradient over 5 minutes. The minor diastereomer (3S,5S)-methyl-2-((S)-2-(tert-butoxycarbonylamino)-3,3-dimethylbutanoyl)-7-(3-chloro phenyl)-8-oxo-2,7-diazaspiro[4.4]nonane-3-carboxylate (C7b) (18 μmol) was treated similarly to give (3S,5S)-methyl 7-(3-chlorophenyl)-2-((S)-2-(2-cyclohexylacetamido)-3,3-dimethylbutanoyl)-8-oxo-2,7-diazaspiro[4.4]nonane-3-carboxylate (E7b) (6.6 mg, 12 μmol). LCMS for C₂₉H₄₀N₃O₅Cl 545.26 [M], found ES+ 546.3 [M+H]⁺ at 3.6 minutes retention time, using 10-90% acetonitrile/water (with 0.1% formic acid buffer) gradient over 5 minutes.

Step F: (3S,5R)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7a) and (3S,5S)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7b)

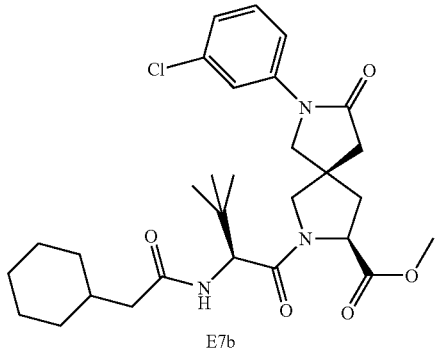

E7b

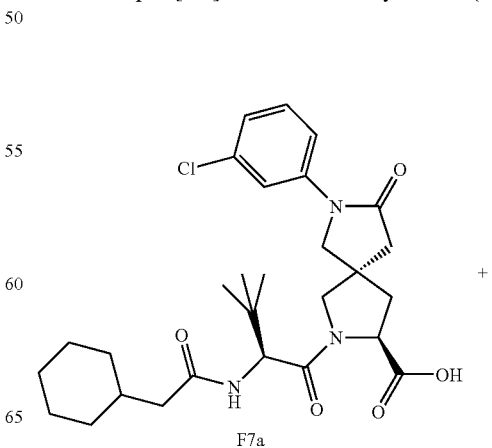

F7a

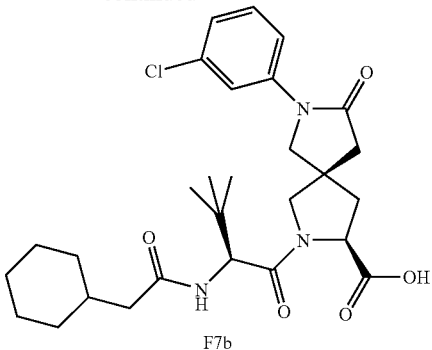

F7b

The methyl ester (3S,5R)-methyl-7-(3-chlorophenyl)-2-((S)-2-(2-cyclohexylacetamido)-3,3-dimethyl butanoyl)-8-oxo-2,7-diazaspiro[4.4]nonane-3-carboxylate (E7a) (12.8 mg, 23 μmol) was taken up in THF (1.0 ml) and MeOH (50 μl) was added. To this was added 1N LiOH in water (46 μl, 2.0 eq). The reaction was stirred at room temperature overnight and quenched at 0° C. with 1N HCl in water (46 μl, 2.0 eq). The reaction was concentrated to dryness to give (3S,5R)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7a) (23 μmol). LCMS for $C_{28}H_{38}N_3O_5Cl$ 531.25 [M], found ES+ 532.3 [M+H]$^+$ and ES− 530.5 [M−H]$^−$ at 3.2 minutes retention time, using 10-90% acetonitrile/water (with 0.1% formic acid buffer) gradient over 5 minutes. The minor diastereomer (3S,5S)-methyl 7-(3-chlorophenyl)-2-((S)-2-(2-cyclohexylacetamido)-3,3-dimethylbutanoyl)-8-oxo-2,7-diazaspiro[4.4]nonane-3-carboxylate (E7b) (6.6 mg, 12 μmol) was treated similarly to give (3S,5S)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7b) (12 mmol). LCMS for $C_{28}H_{38}N_3O_5Cl$ 531.25 [M], found ES+ 532.25 [M+H]$^+$ and ES− 530.25 [M−H] at 3.3 minutes retention time, using 10-90% acetonitrile/water (with 0.1% formic acid buffer) gradient over 5 minutes.

Step G: (3S,5R)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7a) and (3S,5S)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7b)

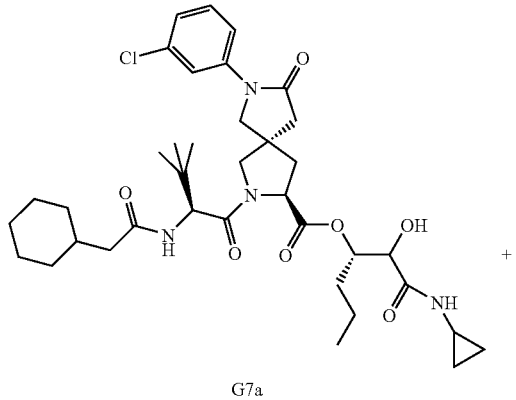

G7a

+

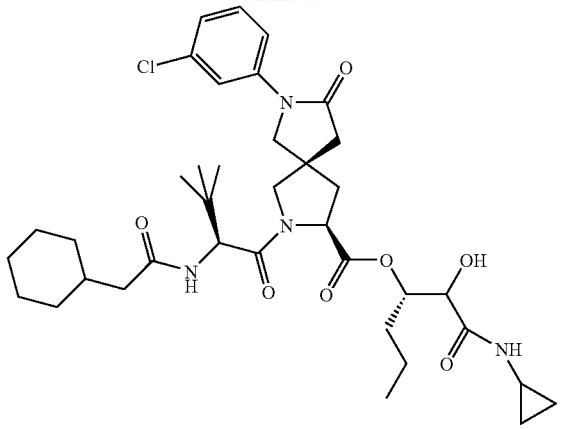

G7b

The carboxylic acid (3S,5R)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7a) (23 μmol) and (2R,3S)-3-amino-N-cyclopropyl-2-hydroxyhexanamide and hydrochloride salt (warhead (5S,8S)-3-(3-chlorophenyl)-7-((S)-2-(cyclopentyloxycarbonylamino)-3,3-dimethylbutanoyl)-2-oxo-1-oxa-3,7-diazaspiro[4.4]nonane-8-carboxylic acid (D3), 20.6 mg, 92 μmol, 4 eq) were dissolved in $CH_2Cl_2$ (2.0 ml). To this was added 1-hydroxybenzotriazole (HOBT, 12.2 mg, 46 μmol, 2 eq), 1-ethyl-(3-dimethylaminopropyl)carbodiimide hydrochloride (EDC, 17.6 mg, 92 μmol, 4 eq), and N,N-Diisopropylethylamine (DIEA, 50 μl, 288 μmol, 12.5 eq). The reaction was aged at room temp. overnight, and extracted with $CH_2Cl_2$ (2×10 ml) and water (2 ml). The organics were dried over sodium sulfate, filtered and concentrated to crude. The crude was purified on silica (1% MeOH/$CH_2Cl_2$ to 20% MeOH/$CH_2Cl_2$ gradient) to give (3S,5R)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7a) (12.2 mg, 17.4 μmol). LCMS for $C_{37}H_{54}ClN_5O_6$ 699.38 [M], found ES$^+$ 700.5 [M+H]$^+$ and ES$^−$ 698.7 [M−H]$^−$, at 3.3 minutes retention time, using 10-90% acetonitrile/water (with 0.1% formic acid buffer) gradient over 5 minutes. The minor diastereomer (3S,5S)-7-(3-chlorophenyl)-2-((S)-2-(2-cyclohexylacetamido)-3,3-dimethylbutanoyl)-8-oxo-2,7-diazaspiro[4.4]nonane-3-carboxylic acid (F7b) (12 μmol) was treated similarly to give (3S,5S)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7b) (8.5 mg, 12 μmol). LCMS for $C_{37}H_{54}ClN_5O_6$ 699.38 [M], found ES$^+$ 700.5 [M+H]$^+$ and ES$^−$ 698.7 [M−H]$^−$, at 3.3 minutes retention time, using 10-90% acetonitrile/water (with 0.1% formic acid buffer) gradient over 5 minutes.

Step H: (3S,5R)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 2) and (3S,5S)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 6)

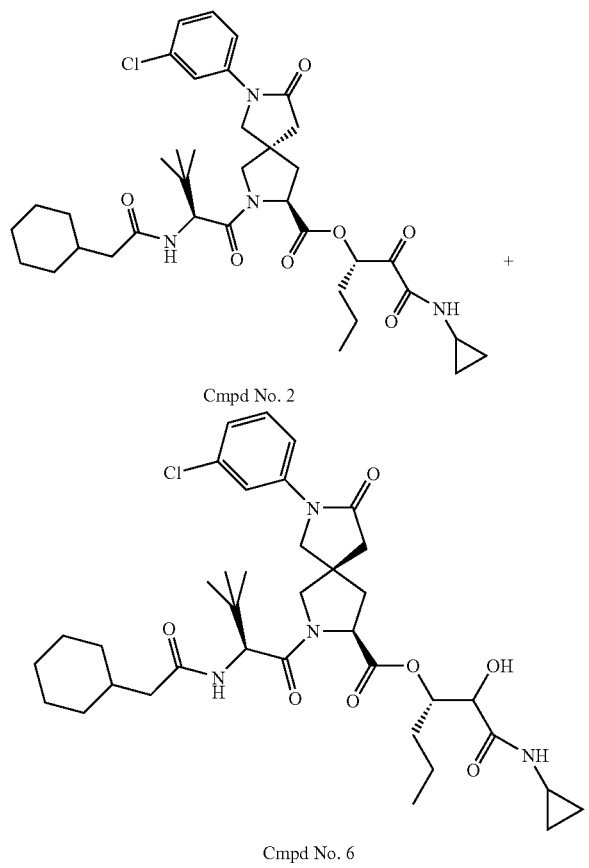

Cmpd No. 2

Cmpd No. 6

The hydroxy amide (3S,5R)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7a) (12.2 mg, 17.4 μmol) was dissolved in $CH_2Cl_2$ (2.0 ml) and treated with Dess-Martin periodinane (DMP, 22.0 mg, 52 μmol, 3 eq) for 3 hrs at room temperature. The reaction was quenched with 1M sodium thiosulfate in water (87 μl, 5 eq). The reaction was loaded onto silica and eluted with an ethyl acetate/hexane gradient, to give (3S,5R)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 2) (12.1 mg, 17.3 μmol) as a white solid. $^1$H NMR (CDCl$_3$) δ 529m, 44H), 3.51 (d, 2H), 3.91 (d, 1H), 4.21 (d, 1H), 4.44 (d, 1H), 4.59 (m, 1H), 5.22 (m, 1H), 5.92 (d, 1H), 6.81 (s, 1H), 7.09 (m, 1H), 7.20 (m, 4H), 7.50 (d, 1H), 7.60 (s, 1H); LCMS for $C_{37}H_{52}ClN_5O_6$ 697.36 [M], found ES$^+$ 698.5 [M+H]$^+$ and ES$^-$ 696.6 [M−H]$^-$, at 3.6 minutes retention time, using 10-90% acetonitrile/water (with 0.1% formic acid buffer) gradient over 5 minutes. The minor diastereomer (3S,5S)-((3S)-1-(cyclopropylamino)-2-hydroxy-1-oxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (G7b) (8.5 mg, 12 μmol) was treated similarly to give (3S,5S)-((S)-1-(cyclopropylamino)-1,2-dioxohexan-3-yl) 7-(3-chlorophenyl)-2-((S)-2-(2-cyclohexylacetamido)-3,3-dimethylbutanoyl)-8-oxo-2,7-diazaspiro[4.4]nonane-3-carboxylate (Cmpd No. 6) (7.8 mg, 11 μmol, 93%). $^1$H NMR (CDCl$_3$) δ 528m, 45H), 3.65 (m, 2H), 3.90 (m, 2H), 4.49 (m, 2H), 4.60 (m, 1H), 5.28 (m, 1H), 5.95 (m, 1H), 6.81 (s, 1H), 7.0-7.8 (m, 10H); LCMS for $C_{37}H_{52}ClN_5O_6$ 697.36 [M], found ES$^+$ 698.5 [M+H]$^+$ and ES$^-$ 696.6 [M−H]$^-$, at 3.6 minutes retention time, using 10-90% acetonitrile/water (with 0.1% formic acid buffer) gradient over 5 minutes.

Reagents and conditions: (l) 1-bromo-3-chlorobenzene, Pd$_2$dba$_3$/xanthphos/CsCO$_3$, dioxane, 100° C., 16 h, 90% (3:1 mixture); (m) HCl$_{(g)}$, EtOAc, 18 h, then HCl$_{(g)}$, MeOH, 24 h, 100%; (n) (S)-2-(tert-butoxycarbonylamino)-3,3-dimethylbutanoic acid, HOBT/EDC/DIEA, DMF, 3 days, 69%; (o) TFA, CH$_2$Cl$_2$, 6 h, 100%; (p) 2-cyclohexylacetic acid, HOBT/EDC/DIEA, CH$_2$Cl$_2$, 18 h, 67%; (q) LiOH, THF, MeOH, 18 h, 100%; (r) (2R,3S)-3-amino-N-cyclopropyl-2-hydroxyhexanamide hydrochloride, HOBT/EDC/DIEA, CH$_2$Cl$_2$, 18 h, 76%; (s) Dess-Martin Periodinane, CH$_2$Cl$_2$, 3 h, 99%.

VI. Assays for Detecting and Measuring Inhibition Properties of Compounds

A. HCV Enzyme Assays

1. Construction and Expression of the HCV NS3 Serine Protease Domain

A DNA fragment encoding residues Ala$^1$-Ser$^{181}$ of the HCV NS3 protease (GenBank CAB46913) was obtained by PCR from the HCV Con1 replicon plasmid, I$_{377}$neo/NS3-3'/wt (re-named as pBR322-HCV-Neo in this study) [V. Lohmann et al., Science, 285, pp. 110-113 (1999)] and inserted into pBEV11 (S. Chamber, et al., personal communication) for expression of the HCV proteins with a C-terminal hexahistidine tag in E. coli. All constructs were confirmed by sequencing.

The expression constructs for the HCV NS3 serine protease domain was transformed into BL21/DE3 pLysS E. coli cells (Stratagene). Freshly transformed cells were grown at 37° C. in a BHI medium (Difco Laboratories) supplemented with 100 μg/ml carbenicillin and 35 μg/ml chloramphenicol to an optical density of 0.75 at 600 nm. Induction with 1 mM IPTG was performed for four hrs at 24° C. The cell paste was harvested by centrifugation and flash frozen at −80° C. prior to protein purification. All purification steps were performed at 4° C. Next, 100 g of cell paste was lysed in 1.5 L of buffer A (50 mM HEPES (pH 8.0), 300 mM NaCl, 0.1% n-octyl-β-D-glucopyranoside, 5 mM (3-mercaptoethanol, 10% (v/v) glycerol) and stirred for 30 minutes. The lysate was homogenized using a Microfluidizer (Microfluidics, Newton, Mass.), followed by ultra-centrifugation at 54,000×g for 45 minutes. Imidazole was added to the supernatant to a final concentration of 5 mM along with 2 mL of Ni-NTA resin pre-equilibrated with buffer A containing 5 mM imidazole. The mixture was rocked for three hrs and washed with 20 column volumes of buffer A plus 5 mM imidazole. The HCV NS3 protein was eluted in buffer A containing 300 mM imidazole. The eluate was concentrated and loaded onto a Hi-Load 16/60 Superdex 200 column, pre-equilibrated with buffer A. The appropriate fractions of the purified HCV protein were pooled and stored at −80° C.

2. HCV NS3 Protease Domain Peptide Cleavage Assay

This assay is a modification of that described by Landro, et al. (Landro J A, Raybuck S A, Luong Y C, O'Malley E T, Harbeson S L, Morgenstern K A, Rao G and Livingston D L. Biochemistry 1997, 36, 9340-9348), and uses a peptide substrate (NS5AB), based on the NS5A/NS5B cleavage site for genotype 1a HCV. The substrate stock solution (25 mM) was prepared in DMSO containing 0.2 M DTT and stored at −20° C. A synthetic peptide cofactor (KK4A) was used as a substitute for the central core region of NS4A. Peptide sequences are shown in the table below. The reaction was performed in a 96-well microtiter plate format using 25 ηM to 50 ηM HCV NS3 protease domain in buffer containing 50 mM HEPES pH 7.8, 100 mM NaCl, 20% glycerol, 5 mM DTT and 25 μM KK4A. The final DMSO concentration was no greater than 2% v/v. Reactions were quenched by addition of trifluoroacetic acid (TFA) to yield a final concentration of 2.5%.

Peptide Sequences Used with HCV NS3 Protease Domain

| PEPTIDE | SEQUENCE |
|---|---|
| NS5AB | $NH_2$-EDVV-(alpha)Abu-CSMSY-COOH [SEQ ID NO: 2] |
| KK4A | $NH_2$-KKGSVVIVGRIVLSGK-COOH [SEQ ID NO: 3] |

The SMSY product was separated from substrate and KK4A using a microbore separation method. The instrument used was a Agilent 1100 with a G1322A degasser, either a G1312A binary pump or a G1311A quaternary pump, a G1313A autosampler, a G1316A column thermostated chamber and a G1315A diode array detector. The column was a Phenomenex Jupiter, 5 μm C18, 300 Å, 150×2 mm, P/O 00F-4053-B0, with a flow-rate of 0.2 mL/min. The column thermostat was at 40° C. Mobile phases were HPLC grade $H_2O/0.1\%$ TFA (solvent A) and HPLC grade $CH_3CN/0.1\%$ TFA (solvent B). The SMSY product peak was quantitated using the data collected at 210 ηM.

Construction and Expression of NS3•4A Protease

Using standard recombinant DNA techniques, a cDNA fragment encoding the sequence for NS3 and NS4A, residues $Ala_{1027}$ to $Cys_{1711}$ from the HCV sub-type strain 1a, containing an N-terminal hexa-histidine sequence, was cloned into the baculoviral transfer vector pVL1392 (Webb N R and Summers M D (1990) Expression of proteins using recombinant baculoviruses, Techniques 2:173-188). Recombinant baculovirus containing NS3•4A was produced by co-transfection of pVL1392-His-NS3•4A with linearized *Autographa californica* nuclear polyhedrosis virus (AcM-NPV) DNA into *Spodoptera frugoperda* (Sf9) insect cells. The transfected insect cells containing recombinant baculovirus clones were subsequently isolated by plaque purification. High-titer clonal baculovirus was routinely used to infect Sf9 insect cells for protein production. In production, Sf9 cells were grown at 27° C. until they reached a density of $2.0$-$\times 10^6$ cells/ml. At this point, the insect cells were infected with virus. After 72 hrs or when the cell viability was between 70-80% the culture was harvested and the cells were ready for purification.

3. Purification of NS3•4A Protein

The NS3•4A protein (SEQ ID NO:1) was purified as follows. Cell paste was thawed in at least five volumes of Lysis Buffer (50 mM $Na_2HPO_4$ pH 8.0, 10% Glycerol, 300 mM NaCl, 5 mM β-mercaptoethanol, 0.2 mM PMSF, 2.5 μg/ml Leupeptin, 1.0 μg/ml E64, 2.0 μg/ml Pepstatin) per gram of cell paste. The cell paste was then homogenized on ice using a Dounce homogenizer. The cells were next mechanically disrupted by passing once through a microfluidizer (Microfluidics Corporation, Newton, Mass.), and the cell lysate was collected on ice. The cell lysates was centrifuged at 100,000×g for 30 minutes at 4° C. and the supernatants were decanted. Optionally, the pellets were resuspended in wash buffer (Lysis Buffer+0.1% β-octyl glucopyranoside), homogenized using a Dounce homogenizer and centrifuged at 100,000×g for 30 minutes at 4° C. Insoluble NS3•4A was extracted from the pellets by resuspending in Extraction Buffer (Lysis Buffer+0.5% lauryl maltoside) using 2.5 ml/g cell paste. The mixture was homogenized using a Dounce homogenizer and mixed at 4° C. for three hrs or more. The mixture was centrifuged at 100,000×g for 30 minutes at 4° C. The supernatants were decanted and pooled.

The NS3•4A protein was further purified using Nickel-NTA metal affinity chromatography. Imidazole from a 2 M stock, pH 8.0, solution was added to the pooled supernatants so that the final concentration of imidazole was 10 mM. The supernatants were incubated batchwise overnight at 4° C. with Nickel-NTA affinity resin that had been pre-equilibrated with Lysis Buffer+10 mM imidazole. 1 ml of resin per 5 μg of expected NS3-4A was used. The resin was next settled by gravity or by centrifugation at 500×g for five minutes. The resin was next poured into a gravity flow column and washed with 10 or more column volumes of Nickel Wash Buffer (Lysis Buffer+0.1% lauryl maltoside+10 mM imidazole). The column was next eluted with three to four column volumes of Nickel Elution Buffer (Nickel Wash Buffer+300 mM imidazole). The elution fractions were collected on ice and evaluated using SDS-PAGE. To prevent NS3-4A proteolysis, 100 μM DFP protease inhibitor was added to gel samples before adding SDS sample buffer and boiling. The peak fractions were pooled and protein concentration was determined by measuring absorbance at 280 ηm and by dividing by the extinction coefficient (e), which for NS3•4A is 1.01.

The NS3•4A was purified further using gel filtration chromatography. A Superdex 200 26/60 column was equilibrated with Superdex Buffer (20 mM HEPES pH 8.0, 10% glycerol, 300 mM NaCl, 10 mM (3-mercaptoethanol, 0.05% lauryl maltoside) at a rate of 3 ml/min. The nickel purified NS3•4A was concentrated in a Centriprep 30 to greater than 2 mg/ml, if necessary, and was filtered through a 0.2 μm syringe filter and up to 10 ml was loaded onto the Superdex 200 column. After 0.3 column volumes passed through, 4-5 ml fractions were collected. Fractions were evaluated by SDS-PAGE. NS3•4A protein elutes in two peaks. Peak 1 contains aggregated NS3•4A and peak 2 contains active protein. The fractions of peak 2 were pooled, aliquoted and frozen at −70° C.

Analysis of NS3•4A Protein

| ANALYSIS | ENTIRE PROTEIN |
|---|---|
| Length | 695 amino acids |
| Molecular Weight | 74,347.78 |

-continued

| ANALYSIS | ENTIRE PROTEIN |
|---|---|
| 1 microgram | 13.450 picot moles |
| Molar Extinction Coefficient | 73430 |
| 1 $A_{280}$ corresponds to | 1.01 mg/ml |
| Isoelectric Point | 6.50 |
| Charge at pH 7 | −3.58 |

4. NS3 Peptide Cleavage Assay

This assay follows the cleavage of a peptide substrate by full-length hepatitis C viral protein NS3•4A. One of three peptide substrates based on the NS5A/NS5B cleavage site for genotype 1a HCV is used to measure enzyme activity. All substrate stock solutions (25 mM) were prepared in DMSO containing 0.2M DTT and stored at −20° C. A synthetic peptide cofactor (NS4A Peptide) was used to supplement NS4A. Peptide sequences are shown below. The hydrolysis reaction was performed in a 96-well microtiter plate format using 100 ηM to 125 ηM HCV NS3•4A in buffer containing 50 mM HEPES pH 7.8, 100 mM NaCl, 20% glycerol, 5 mM DTT and 25 µM NS4A Peptide. The final DMSO concentration was no greater than 2% v/v. Reactions using NS5AB or NS5AB-EDANS as substrate were quenched by the addition of 10% trifluoroacetic acid (TFA) to yield a final TFA concentration of 2.5%. Reactions using FITC-NS5AB-1 as substrate were quenched by the addition of 0.4M formic acid to yield a final concentration of 0.08M acid.

Enzymatic activity was assessed by separation of substrate and products by reverse phase HPLC. The instrument used was a Agilent 1100 with a G1322A degasser, either a G1312A binary pump or a G1311A quaternary pump, a G1313A autosampler, a G1316A column thermostated chamber, a G1321A fluorescence detector and a G1315A diode array detector. The column thermostat was at 40° C. For substrate NS5AB the column was a Phenomenex Jupiter, 5 µm C18, 300 Å, 150×2 mm, P/O 00F-4053-B0, with a flow-rate of 0.2 mL/min using HPLC grade $H_2O$/0.1% TFA (solvent A) and HPLC grade $CH_3CN$/0.1% TFA (solvent B) as mobile phases. The C-terminal product peak ($NH_2$-SMSY-COOH) was quantitated using the absorbance data collected at 210 ηm. For substrate NS5AB-EDANS the column was a Phenomenex Aqua, 5 µm C18, 125 Å, 50×4.6 mm, P/O 00B-4299-E0, with a flow-rate of 1.0 mL/min using HPLC grade $H_2O$/0.1% TFA (solvent A) and HPLC grade $CH_3CN$/0.1% TFA (solvent B) as mobile phases. The C-terminal product peak ($NH_2$-SMSYT-Asp(EDANS)-KKK-COOH) was quantitated using the fluorescence data collected at 350 ηm excitation/490 ηm emission. For substrate FITC-NS5AB-1 the column was a Phenomenex Prodigy, 5 µm ODS(2), 125 Å, 50×4.6 mm, P/O 00B-3300-E0, with a flow-rate of 1.0 mL/min using 10 mM sodium phosphate pH 7.0 in HPLC grade $H_2O$ (solvent A) and 65% HPLC Grade $CH_3CN$/35% 10 mM sodium phosphate pH 7.0 in HPLC grade H2O (solvent B) as mobile phases. The N-terminal product peak (FITC-Ahx-EDVV-(alpha)Abu-C—COOH) was quantitated using the fluorescence data collected at 440 nm excitation/520 nm emission. Alternatively, the ratio of N-terminal product to unreacted FITC-NS5AB-1 substrate was determined using a Caliper LabChip 3000 with detection at 488 nm excitation/530 nm emission, using a chip buffer of 100 mM Tris pH 7.0, 10 mM EDTA, 0.01% (v/v) Brij-35, and 0.1% (v/v) CR-3.

Peptide Sequences Used with HCV NS3

| PEPTIDE | SEQUENCE |
|---|---|
| NS4A Peptide | $NH_2$-KKGSVVIVGRIVLSGKPAIIPKK-COOH [SEQ ID NO: 4] |
| NS5AB | $NH_2$-EDVV-(alpha)Abu-CSMSY-COOH [SEQ ID NO: 2] |
| NS5AB-EDANS | $NH_2$-EDVV-(alpha)Abu-CSMSYT-Asp(EDANS)-KKK-COOH [SEQ ID NO: 5] |
| FITC-NS5AB-1 | FITC-Ahx-EDVV-(alpha)Abu-CSMSYTKK-$NH_2$ [SEQ ID NO: 6] |

5. Determination of Km and Vmax

To determine the kinetic parameters Km and Vmax, the HCV NS3 protease domain or HCV NS3•4A was reacted with peptide substrate under the assay conditions described above. Peptide substrate concentration was varied between 3 µM and 200 µM, with less than 20 percent conversion at all substrate concentrations. The ratio of the product peak area (as determined by reverse phase HPLC) to the reaction time yielded a rate of enzyme catalyzed hydrolysis. These rate vs. substrate concentration data points were fit to the Michaelis-Menten equation using non-linear regression. The value of $k_{cat}$ was determined from Vmax using the nominal protease concentration and a fully cleaved substrate peptide as an instrument calibration standard.

Kinetic parameters for peptide substrates with HCV NS3 or NS3 protease domain.

| ENZYME | SUBSTRATE | Km (µM) | $k_{cat}$/Km ($M^{-1}sec^{-1}$) |
|---|---|---|---|
| NS3 Protease Domain | NS5AB | 25 | $3.0 \times 10^4$ |
| NS3•4A | NS5AB | 30 | $7.9 \times 10^3$ |
| NS3•4A | NS5AB-EDANS | 56 | $1.4 \times 10^3$ |
| NS3•4A | FITC-NS5AB-1 | 15 | $1.2 \times 10^3$ |

6. Determination of Compound Potency

To evaluate apparent Ki values, all components except the test compound and substrate were pre-incubated for 5-10 minutes at room temperature. Then, test compound, dissolved in DMSO, was added to the mixture and incubated for either 15 minutes or 60 minutes at 30° C. Neat DMSO was included as a no inhibitor control. The cleavage reaction was initiated by the addition of peptide substrate at a concentration either equal to Km or equal to one-half times Km, and allowed to proceed at 30° C. for twenty minutes. At the end of the reaction the mixture was quenched, and the extent of reaction was determined as described above. Eleven concentrations of compound were used to titrate enzyme activity for inhibition. Activity vs. inhibitor concentration data points were fit to the Morrison equation describing competitive tight-binding enzyme inhibition using non-linear regression (Sculley M J and Morrison J F. Biochim. Biophys. Acta. 1986, 874, 44-53).

The tested compounds of formula I generally exhibited Ki values from about 0.100 to about 5 µM. In some embodiments, the compounds of formula I exhibited Ki values from about 0.170 to about 3.7 µM. In some other embodiments, the compounds of formula I exhibited Ki values from about 0.150 to about 3.50 µM. In still some other embodiments, the compounds of formula I exhibited Ki values from 0.140 to about 3.200 µM.

Examples of activities of the compounds of formulae (I, Ia, and Ib) on inhibiting serine protease receptors are shown below in Table 3. For compound activities for serine protease measured using the HCV Enzyme Assays, serine protease activity is illustrated with "+++" if activity was measured to be less than 0.41 µM, "++" if activity was measured to be from 0.41 µM to 0.7 µM, "+" if activity was measured to be greater than 0.7 and "−" if no data was available. It should be noted that 0% efficacy is the minimum response obtained with the DMSO only control. The Enzyme Assay 1 refers to the HCV NS3 Protease Domain Peptide Cleavage Assay and Enzyme Assay 2 refers to the HCV NS3 Peptide Cleavage Assay.

TABLE 3

HCV enzymatic assay activities and efficacies of exemplary compounds in accordance to Formulae I.

| Cmpd. No. | Activity | Assay No. 1 | Assay No. 2 |
|---|---|---|---|
| 1 | ++ | | |
| 2 | + | | |
| 3 | +++ | | |
| 4 | +++ | | |
| 5 | + | | |
| 6 | ++ | | |
| 7 | +++ | | |
| 8 | − | | |
| 9 | − | | |

B. HCV Cell Assays

Huh-7 cells were propagated in Dulbecco's modified Eagle's medium (DMEM, JRH Biosciences, Lenexa, Kans.) supplemented with 10% heat-inactivated FBS (fetal bovine serum), 2 mM L-glutamine, and nonessential amino acids (JRH). The cells were transfected with an in vitro transcribed HCV replicon RNA identical to replicon I377neo/NS3-3'/wt as described by Lohmann et al. (1999). Stable cell clones were selected and maintained in the presence of 250 µg/mL G418 (Invitrogen, Carlsbad, Calif.). One of the clones, 24-2, was used in the subsequent HCV replicon assays. The replicon cells were propagated in DMEM supplemented with 10% FBS, 2 mM L-glutamine, nonessential amino acids, and 250 µg/mL G418. The cells were split twice per week in fresh media upon reaching confluence. There are approximately 200-300 copies of HCV RNA per replicon cell.

HCV replicon RNA from cells was measured using the Quantigene Discover XL kit (Panomics Inc., Fremont Calif.) as per the manufacturer's instructions. Briefly, compound-treated replicon cells were lysed and immobilized on to capture plates using HCV specific oligonucleotides over night and the relative amounts Of captured RNA was measured using oligonucleotide probe sets as per the manufacturer's instructions.

1. 2-Day HCV Replicon $IC_{50}$ Assay

On the day prior to the assay, 104 replicon cells were plated per well of a 96-well plate and allowed to attach and grow overnight in DMEM (Invitrogen, Carlsbad, Calif.) supplemented with 10% heat-inactivated FBS (JRH Biosciences, Lenexa, Kans.), 2 mM L-glutamine (Invitrogen), nonessential amino acids (Invitrogen) and 250 µg/ml G418 (Invitrogen). Compounds were serially diluted in DMEM plus 2% FBS and 0.5% DMSO (Sigma Chemical Co., St. Louis, Mo.) without G418. HCV replicon RNA from cells was measured using the Quantigene Discover XL kit (Panomics Inc., Fremont Calif.) as per the manufacturer's instructions. Briefly, compound-treated replicon cells were lysed and immobilized on to capture plates using HCV specific oligonucleotides overnight and the relative amounts of captured RNA was measured using oligonucleotide probe sets as per the manufacturer's instructions. Unless indicated otherwise, each data point represents the average of three replicates. The $IC_{50}$ is the concentration of the compound at which the HCV replicon RNA level in cells is reduced by 50% as compared to the untreated replicon cell controls. To monitor the effect of compounds on cell proliferation or cell viability, replicon cells were treated with serially diluted compounds for 48 h, after which cell viability was determined using a CellTiter Glo assay (Promega, Madison, Wis.). Each $CC_{50}$ is derived from three replicates and is the concentration of the compound at which the number of viable cells is reduced by 50% as compared to untreated cell controls. The $IC_{50}$ and $CC_{so}$ was determined using 4 parameter curve fitting in the SoftMax Pro program (Molecular Devices, Sunnyvale, Calif.).

2. 5-Day HCV Replicon $IC_{99}$ Assay

On the day prior to the assay, HCV replicon cells were plated at a low density of 2500 cells per well in a 96-well plate so the cells would not reach confluence during 5 days in culture. Compounds were serially diluted in DMEM containing 10% FBS and 0.5% DMSO in the absence of G418. Fresh media and compounds were added to the cells on day 1 and day 3. After the cells were treated with antiviral compounds for 5 days, HCV replicon RNA from cells was measured using the Quantigene Discover XL kit (Panomics Inc., Fremont Calif.) as per the manufacturer's instructions. Briefly, compound-treated replicon cells were lysed and immobilized onto to capture plates using HCV specific oligonucleotides overnight and the relative amounts of captured replicon RNA was measured using oligonucleotide probe sets (Panomics) as per manufacturer's instructions. Each data point represents the average of two replicates. The $IC_{99}$ is the concentration of the compound at which the HCV replicon RNA level in cells is reduced by 2 logs as compared to the untreated cell controls. To monitor the effect of compounds on cell proliferation or cell viability, replicon cells were treated with serially diluted compounds for 5 days, after which cell viability was determined using a CellTiter Glo assay (Promega, Madison, Wis.). Each $CC_{50}$ is derived from two replicates and is the concentration of the compound at which the number of viable cells is reduced by 50% as compared to untreated cell controls. The $IC_{99}$ and $CC_{50}$ were determined by 4 parameter curve fitting method using the Prism software (GraphPad Software Inc., San Diego, Calif.) and Excel program (Microsoft Corporation, Redmond, Wash.).

Using the assays above, compounds of the present invention are determined to be useful serine protease inhibitors.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of formula I:

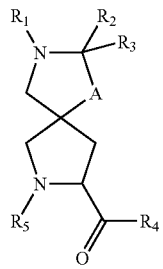

or a pharmaceutically acceptable salt thereof, wherein
R$_1$ is an optionally substituted aryl:
R$_2$ and R$_3$ together form an oxo group;
A is —O—, or —CH$_2$—;
R$_4$ is —NH—CHR$_{4x}$—C(O)—(CO)—N(R$_{4z}$)R$_{4W}$;
R$_{4W}$ is hydrogen, optionally substituted aliphatic, optionally substituted aryl, optionally substituted heteroaryl, optionally substituted heterocycloaliphatic, or optionally substituted cycloaliphatic;
R$_{4x}$ is hydrogen, optionally substituted aliphatic, optionally substituted heteroaryl, optionally substituted phenyl, optionally substituted cycloaliphatic, or optionally substituted heterocycloaliphatic;
R$_{4Z}$ is hydrogen, optionally substituted aliphatic, optionally substituted cycloaliphatic, optionally substituted heterocycloaliphatic, optionally substituted aryl, or optionally substituted heteroaryl;
R$_5$ is

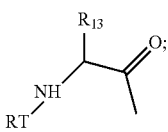

R$_{13}$ is

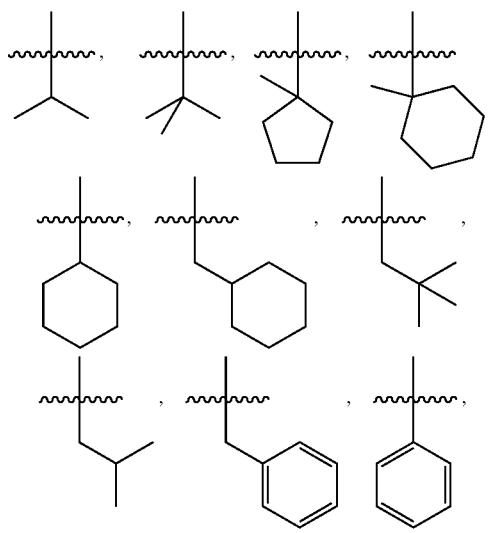

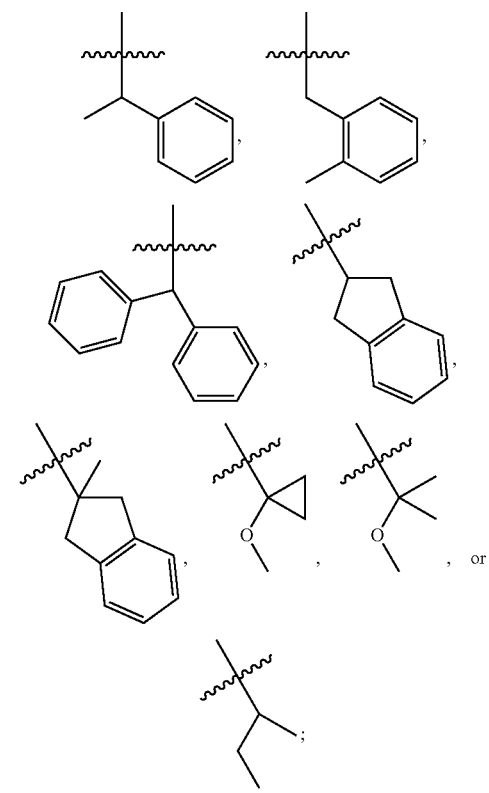

T is —C(O)—, and
R is

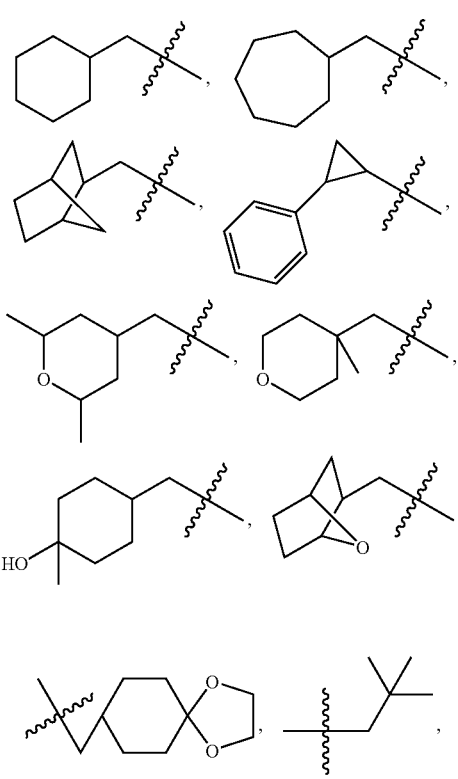

-continued

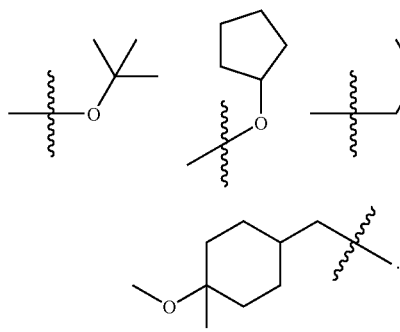

2. The compound of claim 1, wherein $R_1$ is a monocyclic or bicyclic aryl, each of which is optionally substituted.

3. The compound of claim 2, wherein $R_1$ is
phenyl optionally substituted with 1-3 substituents selected from halo, hydroxy, aliphatic, aryl, heteroaryl, cycloaliphatic, and heterocycloaliphatic.

4. The compound of claim 1, wherein $R_4$ is —NH—$CHR_{4X}$—C(O)—C(O)—NH-cyclopropyl.

5. The compound of claim 1, wherein $R_4$ is:

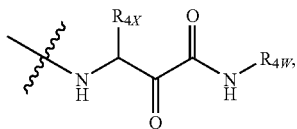

wherein $R_{4x}$ is

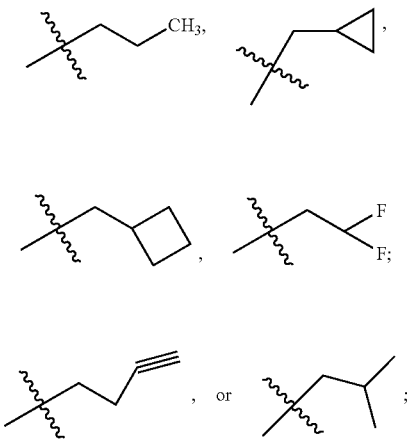

and $R_{4W}$ is

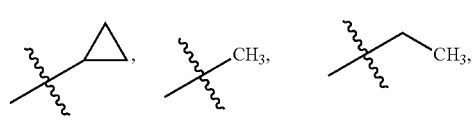

or hydrogen.

6. The compound of claim 1, wherein $R_4$ is one selected from the group consisting of

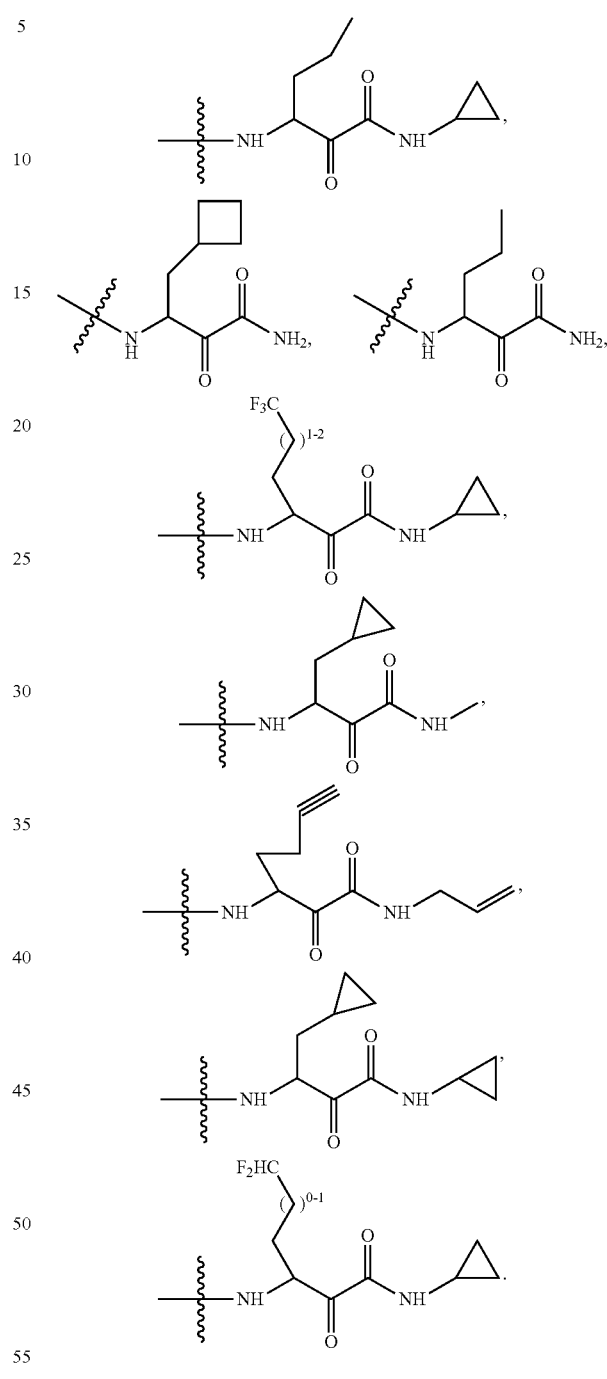

7. The compound of claim 6, wherin $R_4$ is

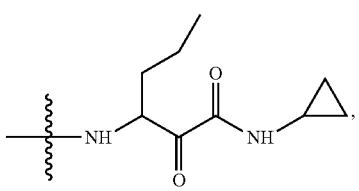

-continued
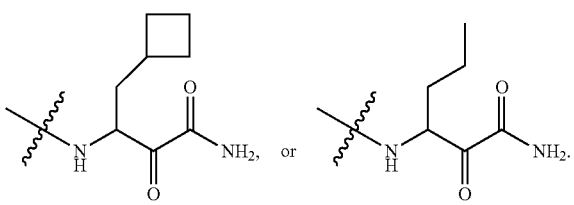
8. The compound of claim 1, wherein $R_5$ is:
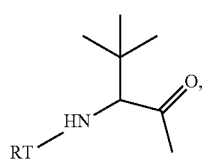
wherein
T is —C(O)—, and
R is
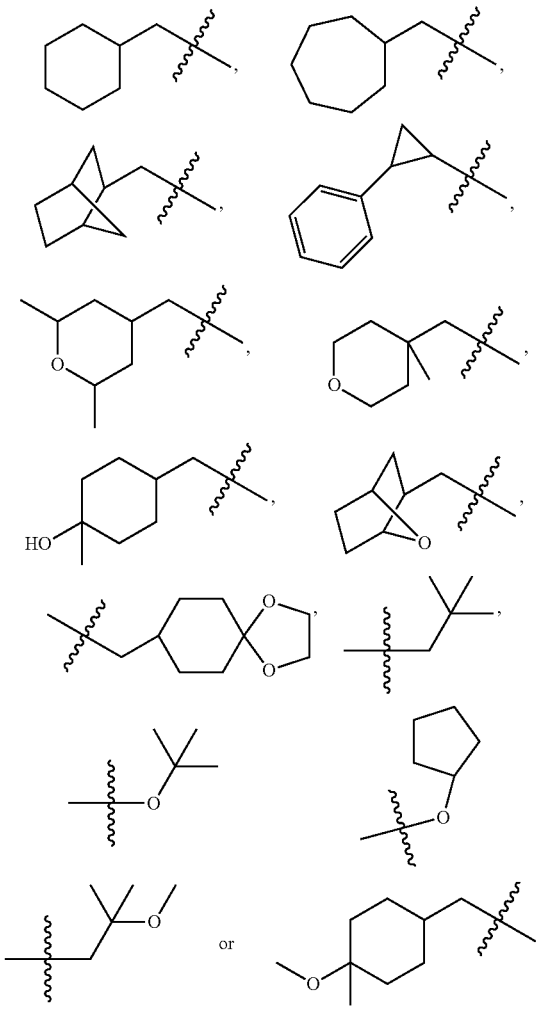
9. The compound of claim 8, wherein $R_5$ is one selected from the group consisting of
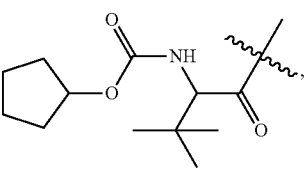 [SMILES: *C(=O)C(NC(=O)OC1CCCC1)C(C)(C)C]
10. A compound selected from the group of compounds:
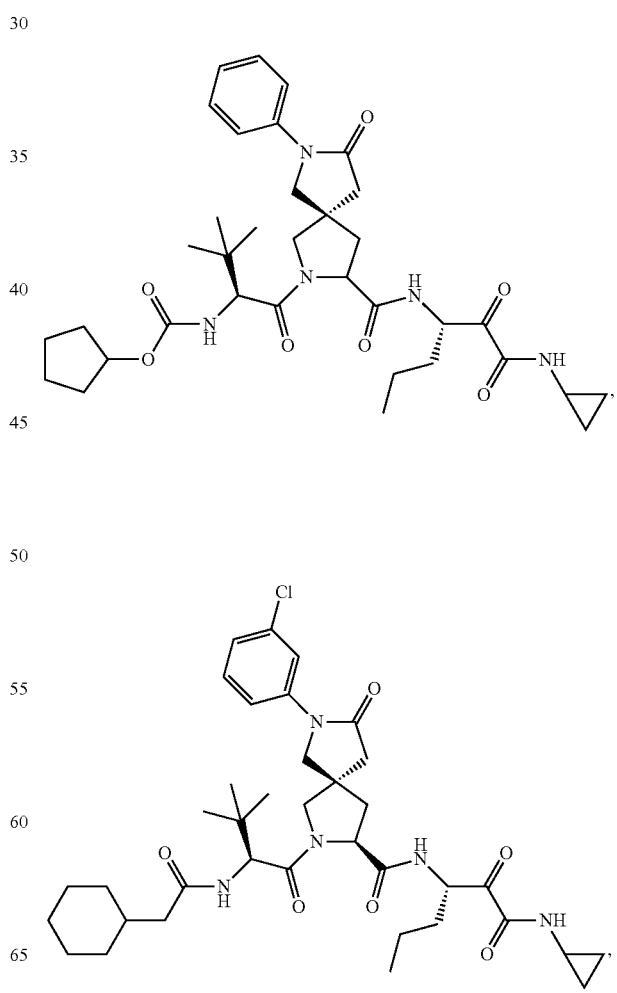

175
-continued
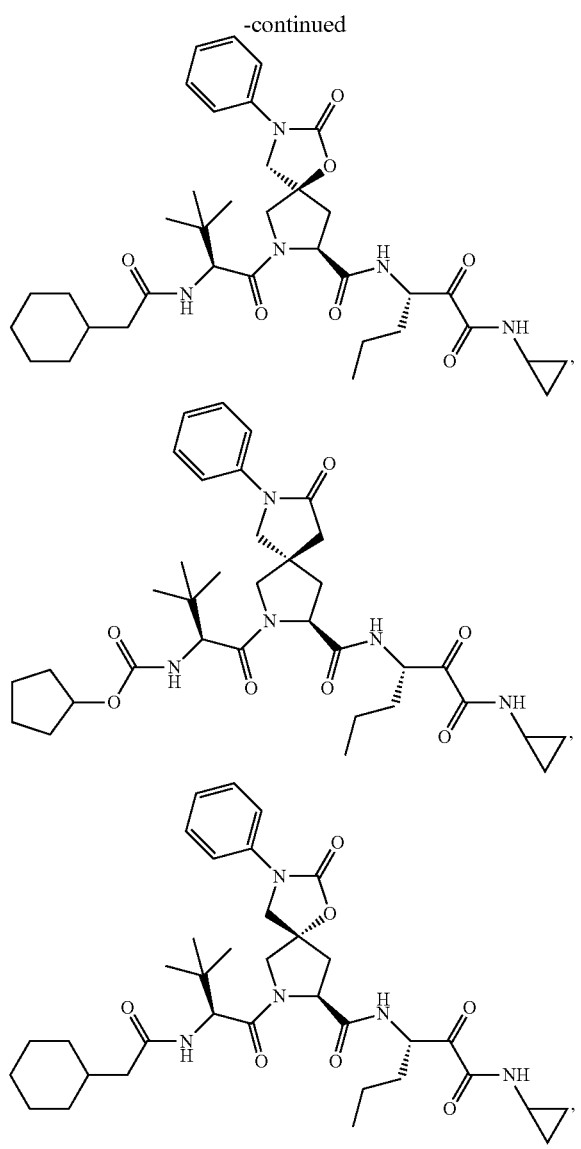
176
-continued
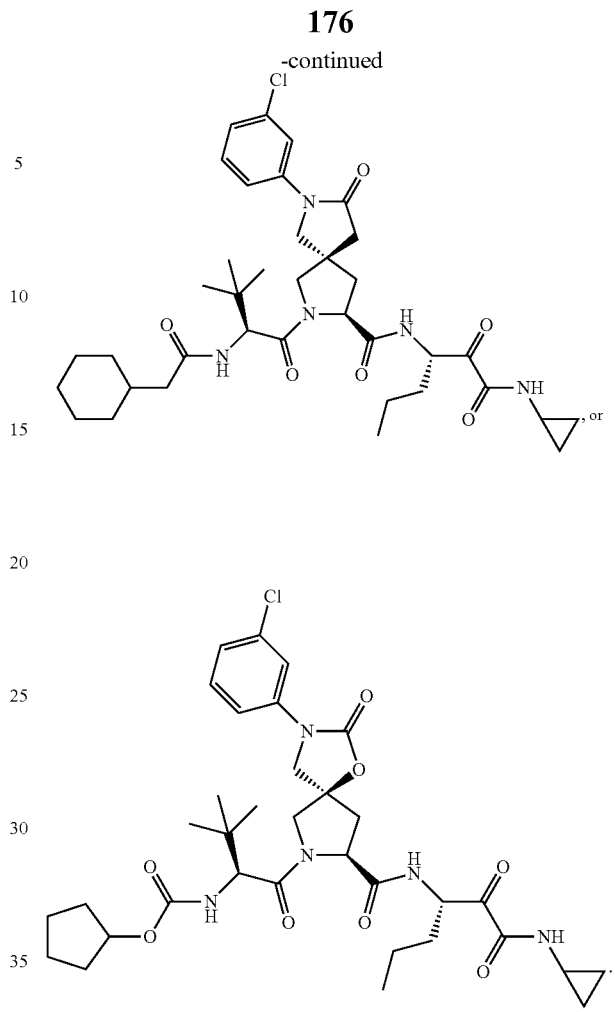
11. A pharmaceutical composition comprising a compound according to claim 1 or a pharmaceutically acceptable salt thereof in an amount effective to inhibit a serine protease; and an acceptable carrier, adjuvant or vehicle.
* * * * *